US007544856B2

(12) United States Patent
Komori et al.

(10) Patent No.: US 7,544,856 B2
(45) **Date of Patent: *Jun. 9, 2009**

(54) RICE RESTORER GENE TO THE RICE BT TYPE CYTOPLASMIC MALE STERILITY

(75) Inventors: Toshiyuki Komori, Shizuoka (JP); Yoshimitsu Takakura, Shizuoka (JP); Yukoh Hiei, Shizuoka (JP); Shoichi Suzuki, Tochigi (JP); Yoshiki Kuraya, Tochigi (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/520,350

(22) PCT Filed: Mar. 17, 2003

(86) PCT No.: PCT/JP03/03154

§ 371 (c)(1),
(2), (4) Date: Oct. 12, 2005

(87) PCT Pub. No.: WO2004/005515

PCT Pub. Date: Jan. 15, 2004

(65) Prior Publication Data

US 2006/0179517 A1 Aug. 10, 2006

(30) Foreign Application Priority Data

Jul. 5, 2002 (JP) ............................ 2002-197560

(51) Int. Cl.
*C12N 15/82* (2006.01)
*C12N 15/12* (2006.01)
*C07H 21/04* (2006.01)

(52) U.S. Cl. ..................................... 800/278; 536/23.6

(58) Field of Classification Search ....................... None
See application file for complete search history.

(56) References Cited

U.S. PATENT DOCUMENTS 7,164,058 B2 * 1/2007 Hanson et al. .............. 800/298

FOREIGN PATENT DOCUMENTS

| | | |
|---|---|---|
| JP | 7222588 | 8/1995 |
| JP | 9313187 | 12/1997 |
| JP | 2000-139465 A | 5/2000 |
| JP | 2000139465 | 5/2000 |
| WO | WO-02/14506 A1 | 2/2002 |

OTHER PUBLICATIONS

Buell et al (Jan. 2002, GenBank Accession No. AAL58263 and AC068923.*
Sequence alignment of AAL58263 with SEQ ID No. 75.*
Falcon-Perez JM et al. 1999, J Biol Chem. 274:23584-90.*
Lazar et al. 1988, Mol. Cell. Biol. 8:1247-1252.*
Hill et al 1998, Biochem. Biophys. Res. Comm. 244:573-577.*
Guo et al. 2004, Proc. Natl. Acad. Sci. USA 101: 9205-9210.*
Fourgoux-Nicol et al 1999, Plant Molecular Biology 40 :857-872.*
Sequence alignment 1 & 2.*
Fukuta, et al., Jpn J Breed (1992) 42 (Supl 1) p. 164-165.
Harushima, et al., Genetics (1998) 148 p. 479-494.
Michaels, et al., The Plant Journal (1998) 14(3) p. 381-385.
Neff, et al., The Plant Journal (199) 14(3) p. 387-392.
Harry, et al., Theor Appl Genet (1998) 97 p. 327-336.
Hiei, et al., The Plant Journal (1994) 6(2) p. 271-282.
Komari, et al., The Plant Journal (1996) 10(1) p. 165-174.
Ditta, et al., Proc Natl Acad Sci USA (1980) 77(12) p. 7347-7351.
Vos, et al., Nucleic Acid Research (1995) 23(21) p. 4407-4414.
Parnaud, et al., Mol Gen Genet (1996) 252 p. 597-607.
Konieczny, et al., The Plant Journal (1993) 4(2) p. 403-410.
Edwards, et al., Nucleic Acid Research (1991) 19(6) p. 1349.
Murray, et al., Nucleic Acid Research (1980) 8(19) p. 4321-4325.
Terada, et al., Plant Cell Physiol (2000) 41(7) p. 881-888.
Hirochika, et al., Proc Natl Acad Sci USA (1996) 93 p. 7783-7788.
Cui, et al., Science (1996) 272 p. 1334-1336.
Liu, et al., The Plant Cell (2001) 13 p. 1063-1078.
Shinjyo, et al., Japan J Genetics (1969) 44(3) p. 149-156.
Huang et al., "Construction of a YAC Contig Encompassing G200 Locus of Rice via Chromosome Walking.", *Chinese Journal of Biotechnology*, vol. 14, No. 4, (1998), pp. 213-219.
Komori et al., "Fine genetic mapping of the nuclear gene, RF-1, that restores the BT-type cytoplasmic male sterility in rice (*Oryza sativa* L.) by PCR-based makers", Euphytica, 2003, vol. 129, No. 2, pp. 241-247.
Akagi et al., "A Codominant DNA Marker Closely Linked to the Rice Nuclear Restorer Gene, *Rf*-1, Identified With Inter-SSR Fingerprinting," Genome, vol. 39, pp. 1205-1209, 1996.

* cited by examiner

*Primary Examiner*—Elizabeth F McElwain
*Assistant Examiner*—Li Zheng
(74) *Attorney, Agent, or Firm*—Birch, Stewart, Kolasch & Birch LLP

(57) ABSTRACT

The purpose of the present invention is to provide the rice restorer gene to the rice BT type cytoplasmic male sterility. The gene of the present invention comprises a nucleic acid encoding the amino acid sequence of SEQ ID NO. 75, or an amino acid sequence which is identical to at least 70% of the amino acid sequence of SEQ ID NO. 75, and which functions to restore fertility. Preferably, the gene of the present invention has the base sequence of SEQ ID NOS:69-74, 80-85 or the bases 43907-46279 of SEQ ID NO:27.

5 Claims, 8 Drawing Sheets

ATG
TGA
#1
2682
117
184
84
246
740
56
693
#2
2680
117
184
84
246
740
56
693
#3
2685
117
194
84
246
740
56
863
#4
2675
390
84
246
744
56
693
#5
2616
390
84
57
107
740
56
646
#6
4376
84
246
740
56
646

SEQUENCE LISTING

<160> NUMBER OF SEQ ID NOS: 87

<210> SEQ ID NO 1
<211> LENGTH: 24
<212> TYPE: DNA
<213> ORGANISM: Artificial Sequence
<220> FEATURE:
<223> OTHER INFORMATION: Synthetic oligonucleotide primer for amplification of R1877 EcoRI marker sequence.

<400> SEQUENCE: 1
cattcctgct tccatggaaa cgtc 24

<210> SEQ ID NO 2
<211> LENGTH: 33
<212> TYPE: DNA
<213> ORGANISM: Artificial Sequence
<220> FEATURE:
<223> OTHER INFORMATION: Synthetic oligonucleotide primer for amplification of R1877 EcoRI marker sequence.

<400> SEQUENCE: 2
ctctttctgt atacttgagc tttgacatct gac 33

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide primer for amplification of G4003 HindIII marker sequence.

<400> SEQUENCE: 3
gatcgacgag tacctgaacg 20

<210> SEQ ID NO 4
<211> LENGTH: 24
<212> TYPE: DNA
<213> ORGANISM: Artificial Sequence
<220> FEATURE:
<223> OTHER INFORMATION: Synthetic oligonucleotide primer for amplification of G4003 HindIII marker sequence.

<400> SEQUENCE: 4
aatagttgga ttgtcctcaa aggg 24

<210> SEQ ID NO 5
<211> LENGTH: 27
<212> TYPE: DNA
<213> ORGANISM: Artificial Sequence
<220> FEATURE:
<223> OTHER INFORMATION: Synthetic oligonucleotide primer for amplification of C1361 MwoI marker sequence.

<400> SEQUENCE: 5
aaagcaaccg acttcagtgg catcacc 27

<210> SEQ ID NO 6
<211> LENGTH: 24
<212> TYPE: DNA
<213> ORGANISM: Artificial Sequence
<220> FEATURE:
<223> OTHER INFORMATION: Oligonucleotide primer for amplification of C1361 MwoI marker sequence.

<400> SEQUENCE: 6

-continued

```
ctggacttca tttccctgca gagc                                              24


<210> SEQ ID NO 7
<211> LENGTH: 27
<212> TYPE: DNA
<213> ORGANISM: Artificial Sequence
<220> FEATURE:
<223> OTHER INFORMATION: Oligonucleotide primer for amplification of
      G2155 MwoI marker sequence.

<400> SEQUENCE: 7

gaccaccaat taactgatta agctggc                                           27


<210> SEQ ID NO 8
<211> LENGTH: 27
<212> TYPE: DNA
<213> ORGANISM: Artificial Sequence
<220> FEATURE:
<223> OTHER INFORMATION: Synthetic oligonucleotide primer for
      amplification of G2155 MwoI marker sequence.

<400> SEQUENCE: 8

tttctggctc caataatcag ctgtagc                                           27


<210> SEQ ID NO 9
<211> LENGTH: 27
<212> TYPE: DNA
<213> ORGANISM: Artificial Sequence
<220> FEATURE:
<223> OTHER INFORMATION: Synthetic oligonucleotide primer for
      amplification of G291 MspI marker sequence.

<400> SEQUENCE: 9

ctgctgcagc aagctgcacc gaaccgg                                           27


<210> SEQ ID NO 10
<211> LENGTH: 24
<212> TYPE: DNA
<213> ORGANISM: Artificial Sequence
<220> FEATURE:
<223> OTHER INFORMATION: Synthetic oligonucleotide primer for
      amplification of G291 MspI marker sequence.

<400> SEQUENCE: 10

acatttttc ttccgaaact tccg                                               24


<210> SEQ ID NO 11
<211> LENGTH: 24
<212> TYPE: DNA
<213> ORGANISM: Artificial Sequence
<220> FEATURE:
<223> OTHER INFORMATION: Synthetic oligonucleotide primer for
      amplification of R2303 BslI marker sequence.

<400> SEQUENCE: 11

atggaaagat acactagaat gagc                                              24


<210> SEQ ID NO 12
<211> LENGTH: 24
<212> TYPE: DNA
<213> ORGANISM: Artificial Sequence
<220> FEATURE:
<223> OTHER INFORMATION: Synthetic oligonucleotide primer for
      amplification of R2303 BslI marker sequence.

<400> SEQUENCE: 12
```

-continued atcttatata gtggcaggaa agcc 24

<210> SEQ ID NO 13
<211> LENGTH: 24
<212> TYPE: DNA
<213> ORGANISM: Artificial Sequence
<220> FEATURE:
<223> OTHER INFORMATION: Synthetic oligonucleotide primer for amplification of S10019 BstUI marker sequence.

<400> SEQUENCE: 13
aacaatctta tcctgcacag actg 24

<210> SEQ ID NO 14
<211> LENGTH: 24
<212> TYPE: DNA
<213> ORGANISM: Artificial Sequence
<220> FEATURE:
<223> OTHER INFORMATION: Synthetic oligonucleotide primer for amplification of S10019 BstUI marker sequence.

<400> SEQUENCE: 14
gtcacataga agcagatggg ttcc 24

<210> SEQ ID NO 15
<211> LENGTH: 24
<212> TYPE: DNA
<213> ORGANISM: Artificial Sequence
<220> FEATURE:
<223> OTHER INFORMATION: Synthetic oligonucleotide primer for amplification of S10602 KpnI marker sequence.

<400> SEQUENCE: 15
agctgttgag agttctatgc cacc 24

<210> SEQ ID NO 16
<211> LENGTH: 24
<212> TYPE: DNA
<213> ORGANISM: Artificial Sequence
<220> FEATURE:
<223> OTHER INFORMATION: Synthetic oligonucleotide primer for amplification of S10602 KpnI marker sequence.

<400> SEQUENCE: 16
tagccatgca acaagatgtc atac 24

<210> SEQ ID NO 17
<211> LENGTH: 26
<212> TYPE: DNA
<213> ORGANISM: Artificial Sequence
<220> FEATURE:
<223> OTHER INFORMATION: Synthetic oligonucleotide primer for amplification of S12564 Tsp509I marker sequence.

<400> SEQUENCE: 17
ctagttagac cgaataactg aggttc 26

<210> SEQ ID NO 18
<211> LENGTH: 27
<212> TYPE: DNA
<213> ORGANISM: Artificial Sequence
<220> FEATURE:
<223> OTHER INFORMATION: Synthetic oligonucleotide primer for amplification of S12564 Tsp509I marker sequence.

<400> SEQUENCE: 18
tttgtgggtt tgtggcattg agaaaat 27

-continued

<210> SEQ ID NO 19
<211> LENGTH: 2240
<212> TYPE: DNA
<213> ORGANISM: Oryza sativa L.
<220> FEATURE:
<221> NAME/KEY: misc_feature
<223> OTHER INFORMATION: PCR marker G4003 HindIII

<400> SEQUENCE: 19
gcggccgctc cgggaagtcg agcgagtaga cgcccctgac gccgtacgcg tcggcgagcc 60
gcagcggcgt ctctggcggt gtgaaggaca gcccgttcag cgtcgcgcgg cgccgcccgt 120
tgatcgtcac cggcgccgtg ctccgcagca ggtacgcctg cgtcacgttg atcgacgagt 180
acctgaacga tccctgtggg ttcggcctcg ccgctccggc actcaggttc cacctgccca 240
atgcaaaaaa ccaaaaccca aaagcttaat gcgaataata catcattcca cgtatttaaa 300
aaaataattt ataggtaaaa tttttataat gtattttagc gacgtaaatg tcaatgctga 360
gaaataaacg ataatacttt aaatgaagtt ctaaaattta aattttggca tcggttgatg 420
ttggataaag aaaacgatgg aggctagtaa tttttcttct tttttaagta tctagattgt 480
catatattga atttttcagt ttttcatccc tttgaggaca atccaactat tattttcctt 540
ttcttatgta aaaggttgaa caacatattc aaacataaaa aaataaaatt aaatgaaata 600
aatttacaat tcataaaatt tacagaattt atgttaagaa aatattcaaa cttagataat 660
aataaagcaa caaaatcgta ctaaaaagaa gtataattgt acattgtata ctactactcc 720
tacaatttta gacttagaat ttttaatttc ctgaaatcta gtaatgccat ttttttcttt 780
ctagttgaac cagacagtaa gtttaactcg aaacttataa gctaatgagc gaagtcgggc 840
aattcactcg tacctgacgg agcgagcttg gttcatggag aaggacttgt cgaactggtc 900
ctggggaggg tcggggagcg ggccggaggc ccgcccccgg gagttggagt agcggaggac 960
ggcgacgccg gcgacgcggc gccacacggt gtcgttcacc atgcgcgcgc tggcgacgac 1020
gtagtagtcg gagctcgcgt tctggtcggt ggtgacgagg aaggagtagg actggccgac 1080
gtggacgtcc aggttggtgt agttctgctg cgtcgtgtag gagccctccg tctccaccag 1140
caccatgttg tgcccctgga tcctgaagtt gaggctcgtc gacgtcccca cgttgtgcac 1200
tcggatcctg tacgtcttgc ctgtgtcccc acaccgacgt cgccgacaca cgcgcaaaag 1260
ataatagact cattgtaagt aggtagtaac cttctccgtt tcatattata aatcgtttga 1320
ttatattttt gttagttaaa cttctttaag ttttttttct ataaacttaa ttaaatctaa 1380
agaattttaa taaaaaaaat caaacgactt ataatataaa atggatggag tagttgcatc 1440
aatttgtgga tgaagcaaac aagattatat ccttttcatg agggtgaaag tattcagtga 1500
acaattcgtc agtttcaagt ttcatgaaat cggacagggt ctctgaaagt ctgtattttt 1560
ggtactgttg gattgactac tctggcttct gttgtcacat cttttgtatc ctagtttcgg 1620
taaaaaaaat tttggcattt ttactcctat cgttgatctg tttaactgaa accattgcat 1680
gatatactac tagcagacaa aactggtgaa aattcacgag aatgaacttt ttgtcagtta 1740
agcattagcg gacagcttca gtaagcagag caggctgcct taaggcttaa agcactatct 1800
tccacaacac tttgtcctac aatcaaattc caaatttact atcacaaaaa gcgaaggaac 1860
taactaaacc ttactcctac tagtactact gctatgacta tgaaacaaga ttccaatcca 1920
aagaaaacac agtgctcgat cagcatgata aaagcaacga aacctgctca tccagctgcc 1980
aaaatgccac cccactgact ctacgtacgt actacgtatt gacgctgtaa aaaactagcc 2040

-continued gtagtacaga gaagaggacc caaagtttcg tcaaaaattt tattttaccc ggatccacat 2100
tgatggtctc gtactcgatg ccggccggga caaggctgtc gttgtacctg tacgggccct 2160
tgccgttaat cagcacgccg tccggcatcc cgaggtcctt gccactgtcc agcatcttcc 2220
tcagatcctg caacgaattc 2240

<210> SEQ ID NO 20
<211> LENGTH: 2601
<212> TYPE: DNA
<213> ORGANISM: Oryza sativa L.
<220> FEATURE:
<221> NAME/KEY: misc_feature
<223> OTHER INFORMATION: PCR marker C1361 MwoI

<400> SEQUENCE: 20
tcttgctgag atccaagttg cggtaacttt gcccttttct ttttttcttc tcttctgaat 60
tttttcatgg tttttgggag agattttcgt aacttgatta cagttctagg aaaaggccac 120
cttgttcaaa cagggctttc ttgaaaggga tcaatttgct aggagtacat gattctaaaa 180
gcgatttcga aataaaacac agttctcgat ctcatacctg aaaacaaaag gcccatactg 240
tgtaaactgt gattatgctt ctgttaaatg ggatatttgt acaaaattga cgccaaccac 300
ctataaacag attgtgagct tttatcttag taaaataaaa tgtgacattc tactcagtgt 360
tcagtgatcc gatgtcgtct cttctgcgta caacttctaa cagccgtttt cggtagtaca 420
aactagcgaa acaccaaaaa cgcagcattt gagttctgga atacgctgaa attgttagaa 480
tcaaccacga aaccaaaatc attgttcaga aacgttgcaa cgagataaaa cacaagaact 540
tgttttaaca aagcatacgg acagtacata tacggttaca acacccagtc tttatacagt 600
tctgctggag ttccatctac tggctgtcat tgtatctcag gacagacagg ttaacatagg 660
tacaacacaa ttacaggcta aaccgaagcg aactacactg tcagcatctc taacagtatc 720
gtcaagcaag cttatttaca gctgctctag taaatttaca acgtccctgg cagaatccct 780
ctcgtttctg gcagcgacga ggcacggtcc atggccttag caggacatct cacccgtcag 840
ctgcatagaa agcaaccgac ttcagtggaa tcacctcctg ctcctgcaaa aaagttggtt 900
cgatcaatca cgcgtttaat ccaaaacaaa atgggtatta attatgctag cctatgaagc 960
tacctcagag ttctctattt gctctgcagg gaaatgaagt ccagtggaac agttctcaag 1020
cacctcaggg ctcttcatcc atgctttgtg tgcttcaatg gctttcagct tatagcgaaa 1080
catctgcgat acggatctaa aattaaggat gtcgacaatt acttaacaca acaaataatt 1140
gaagcaggtc cagttaaaga aaagtagcag cgaagaatag cactctgaag tctgaacctc 1200
agataaagaa atggttggtt tttccagttc atctccctca acatggattc cagtaccctg 1260
gcattctggg caaaggatgg atgttatttt cttaggtgca ttttttgcct ttcttcctcg 1320
attgcttttt cccttgcttg caattttgtc tgctagcatc tcatattggc ataaaatagt 1380
ccagtgcaca aggcaagaag tgtgaaacaa atgaaatgcc tgcaaaatta gccgtacaaa 1440
gtcattggag gttgcagcag aatactacaa atttttaaag aagaaactat acactgtcta 1500
tgttttgctt gaaatgaatt caaccacttt gcattatacg gtttggaatc cctggtttgt 1560
gagaactgta attccattac aacagtgaag aagttaccat aactaatgaa tggaaattag 1620
tcaaatgcct aattttttag gtttgcttta atttatttat ctgtgagaaa tgctaagcat 1680
gtcatgcgtt gctatcttca agaaatacta agaaactgca aaggcaaaga atgtttgaaa 1740
taacttaccc cgcttgagtt tctactgctg caggctagat ttcctgtctt gcagttgagc 1800

-continued

```
aaggtagcta catccttttc aagaagcatt ggtcgcccac aaatatcaca agctttctca   1860
gcagcaaggc gcttctgctt acgcaactcc ctcctcatag atttggtgga taagaggcca   1920
acttgaagat tgtgtgaagt acctgtcggg gaacctgtta tgatagcttg gctattgtca   1980
tgggcggagc tgctttgctc attcgactcc tctgaagatg cttcttgatc tgaaaatgac   2040
ttctttcttc tctttccacg gtgtccagca tcatcaatca cgaagaaaga tccagcagag   2100
ataggaaggt cctgatcatc agaagaccac ttcctgccca actcaattgt ataagagaag   2160
ttgacaatgg caaagtcaga ttgctcatag gtgtcacact catccaagcc atgggagcca   2220
tcctgtccta cccaagcaca ccagatcttg ctaatctttt tacttccttt gctagcttcc   2280
cataacctgt atgcaatatt tccatatccc aaaagatgca caggcaaatc cgaaacaaca   2340
tcctttagca atacactagg aataacgaga ggaccgtcag ttccactttg gtttgacagc   2400
acatgatctt cagatacaga agcagttcta ccattaccat gcgcatttgc accacggcgt   2460
gtgccttttg cgccattgcg agagctagaa tcatctctca acctcgaagt cacttcagtg   2520
tcgttcgctg gaaccagagc cagctctctg gtgttctgcg agctcgagtc cagcaagagc   2580
gggtccttct cgcgcgagtt g                                             2601
```

```
<210> SEQ ID NO 21
<211> LENGTH: 1333
<212> TYPE: DNA
<213> ORGANISM: Oryza sativa L.
<220> FEATURE:
<221> NAME/KEY: misc_feature
<223> OTHER INFORMATION: PCR marker G2155 MwoI

<400> SEQUENCE: 21
```

```
ccctctgctt gatccagtgt acatccatgg gttaggacag attagttact cagttaatta     60
agtgtgagac tggaaaaaaa tatctgacgg cagttttata agttgagtga ttgaactagt    120
gaaagttcag ttaactgtca acggctgtag atttgggatg gcagactgtt ctgagtcaaa    180
atgaagcttt tactgtgcgt ggttaccagg tgcagtaaaa taatttcaga tctaatcgca    240
gtaaaaaaat gtagtactat atgttaagac gagattggtc ggtcaaaatc tatctggccc    300
tttacatctc ccaaatgtta cctcagttgc aggtggtaaa aaaaaatcac tcgtttcacg    360
tgatgtcggc agatcatgga ccatgtctca aatgctgaaa ctctgaacaa tcaacaaaaa    420
aatccaacca gatgagctgt gcaactgata attgatcatc acactatttg caactcatct    480
ttcatgtaga tggaacttca atcccgaaga aataatgaca gcaaaatgct gcgatcctga    540
agaaaggatg gcggcaaaat ggcagcgata aaaaaaaaat ggttggttac tgaagaatta    600
tttgtgcagc agttgagaca gtagcaagat aagagctagc taagctagct aggtagagtt    660
ggatggaaga gtagtagtat gagatagagc atggagcgcg acaactcaag tggatgctaa    720
agtaaaaggc attctcttct cttgtttgga atcagaaaag aaaagaaaag acttgagctg    780
cttggctgga atgtttggtt ggatcatgcg cgctctcctt agcttagctc gccaagaaat    840
cctcgcttca tctctctcaa taattcaaag ccacgagctc tctgctcata tccagtgcga    900
cgattcccgt taatgcaaat gcattatatc cagttcgaaa tgttacaatt cttgcgtttg    960
cagcaagcca gcaagtggtg tgaattgttt aatccctcgt gcatttcaac gaaattctct   1020
cacaaattcg cattgacttc tttcttagca caattagtaa gcagtgacaa ataaagaatt   1080
tttgaacagg atgtctttcc aaggaaggtg agatttttta tgtggatagc aaggatcgcc   1140
tttccttagc atgaagagaa tgtgatcaac tttacacctt gcttacgatt atggccttaa   1200
```

-continued tttttgatac cctaaacagg agcacatcac atgcatgtcg acctgagacc accaattaac 1260
tgattaagtt ggcatttcag atgcatccgt cagttacatg atcaggtgat cgatggatca 1320
actgtaggtt tca 1333

<210> SEQ ID NO 22
<211> LENGTH: 863
<212> TYPE: DNA
<213> ORGANISM: Oryza sativa L.
<220> FEATURE:
<221> NAME/KEY: misc_feature
<223> OTHER INFORMATION: PCR marker G291 MspI

<400> SEQUENCE: 22
cgaacaggat caaaagtaga cgacgagggc atttagaagg agaggaattg tatttgttcc 60
cggtatttaa tttttaaatt tgtggtcgga agtttcggaa gaaaaaatgt gctcatgagt 120
gattattggc tctgaacacc aacctctctt ttcgttgatt ccttctgagg tgttgggtgt 180
tgggacacga tgctgccgcc gacacgacac cgggttccac aatacactaa tctactcgcg 240
acaccttcat tgaactgcat ataattattt agaaagtcca ttaacacatc ttataaaacc 300
ttgttgaatc atataatcat tctataaagt ctatttgaac atcttatgaa aaaataagat 360
ctgacctagt cgttacactc tcttacattt tccattagcc taactaattc cgtgcaggaa 420
acgcccaaaa ataatagtac caatagtcca ctaatcccgt gccagaggcc gccaatgatt 480
agtgattaac ccaaaaaaca taatcatcat cacacgccgc taatgaccag ctctcgctta 540
gctcatccca caggcggccc ccacacgcca ctcctgccat gtgggcccac ctttcacacc 600
ccccaccaac cagaaaaaaa actcccccaa aaaaaaaact tttaatgctt atctcgcggc 660
agtataaaag gcgaccccac cacccacaca caatcacagt cagcgaccca acccaacccg 720
agccgaggag tcgagtcgtg tgaaaattac gaaattgccc ttcgactcca ccaccaccac 780
ccaccggcga ggcgaggaga ggagaaaaat tgggaggaaa aaaaaaggga aaaagaaaaa 840
gggtggagga gatttttgcg aag 863

<210> SEQ ID NO 23
<211> LENGTH: 1510
<212> TYPE: DNA
<213> ORGANISM: Oryza sativa L.
<220> FEATURE:
<221> NAME/KEY: misc_feature
<223> OTHER INFORMATION: PCR marker R2303 BslI

<400> SEQUENCE: 23
tgccatgaag acctatggaa agaatatctt cttctcactc tgtgaatggt gagtttactc 60
tctgtaacat ttagggctag gtcgaaggaa catgaagcat tgctgattca ctccactgtg 120
tttttttttt ctgtataggg ggaaagaaaa tcctgctaca tgggcaggcc gcatgggtaa 180
cagctggaga acaactggcg acatcgccga caactggggc aggttctact catcctctct 240
ttaaccctgt ttacatagtt cttgagtttt tcagtactga tcgtaattgc cctgttattt 300
cagtatgaca tctcgtgcag acgaaaatga ccaatgggct gcctatgctg gacctggtgg 360
atggaatggt aagaacttga gatgtatctg ttcctaggtt gcttaaccat ttgagagctt 420
caaaatgatc aacatatgtt tctgctgtgc aatatcagat cctgacatgc ttgaagtggg 480
aaatggtggg atgtctgaag ctgagtaccg gtcacacttc agtatctggg cactagcaaa 540
ggtaccatag catgttctat gtactaataa ttttgctgca atgttgaact tctttgcatt 600

-continued

```
tcctcactgc aagttttgct tgaattgttc aggctcctct tttgatcgga tgcgatgtgc    660

gctcaatgag ccagcagacg aagaacatac tcagcaactc ggaggtgatc gctgtcaacc    720

aaggcaagcc ttctcagttt cacatgctta gatttagcca tacctcttgg atatttcacc    780

atactcataa tgtaactctc tgaacagata gtctaggtgt ccaaggaaag aaagtacaat    840

ctgacaacgg attggaggta tcccttcaat ggcttccaaa tttgcagttt ctcattgtcc    900

cataagcctt ggcatgatca tgactaactc tgaagctgac aatactttgt gtaaatttgt    960

cggtaggttt gggccgggcc actcagcaac aacaggaagg ctgtggtgct ctggaacagg   1020

cagtcatacc aggcaaccat cactgcacat tggtcgaaca tcgggctcgc tggatcggtc   1080

gcggtcactg ctcgtgatct atgggcggta aagcctttgc tttcttcaga gctcaaagta   1140

gaacatcttc tcttcagaat tcagagttca taacaaattt ctgtcaattg tgcagcactc   1200

ttcgttcgcg gctcagggac agatatcagc atcggtggcg cctcatgact gcaagatgta   1260

tgtcttgaca ccaaactagt cagcaaagaa aagcagcaca ggttagtacg tgtccggcga   1320

atacagctaa attgatcagg attcaggaag aaggtttgca atttgcaagg attggtagag   1380

ctggaaatgg gatgccattt ggttatgtat gtagaaataa gctgtaagcc tgtaagcgta   1440

tatgtaatca gccgtcaaat gctggcgagt gtatttctga agtttgcaac gaaagttgca   1500

gcaataaaaa                                                          1510
```

```
<210> SEQ ID NO 24
<211> LENGTH: 1016
<212> TYPE: DNA
<213> ORGANISM: Oryza sativa L.
<220> FEATURE:
<221> NAME/KEY: misc_feature
<223> OTHER INFORMATION: PCR marker BstUI

<400> SEQUENCE: 24

tggggattct tttctttaag caatttaaca ttattgtcct aacaatatac acaatattgg     60

tttttctttc agtatcaaat aattctttta cttttgaaaa cacatttgca atgtgttgga    120

aacacaatta tatcttgcac ttccttttgg aaatttaatc atttgaaaac tgattcgcgt    180

ttcatggctg taatcttctc ttgcgaacat cgctctttct ttgatggttc tctgttgaga    240

agaagagcaa ccaagtaaat tttcgaaatg tttttttgtt ctttctattc accattgcag    300

gttgtcaaag ccatcgagaa ggccataccg attccgagag cgcaacccat tgccttggat    360

ggcccagcaa gggaagagct gaaggccatg gaggcgcaga aggtcgagat cgaccgcacc    420

gcggcgctcc aggtgcgccg tgagctttgg ctggggctgg catacctcgt cgtccagact    480

gccggcttca tgaggctcac attctgggag ctctcatggg atgtcatgga acccatctgc    540

ttctatgtga cctccatgta cttcatggcc ggctacacct tcttcctccg gaccaagaag    600

gagccctcct tcgagggctt cttcgagagc cggttcgcgg cgaagcagaa gcggttgatg    660

cacgcccggg atttcgatct ccgccggtat gacgagctcc ggcgagcctg tggcctgccg    720

gtggttcgga ctccgacgag cccctgcaga ccgtcgtcgt cgtcgtcgtc gtcttcgacg    780

caggagagcc attgccattc ttactgccat tgccaatgat ctttgtgctg ttctgttctg    840

ttgtcagaat tttttcatgc ccagtttatg gggttaagc tagcttctcc attgtaccgt     900

tctgatgtgc ggatgatgcg atgcaaagca tagtttgttg aagagatgac aaggcagatt    960

ttagcttgaa aacctggagg tgagaaaaaa aaatcctgat gtgtttgtgt gtgtga      1016

<210> SEQ ID NO 25
```

-continued

<211> LENGTH: 676
<212> TYPE: DNA
<213> ORGANISM: Oryza sativa L.
<220> FEATURE:
<221> NAME/KEY: misc_feature
<223> OTHER INFORMATION: PCR marker S10602 KpnI

<400> SEQUENCE: 25
accaccttca tatgaagaaa ttaacggtgt tttcatgagg aatccaacag tcgctgaatt 60
ggtggaaact gtggaattct tcttggctga ggtaaccaat catcacttca ccacaatgca 120
caagtttgta gcttactact acagtacttc taataagttt tgtctgttga gattttattg 180
ctgatttcta tgcatggtca tctttttgac aggccatcca gtcttatcgt gctgagagtg 240
aaactgagct caacctggca gctggtgact atatagttgt ccggaaggta cggccctatc 300
ttcccattgg acatgtttct aaccataaac atatctttgc tggacttttg tgggcaaagt 360
tggctacact aaacttgtgt tcattaacct gctcaatcag gtgtcaaaca atggatgggc 420
agaaggtgaa tgcagaggga aagctggctg gttcccttac gactacatcg agaaaaggga 480
ccgtgtgctt gcaagtaaag tcgcccaggt cttctaggcg ttcaatgagc catacataca 540
taaccctggt gttgtacact gtattatgat cgttcgtgat cttcaaagac cctctgatca 600
gagaaatcac aaatattctt ttgttctatt attgtcatta tcactacccc ttttgtcaaa 660
accagtgcag cctttt 676

<210> SEQ ID NO 26
<211> LENGTH: 1059
<212> TYPE: DNA
<213> ORGANISM: Oryza sativa L.
<220> FEATURE:
<221> NAME/KEY: misc_feature
<223> OTHER INFORMATION: PCR marker Tsp509I

<400> SEQUENCE: 26
gcgagatcat gaacttgatt ttctggttgc catattgggc ttgcttgtta accttgtaga 60
gaaggatagc cttaataggt aagtccctca catgcttcct tccatttgct caattcatat 120
cagtgttact gttctggcag ttccttgggg tcaggactca gaaacatcca attaatgttc 180
atgttctctt aacgactcag aaatacttta taacctctcc acagggtacg gctttcatct 240
gcccgtgttc ctgttgatct atctcagaat ccacagagtg aagagacaca gagagatgtc 300
atagcactcc tctgttctgt attcttagca agtcaaggtg ctagtgaagc ttctggaact 360
atatcaccgg taattcaaaa ttcttcaagt tccttttgta tgtagattat atctttgtaa 420
aactcggcat ttattacctg ctctttgttt caaaaagcag tattttattt tgctccttag 480
cataggtcag cagaacagtt gatcttattc agaaaacaat attttgcatg taacatactg 540
ttatctatga gatgaaaatt aatgcatgtg taataatgtc aatgataaat atttgctatc 600
tgaatccagt ctaccaactc tagttagacc gaattactga ggttctattt caaagaataa 660
tttagtgcac catttgttca actactatga agtaaaatgg tattcccttc tattgacatc 720
gggttagaag tgaaaggcca tcttaatgcg atgttctcaa tgccacaaac ccacaaattt 780
cattaacaca tacagattat tattaacata gctataaatt ggatttccag aagcttgagt 840
tgaatttatt ttgttacaat tgaaagcact gggaacatta gcattttttt ttagttcttg 900
gttattgcaa tttataatgt tatacagaac tgtgtacctc acaatgcatt cattatgaca 960
ttctatgaac catttgattg actgttgctt gtaaacaaca ggatgatgag gagtctttga 1020
tgcaaggagc acgggaagct gaaatgatga tcgtagagg 1059

<210> SEQ ID NO 27
<211> LENGTH: 76363
<212> TYPE: DNA
<213> ORGANISM: Orza sativa IR24
<220> FEATURE:
<221> NAME/KEY: misc_feature

<400> SEQUENCE: 27

```
gatcaactaa caacctcttt gcagcaaaaa agcatacaca caagtgtttg tcttggcctg     60
gggctctgca gatggactga tactctgacc tgcagtgggc ttgggagcta acaatggttt    120
cattcttttt ttttttatgt tttcccctgt tgtttttgct catgttttgt gtaatttttt    180
cttctcatct agcgatgtta tttttcttag catgatggga gtagccctcc tttttttttc    240
tctaattaag tgtaaagtag caacagcata gggatgaatg ttcagtgtag tgtgtggtgt    300
ttcagttatt cagagacgtc catacagttt gtaccttgtg accacacgtc ttaatctgat    360
gaagcttaga ataaatcaca tgttagcaat gcaatatcat ctgcgtcttc tctcactttg    420
gtggccatca aattctgtgt agaagtgtat ggttggtgtg ctgttgcaaa tgccgtattc    480
cgctctgttt tgtggaagtt aagaagtccc tagttgaaat accgattttt catgatctcg    540
gagattgatg caactctgat tgcagcattt ctttttatta gaatgtacac tccatgctat    600
catgatgttt attgtttagt actacaagat ttggttaacc attattttaa tatcataaata   660
attttataaa atcttggagt aacaagttca taatacatga tagcataact ttttgaggct    720
agtctatgta tattgtctcc tttgttttta aactaagcac tcaataaatt attgatggct    780
gtaattttct gaaggtttca ccggtttcgg cccgtgcttt ataaatagct tcggcacaaa    840
agacaaaacg gtccctccaa cacataaatg gttgagttta cgttttcatt atctttggta    900
aaatcaagtc caccacgtag acactcataa caaaagtttg aatatcctca gaaattttga    960
cttgagtcta tcttaccttt gatatcggac atccaaccct ccctccctcc ctgaacttta   1020
tattattcat attacacctg aactttatat tattcatatt acaccctgaa gtggttttca   1080
tttaattgca tacatgctga aatagtttga caacgtgaga tgcactaaaa atctacacgt   1140
tcgtcttaag ttgcaattca ttttatccct tttctttttc tctcttacat aggaatatca   1200
atagtactaa ttcacattac aatatagtat aaattggtaa tcgattattg gcaatatact   1260
atattaaata ttcaaaacta gtcatttaag ctgccaaata agtaaaccac tatcgaaaac   1320
cacaatataa atggcattac aaaacttagg gggttgaata tccaatttta aagttcatga   1380
tgctagagga atttctatca aaagtttatg ggtacatatg gactttttcc tttttaaaag   1440
aagctattct tgtcgtaaac gttaaatatt ttttgtactt tattttttat gattgaaaaa   1500
aaaacttagt tttcaaaatg attggtctgt atacaagcat caattagact taataaattc   1560
atctaacagt ttcctggcag aaactgtaat ttgtttttgt tattagacta cgtttattat   1620
ttcaaatatg tgtacgtata tctgatgtga caaccaaacc caaaaatttt ccctaactcc   1680
atgaggcctt acagatatat ttgatgggtg taaagttttt taagttcttt gggtgcaaag   1740
tttttaaagt atacggacac acatttgaag tattaaatat agacaaataa caaaacatat   1800
tacatattct gcctgtaaac aacgagacaa atttattaag cctaattaat ctgtcattag   1860
caaacgttta ctgcagcatc acattgtcaa atcatagcgt aattaggctc aaaaatattc   1920
gtctcgtaat ttacatgcaa actgtgtaat tggttttttt ttcgtcaaca tttaatactc   1980
catgcatgtc caaatatttg atgcgatctt tttggccaaa ttttgttgga atctaaacaa   2040
```

-continued

```
ggatcaaatt tgctgaattt ttccagacgt cacggcttgt tcatccatcg ttcgcatcgc   2100

gattcgccac cgacgccttg gtttccaacg aattttatca tccgcttaaa tacatccaaa   2160

gctctccatc gccatcggcg gccaacggcg accgctccgc tctacccaat ccacccatcc   2220

actcgccgcc gccccctgat ccaaagcctc cgccgcgccg ccgtcgagag gaggaggagg   2280

aggaggagga ggaggcgtga gcccctatgg ggaccctcct ccggccgcgt ccgcttgccc   2340

acgccgccgg cgccggcgac gccacgccgt cgaccgcgca cggtagccac gcgcctctcg   2400

agaggccccc cccccccgcc gctcgctgat ctctcttctc atcctgtttg ggtttgggtt   2460

tgtgatttgg gtgttttttt tttttccgca gcggtggtgg tgagcggtgg ccgcggccgt   2520

ggcgtggagt gccagccgca tcgggtgcgc cgccgcccgg gtccgcaggt tgcggtggcg   2580

acggcgagct ggaggaggcg gagggagacc gtggtgagat cggatttcgc cgctggtggt   2640

gccgctacca tgggggattc gccgcaggcg ctctcaggtt tgcagcctcc tccactctct   2700

tctcgcaaaa tgtgttgcta tgttcctctc gctgggctgg cctcatagcc attaatgtag   2760

tttgctggaa cattacattc ggaacgttgt tggcaattgc ttgacaaaat gtggaattgt   2820

ggaggggaga aaaatcgttt gaacctgcag tgacaaaatt gccatctata attttaaaac   2880

tgaaggtgtg gaaatcaaac ataatcattg ccagcacatc attcttgtta accaccttga   2940

catattgttg gcttataaca gttagctcca caccaacttg gaaggtgtca atggaatgta   3000

agtataaatt gaggataact ggcagttgtt aagactttct acagaacttg tagcagctaa   3060

aactagctat tgtgcattta tgtttcatgg aatttgagcg gcaatggata tttcttacta   3120

agacgtataa tgcaaaaaaa aaaaaaaaac tatgtctatg cagtttacat gtaatgtgcg   3180

gatgcaaata aaatcatgtt catggacaaa ctaatgggat tcataccaaa ttccagaatt   3240

gcatttctta tgtggttact tttgtttgtt gatttggtta ccagacatcg atgtggtttc   3300

aagggtcaga ggggtttgct tctacgcggt gactgcagtt gcagcaatct ttttgtttgt   3360

cgccatggtt gtggttcatc cacttgtgct cctatttgac cgataccgga ggagagctca   3420

gcactacatt gcaaagattt gggcaactct gacaatttcc atgttctaca agcttgacgt   3480

cgagggaatg gagaacctgc caccgaatag tagccctgct gtctatgttg cgaaccatca   3540

gagtttcttg gatatctata cccttctaac tctaggaagg tgtttcaagt ttataagcaa   3600

gacaagtata tttatgttcc caattattgg atgggcaatg tatctcttag gagtaattcc   3660

tttgcggcgt atggacagca ggagccagct ggtatggctg tagtctcatc cctgctttct   3720

taagtagaca tatatacatt tacagtattt ggtaaataaa caagatttta tgaatcatat   3780

atgattttgg ggaaaacaca aaactctctt tgttggctgc cttgaacata gttctgttca   3840

cacagttata gcaccttctt taaaatgaag aactttgttg catacacata aggccaaacc   3900

acataatgaa ttttgtttat ttctatcttt gaatgttagc atcgtttttg tttaatgcat   3960

gatcgccttc ctatatattt gtagtatgtc aacattgtat tccatgctga gcataacaaa   4020

tggtttgtta aaattcagga ctgtcttaaa cggtgtgtgg atttggtgaa aaaaggagca   4080

tctgtatttt tctttccaga ggggactaga agcaaagatg gaaagctagg tgcatttaag   4140

gttcagtaac caaacttagg ttacattaca tctaatgaga tttttatatt cagtatataa   4200

tgttaacctt ctcatggtgt actgacgtgg ttataaatgt ccccagagag gtgcattcag   4260

tgtggctaca aagaccggtg ctcctgtgat acctattact cttctcggga cagggaaact   4320

gatgccttct ggaatggaag gcatccttaa ttcaggttca gtaaagctca ttattcacca   4380

tccaattgaa gggaatgatg ctgagaaatt atgttctgaa gcaaggaagg tgatagctga   4440
```

-continued

```
cactcttatt ctaaacggtt atggagtgca ctaaagaaag atggtgtttt tttttattat   4500
atggaaccta ttcaaaggca cagacaggct ttcaaggcta agcttgttac aggtactgat   4560
actagttact aattactttc gtaatcagta taaataagct tgtgtagtgt aatggcattg   4620
tacatttctg cacttggtaa atttacagaa gaggcaagta atattttaga ggattgagtt   4680
tattcaccca gtcatatagt tgaagaggca agtaacctgt aagagaggac tgaacattaa   4740
cacctcttgt tcgattaaaa atgaccaaag agcatcaaac atgtattcga ggctgttact   4800
ttagatatgg cccattaatt tgtttagttg tctatgtaca tcctagttgg tgtaaatgcc   4860
agttaccatt tctatgatct aaaacaatca actcttttag tatattttca aaaacgaaat   4920
tcagtacaca tgtatgaatc ttaatattct tctctagctc gttacaaaag caacaaaggc   4980
accgtgtcag ctggttcaca ttagctagtt tgtacttagc attatccact agcaccttat   5040
tttcatgcat atcatgctaa tttgcttgcc cacgttgagt gggaattttt ttcatgtttt   5100
ataatttata tatgttttag acttctagtc cacaatttat gtacttcatg ttcctgagcc   5160
tctagtatgg ctgatagcag actaggtgct gagtgctgtc ctttttgca gactgaagag   5220
agaagaaata caagactgtc cattgttagt cagatttgta aaaatagact ctgatgtagt   5280
ttacttttgc ccctatttta tttttaacaa tacaaatata taacagatcc taagaactta   5340
tcttaattta ggagaagttg ctcgtttcat taaattaaat tgtgaagtaa aaatgtgtgc   5400
tcgagtctgt caatgcaatc ctgtgttctt gtttgaagat atggtgtagg gcaggccagg   5460
attgaacact gaatggtaag actgcttctg ccttcagacg ttattgctaa atttttagct   5520
acttgcagtt agtgctgcca cgccgattaa gcagtagaac aaagtagttt tgtcgtgcac   5580
aaatgagtta tatttcattg gaaatcgaag cgaaaacgaa tcaaaagtta gaagaaaagg   5640
ggaaacttgg taattactcc ataaagagag tgcattttat tggtaagatg gtatccggaa   5700
gctgtgagct ccgggctgta tgtattctgg caaatttgat atgagatgct cgattattgg   5760
cttaagttag cgatatcaaa tttggggaag caccaaagga attattgtga aggagttatg   5820
ggtgcgtgac gttatctgct aggttcaaat ccttgtggct atgaatattt atctgctagg   5880
ttcaaatcct agtgactatg aatattaatg ggtaaggtaa gggatttatt gttaatttta   5940
gtttctttaa gattgtgcca tcggacgcca ttcggtaact gtaataatgc tttgtattgg   6000
attcacttgt gttacatgca cgcactaaac atgtgcttta ccttttcatc tgtttttgcg   6060
ttctgggcta gaaactcaaa cgttgaattt tccatggtct gctcaacttg acaattactg   6120
cgtgtcaagc gatcttatac gcatactatg cgcacaagtg attgtatacg gatatgatga   6180
cagtataacg tgtgatattg attttttaa taaaaaaatg atgttcattt ccttgatgaa   6240
ggaacaaaga cttttttaa aagaagggta ttactaaaaa caaaaatgac aaaaacaaaa   6300
tatcagtgca catggcaagt gtgctcggca atttttctc tgtactttaa acaaaaatac   6360
ttctatatgt tctttttat aagggtggca caaatctttt aaatgagcca aatatctaca   6420
ttggatttat taaaaactgt ataaattata atttatactc tgaaaggttg tgtgcatctc   6480
tcttggagaa aatgtataag ttgcaaacaa acattaatcc acgttatgta acttttttc   6540
gccggaaagg ccgaaggagg cctgacggag cgtggggctc ctcaccggga gaccgcgcag   6600
gccccccttt gccggttcgg ccggggactc agggtgaaat tctaagctct ctgtatgtgg   6660
aaggttcgcg accgtcgaaa gagcataaga cacgggcgat gtatacaggt tcgggccgct   6720
gagaagcgta ataccctact cctgtgtttt gggggatctg tgtatgaagg agctacaaag   6780
```

-continued

```
tatgagccag cctctccctt gttctgggtt ccgaatctgg aaaagtccag tccagtcccc   6840
ccctctaagt gggcaaggtc ctccttttat atcttaaggg gataccacat gcaccatctc   6900
cctcctttct gtggagactt accctacctt ttcataaatg gacggagatt tgtatagttg   6960
ccgtccgaat gaccttctga taggacggcc catacctacc tccacttccg ccgaaagcag   7020
gtgcgacgtg ggattatggc tgtctgctga cgacatgacc agtgtcagac tggtcacaaa   7080
ttgctcattc ctgtccacca cgcgtcagtt tagcaatcta catgttggcc cttcttcaca   7140
caacatcttg cctgtaatgg ttaggatgaa gcctggcata tatctaacca ggactaacgt   7200
gccatctcta ggaggtaaca cgctagctcc agctggggac gagcgcctag aagccctcgt   7260
cctgacggga tggggcgagg cgtgcgtcag atcgcctgtc gccacctaac ctgcgatctg   7320
accggtctgt gactggtcac agaccggata aacgagtgca ctgcacttcg ttacatgcag   7380
cgtgacacgc tcagccaaac cgcaataaat gtggttaggt gagccccgct gtgctcacct   7440
aacccataca cgcggagcaa aaacccacga ggggtcgggg cgcctcggcc ctcggggccg   7500
aggcgggtgc ggtccgaccc cctcgggggg actaagagga gggcgaacac atcaccctcg   7560
ggcccgacgt cccccgaggg tgccaggcca cgtgggcgat tgtgtctgcc tcaaacctct   7620
agtcatgata ctcctgatcc catgtcaccg acagtagccc ccggcgttat gccagggcga   7680
tcgccctctt taagggaagc ggtcgggcgt gacgccactc ctaaggcctg gtgacaggtg   7740
ggaccggtct ccacaattgg gcagaaaccc aacggtcaca aatcacgcac atcggcaatg   7800
gtaactctac tatcaataat gagcggtctc ttcaagactg ccacattact cgagtagcac   7860
acgaatctgg acatggcgat tcgtttcgtc tggagatatg gtaacgtcgc tttggtcggc   7920
gagcgtaatt aacgcgcgca cgatatgatc tatctcgact gccacaaccg catatccacc   7980
tcatgcgccg caagcgggcg aatgggatta gtggaagcgt gggcgcgaga aacgaggggg   8040
cgaaatagtg ggcgcgagaa gcgaggagcc gggcacagcg ttggcaagag tataaaggca   8100
ctgaggaaag gatctgtttc cttcctttcg ccatcatttc ccttgtcttc gccgcttgcg   8160
ccctaactcc ttctttcctg tgctctactt tcgccacacg cgctcgctct caatcttctc   8220
ttcctccggc gccatggcac ggggctccgc tctgctcgat ggtagcgtgc tgccgccttc   8280
ccgcatcgtg agcgagaggc aggctgggct gccgcgccgc ttcatgccgg aatctgccac   8340
cggccgggag atagtcacgc tgggcgaggg acgcccggcg ccagactacc cggggcggtc   8400
cgtcttcttt ctcccctttg caatggcagg gctggttccg ccattttctt ctttcttcat   8460
ggatgttctg aagttctacg atctccagat ggcgcacctc acccccaacg cggtgatgac   8520
attggccatc ttcgcgcatc tgtgcgagat gttcattggg gtgcgcccat ctcttcggct   8580
gttccggtgg ttcttcaccg tgcagtcggt gtcgccgcca tcggtagttg gtggctgcta   8640
cttccagcca cgggggccgg tgctgaatcg ctacatcccc tgcgccctcc gcaagaagtg   8700
ggacgactgg aagagcgact ggttctacac ccccctcgcc gacgaagcgc gcctccgact   8760
tccgagccag cccccggcgc aggcctccag ctggcgggcg ccggtagatc tgggggatgg   8820
ctatgacgcc gtcctcgacc gcctggcggg cctacgatcc caggggctca cagggaccat   8880
ggtgtacggc gactacctcc gtcgtcggat tgcgccgctc cagcggcgcg ctcggggcgc   8940
ctgggagtac accgggtccg aagactacat gaggacccac cagggagtca gatgggactg   9000
ggctcctgag gatttcaaga tagtggtcca acgggtgctg aatctcaact ccatggaggc   9060
gtccctcatt ccccaaggaa tcctccctct ctgcagcgat ccagaccgcg cctccatcct   9120
gaccattatg acggcggtcg gggcctcaga ggagtgagct ccaaagggcc acgacggcgc   9180
```

-continued

```
aggcgggagc cgtagggggg atcaatctac ccggggaggg ggtcgtgctt ctgggtctcg   9240
cgacggaggc ccgaggagca gccgccctgc cgacgcccgg gggaagagga agcagggagg   9300
aacacctccc ccatctcctc cccgaggggg cggggcggtg cgtgccagca gcaggcgccc   9360
ggagggggcc gcgccgacat cgcagcccga gggggagcgc aagaagaagc ggctccgcaa   9420
gatgggggag acagaaccat ctcagggaaa ccttatttcc cctctaaagt ggtcgtttaa   9480
ccgacccccct cgcaggttcg tctctcaccc atcgtggctg tattcattct ctcaacgcga   9540
gttttcactc acccatcttg ttcgtcttct ggtcttttct tctgtttcag cgagatcccg   9600
tcgcgtccct cccgccattc caagtccggc cagtctgagg ccgaggatcc ggcggccgca   9660
gaggcccgga ggcgggaatc tgaccggcga gaggccgcgg atcgcctacg ggaagccgag   9720
gaggccgccc aggaggccgc ccgggctcgc caggtcgagg aaaccgctcg ggaggaggcc   9780
gcccgggccc gccaggccga ggaagccgct cgggaggagg ccgcccgagc ccaccaggcc   9840
gaggaagccg ctcgggagaa agccggattt cgccaggacg aggcaatggc gacttccgag   9900
gcagctcgcg atgaggtcgc gggcgcgtcg cttgagccca cttcctcggg cgacgctcag   9960
gcgacaactt ccggggcagc tggcgacgag gctgcgggcg cgtcgcttgg gcccactccc  10020
tcaggcgacg cccaggacca accaggtccg agggacatcc ctgagtccgg cacttccatc  10080
ggcggcccga gccgcgtggc atcctctcca aggcggctct tccccacgcc ttctatcgcc  10140
ccactgagcg cagagcccct tctgcaggcc ttggccgccg caaacaccgc ggtgttggac  10200
gggcttagtg cccaggtgga ggccctgcaa gcagagtggg cggagctcga cgccgcgtgg  10260
gcgcatgtcg aggaggggcg gcgctcagtg gaggccatgg tggaggtggg ccgcaaggca  10320
caccgccggc atgtctcgga gcttgaagcc cgtaagaagg tgttggcgga aatcgccaag  10380
gaagtggagg aggagcgggg ggctgccctc attgccacca gcgtgatgaa cgaggcgcag  10440
gacaccctcc gccttcaata cgggagctgg gaggcggagc tagggaaaaa gctcgacacc  10500
gcccaggggg tgcttgacgc tgccgctgcc cgagaacagc gggcggggga gaccgaagcg  10560
gcgtcccgac ggcgcgaaga gacccttgag gcgcgcgcca tggcgctgga agagcgcgcc  10620
tgcgtcgtgg agagggatct ggcggaccgc gaggccgccg tcactatccg ggaggcaaca  10680
ctggcggcgc acgagtccgc ctgtgccgaa gaggagtccg cactccgcct ccacgaggac  10740
gcgctcaccg agcgggagcg agctctcgag gaggccgagg ccgcggcgca acggctggcg  10800
gacagcctgt ccctccgcga ggcagcgcag gaggagcagg cgcgccgcac tctggaatgt  10860
gtccgcgccg agaggaccgc actgaaccag caggccgctg acctcgaggc gcgggagaag  10920
gagctggacg cgagggcgcg cagcgacggg gcggctgcgg gcgaaaacga cttagccgcc  10980
cgcctcgctg ctgccgaaca taccatcgcc gatctgcagg gcgcgctaaa ctcgtccgcc  11040
ggggaggtcg aggccctccg cttggcaggc gaggtagggc ccggcatgct ttgggacgcc  11100
gtctcccgcc tagatcgcgc cggtcggcag gtgggcctct ggagagggcg gaccgtaaag  11160
tacgccgcca accatggagg cctcgcccag cgcctctcga agatggccag ggctctccaa  11220
cggctccccg aggagctcga gaagacaatt aagtcatcct cgagggacct cgcccaagga  11280
gcggtggagc tcgtactggc gagttaccag gccagggacc ccaatttctc tccatggatg  11340
gcgctggatg agttccctcc tgggaccgag gacagcgcgc gcgcaggtcc gggatgccgc  11400
cgaccatatc gtccacagct tcgagggctc agcccctcgg ctcgcgttcg cccccaactc  11460
cgacgaggag gacaatgccg gtggtgcaga cgacagtgac gatgaggccg gcgacccggg  11520
```

-continued

```
cgtatcggat tgatccccca agcccccgcc attctttagt tttttcttct tttccttctt  11580
ctaaggcctt cgggcctctt ttttgtatag atcaacttaa tctgtaatca aaaatgaaga  11640
aatttttgtg tcaatttcat cttgctgtgt gtatgagatg aggatgatct gtgacgtggt  11700
ccttttgcgt cttagcttga ttaagggctc gtgcccaggt cccagtcctc aaaaggcgtg  11760
ggtcggggct agtgcctggg gagatccaca tgtcgagact ggccaggccg ggaacgtggt  11820
gaccgagggt tatgggtgac ccgattgtgg gtttttgccg attccccccc ggagttcacc  11880
acgccccggg gcacggctcg gttctgggcc ccgtttggcg attttagccg acccgagccc  11940
ccgagggcag gattgagcac gagtgaccta tttcaagtca agattcttca aaaggaaaaa  12000
aaaacacaga tacagccttt aggaaattga aactgctttt attgaaatac tgaaataaga  12060
gaaataagaa tgtgcatgtg tggcagcccc cggccaacgc tgcacgcccg agggggtgcg  12120
gggttggccc gagcccgaaa cctgacaccc gacccccccc tcaggggtag aagcgacgaa  12180
ggtgttcgat gttccacggg ttaggcagct caatgccgtc gcccgtggcc agccgtatgg  12240
agcccggccg ggggacgccg accactcgat acggaccctc ccacattggt gagagcttgc  12300
tcaatccagc acgcgtttgg acgcggcgta ggacgaggtc gtcgacgcag agtgatcggg  12360
cccggacgtg acgctgatgg tagcgccgca ggctctgctg gtagcgcgcg gctctgaggg  12420
ccgcgcgccg ccttcgctct tccaagtagt cgaggtcatc tctgcgaagt tgatcttgat  12480
cagcctcgca gtacatggtg gcccgaggag acctcagggt gagctcggat gggagaaccg  12540
cttccgcgcc gtagacgagg aagaaaggcg tttccccggt tgctcggctt ggtgtagttc  12600
ggtttgccca gagcaccgct agcaactcct cgatccatga atcgtcgtgc ttcttgagta  12660
tgttgaaggt cttggtttta aggcctttga ggatttctga attggcgcgc tccacttggc  12720
cattgcttct ggggtgggca ggtgaggcga agcagagctt gatgcccatg tcttcgcagt  12780
agtcgccgaa gagttcacta gtgaattggg tgccattatc cgtaataata cggttaggca  12840
ctccaaaccg ggccgtgatg cccttaatga atttaagtgc ggagtgctta tcgatcttga  12900
cgaccggata agcctcgggc cacttagtga acttgtcgat cgcgacatac agatactcaa  12960
acccgcccgg ggcccgccta aacggtccca ggatatcgag cccctagaca gcaaatggcc  13020
acgaaagtgg tatggtctgc agggcctggg ccggctgatg gatttgcttg gcgtggaatt  13080
gacacgctct acatcgccgg accaggtcga ccgcatcatt gagagctgtc ggccaataga  13140
aaccctggcg aaaagcttta ccaaccaagg tgcgcgaggc ggagtgggct ccgcattcgc  13200
cttcatggat atcggcaaga agcacaacgc cttgttcccg aggaatgcac ttcaggagga  13260
ttccattagc cgcgcgccga tagagggtcc cttctaccag cacgtagcgt ttggagatgc  13320
gatggacgcg ttcactccct tcgcggtcct cgggtaaagt cttatctgtg aggtatgctt  13380
ggatctcggc aatccaagca atcaatctaa gggagctggg agcgctcccc tcgggtcccg  13440
aggcctggac ttcgacgggc ctcgggggcc ggtcaggcgc gtccgtctcc cctaaggggt  13500
cgggtcgcgc cgacggctgg gcaagccttt cttcaaaggc gcccggtggg gtctgggctc  13560
gcgtggacgc gagccgtgag agttcgtcgg caatcatgtt atcccgtctg ggcacatgcc  13620
gaagctcaat cccgtcaaaa tggcgctcca tacgccgtac ttggcgcacg taggcgtcca  13680
tctgcgggtc agagcaccgg tactccttac agacttggtt aacgaccagc tgggagtcgc  13740
ctaacaccag gaggcggcgg atccccagtc cagctgccac tctgagtccg gcaaggagtc  13800
cctcgtactc tgccatattg ttagtcgctc gaaagtcgag gcggaccaag tatctgagga  13860
cgtctccgct cggagaggtc aacgtgaccc ccgcaccggc gccctgaaga gacagggagc  13920
```

-continued

```
cgtcgaactg cattacccag tgggcggtgt gaggcagctg cgaggggtcc gtgctggcct  13980
cggggattga gacgggctcg ggagccgggg tccactctgc cacaaaatcg gcgagagcct  14040
ggctcttgat agcgtgacgt ggttcaaagt gcaaatcgaa ctcagaaagt tcgattgccc  14100
atttcaccac ccgtcctgta ccctctcgat tatgcaagat ttgaccgagg gggtaagacg  14160
taaccacagt gacccgatgc gcctggaaat aatggcgcag tttcctcgag gccatcagaa  14220
tagcgtaaag catcttctgg gcctgagggt atcgggtttt ggcgtcccgg agggcctcac  14280
taacaaagta gacgggccgc tgcacctttc ggtggggccg atcctcttcg ctaggggccg  14340
catccctggg gcactcttcg tccaagcagc ctcgcggggc gcacttgtct tctgtgctga  14400
tgacctcggg gtcggaggat aacaggggcg gccttcccac agtggctttg gggccgtcct  14460
gggggtcagg ggctcctggc gtcgtcggac aagcgggcaa agggccaact ccggtcgtca  14520
ggggccttag gcctccgttc ggctcggggg cctcttctcc ctgctctttc ccgggtcgag  14580
tcagcacagg gttagcctcg gggtcaaagg gcgataggtg cggccttccc acagtggcct  14640
cagggccttc ctgggggtcg gggctcccta gcaccgtctg acaagcgggc agagggccaa  14700
ctccggtcgt cgggggcctc aggccaccgt tcggctcggg ggcctctcct ccctgctctc  14760
tcccgggcca agtcggcaca gggtggggaa gcgcgaaatg agaattatcc tcatcgcgct  14820
ccacaaccaa tgccgcacta actacttgcg gggtcgccgc taagtagagt agcaagggct  14880
cgtctggctc cggggcgacc ataactgggg gagagcttag atacgccttc aactgggtga  14940
gggcattttc agcttccttc gtccaggtaa acggtccgga gcgtttgaga agcttaaata  15000
agggtaacgc cttctctccc agcctcgata tgaaccgact tagggcggcc atgcaaccgg  15060
tgacgtattg cacatcccta agtttgctgg ggggcgcatc cgctctatag cccgtatctt  15120
ctcggggttg gcctcaatgc cccgggcaga gaccaagaac ccgagaagct tgcccgcagg  15180
tacaccgaac acacacttat cggggtttaa ttttatgcgg gcggagcgga gactctcaaa  15240
agtttccgct agatctatga gtaacgtttc ctggttgcgc gtctttacaa ccaagtcatc  15300
gacataagcc tcaatattac gtcctaattg gctaccgaaa gaaattcgag tagtacgttg  15360
aaaagtagga cctgcattct ttaacccgaa gggcattgtc gtataacaat aggttcctat  15420
gggggtaatg aacgcagttt tttcctcatc ctccctagcc atgcgaatct gatggtaacc  15480
agagtatgca tctagaaaac acaaaaggtc gcaccccgca gtggagtcga caatctgatc  15540
tatgcgaggc agggggtaag gatccttagg acatgccttg ttaaggtcgg tgtagtcgat  15600
gcacatccga agcttgccgt tcgccttggg aacgaccacc gggttcgcca gccactcggc  15660
ggggttgacg ctgccatcat atttttcggc gatggtgggc cggaaccttg gggccaacg  15720
gacattccga agactcgcca caaaggctct acagccgaca ccaccaaccg ggggcacgga  15780
gggctgattc ccgcgtccgt gttgaggtga cactctggac gaggaagcgc cctccgttgc  15840
gtgggcagca cttcggtcat tacgccggcg ctcgatgctg gtgcgggcgt ccggcccccc  15900
acgcagatct ttctgggtcg aaggagtcga cgaaggagtg gcggccgaat ggcgaacagc  15960
ggctgccgct cgtcgtgccc tccgtcttga cgacgcggag ccggtggtag cagcaccaga  16020
ggccttggtg gcggaggacc gcccaccagc atctaggcgc tgccgtgccg tcatgactaa  16080
tttggccacg tcgtccagcc atcgttgggc tggagactcc gggtcaggga cgacaggcgg  16140
gtgacgtaag agcgcgcccg cagcttggag cgcgccctgg ggcgtgctgc cgtcgccgta  16200
gacgaggagg cgacgctccc catctcgccg ttcttctcca tcgcccgcga tcggtgaagt  16260
```

-continued

```
cgcggatctt tcgaccctct cgagcgcctc cccccgctta ggactttggc atggagggag  16320
cggtggagta cgagctcgac ggcgtgggtt cggctccccg tcgtcgccac tcacactcgg  16380
agagaggtcg tgcgcctttg cttgctcggc catcaggctg aacaggaaaa gcttggcgca  16440
cacggaagag tacgagagct cagaaaaaca cacactgagt cccctacctg gcgcgccaga  16500
tgacggagcg tggggctcct caccgggaga ccgcgcaggc ccccctttgc cggttcggcc  16560
ggggactcaa ggtgaaattc taagctctct gtatgtggaa ggtttgcgac cgtcgaaaga  16620
gcataagaca cgggcgatgt atacaggttc gggccgctga gaagcgtaat accctactcc  16680
tgtgttttgg gggatctgtg tatgaaggag ctacaaagta tgagccagcc tctcccttgt  16740
tctgggttcc gaatctggaa aagtccagtc cagtccagtc ccccccctcta agtgggcaag  16800
gtcctccttt tatatcttaa ggggatacca catgcaccat ctccctcctt tctgtggaga  16860
cttaccctat cttttcataa atggacggag atttgtatag ttgccgtccg aatgaccttc  16920
tgataggacg gcccatacct acctccactt ccgccgaaag caggtgcgac gtgggattat  16980
ggctgtctgc tgacgacatg accagtgtca gactggtcac aaattgctca ttcctgtcca  17040
ccacgcgtca gtttagcaat ctacatgttg gcccttcttc acacaacatc ttgcctgtaa  17100
tggttaggat gaagcctggc atatatctaa ccaggactaa cgtgccatct ctaggaggta  17160
acacgctagc tccagctggg gacgagcgcc tagaaaccct cgtcctgacg ggatggggcg  17220
aggcgtgcgt cagatcgcct gtcgccacct aacccgcgat ctgaccggtc tgtgactggt  17280
cacagaccgg ataaacgagt gcactgcact tcgttacatg cggcgtgaca cgctcagcca  17340
aaccacaata aatgtggtta ggtgagcccc gctgtgctca cctaacccat acacgcggag  17400
caaaaaccca cgaggggtcg gggcgcctcg gccctcgggg ccgaggcggg tgcggtccga  17460
ccccctcggg gggactaaga ggagggcgaa cacatcaccc tcgggcccga cgtcccccga  17520
gggtgccagg ccacgtgggc gattgtgtct gcctcaaacc tctagtcatg atactcctga  17580
tcccatgtca ccgacaaggc catccgaatg tattaaggag taaaagttac aagaaaaaac  17640
accataatgc accaatgtgc atgaccacac accatacact acccccaagc acaaaccact  17700
gagggtgaag cctagcacca aacgaccgcc actaagtgtg accaaacgcc gctaggccta  17760
cggcagcaac acatagatga gacttcgaaa acgatgccac caaggtggtc acgacatcta  17820
ggatgctgcc atcgtccatc taaaaagatg tggttttcac ccagagaaac tcatcaagaa  17880
ggggagaggg taacccttga cagcgcccca aggaggttac gacgcccgaa ggcgtagccg  17940
ctgccggtcc ggtgaaccac cggactaggc ttccgcctag gaccctatag ccttgatcgc  18000
agatcaccgt ccaccactca gaaccaccac acagacaaaa ggtagcacgt agcttccacc  18060
acaccgcacc gacgcccctt cgtcggccga ctccatcgaa ccaccatccc tgagagctgg  18120
cccaggaccc ctccgttcca ccacccgccg gccgccttgc cagttttggc caaaggagaa  18180
cccgggactg ggtgacattg cttcggcagc ctgagcttcc cccgctggcg agctgctgtc  18240
tcaatccaac ctagaaactc cccgcaaaag aaggggatga gctctaggaa gggcgagggt  18300
gccgaccggc aacgaggaag acaacccatc gactccagct ccctttgcac taccatctgg  18360
ccctgcgcca atgccggata cgctgtcgct ccggctccgg cgccacccac ctgcaccccc  18420
tttgcctggt ctccgcgccc ctcctggctg cgtcgcgccg cccagctggc cgctaagggc  18480
accgcgacgg ccgcccggct accgaggcct ggccgcgcca tgggacagct cgcgctggca  18540
ccagcgagcc acggccgtcg cgctgttgcc ggcgccagcg agcacaaccg ccagctccaa  18600
gggccgagca tgccactgag ccgccgccgc tgccgcccgg gccggctgca cgtcaccggc  18660
```

-continued

```
gcacacgacc gcacgccgcc acgctccgcc tccgcgcccg aggcagcccc atgccattgc  18720
cgcgcacctc gcccgcccgc tgccgagccg ccaccgcgca ccttgctgag ccgccaccgc  18780
cgtccctagc cgcctcgtgc cgccgccacg ccagatccag gcgcgggatg gccggatccg  18840
gccttggggg cgccggatcc accgcctccc cacaccgcca cggcgtcacc acctccgacc  18900
gcagtgaggg cttcgtcgtt tgccccatcc tcatcgcgtc gaggaggaag acgccaagaa  18960
aaaagggcct cgccgctgcc ttccttgctc gctgccggct tcgccgccgg cgagctccgg  19020
cggcggcgag gtgggggaga agaagtgggg agtgggcagc tagggttttt tcgcccccca  19080
agccgcccgt gcgagagcga cggtgggggg gggggggact ttccaacctc ttccagtgtt  19140
ctagttctcc acgttatgta actcaatttg tttaaccata gaaagtaaga aacctaccag  19200
cgtgttaagc tctctttcat tccctttctt cttcctggtt ttgcttccat cacatgtcaa  19260
gtgaagggtt cttaactacc attactccta cacatctaat ttttttctca gatctttcgc  19320
aggtatatat tgatgctaca ttttatgatc ttaagataat ctccttcaca ttaccctctg  19380
ctgaaacttt agcttgaacc gtcatcttca ccacaatttg agcccaattt gcacagagca  19440
caacgagcaa tagcttgccc ttacgttcat tatttagcat gaactactac taactaccca  19500
agaatcaata caccggttta ataacgccat tttatcacgt taatatatgt ttcattcaac  19560
acaccggttt tggcacagtt gcaaacttgc aataaattct ttcctacttc tccatcccat  19620
aatataacaa attggtatgt ctcgtctggt actaagttac tatattatga gatggaggga  19680
gcacttcttt tcttccaaaa tataagaata tagtattgga ttagatatta tctagattca  19740
cgaattcgat taggttgtct agatttatag ttgtatgtaa tgtataattc ggtaataggt  19800
tattacctct caggatggag ggagtagttt tgactttttt tttcttataa atcgctttga  19860
tttttatatt agtcaaattt tatcgagttt aactaagttt atagaaaaaa attagcaaca  19920
tttaagcacc acactagttt cattaaattt agcatggaat atattttgat aatatatttg  19980
ttctgtgtta aaaatgctgc tatatttttc tataaacgta gtcaaattta aataagttag  20040
actaaaaaaa atcaaaacga cttataatat gaaatggagg aagtagtaga ctataacaaa  20100
tttaaaccgt gctttgattt tagagcatca ctaatatgtt agcaataatc tatccctaaa  20160
atttattttt tttcctaaac tgaaaatagg aagtggaaat actcctccat ctaagagaga  20220
gcctaaattc aataaaaaac taaaaaacta aaggtggatc cctctattaa actaccgcaa  20280
aaaatttatg ttttttttct cttccacgcg cgcagaacag atatctcgat caagttagca  20340
tgtaaaattt ttaaagagat accttatacg actccttccg tatttccaaa agcaaacgga  20400
tttaaaatct gactcaaata aagatctata tatccaattt acatgacaca tgtttcgccg  20460
aatttttata ttaataataa ttaatatttt taaaattaaa ttattagcaa tttgtttgga  20520
ggatttatca aaacaggatg gacgttgttt ataacagcgt ctagacctag acgcgcttgc  20580
aaactgcggc caccctttta tcacacaaat ttttgacaat ttgacacttt ccaaaaatta  20640
attttataaa ttaaccgtga ccaaaactta tttaaaaatg atctttttgt tgagcgcaaa  20700
atcgtatact tcagcgccaa atagcacggc gccgacctcc cccttcccct cccctctatc  20760
ctccactgct gccgcccacc tctccgtatc agctgcgtcg cgttggtttc cgccggcgct  20820
gctgctgctg caccagtccg ctagggcggg cgggcatggc gcgccgcgcc gcttcccgcg  20880
tccgcgccgg cgctgttggc gcccttcgct cggagggctc gacccaaggg cgagggggcc  20940
gcacgggggg cagtggcgcc gaggacgcac gccacgtgtt cgacgaattg ctccggcgtg  21000
```

-continued

```
gcaggggcgc ctcgatctac ggcttgaact gcgccctcgc cgacgtcgcg cgtcacagcc  21060
ccgcggccgc cgtgtcccgc tacaaccgca tggcccgagc cggcgccgac gaggtaactc  21120
ccaacttgtg cacctacggc attctcatcg gttcctgctg ctgcgcgggc cgcttggacc  21180
tcggtttcgc ggccttgggc aatgtcatta agaagggatt tagagtggat gccatcgcct  21240
tcactcctct gctcaagggc ctctgtgctg acaagaggac gagcgacgca atggacatag  21300
tgctccgcag aatgacccag cttggctgca taccaaatgt cttctcctac aatattcttc  21360
tcaaggggct gtgtgatgag aacagaagcc aagaagctct cgagctgctc caaatgatgc  21420
ctgatgatgg aggtgactgc ccacctgatg tggtgtcgta taccactgtc atcaatggct  21480
tcttcaagga gggggatctg gacaaagctt acggtacata ccatgaaatg ctggaccggg  21540
ggattttacc aaatgttgtt acctacaact ctattattgc tgcgttatgc aaggctcaag  21600
ctatggacaa agccatggag gtacttacca gcatggttaa gaatggtgtc atgcctaatt  21660
gcaggacgta taatagtatc gtgcatgggt attgctcttc agggcagccg aaagaggcta  21720
ttggatttct caaaaagatg cacagtgatg gtgtcgaacc agatgttgtt acttataact  21780
cgctcatgga ttatctttgc aagaacggaa gatgcacgga agctagaaag atgttcgatt  21840
ctatgaccaa gaggggccta aagcctgaaa ttactaccta tggtaccctg cttcaggggt  21900
atgctaccaa aggagccctt gttgagatgc atggtctctt ggatttgatg gtacgaaacg  21960
gtatccaccc taatcattat gttttcagca ttctaatatg tgcatacgct aaacaaggga  22020
aagtagatca ggcaatgctt gtgttcagca aaatgaggca gcaaggattg aatccggata  22080
cagtgaccta tggaacagtt ataggcatac tttgcaagtc aggcagagta gaagatgcta  22140
tgcgttattt tgagcagatg atcgatgaaa gactaagccc tggcaacatt gtttataact  22200
ccctaattca tagtctctgt atctttgaca aatgggacaa ggctaaagag ttaattcttg  22260
aaatgttgga tcgaggcatc tgtctggaca ctattttctt taattcaata attgacagtc  22320
attgcaaaga agggagggtt atagaatctg aaaaactctt tgacctgatg gtacgtattg  22380
gtgtgaagcc caatatcatt acgtacagta ctctcatcga tggatattgc ttggcaggta  22440
agatggatga agcaacgaag ttacttgcca gcatggtctc agttggaatg aaacctgatt  22500
gtgttacata taatactttg attaatggct actgtaaaat tagcaggatg gaagatgcgt  22560
tagttctttt tagggagatg gagagcagtg gtgttagtcc tgatattatt acgtataata  22620
taattctgca aggtttattt caaaccagaa gaactgctgc tgcaaaagaa ctctatgtcg  22680
ggattaccga aagtggaacg cagcttgaac ttagcacata caacataatc cttcatgggc  22740
tttgcaaaaa caatctcact gacgaggcac ttcgaatgtt tcagaaccta tgtttgacgg  22800
atttacagct ggagactagg acttttaaca ttatgattgg tgcattgctt aaagttggca  22860
gaaatgatga agccaaggat ttgtttgcag ctctctcggc taacggttta gtgccagatg  22920
ttaggaccta cagtttaatg gcagaaaatc ttatagagca ggggttgcta gaagaattgg  22980
atgatctatt tctttcaatg gaggagaatg gctgtactgc caactcccgc atgctaaatt  23040
ccattgttag gaaactgtta cagaggggtg atataaccag ggctggcact tacctgttca  23100
tgattgatga gaagcacttc tccctcgaag catccactgc ttccttgttt ttagatcttt  23160
tgtctggggg aaaatatcaa gaatatcata ggtttctccc tgaaaaatat aagtccttta  23220
tagaatcttt gagctgctga agccttttgc agctttgaaa ttctgtgttg gagttctttt  23280
ctcctacagt cgtattagag gagggatctt ctctttatgt gtaaatagcg aggtatgtat  23340
gtcacctctc cgaattattt ttactctggt tcctagacgg taaacaagca attatgttct  23400
```

-continued

```
gcctttgatg ccagaaaaaa cacaaaagtt tgtcgttatc tctactaacg gatcataaag  23460
gaatttgtaa ctggagtttc aaacttaatt tgtctaggca gtagttttgg cattagatcc  23520
aacattgtgt aggattcatt tgtgtgtatc aatctatagg gtttcattaa atttcgttta  23580
tgtgtactgt ttaggtgttg aatagtttga cttgtttttt aactgaacaa aagatactga  23640
aatcgttcca ttcaacaaac acatgttccg ttaatgaaat tattgtacgt taccttttgt  23700
tttcttactc acaagtgtcc tcttttctta tatcctatag attggtacaa caaattattg  23760
attcaatttt ggttttgaac attgatgatc ctccctgcac tattggtgca gctgctcttc  23820
tattcatttt gtgaagtgat gtgagtacct ctcaatccca tccttatgct tctgtgcatg  23880
cttcattcca attttttacg catatcgatt gttttctttt atataacagt ccataaagat  23940
aatcacatca tgacaaagtt atttatttct acagtatagt tatataagta ttcaccagtt  24000
ttccatgaat attttggcat gtgattacaa agaagattat ttgagaaaat ccatgctttt  24060
atttcatcat tttgtttgaa gttgaacttt aatttatggt gtaaatttca gttattattg  24120
ctagcagctc gtactcttta atggtataac ttcacttgtg cttattctcc aatatctccc  24180
ttcttgttgt tcaggttcaa gaaaatcatt tgttggattc agaatctggt gtccattttc  24240
ttcttaaatt attaaatcct ccagtgaatc ttgttgattc caaagcacca tcgataggtt  24300
ccaaacttct tggaatcagt aaagttcaaa tgcttaatgg atcaaataag gattctgact  24360
gcatttcaga ggaaatcctt tcaaaagttg aagagattct cttaagctgt caagtgatca  24420
agtcgctcga caaagatgac aagaaaacaa caaggccaga actgtgtcca aagtggcttg  24480
ctttgttgac aatggaaaat gcatgcttgt ctgctgtttc agtagagggt aagttttaat  24540
caaatttctt ggtcatgatt tccctttatg accattatat ttatttatat gagccaaata  24600
agcagttgtc aacttgtcat aagttacata gcacctattt gcaatattca tgggtggttt  24660
gcttagccct tttcttcacc tgcttttgat tgatgacttc catctgtgtt gcagaattga  24720
attggagtag tggactgcac tagaagcacc tatggccatt gtcatactag gaaggttttc  24780
ccttatcaaa tatttgattg ttacagagac ttctgacaca gtgtccagag ttggaggaaa  24840
ttttaaagag acattaaggg agatgggagg tcttgatagt atttttgacg ttatggtgga  24900
ttttcattca acattggaga tgagatctcg ctaacatcgc atattttaca tttcctttgt  24960
tcaactctaa tagattgtgc aggcttgttc cttttcgcca ttttagcttt aatgcgcttg  25020
aagccacatg aaagtaatgc ttgtccagat acatagccaa aggttgttat attttggggc  25080
atggaaaatg cttgaggtag taactatttt catcaggaca tggaaaattg gctgcaacac  25140
aaattatgtt gttttatgtt gcaaaaatag ttttttaata ctttttttatt ctgcatgtgg  25200
tgttagtatc ttacagttcc tctgatgatt atatccccca cgataataac acttgaaacg  25260
ataataacac ttgacatatc tacaccaagt gaacattatt catttggatg ttacttttcc  25320
agctatactt gctgttcttg catgtgtaag caagtttgga gtaaattgcg cattaattta  25380
aatgcttggt gttcctatct gtgtactttt tattccccaa ctaataatgc aatcatatta  25440
cgctgataaa ctgaataaat aaattaacaa tatacttctg gtggcaaacc ttgtgtatca  25500
gaatctcata aaggatacat ccacttcagc tttggaccga aatgaaggaa catctttgca  25560
aagtgctgct ctcctcttga aatgtttgaa aatattggaa aatgccatat ttctaagcga  25620
tgataacaag gtaatgctcc ttatatgttc tgtttcagtt tagtacccat ttccttcttc  25680
tgtactatct tctctcctga tttgttctgt gcaaaatgtg caaacagtgc gactttgtat  25740
```

-continued

```
gtctgcttaa caattttctt ttcttcctga aaaagcaata tgaactctta cattcatttt  25800
gcttcttgca gacccatttg cttaatatga gtagaaaatt gaacccgaaa cgctccttgc  25860
tttcttttgt tggtgtcatt atcaatacta ttgagttatt atcaggtatt tttcttaata  25920
atacaatgtg ttcgctaaca caataaaatg ttttaaacat ccagtatgtt aaagttgcag  25980
tctgacgcct attttgtttt gctgcagctc tttcaatact tcagaattct tctgttgttt  26040
ccagctctac atatccgaaa tcgtctaaag tctctcaaca gagttactct ggtaataaca  26100
aacaccaatt ttgtttgatc agttgatctc gttggctttt ctatgcactg tctcaatata  26160
gtttggtcgc cattcaagtc tcactacaga tgttgaactt ggcctgacac caaatattta  26220
taaaatgcta cctgatattt ttaatatttc atgtttcctg acccagatta tcttgttggt  26280
tcctcgtata agtttaatta gtgacattct tgaagctttg ttatgcagca gatgtcatgg  26340
ggggaacttc atttaatgat ggaaagagca agaactcgaa aaaaaaaaac ttttgtcgaa  26400
ccagacacgt cattgttgct tatcttcaaa atcagaagtt tctcatatta ctatatcttc  26460
tggtagtgat gctggtctgt cacagaaggc attcaattgt tctccattta tatcaagcaa  26520
tggggcatca agtggttcat taggcgagag gcacagcaat ggtagtggtt tgaagttgaa  26580
tataaaaaag gatcgtggca atgcaaatcc aattagaggc tcaactggat ggatttcaat  26640
aagagcgcac agttctgatg ggaactccag agaaatggca aaaagactcc gtctatctta  26700
aaatgtaatc accgacagtg gtggtggtga tgaccctttt gcatttgacc gccgcgtcgg  26760
cgtcgccacc acgtaatcgc ccacgtcgct gcccccgctg ccacgtcgtc gaccgcgcac  26820
ggtaatcaca cgcatctcga ggccgccgct agctgatatc ttctcatccg gttgatttgt  26880
gattttggcg tttttgcagt ggtgatggcg gggggcgacc gtggccgagg cgtggagtgc  26940
catccgcatc agggtgtatc ggccgcgctg ctccgccctg gtccgcaggc tttggcggcg  27000
agctggcggc ggagggagac tgtggtgaga tcggatttcg ccgctggtgg tgtcgctacc  27060
atgggggatt cgccgcaggc gctctcaggt ttgcagcctc ctccactctc ttcccttttt  27120
tattttttt tctcgcaaaa tgtgttgtga tgttcgtctc gctgggctgg cctcatagcc  27180
attaatgtag tttgctggaa catttacatt tggaacgttg ttggcaattg ctttacaaaa  27240
tgtggaattg tggaggggag aaaaatcatt tgaacctgca gtgacaaaat tgccatctct  27300
aattttaaaa ctgaaggtgt ggaaatcaaa cataatcatt gccagcgcat cattcttgtt  27360
aaccaccatg atatattgtt ggttataaca gttagctcca caccaacctt gaaggtgtca  27420
atagaatgtt tagtataaat tgaggagaac aggcagttgt taagactttc taaagaactt  27480
gtagcagcta atactagcta ttgtgcattt gtgtttcatg gaatttgagc agcaatggat  27540
atttcttact aagatgtatg atgcaaaaca aaaaactatg tctatacagt ttacatgtaa  27600
tgtgcggatg caaataaaat catgtacatg gacaaactca tgggattcat accgaattcc  27660
agaattgcat ttcttatgtg gttacttttg ttgttgattt ggttaccaga catcgatgtg  27720
atttcaaggg tcagaggggt ttgcttctac gcggtggctg cagttgcagc aatctttttg  27780
tttgtcgcca tggttgtggt tcatccactt gtgctcctat ttgaccgata ccggaggaga  27840
gttcaggaaa aaaatttgaa aatacccatt ttttgaaaaa gatttacgtt tatatacact  27900
agtatgaaga atttgcgaaa atataactaa tccgcagatc ggttatgcgg gagcgcaaca  27960
aaagtatggc gtggcggcgc ggagtggacg gccgaggcgt tcgcgcggaa tggggctgcg  28020
ggaccgagcc agtctcgctt gccggtaacg cggaaccggt acgctcccgc agcgccagtg  28080
tgcggaaccg cggcgccaac attttttac tgcatggcac tgtgtttaat actgtttgac  28140
```

```
actgtttctg gtactgtttt acacagttcc cgggtcagtt ccgcacaatg gaggcgcggc  28200
accgaccatg aacaatgtgt gaacagtgct gcacagggtt aaaacagtgt ataaactgcg  28260
ctgcacagtg ctggagtcgc tggccactgc ggttccgcgt tttggaaccg cgggaccgtc  28320
gcgattccgc gttttggagc tgccggacca tgacggttcc gcgcaggatc gtcggtcccg  28380
tattttgaat ctgcggaacc gtcgctgtcc cgcgtttcca tttcgcggga tgcgtatatt  28440
tttataaaac ctctccatgc atgtatataa acataaatta ttgaaaaaat aagtatattt  28500
gcaaattttt ttcgagagct cagcactaca ttgcaaagat ttgggcaact ctgacaattt  28560
ccatgttcta caagcttgac gtcgagggaa tggagaacct gccaccgaat agtagccctg  28620
ctatctatgt tgcgaaccat cagagttttt tggatatcta tacccttcta actctaggaa  28680
ggtgtttcaa gtttataagc aagacaagta tatttatgtt ccgaattatt tgatgggcaa  28740
tgtatctctt aggagtaatt cctttgcggc gtatggacag caggagccag ctggtatggc  28800
tgtagtctca tccctgcttt cttaagtaga catatatgca attacagaat ttggtaaaca  28860
aacaagattt tatgaatcat atatgatttt ggggaaaaca ccaaactctc tttggtggct  28920
gccttgaaca tagttctatt cacacagtta tagcaccttc tttaaaatga agaactttgt  28980
tgcatacaca tatggccaaa ccacataatg aattttgttt atttctatct ttgaatgtta  29040
gcaccttatt ttcatgcata tcatgctaat ttgcttgccc acgttgagtg ggaatttttt  29100
tccatgtttt ataatttata tatgttctag acttctagtc cacaatttat ctacttcatg  29160
ttcctgagcc tctagtatgg ctggtagcag actaggtgct gagtgctgtc catttttgca  29220
gactgaagag aggagaaata caggactgtc cgttgttagt cagatttgta aaaatagact  29280
ctgatgtagt ttattttagc ccctatttta tatttaacaa tacaaatata taacgtatcc  29340
taagaactta tcgtaattta ggagaagttg ctcgtttcat taaattaaac tgtgaagtaa  29400
aaatgtgtgc tcgagtctgt caatgcaatc ctgtgttctt gtttgaagat atggtgtagg  29460
gcaggctagg atcgaacact gaatggtaag actgcttctg ccttcatttg tgcacttggt  29520
gctgccacgc cgattaagca gtagaacaaa gtaattttgt cgtgcacaaa tgagttatat  29580
ttcattgaaa atcgaagtga aaatgaacca aaagatagaa gaaaagggga aacttggtaa  29640
ttatatactc cacaaattta ttggtaagat ttgatattag acgctcgatt acttggctta  29700
agttaaggat atcaaatttg gggaagcacc aaaggaatta ttgtgaagga gttgtgggtg  29760
cataacgtta tctactagtt caaatcctag tgactatgaa tattaatgag taaggtaagg  29820
gatttattgt taattttagt ttctttaaga ttgtgtccga gtacaccatt cggtaagtgt  29880
aataatgttt tgtattggat tcacttgtgt tacgtgcatg tgcttttacc ttttcatttg  29940
tttctgcgtt ctgggtatga atttgacgag attccatggt cagctcaaca tatcagttac  30000
tgcgtgtcaa gcgatcttat atggtatgcg cacaagcgat tgtatacgga tatgacagta  30060
taatgtgtga tattgatacg atgttccttt cctttataaa ggaacaaaga cttttttttaa  30120
aaaaagaagg ggtattacta aaaaccaaaa tgtcaaaaac aaaatatcag tgcacatggc  30180
aagtgtgcac gagcaatagc ttgcccttac gttcattatt tagcatgtac tactactaac  30240
tacgcaaaaa tcaattcacc gattattaaa ctgttaacat cattttagca cgttaacata  30300
tgtttcattc aacacaccgg ttttggcaca tttacaaact tgcaaagttg caatactccc  30360
ttcgttacat agcataagag attttaggtg aatgtgacac atctatccaa attcattata  30420
ctagaatgta tcaccgcctc cacgccggga gggagagcgc cgccggtgga gaaaggggga  30480
```

-continued

```
gggagtggtc gaggggaacc agtagggtgc cctccccgtc gccgcctccc cgtggccgcg  30540
ccggcgagac aggaggaaga gggggagatg gagcggcgcc gccggtgagg gcgcgcgtgc  30600
gcgggggggg gggggggga gcggcgacgc cggtgaggaa gggaagggga gtggtggctt  30660
tgagagagat aggggagagg gaaaatgatt ttagagttag ggtttgggct gctgagtttt  30720
tatatagatc gggatcaatc aggaccgtcc atcagatcgg acaactacgg tttctcccgc  30780
gttgggccgg gtgccactcc taggttgccc acactattgg gccacatgta cgctccgcgt  30840
gaaataagtt cactttaggt cctttaagtt gcctctgaat tgttcccagg ccggccgcac  30900
tattgggcca ccccataggc catgtgtacg ctccgcacag aataatttcg ctttagctcc  30960
cttaatttgt cccctcaaac ttctaaaacc agtgcaaatc tttaattttt agttcaccca  31020
ttgcaactca cgggcatatt tgctagtgac atataatatg aaacgaagga tgtagcagac  31080
tatagaattt aaactgtgct ttcattttag agcatcacta actgttattt agatttttat  31140
ttaaataaat gcagaaatga tgtttttatt atgaaaatta gcaataaagc tcccaaaatt  31200
tcaaaaaaaa attaaaagag atttattaat catggttaat ttaattaaaa attaaatcta  31260
accatatcat attatttcac ggtccgtgat gaggaaatgg cagctgctat cacttatggt  31320
gggagagaag gggcattgtt tatttttata actatctctt ataactccca tgaaactata  31380
aaataaatat aatcattatc ataacattag tttttttcca ttgcaacgca agggtaattt  31440
ttcagtacaa taaaaaaata aaagtgggcc attctgaacg gaaatttctg gttttttttc  31500
ccaagagcgc cgcacacaac tgcgcaagag atcgatcgcg atcaccctgc tcgtcgccga  31560
tctcctacac catccctgcc atctccttcc cctccactgg ctgctgctgc acctgtcagc  31620
tagggcgggc atggcgcgcc gcgccgcttc ccgcgctgct ggcgcccttc gctcggaggg  31680
ctcgatccaa gggcgagggg gccgcgcggg gggcagtggc ggtggcgcgg aggacgcacg  31740
ccacgtgttc gacgaattgc tccgtcgtgg cataccagat gtcttctcct acaatattct  31800
tctcaacggg ctgtgtgatg agaacagaag ccaagaagct ctcgagctac tgcacataat  31860
ggctgatgat ggaggtgact gcccacctga tgtggtgtcg tacagcaccg tcatcaatgg  31920
cttcttcaag gagggggatc tggacaaaac ttacagtaca tacaatgaaa tgcttgacca  31980
gaggatttcg ccaaatgttg tgacctacaa ctctattatt gctgcgctat gcaaggctca  32040
aactgtggac aaggccatgg aggtacttac caccatggtt aagagtggtg tcatgcctga  32100
ttgcatgaca tataatagta ttgtgcatgg gttttgctct tcagggcagc cgaaagaggc  32160
tattgtattt ctcaaaaaga tgcgcagtga tggtgtcgaa ccagatgttg ttacttataa  32220
ctcgctcatg gattatcttt gcaagaacgg aagatgcacg gaagcaagaa agatttttga  32280
ttctatgacc aagagggggcc taaagcctga aattactacc tatggtaccc tgcttcaggg  32340
gtatgctacc aaaggagccc ttgttgagat gcatggtctc ttggatttga tggtacgaaa  32400
cggtatccac cctaatcatt atgttttcag cattctagta tgtgcatacg ctaaacaaga  32460
gaaagtagaa gaggcaatgc ttgtgttcag caaaatgagg cagcaaggat tgaatccgaa  32520
tgcagtgacg tatggagcag ttataggcat actttgcaag tcaggcagag tagaagatgc  32580
tatgctttat tttgagcaga tgatcgatga aggactaagc cctggcaaca ttgtttataa  32640
ctccctaatt catggtttgt gcacctgtaa caaatgggag agagctgaag agttaattct  32700
tgaaatgttg gatcgaggca tctgtctgaa cactattttc tttaattcaa taattgacag  32760
tcattgcaaa gaagggaggg ttatagaatc tgaaaaactc tttgacctga tggtacgtat  32820
tggtgtgaag cccgatatca ttacgtacag tactctcatc gatggatatt gcttggcagg  32880
```

-continued

```
taagatggat gaagcaacga agttacttgc cagcatggtc tcagttggaa tgaaacctga  32940
ttgtgttaca tatagtactt tgattaatgg ctactgtaaa attagcagga tgaaagatgc  33000
gttagttctt tttagggaga tggagagcag tggtgttagt cctgatatta ttacgtataa  33060
tataattctg caaggtttat ttcaaaccag aagaactgct gctgcaaaag aactctatgt  33120
cgggattacc aaaagtggaa ggcagcttga acttagcaca tacaacataa tccttcatgg  33180
actttgcaaa aacaaactca ctgatgatgc acttcggatg tttcagaacc tatgtttgat  33240
ggatttgaag cttgaggcta ggactttcaa cattatgatt gatgcattgc ttaaagttgg  33300
cagaaatgat gaagccaagg atttgtttgt tgctttctcg tctaacggtt tagtgccgaa  33360
ttattggacg tacaggttga tggctgaaaa tattatagga caggggttgc tagaagaatt  33420
ggatcaactc tttctttcaa tggaggacaa tggctgtact gttgactctg gcatgctaaa  33480
tttcattgtt agggaactgt tgcagagagg tgagataacc agggctggca cttacctttc  33540
catgattgat gagaagcact tttccctcga agcatccact gcttccttgt ttatagatct  33600
tttgtctggg ggaaaatatc aagaatatca tagatttctc cctgaaaaat acaagtcctt  33660
tatagaatct ttgagctgct gaagcatttt gcagctttga aattctgtgt tggaattctt  33720
ttctcctaca gtccgattag aggagggatc ttctctgtat gtgtaaatag cgaggtatgt  33780
atgtcacctc tccgaattat tttgactgtg gttcctggac tgtaaacaag ctattatctt  33840
ctggtgttga tgccagaaaa aacacaaaag tttgtcgtta tctctactaa cggatcataa  33900
aggggtttgt aactggagtt tcaaacttaa ggtatctagg cagtaggtat atattgatcc  33960
tacatcttat gatcttaaga tgatatcctt ctcattatcc tctgctgaaa ctttagcttg  34020
aaccgtcatc tacaccacaa tttgagcccc ttagcacaga gcacaacgag caatagcttg  34080
cccttacgtt cattatttag catgcactac tactaactac ccaataatca atacatcggt  34140
tattaaactg tttgtacagt ttaataatgt cattttatca cgttaacata tgtttcattc  34200
aacaccacac cggttttggc acagttgcaa acttgcaata acatttttac tacttctccg  34260
ccccataata taacaatctc gttccatact atattgctat attacaggat ggatgaagta  34320
cttcttttct tccaaaatat aagaatctag tactagatta gatattattt ggattcacga  34380
atttgattag gctgtctaga tttgtagtcg tatgtaatgt ctaattcggt aataggttat  34440
tacctctttg gatggaggga gtagttttta tttcgtactc cctccgtttc atattataag  34500
ttgttttgac ttttttctta gtcaaatttt attgagtttg attaaattta tagaaaaaaa  34560
ttagcaacat ttaagcacca cattagtttc attaaatgta gcatggaata tatttttata  34620
atatgtttgt tttttattaa aatgctacta tatttttcta taaatgtagt caaatttaaa  34680
gaagtttgat tatgaaaaaa tcaaaatgac atataatatg aaactgagga tgtagcagac  34740
tatagcaaat ttaaactatg cttttatttt agagcatcac caaaagatta gcaataattt  34800
atccctaaaa ttcaagtttt gggtttctta aactgaaaat aggaagtgaa aaatcttttc  34860
cgtccaagag atagcctaaa tcttatctta actaattaaa atattcataa ttttcctttc  34920
gtcacattaa attttcgtcc gtaaatctga ttgaaatcca attggacaat ccaaaaaata  34980
gagaaaaaga acagaaaaaa taataaaaag cacacaaatc ttatctcaat cccgcgggaa  35040
gctgccgacg ccgccgaatc cgctcgagcg ccgccgccgc cgctcacggg gaacgatgtc  35100
gctgctgtcg cacgcggtat gggagggcgc cgctgccact gcttgggaga taggatatgg  35160
agagagaagg aaatgtgagg gttagggtta ggtttttccc cgtccgtatc ttcagcgaca  35220
```

-continued

```
cggaggcgat ccaagctgtc catcagatcg gacggctcag aatgcctcca tcgtcgggcc  35280
gcgcatgctt gatgggccga gggaaggccg gagggtcgaa caaacgcaat caaaggagga  35340
gttggaggag gtaaattaga atttatttgc gggctgagat agtaaatgga ctgaaaatgg  35400
cccatagaga aattgggaat tttatttaaa taaatgttga aaaggtgttt atattatcaa  35460
aattaaaaat taagctccga aaattctaaa aaatattcaa agagcattat taatcatggt  35520
taatttaata aaaattaaat ccaaccatat catattattt cacggcgcgc ggtaggaaaa  35580
tgcgcagctg ttgtcgttta cggtgggaga gaagggacat tgtttatttc cagaactatc  35640
ttttataact cccatggaac tttaaaataa atataatcat tattatagca ttagtttttt  35700
tctgtctttt ttttccccaa gagcgccgcg cagaagagat cgatcgcgat ctccctgccc  35760
cgacgtcgcc ggccgatctc tcattctctc cacgccctgc tcgtcgccga tctcctacac  35820
catccctgcc atctcctcct tcccctcccc tctatcctcc actggtgccg cccacctctc  35880
cgtataagac aaactgcgtt gcggcgttgg tttccgccgg cgctgctgct gcacctgtca  35940
gctagggcag gcatggcgcg ccgcgccgct tcccgcgctg ttggcgccct tcgctcggac  36000
ggctcgatcc aagggcgagg aggccgcgcg gggggcagtg gcgccgagga cgcacgccac  36060
gtgttcgagg aattgctccg gcgtggcagg ggcgcctcga tctacggctt gaaccgcgcc  36120
ctcgccgacg tcgcgcgtca cagccccgcg gccgccgtgt cccgctacaa ccgcatggcc  36180
cgagccggcg ccggcaaggt aactcccacc gtgcacacct atggcattct catcggttgc  36240
tgctgccgcg cgggccgctt ggacctcggt ttcgcggcct tgggcaatgt cgtcaagaag  36300
ggatttagag tggaagccat caccttcact cctctgctca agggcctctg tgccgacaag  36360
aggacgagcg acgcaatgga catagtgctc cgcagaatga ccgagctcag ctgcatgcca  36420
gatgttttct cctgcaccat tcttctcaag ggtctgtgtg atgagaacag aagccaagaa  36480
gctctcgagc tgctgcacat gatggctgat gatcgaggag gaggtagcgc acctgatgtg  36540
gtgtcgtata ccactgtcat caatggcttc ttcaaagagg gggattcaga caaagcttac  36600
agtacatacc atgaaatgct tgatcggagg atttcaccag atgttgtgac ttacagctct  36660
attattgctg cgttatgcaa gggtcaagct atggacaaag ccatggaggt acttaccacg  36720
atggttaaga atggtgtcat gcctaattgc atgacatata atagtattct gcatggatat  36780
tgctcttcag agcagccgaa agaggctatt ggatttctca aaaagatgcg cagtgatggt  36840
gtcgaaccag atgttgttac ttataactcg ctcatggatt atctttgcaa gaacggaaga  36900
tccaccgaag ctagaaagat ttttgattct atgaccaaga ggggcctaga gcctgatatt  36960
gctacctatt gtaccctgct tcaggggtat gctaccaaag gagcccttgt tgagatgcat  37020
gctctcttgg atttgatggt acgaaacggc atccaccctg atcatcatgt attcaacatt  37080
ctaatatgtg catacgctaa acaagagaaa gtagatgagg caatgcttgt attcagcaaa  37140
atgaggcagc atggattgaa tccgaatgta gtgacgtatg gagcagttat aggcatactt  37200
tgcaagtcag gcagtgtaga cgatgctatg ctttattttg agcagatgat cgatgaagga  37260
ctaaccccta acattattgt gtatacctcc ctaattcata gtctctgtat ctttgacaaa  37320
tgggacaagg ctgaagagtt aattcttgaa atgttggatc gaggcatctg tctgaacact  37380
attttcttta attcaataat tcacagtcat tgcaaagaag ggagggttat agaatctgaa  37440
aaactctttg acctgatggt acgtattggt gtgaagccca atgtcattac gtacagtact  37500
ctcatcgatg gatattgctt ggcaggtaag atggatgaag caacgaagtt actctccagc  37560
atgttctcag ttggaatgaa acctgattgt gttacatata atactttgat taatggctac  37620
```

-continued

```
tgtagagtta gcaggatgga tgacgcatta gctcttttca aagagatggt gagcagtggt  37680
gttagtccta atattattac gtataacata attctgcaag gtttatttca taccagaaga  37740
actgctgctg caaaagaact ctatgtcggg attaccaaaa gtggaacgca gcttgaactt  37800
agcacataca acataatcct tcatgggctt tgcaaaaaca atctcactga cgaggcactt  37860
cgaatgtttc agaacctatg tttgacggat ttacagctgg agactaggac ttttaacatt  37920
atgattggtg cattgcttaa agttggcaga aatgatgaag ccaaggattt gtttgcagct  37980
ctctcggcta acggtttagt gccagatgtt aggacctaca gtttaatggc agaaaatctt  38040
atagagcagg ggttgctaga agaattggat gatctatttc tttcaatgga ggagaatggc  38100
tgtactgcca actcccgcat gctaaattcc attgttagga aactgttaca gaggggtgat  38160
ataaccaggg ctggcactta cctttccatg attgatgaga agcacttttc cctcgaagca  38220
tccactgctt ccttgttata gatcttttgt ctgggggaaa atatcaagaa tatcatagat  38280
ttctccctga aaaatacaag tcctttatag aatctttgag ctgctgaagc attttgcagc  38340
tttgaaattc tgtgttggaa ttcttttctc ctacagtccg attagaggag ggatcttctc  38400
tgtatgtgta aatagcgagg tatgtatgtc acctctccga attattttga ctgtggttcc  38460
tggactgtaa acaagctatt atcttctggt gttgatgcca gaaaaaacac aaaagtttgt  38520
cgttatctct actaacggat cataaagggg tttgtaactg gagtttcaaa cttaaggtat  38580
ctaggcagta gttttgacat tagatccaac attgtgtagt attcatttgt gtgtatcaat  38640
ctatagggtt tcattaaatt tcatttgtgt actgtttagg tgttgaatat attgttttac  38700
ttgtttttta actgaacaaa agatagctga agctttgttc tttaccaaat gcagtagtga  38760
tcatcacaat atattttttt acggaacagg agattgtata aaatggtttc catcggcggc  38820
caacggcgac cgctctgctc tgacccacca cccaatccat ccatccactc gccgccgccc  38880
ctgatccaag cctccgccgc gcgacagcga cgcaccgccg tcgagaggag gaggcgtgag  38940
ccccatgggg accctcctcc ggccgcgtaa tgccgctgca cggtaaccac gcgcctctcg  39000
aggcctccgc cgctagctga tctcttctca tcctgtttgg gtttgggttt gtgatttggg  39060
tgtttttttcc gcagcggtgg tggtggtggt ggttgcggcg ggagggggcg gtggccgcgg  39120
ccgtggcgtg gagtgccagc tgcatcgggt gcaccgccgc cggggtccgc aggttgtggt  39180
ggcgacggcg agctgaggag gcggagggag actggtgagg gacacaggca ggcaggctct  39240
caaggctaag cttgttacag gtactgagac tagttactaa ttactttgat aatcagtata  39300
aataagcttg tgtagtgtaa tggcattgtg catttctgca cttgtaaatt ttacagaaga  39360
tggtcattca atttgaacct gcatctaata ttttagtggt ttgagtttat tctcccagtc  39420
acagagttga agaggcaagt aacctgtaag agaggactga acattaacac ctcttgttcg  39480
attaaaaatg accaaagagc atcaaacatg tattcgaggc tgttacttta atatggccca  39540
ttaatttgtt tagttggcta tgtacatcct agttggtgca gtgttgtgga aaacggaata  39600
cgggtgtcgg atggacgagg tgccgtcaag cgattaatcg taatacggat gattaaacgg  39660
aattatatgg atttttggcg ttcgcactaa gatgtacata attgatgtta atggcaatgg  39720
tggagacaaa atgcatcatc ttaataaaaa atatttgtat aaatctctaa ctatattatg  39780
aaaatgccat ttattagttc aatagatatc aacactgatg gttagtagcg caatagcatt  39840
gggcttgtta gtcaaaatag tgcagctggg ctgcaagttg caagtttatg ttagtttcat  39900
aaacagacat ctgatttgtc gataaataac cgactaatcg tgccatacaa ctgtataatt  39960
```

-continued

```
actctgaaat agtaatgttg ctccgacttg atgatacggt acggtctggc taccgtttcc  40020
gttttgacag acgattaaac ggctgtgccg gtcgacttcc acaacactga gttggtgtaa  40080
atgccagtta ccatttctat gatctaaaat aatcaactct tttagtatat tttcaaaaac  40140
gaaaattcag tacacatgca tgaatcttaa tcttcatatc tagctcgtta caaaatcaac  40200
aaaggcaccg tgtcagctgg tgcacattag ctagttcgta cttagcatta tccactagca  40260
ccttattttc atgcatatca tgctaatttg cttgcccacg ttgagtggga attttttttcc  40320
atgttttata atttatatat gttctagact tctacttcat gttcctgagc ctctagtatg  40380
gctggtagca gactaggtgc tgaatgctgt cctttttttgc agactgaaga gaggagaaat  40440
acaagactgt ccgttgttag tcagatttgt aaaaatagac actgatgtag tttatttttg  40500
cccctatttt atatttaaca atacaaatat ataacgtatc ctaagaattt atcgtaattt  40560
aggagaagtt gctcgtttca ttaaattaaa ttgggaagta aaaatgtgtg ctcgagtatg  40620
tcaatgcaat cctgtgttct tgtttgaaga tatggtgtag ggcaggccag gattgaacac  40680
tgaatggtaa gactgcttct gctttcagac gttattgcta aatttttagc tagttgcaat  40740
tagtgctgtc acgccgatta agcagtagaa caaagtaatt ttgtcgtgac aaatgagtta  40800
tatttctttg aaaatcgaag cgaaaacgaa ccaaaagata gaagaaaagg gaaacttggt  40860
aattactcca caaagagaac aaatttattg gtaagatttg atatgagatg ctcgattact  40920
tggcttaagt taacaatatc aaatttgggg aagcaccaaa agaattattg tgacttaagt  40980
taaagatatc aaatttgggg aagcaccaaa ggaattattg tgatggagtt gtgggtgcat  41040
aacgttattt gctttgttca aatcctagtg actatgaata tgaatattaa tgcgtaaggt  41100
aaggaattta ttgttaattt taggttcttt acgattgtgt ccggggacgc cattcggtaa  41160
ctgtaataat gttttgtatt ggattcactt gtgttacatg cacgcactaa acatgtgctt  41220
taccttttca tttgtttgtg cgttctgcgt ttgaatttga cgagattcca tggtcagctc  41280
aacatgtcag ttactgcgtg tcaagcagtt actgcgtgtc aagcgatctt atatggtatg  41340
cgcacaagcg attgtatacg gatatgacag tataacgtgt gatattgatt tttttatata  41400
aaaaaatacg atgttacttt ccttcataaa ggaacaaaga cttttttttt aaaaaaaaga  41460
aggggtatta ctaaaaacaa aaatgtcaaa aacaaaatat cagtgcacat ggcaagtgtg  41520
ctcggcaatt ttttgtctgt actttaaaca aaaatatttc tatatggtat tttttacaag  41580
ggtgtcacaa atattttaaa ttagccaaac atctgcattt tattaaaaac tgtataaatt  41640
ataatttata ctctaaaagg ttgtgtacat ctctcttgga gaaaatgtat aagttgcgaa  41700
caaacattaa tccacgttat ataagtcaat ctgttattta accatagaaa gtaagaaacc  41760
tactagcgtg ttaagctaag ctctctttca ttctctttct tcttcctggt tttgcttcaa  41820
tcacttgtca agtgaagggt tcttaactac cattactcct actcaccaaa tttttttctc  41880
agatctttcg taggtatata ttgatcctac atcttatgat cttaagatga tatccttctc  41940
attatcctct gctgaaactt tagcttgaac cgtcatctac accacaattt gagcccctta  42000
gcacagagca caacgagcaa tagcttgccc ttacgttcat tatttagcat gcactactac  42060
taactaccca ataatcaata catcggttat taaactgttt gtacagttta ataatgtcat  42120
tttatcacgt taacatatgt ttcattcaac accacaccgg ttttggcaca gttgcaaact  42180
tgcaataaca tttttactac ttctccaccc cataatataa caatctcgtt ccatactaga  42240
ttgctatatt acgggacgga tgaagtactt ctttccttcc aaaatataag aatatagtac  42300
tagattagat attatttgga ttcacgaatt tgattaggct atctagattt gtagtcgtac  42360
```

-continued

```
gtaatgtcta attcggtaat aggttattac ctctttggat ggagggagta gtttttattt  42420
cgtactccct ccgtttcata ttataagttg ttttgacttt tttcttagtc aaattttatt  42480
gagtttgact aaatttatag aaaaaaatta gcaacattta agcaccacat tagtttcatt  42540
aaatgtagca tggaatatat ttttataata tgtttgtttt tttattaaaa tgctactata  42600
tttttctata aatgtagcca aatttaaaga agtttgatta cgaaaaaaaa tcaaaatgac  42660
atataatatg aaactgagga tgtagcagac tatagcaaat ttaaactatg cttttatttt  42720
agagcatcac caaaagatta gcaataattt atccctaaaa ttcaagtttt gggtttctta  42780
aactgaaaat aggaagtgaa aaatcttttc cgtccaagag atagcctaaa tcttatctta  42840
actaattaaa atattcataa ttttcctttc gtcacattaa attttcgtcc gtaaatccga  42900
ttgaaatcca attggacaat ccaaaaaata gagaaaaaga acagaaaaaa taataaaaag  42960
cacacaaatc ttatctcaat cccgcgggaa gctgccgacg ccgccgaatc cgctcgagcg  43020
ccgccgccgc cgccgccgct cacggggaac gatgtcgctg ctgtcgcacg cggtatggga  43080
gggcgccgcc gccgctgctt gggagatagg atatggagag agaaggaaat gtgagggagg  43140
gttaggtttt tccccatccg tatcttcagc gacacggagg cgatccaagc tgtccatcag  43200
atcggacggc tcagaacgcc tccatcgtca ggccgcgcat gcttgatggg ccgagggaag  43260
gccggagggt cgaacaaacg cagtcagagg aggagttgga ggaggtaaag tagaatttat  43320
ttgcgggctg agatagtaaa tggactgaaa atggcccata gagaaattgg gaattttatt  43380
taaataaatg ttgaaaaggt gtttatatta tcaaaattag aaattaagct ccgaaaattt  43440
taaaaaatat tcaaagagca ttattaatca tgattaattt aataaaaatt aaatccaacc  43500
atatcatatt atttcacggc gcacggtagg aaaatgcgca gctgttgtcg ctgacggtgg  43560
gagagaaggg acattgttta tttccagaac tatcttttat aactcccatg gaactttaaa  43620
ataaatataa tcattattat agcattagtt tttttctgtc tttttttttcc ccaagagcgc  43680
cgcgcagaag agatcgatcg cgatctccct gccccgacgt cgccggccga tctctcattc  43740
tctccacgcc ctgctcgtcg ccgatctcct acaccatccc tgccatctcc tccttcccct  43800
cccctctatc ctccactggt gccgcccacc tctccgtata agacaaactg cgttgcggcg  43860
ttggtttccg ccggcgctgc tgctgcacct gtcagctagg gcgggcatgg cgcgccgcgc  43920
cgcttcccgc gctgttggcg cccttcgctc ggacggctcg atccaagggc gaggaggccg  43980
cgcggggggc agtggcgccg aggacgcacg ccacgtgttc gacgaattgc tccgccgtgg  44040
caggggcgcc tcgatctacg gcttgaaccg cgccctcgcc gacgtcgcgc gtgacagccc  44100
cgcggccgcc gtgtcccgct acaaccgcat ggcccgagcc ggcgccgacg aggtaactcc  44160
cgacttgtgc acctacggca ttctcatcgg ttgctgctgc cgcgcgggcc gcttggacct  44220
cggtttcgcg gccttgggca atgtcattaa gaagggattt agagtggacg ccatcgcctt  44280
cactcctctg ctcaagggcc tctgtgccga caagaggacg agcgacgcaa tggacatagt  44340
gctccgcaga atgaccgagc tcggctgcat accaaatgtc ttctcctaca atattcttct  44400
caaggggctg tgtgatgaga acagaagcca agaagctctc gagctgctgc acatgatggc  44460
tgatgatcga ggaggaggta gcccacctga tgtggtgtcg tataccactg tcatcaatgg  44520
cttcttcaaa gagggggatt cagacaaagc ttacagtaca taccatgaaa tgctggaccg  44580
ggggatttta cctgatgttg tgacctacaa ctctattatt gctgcgttat gcaaggctca  44640
agctatggac aaagccatgg aggtacttaa caccatggtt aagaatggtg tcatgcctga  44700
```

-continued

```
ttgcatgaca tataatagta ttctgcatgg atattgctct tcagggcagc cgaaagaggc  44760
tattggattt ctcaaaaaga tgcgcagtga tggtgtcgaa ccagatgttg ttacttatag  44820
cttgctcatg gattatcttt gcaagaacgg aagatgcatg gaagctagaa agattttcga  44880
ttctatgacc aagaggggcc taaagcctga aattactacc tatggtaccc tgcttcaggg  44940
gtatgctacc aaaggagccc ttgttgagat gcatggtctc ttggatttga tggtacgaaa  45000
cggtatccac cctgatcatt atgttttcag cattctaata tgtgcatacg ctaaacaagg  45060
gaaagtagat caggcaatgc ttgtgttcag caaaatgagg cagcaaggat tgaatccgaa  45120
tgcagtgacg tatggagcag ttataggcat actttgcaag tcaggcagag tagaagatgc  45180
tatgctttat tttgagcaga tgatcgatga aggactaagc cctggcaaca ttgtttataa  45240
ctccctaatt catggtttgt gcacctgtaa caaatgggag agggctgaag agttaattct  45300
tgaaatgttg gatcgaggca tctgtctgaa cactattttc tttaattcaa taattgacag  45360
tcattgcaaa gaagggaggg ttatagaatc tgaaaaactc tttgagctga tggtacgtat  45420
tggtgtgaag cccaatgtca ttacctacaa tactcttatc aatggatatt gcttggcagg  45480
taagatggat gaagcaatga agttactttc tggcatggtc tcagttgggt tgaaacctaa  45540
tactgttact tatagcactt tgattaatgg ctactgcaaa attagtagga tggaagacgc  45600
gttagttctt tttaaggaga tggagagcag tggtgttagt cctgatatta ttacgtataa  45660
cataattctg caaggtttat ttcaaaccag aagaactgct gctgcaaaag aactctatgt  45720
taggattacc gaaagtggaa cgcagattga acttagcaca tacaacataa tccttcatgg  45780
actttgcaaa aacaaactca ctgatgatgc acttcagatg tttcagaacc tatgtttgat  45840
ggatttgaag cttgaggcta ggactttcaa cattatgatt gatgcattgc ttaaagttgg  45900
cagaaatgat gaagccaagg atttgtttgt tgctttctcg tctaacggtt tagtgccgaa  45960
ttattggacg tacaggttga tggctgaaaa tattatagga caggggttgc tagaagaatt  46020
ggatcaactc tttctttcaa tggaggacaa tggctgtact gttgactctg gcatgctaaa  46080
tttcattgtt agggaactgt tgcagagagg tgagataacc agggctggca cttacctttc  46140
catgattgat gagaagcact tttccctcga agcatccact gcttccttgt ttatagatct  46200
tttgtctggg ggaaaatatc aagaatatta taggtttctc cctgaaaaat acaagtcctt  46260
tatagaatct ttgagctgct gaagcatttt gcagctttga aattctgtgt tggaattctt  46320
ttctcctaca gtcctattag aggagggatc ttctctgtat gtgtaaatag cgaggtatgt  46380
atgccacctc tccgaattat ttttactgtg gttcctagac tgtaaacaag caattatgtt  46440
atgctgttga tgccagaaaa aacataaaag tttgtcgtta tctctactaa cggatcataa  46500
agggatttgt gactggagtt tcaaacttaa tgtgtctagg cagtaatttt gacattagat  46560
ccaaaacaat ttatagggtt tcattaaatt tcatctatgt gtactgttta ggtgttgaat  46620
agtttgactt gtttttaac tgaacaaaag atatgtctga agctttgttc tttaccaaat  46680
gcagtactga tcatcacaat atattttta tggaacaaga ttggattgta tagaatggtt  46740
tctgatctga ttatcttatc tcaacgtatt attatgcaca tgtactaatc atgaaatatc  46800
tgatggaatg atgtttctat ttacctgtgt gaggcagcaa ggagtgagat ggataacacc  46860
acatactccc tctgtcccag aatataagaa gttttagagt tggacacgat tattaagaaa  46920
gtaggtagaa gtgagtagtg gagggttgtg attgcatgag tagtggaggt aggtgggaaa  46980
agtgaatggt ggagggttgt gattggttgg gaagagaatg ttggtagaga agttgttata  47040
ttttggggag tacattatta ttctagaaca atactgttgt gctcaagaag cgttccaaag  47100
```

-continued

```
atgtttcaca acctgtgctc gatgggtttt gagcttaatc ctgggacatt cagtatcatg  47160
atctgtctca ttcttaaaca tggaataaag gatgacagca tgatttcttt gtctctataa  47220
tcttttggct acccacagat aatagctgta aatctatact actttaaaag gagtagtggt  47280
ggtggtgagt ggtgaatctg ccaccacccc accaccaact ctcaaaattc tgacatgtgg  47340
gatcactgtc aatcccttct ccaagacatg tgggatcact gtcaatccct tctccaaacc  47400
aattgtatga tagaacagtg gaaatcacgg acagaccatg gagctctcaa ccataatcat  47460
ccttgcgagt taataacaaa tggagcgtaa acttggcaag caaaaaactc aaattaattc  47520
taaaattaag ctctaggatt caaaatagat ttcctctctg cattgtgctg ttatgatttt  47580
taattccgta acaacgcaaa tgcattttgc tagtcttata aagaagggtt aatgcaaata  47640
ttctgattaa atgattgtat ctatgaagtt tgaatgctag tggaagctcc tttgaccatg  47700
ttttgttgtg cgagcattta agagagtgaa gagaatgctt ctttggtgct gttctggtat  47760
ggaaggatcc acagataaaa ttcaggttct actgcttctc tgcttgtaat tttcatgaag  47820
ctgcagtgaa taccttgttg accacttgat ctgttgcttt gaaggagaat atagtagtgg  47880
ccaaggttgg tgacggtgat ggtggcatgt gatcccccag atcttcagtg acccagagag  47940
gaggggacgg cgcgtggtga gctacaaggc atactcagtg gagggcaaga tcaaggcctc  48000
ccgtccgtag gggactccgc tgcatcaagg ccaactgctc cgaactgatc aatttctggt  48060
acggatcact tctcctttcc tttttttttt caccttaagc actctcttga ttcttcgctg  48120
ctacctccct taatttcttt caatatattg tggcacttga tcatggcgga gacccacctt  48180
ccagtgtgaa tggattttgt caaagaacta aatttattcc attagcttat tttccgatta  48240
catggaagac attcttttct ggaataaata cagaactaaa tcctgtttcc tgaataaaag  48300
ttgttagtgt gtggcatggt gcatttccgc gcttctaaat tttataaaac ctgttcattc  48360
aatttgaacc tgcatccaat ccaatatttt aggtgcagac aggtgcttgc ggtcaggtta  48420
aagaagttgg caaaaatgct tctgaagaaa ggttaattgt tgtttcatct caggaggtaa  48480
tatgcagatg attattccaa ttggcattgc cttgccattt ttatcacgag tctttacaat  48540
tttatatcct cctacatatt ctttccagat tccagatgat ccagtgtctc caacaattga  48600
ggcgcttatt ttgctccata gtaaagtaag tacacttgct gagaaccacc agttgacaac  48660
acggcttgtt gtaccatcaa acaaagttgg ttgtattctt ggggaaggtg gaaaggtaat  48720
tactgaaatg agaagacgga ctggggctga aatccgagtc tactcaaaag cagataaacc  48780
taagtacctg tcttttgatg aggagcttgt gcaggtaatt tatttggcca tacctacacc  48840
agagatccat atattacttt tataactgca gtttttactt gttaacattt cattgtgctt  48900
ttacatttgt tccaagcttt caggttgctg ggcttccagc tattgaaaga ggagccctga  48960
cagagattgc ttcgaggctt tgaactagga cactcagaga tggaagttct tccaataatc  49020
cgacaccttt tgcccctgtt gatggtcctc ctgttgatat cttgcctaac aaggaattca  49080
tgctatatgg acgatctgct aatagtcccc catatggagg gcctgctaat gatccaccat  49140
atggaagacc tgccattgat ccaccatatg gaagaccaat atccacaata tggaagacct  49200
gccaatgatc caccatatag aagacctgtc aatgatacat catattgagg gttgaacaat  49260
gatgggcctc gtgatcaggc ccggtcctga ggggggtcga atggggcgat cgctccgggc  49320
cccccgattc ccagggcccc cacctatctg tgcaacgagt agtagcgatc ttccagcgcg  49380
caacgtgagg cgatgtttct ccgtgatttc gccggcctgc aactgcgaga tcgcgagtat  49440
```

-continued

```
aacgatcagc cgatcgatct catctgccga ctgccatgct gatgccacac gcaagcgcag  49500
catatcagcc ttatcttggt tgatcggcat gctggacgag cacatctgtt gtcgcatcaa  49560
ctgctgactg ctatatatgt gctggtgctg aatcgatcga ttgtcgtcac ggaagtgaag  49620
aacaaccacg gcactgctgc ctgctgggct ctagccgcca tcagtaagta cgctatactg  49680
cctatctaga tctagatcga gattacatag tggaattatc tgtttataac aaaattacaa  49740
ggtatcaatt gataatttaa ggttataacc gtacaaactt cagtgatttg ctggtttcac  49800
attggttaga tttgtttcaa ctaatttggt acttctgtag ccttgtaatt tacgaatcta  49860
gtattaatat tttcttaagt attagcctgt tccttgatat tatgctgttg agaaagtatg  49920
caatagataa caaaaacaag taggtgtgtt gaggatgctc aagagtaata caggcacttc  49980
aataattctg atattatcag gacatcatca ataattctgc gcctacaaat cttcaaagaa  50040
aattttaata taatgcgtat gattttttaa atacgaatat tgattgctat ttaaagatat  50100
ttatattata tggtaattat tatttgaagg tttataataa aggcctccgt ttttagtttc  50160
acgctgggcc ttcagaatct caggaccggc cctgctcatg atccttacac cgtgtatcct  50220
gtagagtact tctctaaaag agagtaccct agtggaagta gcaaagttgc accatctgct  50280
tcatacgaaa gatatgcagc aactactcgc ttgcctaata gagaactgcc ctcatctatt  50340
agtcctggtg ccgattatat gtcctgccgt tcttatcttg accaagtacc tactgatagg  50400
tactctaata gggttacact acaattaggc ctcttgagag ccgggaatag taatgtgcaa  50460
caattaggaa tcaccagagc tggaaattcc aatgcttatg attatactga ggtacatttc  50520
caatgcgtta gcttgcctct tctttgcaaa tggccctcgc ctgatatgtt tccattagaa  50580
acatgaaacc atatatttga ctgttgcatt atgtctattt tcttccatga tggttcagac  50640
gtctgaaaaa aggacaaaaa tattctagaa tatgtcatgg tgatccaaat atatccttct  50700
gtcttgtgcc cactctaata tctatcgttg gtaacactat tcaattgtta ccatgttgtt  50760
gcaaacccta gattcagtta ttcagctgtt ctctgctgct gttgcttacc agttttctta  50820
gttgggtgtt gatcttttct catttttat ttccttgttt cctggttcac ctgctgcctc  50880
tctgatgcat ctgaatgtat atttttgttc tcttcagtgc ttaatagatt taaatttcat  50940
tcttttcagg ctgcggagct gatccatgga cgtgaggatt accgaagact gtcaggtctc  51000
actgggtatg gcttacgcag actgaatttt tacaggacac aaacatgaat tttgtcctca  51060
taatcattga gtgatgatct ctttgcaggt atccaggtgg ctctgtcgaa ttgtggattc  51120
caaatagtta actggagtct gtcattggtg ttggtggtgt caatctagct gagatccgtc  51180
tggtatagcg taagagaaac atcatgcact atccccagtc ataaccatgc cccaatggcc  51240
accaatagtt ttcctcgtga aaatctcccc ttgatcccag atctctggtg cgagagtgaa  51300
gttgcacgaa gcccatcctg gttcttccga gtccattgtg gagatccagg gcattccgga  51360
tcaagtgaaa gccgcacaga gccttctgca aggcttcatc ggcgcaagca gcaacagcag  51420
gcaggcgccc cagtcctctc gcatggccca ttatttttag taagctggag gacattcgca  51480
acaggggggt cagtggtcac tgcaaagctg agtttgttct tcagttcaac tgcagaaaat  51540
tgcagatcgg ttgccgtagt tgctagaacg gtacatagtt gccacctaac tgtagcgagt  51600
ggcataactt attgtgtgtt actgcccaat gttgtctctc cttgtgttca tggattcaga  51660
cttgtgattg tagtatttct ggatcagact ggagtaaaag aaaaaaaaaa aggaagacat  51720
gggtttaaca gtaagctcaa aacgttgaca gtagtaaaat aaaaggggtt tgttcacttt  51780
atttccaata tcaaccttac caacatttgg cgttgaatca tttataccac atcgcttgtg  51840
```

-continued cagctgaatt tggggctgtt taaaagatgg tctcttggat tgctaattgc ctcgcggcaa 51900
gcgtggtacc ttgtacaata taaatataat tataactatt taatttcata attaaacatg 51960
ttgttacaaa tctctactat tataaaaatt gaagatgttt tttgccggta ttttggtacg 52020
tcatctgtgt atgaatccgt ttttaagttc gtttgctttt ggaaatacat atctgtattt 52080
gattcagttt ataagatcgt tcacttttgg taatacagaa ggaatcatat aagaattctg 52140
tttaaaaaca ctcgtatagt aacttgagac gatcagacgc ctaactacag ctcatgattt 52200
tctaaatata tatatatata tatatatata tactagaaaa aatatatgtg tgttaaaagc 52260
tatcttaatc ttattattgt tatatatttt agttaacaag aaatctattg tgggaacttg 52320
tttggatata tattttttta aaaaaaatca tgagctgcaa ttaggaatcc aatcgtctca 52380
agttagcagg agggcgagtt tttttaaaga gatttcttat acgatttctt ctatatttct 52440
aaaagcaaac gaacttaaaa accgactcaa acatggatct gtatttccaa aaacgaataa 52500
acttaaaaac cgactcatgc acagatgatt aatttttata atagtagaga taaacgaact 52560
cccacagtga attttatttt aactgaacca tataacaata ataagattaa aatagacttc 52620
acccgttgca atgcacgggc attttttcta gttaaagaag aaataaaaaa acacaaaaat 52680
ttataaaatg taaaaaagaa aaatattata attttgttag aattattatt ataatataga 52740
aaaatagttg ccaaaatttc tcaacgaatg tcgaataaac tcagcaatgt catatattta 52800
aatatgatgg taatatttgt tcgcaaaact ttaatcttca atccttcaac aacatagata 52860
tacaacgtcg taatcgccaa caagcccgag tgaccataca ggatagccga gcggtggatc 52920
tgtactgttc ttgggtgaaa taaatctagt acattgtata tcttatctta atatctacta 52980
ttataaaaat tgaagatatt tcttcaaaga tttccatacg ttctctactc cgttacaata 53040
tcggttctac tccgttacaa tatcggtttt gtacaccccg cgcacgcgtt gtgtgttctc 53100
ccgttccaat acatgaagct agagtcttgc ttctccctgg tctggcaggc cctttttcca 53160
ccatccccac cagggccagc gggttacatt gaccgatcac ggcccacatt agtggatgca 53220
gccagccacg ctcttcacaa atcatgtgat gaacattagc tgagttaaaa tttatccttt 53280
gatgattgtt agaaatgttt ttttctccac atcttctctt tcaattttgg aaaaatagat 53340
ttcttgattt ttgtgctcgt acatcactaa taaatcagtt gttacccttc cacacattgt 53400
caatttacca tgtctatttc agctcttacc ttgtatagtc ttgactcttg agtcctcgct 53460
attgactaag ttgctacatg cctcctacaa atcaatagac tgccataaca atattttcta 53520
cgacatgatc catattagtc catgcaatgc aagtacacac acactactgc acgaaaaaac 53580
tatgcaccat aacttcaaaa ctaacatgtt agaatgacgt taatttttca ttacaattat 53640
attcatcgac cgttaattta ctaggcatcc tgtttaaaaa aaatattcac cgaccatacc 53700
cacatgttcc gtagttcatt aggtgatgga tcggtagtta cagcagctgg atttttatat 53760
tttggtcatt ttgaaaaatt tatttcgcaa atagactcct gaaaaaactt atcccagaaa 53820
tagtcccttt tggagcgtca gagtggctgg cgccgtggtc caacgggaca gcgccaacct 53880
ctctggcgcc gccccccgcc tctattcttg tttctctata tagagttgca aactttttat 53940
ttttgtttta tttttttgga tgtttttca ctcttagaat cacgatacaa ccaactacaa 54000
aaaaaattaa actcgaacgg aatatatcac ttagctagaa gtctgaaaat atagcatacc 54060
acttatctac tttgcacctt caccaaaatt agaccataac ttctttagta aaatcctttg 54120
atcagcatat taaacataat gcactctatc actaggtgaa attacttaat ctaattcaaa 54180

-continued

```
atataactac atgtagcctt gaaaaattct acatgccaca tatttcgtcc gtttgagttt  54240
attattttta tggttcgttc atgtgagttc ccaagtgtga aaaaaaaata aaataaaaat  54300
aaaaaagttg cacatcctct cctctgcatt agagaggaga ggagaggaaa aattctacag  54360
gtcacatatt tcgtccattt gagttcattt tttctatggt tggttcttgt gtgttcctaa  54420
gcgtgaaaaa aatatcaaaa aaataataat aaataaaaaa attcgggggg gggggggcgcc  54480
agccactctt aggggtgaaa acgatcggat aatatccgat ccaatctgct ccgaatccat  54540
ccgaaataag gatatggtat gggtttttag aaatctggcg gatatggatg cggatgagga  54600
tatggtatct ccgaaatacg acggattatc cgacattttt gtcggattat ccgataggcc  54660
ctttaccgga taatccgaaa ttatgaacac atgtaaccac tctatctatt gcatataaca  54720
taagttggtc catccaatga cctaattcat caattaccct agatttctta ctatgtggtt  54780
ttcaccattt catgtcacac ttgcgtagct gtatttttat aaaatggaca tcatgtattt  54840
atgttgttta gcacttaagc acataattat tacaatgggt cgtttattga cattgtgtta  54900
tttttacttg cattgctaac tcaatgttgt attgattgca tacacacgta acatctgata  54960
aaatttaatc cgtttctgaa ccgattccgc accatttccg acatctgcat ccgtacacta  55020
tccacaccca ctccgaatcc gcttaaaaat atggtttagg atatggtatg accactatcc  55080
gtccgaatcc gctttatttt cacccctagc cactctggcg cgcttcccct gccacctcag  55140
catcgtccca ccacgtcggc agaaggacgg cggctccagc cactctggcg ccacaaaaaa  55200
ggaccatttc tagcataagt ttttttaggg gtctatttac gaaataagtt tttaaaagga  55260
ccaaaatgtg aaaaatccag gttacagcag actgtgataa gcaatagcta tattgcctat  55320
atatacacgt atatgcattg ctaatccttc aattttgtcc aattctttta aattgtcttc  55380
acctgttgca acgcatgatt tttttctag tcttaacctt aactaatctt aataactaac  55440
taaaagattc gtatctttcc gatcgtcacc ttgtccatac gctaattttt cgtccgtccc  55500
ccctccccct caaaaaaaaa gggaaaaatc cattttacac cctcgaactc ttatgcttgt  55560
ctaaaataca cccccgaact ataaaaccgg gtataataca ccctcgagct atcaataccg  55620
gacagttcaa gggtgtatta tacctggttt tgtagtttgg gggtgtattt tagataagca  55680
taagagttca agggcgtaaa tggacttttc cccaaaaaaa atcccagtcg ttactttcca  55740
tcctgagaat cggagacagg gaaaactgaa gcatacacgc aaatagaatc aaagataggg  55800
aaaactaagc atatacacac aaatatatcc aaaaattccc atgcagctag atcgggtgcc  55860
accgttgttg ccaaaccacc acattgcaat gtaaatctaa gactaaagcc taaatcctat  55920
gctaagtcat caaattagac tcggttctac caatttggta atatatcaaa ttagacttga  55980
tttttactga tttgaggttc tcgaggtgtc acactatgaa acggaagttt ttcccgttgc  56040
aacgcacggg cactatgcaa tatcttaact aattaaaaga ttcatatttt tcctttcgtc  56100
acaccgatct ttcgtccgtc tgtaacatca cgtgcacctc ctctccaaat cccacatcat  56160
cataatccga cccaaaaaca aaatctcaat ctcaatccaa tcagaatcat cacaaaatca  56220
tccaaaatat caagagatga ttataggaga tggaggggtg agcaggagca acatcatcat  56280
cgcataaaaa ccccaaaatc aatcacaaca acgacatcat tatcacataa gaaaaacaat  56340
acaaacaaca tacacaatca acaacactgg cggatccagc cgaggggaca acggcgtggc  56400
agcgggcaga tcctctcggt cagatccgcc cacgggtgcc actgacgtcg ccgccgccac  56460
cggatccaag ggagaagctt cggacagagg gagagggggg tagaggaccg ctaaatccgc  56520
ccaccggaaa tgccgccgcc accacctccg tcggatttgc ccgagggagc gccgatgccg  56580
```

-continued

```
ccaccgccat cgcgggagaa gcttgggcac ggagggtgag gaggaggggg ggtagagaat  56640
cgccggatcc atccgctgga aaagcctccg ccggatccgc ctgccggaaa caccggtgtc  56700
gccgcctccg ccggattcgg tagcgggagc cgccgatgcc accaccgccg ccggatccgg  56760
tcggtgggag ccactgacac catcgccgcc gcctcctctg ctaccgacaa gggagagacg  56820
agaggggcgg gggcgagggc gggggacgag agggttagag ggagggaccg agtgggagag  56880
agagggacga gtgagaggag ggggacgagt gaataaggat gcgtgacctt atccactcgc  56940
gcggtcgcac cccggctctt tctctcgctc agctgttgcg cttgtggaga ggatgcgaga  57000
tttttttttg agtaaaatgc acgggcggtc cttaaacttg tagcggtctg tcatctaggt  57060
tcccaaactc tcaaaatgca tatccaggtc ctagaatttg tcaaagtgta tcatctagat  57120
cccaaaccga cacatcctct cttggatcct acatggcgct aatgtgactt gtcacatgga  57180
cgtgacacgt cttttttttt cttcttttct ttttcttttc cgttttcttc tcattcttct  57240
ttttttccat cttctgctcg ggtcacatag aaaggaaaag aaaggaaaat acaagagaag  57300
aaaaaaagaa aaaagaaaat ttttaaatgg gtctcattcg tcagtcaaaa ttatgccaca  57360
tcatgtccct gcgacatgcc acatcagcac cacgtagcat cctgaagggg ttgtggcgat  57420
ttgggaccta aatgacacac tatgacaagt tctaggactt ggatatgtat tttgagagtt  57480
taaggattta tatgacacac tactataagt ttaaggaccg cccatgccct ttactttttt  57540
tttttacacg gagagaatgc gaatttgttg gttagttgcg gctgagggtt tctcgcacgg  57600
agaaatttgc ggtgggagaa tttttttttcg aggttctttc tattgggaga agacgggatt  57660
atagggatta ttactggtgt ggtggcccct gttttctttc tttttcgagc ttctttccgt  57720
taaattcact tttctctctt caaggagcgt aggacatgac tgaatgcagc tgctgtaaat  57780
tagaaataaa aaagaaacat attctgtttt tcattttttt caataggtaa atataaagat  57840
ttttaagtaa tatttaaaaa tatatagtgc tgatcaacga cattgttaag tgagattttg  57900
ctgttactat cacttttttt tccattgggc tcacgtacgg cattaaaagt tttagttttg  57960
gttctctcct tttgagtttg ggcatatacc aatattgaga taggtatact aaagttcatt  58020
tggattttat tcgattcaac ttttttgggt tttgttcagt tctttttttac atgtttctca  58080
tctgaaatta ggaaattagg tttggtaaag tcttgaatag ataacgctgt tgacgtttga  58140
acatatattt atctatttat ttatttaaaa atatatgaat aatttttatt ttgttatgac  58200
ttttgtcggt gacatgggac cgggagtatc atgactagag gcttgggcag gagcgatcac  58260
ccacgtggcc tgatgtaaca tcctgaaaat tcccaacaat aaaaatcact aaaattttga  58320
actttttaaa acttttgcat catgctggtt gttatgattg ctattgcttg ccaaaccgta  58380
aatgatcaca aagaaagtaa agtaaggatc taaaatttaa gtaatagata aatttacgag  58440
aatataatat ttaattgcta accctacaaa taattacgca caagaaaaca aagccagaca  58500
aacggaaggt taattactaa tttaaattat ggattaatta ttaaatactt gaaccatgtg  58560
ttgcgtgcca tggcatctaa atacacatga aataatggtc atataattaa attaagcttt  58620
ataaaattat gtgaggtttt aattaagcaa ttagcttaat gttgtaccga gtcttaatat  58680
actatttata gaataaataa attcaaccta tccgtgtaaa atatattgct ataagttcat  58740
tcaatgtact attgtaataa taatggccac attaggatat tttaattaat tttggaaccc  58800
tcaaagcctc caaaattatc taggttaatt ttgaaattat acctcattta agtaatgcaa  58860
tagaaaaata tacataaaaa taaaatatgg gtaatattag aaattgagta aattttcatc  58920
```

-continued

```
taaattaaaa catatattgg gtaaacctcc tttatgtaaa aattaagatt tatagaatga  58980
aatttgtaca agggataaac taaaatcggg ttaaatagaa aatggcactg ttcattgcac  59040
tctaggtgct cgacgtggtc cctggcccta ttttccccct cagccgcgcg cgcctggctg  59100
cctcgcgccc cgcgccacgc cacccgcgtc gcgtcgccgc tgccgcgccg tcgccgtcgg  59160
ccgttccgcg ccgctcgtcc gtcgctccgc cgcctcgcgc cccgcgccgc gtcgtcatcg  59220
cgtcgccgtc gccatcaccg cgcctggccg cccctgaccc cgcgccgcgc cgcgccgtcc  59280
cgtagccgcg tgcgcgttcc atcgccgctg ccgcgccgcg cgccgtcacc gcgcgccgct  59340
cgtccgccgc gcatagcccc gcgccgccgc gccatcgtgt cgccgcgccg tcgcgtcgct  59400
ctcgagcccc gcatccctct cgagccccgc acgtcgcgtc ttgtcgccgt tgctgccgcg  59460
tcgtcgtcgc cgatgctgtc gcgtcgccgc tgccgcccgt cgcgtcgcct tgcgccccgt  59520
gccgccgctg ccgcgttgtc gctgtcacct tcgcgtcccg cctcgtgccg cgcgccaccg  59580
ctgccgcccc gtcatcgccc gctcgtcgcg cgcgccgccg ccgctgccgc gccgtcaccg  59640
tcgtgtcgcc gtcggcctcg cgccttgagc cgccgcgcgc ccgtcccctc gcgcctgcgc  59700
cccgccgcac ggccgtcccc tcgccgtcgc cctgcgccac tgccgcgccg cccgtcccat  59760
cgcgccgagc cccgtgccgc cgcgcgcgtc gcgtcgcccc gcctgtcacg ccgctcgccg  59820
cctcgagcca cacgcgtcgc gccgtcgcgt cgccattagg gccggccacc cctttccccg  59880
cgccctataa aaccccccgg ccaccccccct ttcaccccac accatcccca cccattcccc  59940
tcttcctctc ctccttcccc tcttcgtccc ctccaccgcg ccgcgccgcc gccttcgtgc  60000
cgccgcgccg tgcgccgtcg tcgcgccgcc ctcgcgccgc cgcaccgccg ccttcgtgcc  60060
gccgcgccgt gcgccgacgt cgtgccgccg tcgccgtcgc cgtcgtcgtg ccgccgtcgc  60120
cgtcgccgtc gtcggtaagc cgccgtccct tccctcgttc cgacgccgtc gccgcccggg  60180
tgggaaggag ccgagagaga gagggaggaa ggagccggga gtaggaagaa agaaaagaaa  60240
agagagagag agaaaagaaa agagaagaaa agagaaaaga gagaaaagaa aagaaaagag  60300
attagagaag ggagggaaga gtgggcccca cctgtcatta gccccatcca attcccctta  60360
gaaaaataat tctgtagaaa agaaaatcaa gatcttgacc ccacctgtca gtcactatag  60420
cgtgtggata aggttgtatt aaaaataaat gaattaggaa cagtactatt tcgcaactat  60480
tagaattaat tcaaatttga atctttacac tagcataact aattcatttt agctccgatt  60540
tgagtggaac ttgaacctaa attcatctaa attcataagc tttccaatgg tatataattt  60600
actattaaat aaaatatatt tataattatt aagtaattaa tatcatatga ttaggttatg  60660
gtcaacttaa aaatatgcta ataaataaaa ttagtattgt ggatgtaata atatttgtct  60720
ctaacatgtc ttgccactgt aacaaccaca caaactaata ttaagtgatg tctgaaatga  60780
atgaatgaat aggaaaatac tagtacttgt ttaatattcg atagccatat aattaaaccc  60840
atggcttata ggttatttaa atcaaatgta gccttgtgat tatgcaacta aaatataaac  60900
acatatagat gaatctttag cttgattagg aggaataata acagagctag tgtgactagt  60960
tatgatatag cttgttgtcg gttgcctata tttagtaaat ggttcaatgt taatacactg  61020
atgcacacac ataccctttt tgataaccta ctagttgcat atattaaact tggtaataaa  61080
tgaagaacca atatattagc taaatactgg tgctagttat aaatcttgac cacacataat  61140
tttagttcaa accacacctg aggattgttc gttataaagt tataaagtta taaagttata  61200
caaaagataa tatgtaacta taatagtatt aaaccacaaa tctaaaatac agggcgcata  61260
attgtcaacc ttttatgcaa acggataata tccatatata tacatcatgt ggataattcg  61320
```

-continued

```
aataatagct ccattggtaa aataataatg taggcgaatc atggtgatga gatggtttat  61380
cctaaacctc cccatcgaca tagccatgct atagggacct gaccatttta ccttcataac  61440
agatctcttc cataagccaa tagctagact aaaccacaga ttagcaaatg tgtacatcat  61500
atattgtgct agttagtacc aatagaacca tcaggacaat ataaatacta aggaatctta  61560
gctcttagct tgattagaat ccaatagcaa acacgagtag tatgagcagc cttaggttcg  61620
acctcaataa ttatattttg cttgtgcata attgcttctt gttgaatatt ggtttttctc  61680
gcatattata gaaattgtat atcggttagt cgtgaggcaa cgtatgcagc tttcaggagg  61740
tgaaggttga tcaagattgt atcaagaata atgactattc taagcaggca agtcatcact  61800
attccttgaa catgttgatc ctaattgcga aattattttg tttacaaata aaattgcatg  61860
caatgatgaa catcctactt gtgattatgc catgccttga ttattgttta cccttaaaat  61920
ccttgtaacc atgattacgt atgagtccct agtcaattat gacaattgct tagagatgct  61980
attctagaat catgcatact catatttatc aaatgctata tgcttgggca attacctttg  62040
ggaaggtaat tgagatgcgg catgtggaga catgaacgcc acattgccat gatattaatg  62100
acatgatttg tgaaaggaga aataaaatta aacaactgtt ttcgactggg gcggacggag  62160
gatttgggtg gtatctggaa aaggctagta ccgtccccgg tcaattaagg accgagccat  62220
gaagttaagc atgaaacgac ccccgtacaa ccgcacttct cgtatgggta tagacctagc  62280
ggagtagata gctgagcgga ggcagtatcc atgcatagtg gtttcttgat gtgtgaggca  62340
ggggctctac ggtggggcag ccattggtag gaccgcaagg cgggtatcta cagtggtgtc  62400
gccatcggta ggactgccat gtgagaatct aaaacataat tataacttaa tgcatgtgtg  62460
agtcttccct tcccgggtgc gccagaactc ctctcactgc tagaaaccgt gtacgcctag  62520
agtgcatgag gatgaaaagt tcatggagcg ggtactgcca atgcgaggtt atcgaaaagc  62580
tctgccgtga cgcatctcat gtgttgggac gaggctcatg tgttgggcag tcgcggagtg  62640
cgggtaaagt gtacatccac tgcagtgtga gtaaaccaaa tctattcgaa tagccgtgct  62700
cgcggttatt gagcaccggg acatgtatta cacttggcta gactctaaat tcttaacttg  62760
tggggaatgg gatattgcat gatgaatttt atgctgatgg agccacatcc cgagaggagg  62820
gaaggtggac atcctcagaa aaccatgacg attcaatggc gggaagctat ccttgggatc  62880
acaatggatg gtggacagaa ccgtcgttgt ttaaagtgaa cactggtact aaaatttgat  62940
cgatctatgc taggttttag gcttgtgaaa agaattgtaa aattagcttt atgcaaaagg  63000
acctgaagcc attccttgaa ataccctcta tcatatgcat tgttattatg gtggcttgct  63060
gagtacggtt ggtactcacc cttgctattt atatatcttt taggagagtg ttgaagagaa  63120
gcccttgtcg gtacgcttgc gtatcccaca agatgatcgg agtgcggtct tgttctaggt  63180
ctcgtttccc cagtcgactg cctgtggcat gttaaccggg cccttatatt attttgtctt  63240
tcgctgttgt tctctgatag ttgttggcct acctggccct aatgtaagta tttaactctt  63300
ttagcctaaa ttcattcgtg atatgttgtg atccaactat gtatgtgtgt accaactact  63360
gatccaggga ttggtacgga taaacacaga agatttccga tttccaaaat cgggggtcta  63420
cacctgaccc cctcaggggg ggggggtcgg gcccgagggt gatgtggccg ccccccctctt  63480
tgtctccccg aggggtcgga ccgctcccgt ttctgccccg agggctgagg cgccccgacc  63540
ccttgtgggt tttgcgccgc gtgtatgggt taggtgagca caacggggct cacctaaccg  63600
tatttattgt ggtttggacg agcgcgtcac gccgcatgta gcgcagtgca gcgcgctcgt  63660
```

-continued

```
ttatccggtc tgtgaccagt cacagaccgg tcagatcgtg ggttaggtgg caacaggcgg  63720
tctgacacac gcctcgcccc atcccgtcag gataagagcc tccaggcact tgtccctagc  63780
ccggagccag catgctaact cctggagatg acacgttggt cccggtcaga tatatgccag  63840
gcttcatccc aaccattaca agcaagatat tgtatgaaga agggcgaaca tgcagattgc  63900
tggactgaca cgtggtggac aagaatgacc gatttgtgac cggtctgaca ctggtcatgt  63960
cgtcggcaga caaccatgtt cccacgttgc acctgctttc ggcggagtgg aggtaggtat  64020
gggccatccc atcagaaggt cgttcggaca gcagccattg caagtctccg cccatttatg  64080
aagagatgac agggtgatcc cctggagaga aaaaaaggag gaccttgccc acttaggagg  64140
tgaggacgac tggaagggga gaggatctgg agagtagatc ccacgagagg aaaaaaggga  64200
gaagagggtt tctagagtaa gagctctctg actctccagc tctttgtagc ttcttcgtac  64260
acagatccac cagaaaatag gagtagggta ttacgcttct cagcggcccg aacctgtata  64320
catcgcccgt gtcttgtgct tttttcattc tcgcgaactt tccacagact aggagcttag  64380
aatctcgccc agggcccccg gccgaaccgg caaagggggg cctgcgcggt ctcccggtga  64440
ggagccccac gctccgtcaa ctttggctta taattaaaaa tactctaagg atattttttt  64500
atattttatt ttcttatgtc tatatgaaat tttaaataag atagatggtt aaacatatat  64560
tggaaaaaca tatatccaaa agtccactat cacaagcgta gcatagatac gattacaata  64620
cgtttccgcg aagactgttt atacctactc tattccctgt tccttgtgcg gttgtgccat  64680
ttggggctgt tttttcatct cggattaact cgcgtggaaa ccgcgagacg aatgttttga  64740
gcctaattaa tccgtcatta gcatatatgg gttattatag cacttatggc taatcatggc  64800
ctaattagac ttaaaagatt cgtctcatga tttacatgca aactatgcaa ttagtttttc  64860
tttttatcta tatttaatgc ttcatatatg tgtccaaaga tttgatgcga tgttctggga  64920
aaatcttttt ttaactaaac atgcccaagg tgtttctcca attaagttga cccaaaatca  64980
ttcggcgtca cctttgtctt tcactttcct tccactacaa ggtgatgaca ctgacaaaag  65040
gtccaaaagc tacaggatct gatttttgtt catccatctg tgatgtgtcg gcaagccatc  65100
catggagttc atccactcaa ctcctctctc tcagagagag agagagagag agagacagac  65160
agacacatgc atgatagatt gtgctagtac ggtagtaaca ttttattgcc tccttttcta  65220
aaattctagg ttgtttggaa aacaaaaatt ctagattgtt caataaatta ataatattag  65280
gtatttattt taagtcactt taggtgttaa tttttgaatt ttaaactgct taaactctct  65340
ttcgacgcat ctgagagcag gtacaatagc agactataag ccagctataa atatatttta  65400
agtagataaa agaggaaaaa taagagtagc gggctataga tttgtagaca gctgcagcgc  65460
gagctccaag atacatatgt gtatgacatg tgagaccaaa cattaattat gtagtatatg  65520
tttatatgta tctattgtat gaattggcta ttaaattgac tatgggtgtg ttcggaggtg  65580
ggtgttggga accatctccc aagcacggaa aacggagcgg tccattatgg cgtgattaat  65640
taagtattag ctatttttta aaaaaataaa tcaatatgat ttttttaaac aacttttgta  65700
tagaaacttt ttgcaaaaac tcaccgttta gtagtttgaa aagcgtgcgc gcggaatatg  65760
agggagaggg gttgggaacc tcctcatccg aacgcagcct atacatgatt tggagccaat  65820
agttggctat aatattaaac ttgctctgag tggctcttga atcatcgaag tgatagaaat  65880
catatgcaga aatgtttata tttgtgatgt aaaatttgaa tctaaaatta tttatatttt  65940
gaaatggagg aagtactacc taaaacaagt atgagaaaga gacatgaaaa acacaaaatc  66000
tagacttaaa aataattgga attactagca ggaggtcgaa gtcaatcaag acggcgaaga  66060
```

-continued

```
aaagcacagg ggacagcaga cacgttaaca cgtaagtaaa caaacaagtg gttaattaat  66120
tagggggccc tcaagtctcc cctaaagcca ctaaacatga caggtttgtg taccatggaa  66180
aaaagggtga agcaaaactt tattctctct ctcattagat taccagttgg aaagcaatcc  66240
tgggacctct agctaatctc attattgtag aacaacgttt tcttagagag agagagagag  66300
agaaataagt caataaaaat tactactaat ccacttgaac cagttctgtc ggtgtcggat  66360
gatttaccac atttgacgaa acggactatt tattcgacgt ttcgaaaaac acactttttt  66420
agaaaaaaaa aactttcctc tattagccac tcgttttagt tatataccta tccgagtatc  66480
tgttaagttt atttatcaaa atatttaatt tatctctata attaaatata caatccgtaa  66540
aaacaatcac gcagtaattc gtttcaaact gagcctcagc tagaaaatca aaatggaaat  66600
gaataacaat agcaacagta gagttagttt ttcggcttat catccgcaac ccaaatgcga  66660
attttaaact tagccttaga gttaattttt aaggcttgtt taccatactt cattttccca  66720
gcattagttt cttttgtcac taaaaattgt ttttttaagt tgtttcgttc attttctcac  66780
ggtttatcag cagtagagcg aagccattct tggagcctgt ttggcacagc tctagctcca  66840
gctctagctc cactctttct ggagctggag ctcagcccaa cagttttagg tgcaccaaaa  66900
ttaggagtgt agttgggtgg aactctctca caaaaaattg tggagctgga tttagacagc  66960
tccacaactt cactccaaac ccaactcctg aagttaaatt gataagttga agctctatct  67020
atcaagccct ttttcttgat catgcttcta cctactccat ttttgtttct tggccctcac  67080
aggaattgga aaggaaaggc gtatatgcat caatgcatgc atgcgcacat caacctcgtc  67140
catcaaccat cataatcatc atcatctcgc cagctgacga aaatgacctg catccatcca  67200
tcacggacaa tccaagcgaa caccgctacc aacatcacag ccaacctgtt tatcactagc  67260
tcttgatacc actcctacat aaacactacg cgcaggttaa ttaattaagc gtgattactg  67320
aagtaacatc taatcacgtc ctggttagcc tttaataaga caacagttag agcaggtaca  67380
atagcagcag gatataagcc agctataaaa aaagagagaa aagagcaacg ggctacagat  67440
ctatagccag ctgtagcatg gacttcaaga cacaacgtgt gtataacagg tgggaccaga  67500
taataatagt gtagtatagt aagtaactat tatatatatt gactatagat gatttggagc  67560
tattagtgtg ctatagtatt aaacttgctc atagagcagg tacaatagta ggatattagc  67620
cagctataaa catattataa tgagataaac attgatagag aagagcagcg ggctacagat  67680
ctgtagccag ctacaacacg gactccaaga cacaacgagt gtatgacaga tgggaccaga  67740
tattagtagt atagtaagca actattatat aaattaacta ttacattggc tatagatgat  67800
ttggagttag tagtgggcta tactattaaa ctttttctct tagcaaaaat caagcgccta  67860
atcacattag aggagtagct ttgagacaaa ccaattagcg gcgaatcaag cgatctgcgt  67920
ggtcgtacag tgatgggccg ggccgggccc acagcccgac agtgacaggg ggcctgacgc  67980
atgtcagcct cagccctgga cgggagctag ccgttgtgtc cccgggggag gggagggggg  68040
cattcccatc atttcgcccc tcctccgggc ccacatctca gtgggggtaa aggtgtaaat  68100
tactgcgacc gcgagtccag cgagcctaga tttggacctt gtgtccgttt gactgaaccg  68160
gagctactcc ccaatacggg gggattgcgt tgtgtgcatg ccatgtgggc ccgagcgccc  68220
tttgttcgtg gctttgggtt ggaaaggtga ccgtgtgagc tgtgcggtgt tgtactacgt  68280
attagtataa atcatttttg ggtactactc cctccgtcca aagcttattt ataatttgtt  68340
gtactccaac cgtccgtctt atttaaaaaa aatataaaaa aaattaaaaa aataagtcac  68400
```

-continued

```
acataaaata ttaatcatgt tttatcatct aacaataaaa aatactaatt ataaaaaaat  68460
ttcatataaa acggacagtc aaacattgtc acgaaaatct aatgtttgcc ttttttttta  68520
agaccaaggg agtatctacg aacaaagata atacatgtta taatcatgaa gcccatgatg  68580
tgattagccc ggccgtttga ctaacctcac gagctacgtg gctgacaagt ttaacttgtt  68640
aactccatca tttcggatac ttagagcatg tacaatagca gactattagc cagctataaa  68700
catattttaa tgggataaaa gatgagagag aagagcagcg ggctacagat ttatagccag  68760
ctgcagcacg gactccaaga cgcaatatgt gtatgacagg taagaccata tgttaatagt  68820
atagtaagca actattttat aaactggcta ttagatcggc tatagataaa ttggagctag  68880
tagtggacta tactattcaa cttgctctta tatgatataa atattgatat aactatatga  68940
ttttgttaat gacatgtttg tttatggatg gactatgtgg ggtcggtcgc ctccgtagct  69000
gaccaaaata caaacttaaa acccctatct ataaaaatct aacttttgtt tataaatata  69060
gatataaaag ttcataatta gagcctcatc ttttaaacga aaagagtact atgaaaacaa  69120
ctcgtaatac aaagactaat tacgacgaaa agaaaatagt actgacaaga ggaaagcagt  69180
gaacttgcat actccctccg taaaaaaaac caacctagac acggatataa cactatatat  69240
ctagattcgt tcgttgtaat gaagtgtcac ctccgtatct aggttggttt tttcgtacga  69300
aagaagtatg agtaaatcta aagctatgta tacccttcgt caaaaaaaaa aagtaaacct  69360
tgtactggtg cgtgtcacat cctaatataa tattgttttt tatggagggt gtacagttga  69420
aaaaaattga tgtgttttaa ggatgaaaaa tattggtaat gttggctatg taactctaga  69480
aaaaaaaatg cagtaataat aaaatgctaa tttgctggag tactagatta tagacaatcc  69540
agtccaggac acgacaccct ccctactctc tccacttcca ctctcaccgg ccaccgcgcg  69600
ctctctctct ctctctcccc cttctcccgc aagattcttc ccccaaatcc cacccgatcc  69660
accgccgccg cccgctcgcc ggagtcccat cgctgccacc gccgccggag ccgcggcccg  69720
acgcccgccg ggcctgcttg ctgtgtgtgt gaggaggtgg agttgctcgc gctcgttccc  69780
gcggccacct ccgcctgctg ctgcttctgc ttccgctggc attgcgggga ggtcgtgtgc  69840
cgggggacgt gggggctcgt gttggagcgc ggctgccggt gaggtggggg gtgcggcgcg  69900
gcgcggctcg cgctcgtgcg ccggtggcgc gggcgcgggg ggaagcgtac gggggagggg  69960
gagtgtggcg gcggcggcgc gcggggtagg gacgggcgcc gccaccacca ccggctcgtt  70020
cgctggcagg cgctacgcgt ccagatccgt acgccggtat gcttcgtctc gccgcaactc  70080
tctccatttg attagtatcc cctcgccgaa acgaggcctg tgaggcgccc gctttctggc  70140
tggcttccct gtactcgctg cttgctcctg cctgttgggt taacccgttt ccatcgaatt  70200
tgggtaagcg aaacatcgcc tcatatgggc atttggggtt ctggcagcct taggctcgcc  70260
atccgtcgcc gagcttccaa gtgaccggcg cttgttggta tatttgcttg cttgttcctg  70320
tttggtggct gcgctaaatc ttttgtgctg cattgaattt atgccaccca tatacagcaa  70380
attactgagc tgaaataatt cggctaatta ggtccagcaa tatgacatct cgtggattga  70440
atgctaagct gacattgtat cactgatgct ggcttatata taggttgttg agaagtgaag  70500
atgtcgacag gtgaaaccct gcgtgcagag ctatcatcca ggacgccgcc tttcggtttg  70560
aggctatgga ttgtgattgg aatcagtatt tgggtggtga tcttctttat actaggtttc  70620
atgtgcctct ggtccatata ccgaaggaag ccgaagaagt cctttgataa gattccagta  70680
tctcaaatcc cggatgtttc caaggagatt gcagtagatg aagttcgtga gcatgctgtt  70740
gtcgaaaact tccgtgtgca agaaagccac gcgatatcgg tgcaggagaa acattacgag  70800
```

-continued

```
aaagattcag ggaaaatgct ggcacacttg gttaggagta aatcgagtga tgccgataat  70860
ttgagccaat gcagctcggt gtaccaatgt gatagggctg gtagctcgta ttctggtgat  70920
gaaggcagct cgggcaatgc taggaggcac ttttctcaat atgcaactgt ctcagcatcc  70980
cctctggttg gtctcccaga attctctcat ctgggctggg gtcattggtt tactctgaga  71040
gatttggagc atgcaacaaa tcggttttcc aaggagaatg tcattggaga gggtggatat  71100
ggggtagttt accgtggtcg actcataaat ggaactgacg tcgcaataaa gaagcttctt  71160
aataatatgt aagagatcct gaaatctatt ctgcgtttta cagaacttgt gactccttct  71220
gatgccatca tattaatttt cttttgatat ggtgctgcag gggccaggca gaaaaggagt  71280
tcagggttga agttgaggct attggccacg tcaggcataa gaatcttgtc cgccttctag  71340
gatattgtgt tgagggaatc cacaggtaaa gctatttatc aatcaccttt gctgatggat  71400
ggctagcttt tgtttctact ggcacattat ttacttgcat agggatgtag gattgctctt  71460
ggtctatgtc cacctactca ccagattatc tcaagggata ggttattcct gactgcactc  71520
cttatgctat cgattttttc ccttccaaat ctgatggtgg gattcagcat gcccagtgac  71580
agattatgct cagtccacag aaaccttctt tggaccacca ttcttttacc atgaaaatgt  71640
ggccatagct ccgaaagcta ggattcacta gaagcgcaca actgcttatt ggtttgttag  71700
ttggctataa caaggtctta ctgaaatgta cttccatagt tcattacttt gtgaatgcct  71760
gttcttgttc ttcacgtttc ttctcatgca tgttcaattc taaatttgta ttcatgatat  71820
gtccaagcta ctgtattctc caaagaaaat cagaagtcca ttcacctatg tattttccag  71880
ttttccgcca ttttggatac tgctctagaa acaagttaat aatatagata tttatatggt  71940
ttggccagtg ctgcttaagt gaccatcgag atagaaattg cttaagaaat atactaagat  72000
gttgagtgtc aggtgttttc ggataatctt gttaccaaca aataggtcct atgaatataa  72060
tggtgtctgc ttcacgtaat tcaaaatcca cactcagcca aaataatctg caatagggtg  72120
ttgaaaatat gattatgttt ctcccttgtt ttcatcatga ctacagaaat gaacaatgtt  72180
gctacatctt gtaataattt gtggttttca attgaacaaa acatccatca aatgatatct  72240
acagcaatat attttgcact tctgagcaca caataggttt gagtgtattc gagtcatggt  72300
cattgattta agctttttat ttcactacat aaccattgat ttgagtgtat ctaaggagtt  72360
ctgtttccac aagtacttta tgttaatggt gtctccttat gctttggcca tccaaactca  72420
ttactgttgt ttaatatttt tagtggttag tggtgtccaa atctttcttt gtgtacatca  72480
tactatgttt ttgtagtcta ttaaacttcc atcctatcat ctgacttgtt atattccagg  72540
atgcttgtat acgaatatgt gaataacggg aacttagaac agtggcttca tggtgccatg  72600
cgccaacatg gtgttcttac ctgggaagcc cgaatgaaag ttgttcttgg aattgctaaa  72660
gcgtaagaaa caaaccatcg tccccgtcaa aaagaaaaga attgttcttc actttagctc  72720
ttttatatgt atatgtttag ttgcataacc cattttccat aactgaattg gtatacaggc  72780
ttgcttattt acatgaagca atagagccaa aagttgtaca ccgggatatc aaatcaagca  72840
acatactaat cgatgaagaa ttcaatggca aactttctga ttttggcttg gctaagatgc  72900
tgggtgcagg gaagagccat atcacaactc gagttatggg aacttttggg tatgttgata  72960
ttttttgga gttagtatta atctttccta tgcttagctt ttactgttgg aatgtgcagt  73020
acttcgctta ttcatacagt ataaaatttt acatgctgcg aactttgtcc ttcgtatatt  73080
ataacaggta gctttctcat tgctatcatt gattcatttc aggtatgtgg cccctgagta  73140
```

-continued

```
tgccaacaca ggtctgttaa acgagaagag tgatgtctac agttttggtg tgctattact  73200
ggaagcagtg actggtagag atccagttga ttatggccgg cctgctaatg aggtgagcat  73260
atatcctaca atctcatgcg tattatgtat gttacaaaag tccgtactat tggaaattat  73320
tttacggcaa aataacgtct atactaggag agacgaattt gcttcaggtg tatggctgtc  73380
tggcagttgt ctactgtcta gttacccttg tctcactttt acagtctatt gttttatttt  73440
tcaggagctg actagctgta taccttgtca tatataacaa cactgtaacg tggatgcctt  73500
gcaggtgcat ctagtggagt ggctcaaaat gatggttggc acaagaagag ctgaagaggt  73560
agttgaccct gacatggagg tcaaaccgac cattcgggct cttaagcgtg ctctcctagt  73620
ggcactgagg tgcgtcgacc cagactctga gaaaagacct actatgggtc atgttgttcg  73680
gatgctcgag gcagaagatg tcccatcccg tgaggtggta acgctttctc ctttcctgca  73740
ataacattca tcatattata tcattgcaat aaatctgaag cttttgctgt aatcctactg  73800
aaggaccgga ggagccggag gggcaacact gccaatgcag ataccgagtc caagacaagc  73860
tcaagcgaat tcgagataag tggcgataga agggactcag ggccatcagc aaggtttcaa  73920
ctctaagaag acggtgatca tagtcaagaa caatggcttc aaaactctat gcagtaacat  73980
ggtggttggc agagaaaaag gggtatttct ggagggcatt gcattttgta ttgtaggtct  74040
gcatggcggt agagactgga gagagcacag tgtctgatga tggatacccg gagacctgta  74100
attcccattc agtattctgt ttgttagtca agcagcttgt acagatcgtt gtctgttcca  74160
ttttttcatt cttctggttt ttttgtttag gaggctcttg gattaccagt acgaaccgct  74220
gtctcttttc tagaatcacc aacatggaac ctatcaatat ttactactag tactacgact  74280
tgctttcttc ttgctgagat ctatcatgta ctgtacataa ctgacgtgtt cagctgcact  74340
tggacaagta gatgctcgtt ctgtatgtcg aatttacttg atgaggtcga gcattaagta  74400
ccatggctgc agccggcttc tgtttagttg tgctgacatg cggcggcgac ctcacgctgt  74460
gtggcccatt cttgatcttg ggccgaaact gtagcaacgg gcgtacggcc catctatatc  74520
gggattgttc ggcccgttgt agatgggccg gatcgggatt gcgacttacg tgcgacccat  74580
ttcggttggg ccggtggtcc gctacttcat ctagcagtgg tcggcggcag ggttcacaat  74640
tccaatagaa tccaaacatt attggattga gttaaaaaca caaaccaatc ggctttttgt  74700
caggttcaga aaattttaaa ctgaatttta attttttgac aaaaatctat ttagatttcg  74760
tctgtttttt taggtttgtc aacggattca gcgaaatccg atgatatcgc tcgtgagtgg  74820
atttttgatc cggtatcgag attgtgaacc cttgtcgcgc attgcctgac aaagacaacc  74880
agtgaagcgc cgtgcgcgcc gcgtgcgcgc cgcgtgacgc gaagatgcgc aggaaggaac  74940
aagctggcaa gcggcgcgcc catgacggcg gcggcgacga cgacccgcgc gcgtgcgtgc  75000
gtcaacgcac gcgaccggcc gagatccgtc agtggccgcg gctatatata atacatcgtc  75060
gcctcacacc ccccacacac cgagtcatcg ctcgccggag ttagagttcg tagcggcgaa  75120
ggatatagcc atatattata gatggcgatt ggtgttggtg gctgctgcgc cgtgctgctc  75180
gcggcggcgc tgctcttctc ctctccggcc accacatgta agcacgccca tcttcttctt  75240
cttcttcttt ttttctttct tttttttttt tttttggaaa tgagccgcag ctgacaaaaa  75300
gatcactcac acatggatac actgtcgtga cactaaccaa tgcctaagcc attttgtttt  75360
cttgttttgg atttttcttt ttatgtgtat cacttttgct tgttgctctt gcagatgctt  75420
atgattccct ggatccaaac ggcaacatca cgataaaatg ggatgtgatg caatggactc  75480
ctgatggcta tgctgtaagt agcggtggca gtacaccaac atctctacct ttattttcgt  75540
```

-continued

```
ctcaacctgt acatttacac tatcttgttc tactacctct aataaaaaaa tatatttgat  75600
gttttaaaat ctattaagtt ctagagatta ggaaagctac acatggtttt atgttttgat  75660
actattaagt agtatatttt ataagttata ttgaaggctg gggtttcaaa agtttgacta  75720
cactagatct tattcaaagc gtctaatgat tactgaacgg aggaagtatg aacttataga  75780
cttgaagtta aacagcatag ccacatctct tcatgtatac ttcatccgtt tcatattata  75840
agattttcta gcattatcca tattcatata tgtgcgtcta gattcattaa tatctatatg  75900
aattgggcaa tgctataaaa tcttataacc tgagaaacgg agggagtatg tcgcaaacaa  75960
caacaacaat aacaacgagc aaaatctgta tcgaatccgg tttccctctt gtaactgtat  76020
caaagatctg tcctctgaaa cgtcccctgt tcatcaggcc gttgtcacac tgtccaacta  76080
ccagcaattc cggcacatcc agccaccggg gtggcagctg gggtggacat ggcagcagaa  76140
ggaggtgatc tggtccatgt acggcgcgca ggccatcgag cagggcgact gctccatgtc  76200
caaggagggc agcaatgtcc cccacagctg caagaagcat cccaccgtcg tcgacctcct  76260
cccgggcacc ccaatcgacc tgcagatcgc caactgctgc aaggctggat cactgagcgc  76320
attcagccag gacccggcaa attctgccgc gtcgtttcag atc                   76363
```

<210> SEQ ID NO 28
<211> LENGTH: 53905
<212> TYPE: DNA
<213> ORGANISM: Orza sativa Asominori

<400> SEQUENCE: 28

```
gatcagtgag tgagagtgat gtgctattga ttttcgtcta ggattttgct gtgctcttct     60
tcttcttctc ctctctacca agaaagatcg atggaggaga atttgtagga cgcgtttctc    120
acgaattact tagctgttaa tgatcagctt gatgtgtacg atatgatggt gcagagtgaa    180
agttgtgttg ttcactggtg gatcatggga tgggaatatg ggattgttgt aagatgtaac    240
tcaagtgttt tcttttttgg gattactttt ggtaataaga gcttgggtga tcgaaaacta    300
cagatggttt ttcttttaag ttgtatgatc tctgtagagt ttttgagtaa tttgtagttt    360
tgtaccctat caaagatcat ctctagctgc ctctgagctc tccaactcta tatgtccatc    420
tctagtatat atgtcccata tttctgactg aaaattttca agtcggttgg ttccctccgc    480
ctggatattc tttcagctaa ttagattttt tttaaatgat aaatttgcta aaagcttgtt    540
caaattcagc taagatctat tcaaacttca atttctctat cgaaattccc ggaaatttca    600
attcaatcat tccccaatac atgccgattt ccgtaatatt gaaccatgac atgtaaacaa    660
cgaaggaatc aagggcatat ttagtttcat ctcacatcga atatacggac acacatttga    720
agtattaaat gcactctaat aacaaaacaa attacagatt ccgccagaaa actacgagac    780
gaatctatta agcctaatta atacatcatt agcaaatgtt tactatagca ccacattgtc    840
aactcatgac gcaattaggc ttaaaagatt cgtctcgcag tttcctgacg aaccgtgtaa    900
ttattatttt ttctacgttt aatactttat gtatgtgccc aaatattcaa tgtgacaacg    960
tgaaaatttt tatttggaac taaataggcc ctaatattct ttcaagatat tagaatagtt   1020
atccctctcc acctccctgc acaaacagtg aacttctttc tccttgggca caggagtagt   1080
agcagctccc ggaaacagaa agcaatcaag caaagtcctg aacctgaagc atcctgaaac   1140
cagcagacgg cagaaaccag tgggcgcagg cgatagcagt tttcgtggt ccggcgtaca   1200
gccaaaatac tggccatcgg gtgcctacat agaatgagtc cactggacgc agctaccacc   1260
```

-continued

```
gtgtgtgcta cactgaccgc cgctgctcgt cgaccagttg tacggggctg acttattctg   1320

aatttctaat ggtttatttg gggtttaga acactgaggg gtgctttaga tccaaagatg   1380

tgaagtttgg gcgtgtcaca tcgggtatta tatatagtgt cgcacagggt gtttgggcac   1440

taataaaaat actaattatt gatcctatac gataagctat ataatactcg atgtgacacg   1500

ccaaaacttt acatccctga atctaaacac ccttttaaat agagtatttg gtgtgaaata   1560

taattttgat ttgggaagaa ggtgagtgag atttggaaaa aaaaagcatt tcaattaaaa   1620

aatttgccag cagtaaataa agaaactact cggttttgta attaaagtga ggttttggca   1680

cttctttgcc ctaaactggc ctccatttta taaagtgaga accgtgcagc aaaagcctga   1740

aaaggcaaaa agaaagaaat tgtagaggtt tttcaggagg atacaactag gtgggtctct   1800

aactctctat gcagctgtgg tctgtggagc aaaacgatga aatggaagac gggacgttga   1860

cgagggtgaa gaaaacgagc gtttgaccag cgtcaaccat ggcgtgaaca gtagcaccac   1920

taacctgacc gagaggttga agaagatgca atcaacgggg tactatagtt cccacgaatt   1980

tcccagcaac aacgggttgg ttctcactac tcacgaattc cctgtggctc aacaactact   2040

agtacatcct tttgtccatt atgataaaag ttctatctta atttttattt acacgttttt   2100

caaactgttt tttaattttc tatataaaaa atacttaaaa tatcaaataa aatctatttt   2160

tggagtttta aaaaactcaa ttaatcatat atattattga cttattttat tttacgtgga   2220

ctaaaatatc ttcatcttca tttaggttat gttcttttct catcaagata catgatacat   2280

tagcatgttt ttcaaactgt tttttaattt tgtatataaa cttactctaa aatatcaaat   2340

aaaatttact tttagggttt ataaaagtaa aactcaatta atcattacta acttgtttca   2400

ttttacgtgg actaaaatat cttcatcttc atctaaggtg gtgtttggat ccaaggacta   2460

aattttaatc cctatcacat cggatatttg acactaatta gaagtattaa acatagatta   2520

atgatgaaac ccattccata accctggact aattcgcgag acgaatatat tgagcataat   2580

taatccatga ttagcctatg tgatgctgta gtaaacatgt actaattacg gattaattaa   2640

gcttaaaaaa tttatcttac gaattagctc tcatttatac aattaatttt attgttagtt   2700

tacgtttaat acttttaatt agtatacatc cgacgtaaca ctgatcgata caaacaccaa   2760

ctaaatcgaa aatcaccgaa tggctcgtca tcctcccaca tgagatgcca agatggaaca   2820

ccaacaatcc aacggctagg aagcgcccca tcccacccac cgcctaaccg ccttcctatg   2880

caagtgggtc ccaccccttc cttccttttt tttttctttt tacaaatccc cttccctttc   2940

ttggctagct agctagcttg gcccaacgcc acgagccgag ccgagcacat ccggagccaa   3000

gccgagctca gcgcctcagc tccccctcct cctcgtccca ttcccggttt cctcctccga   3060

tttcccccaa atccgcacgc ctctcccctc cgcctccatt tttcccgatt cccaattccc   3120

aaatccggat cagccgcagc cgcagcagca aaaaatttcg aaatccaaat ccaaacccat   3180

cccccccacg acgacgtcac ccacatcccc acccccgcga gacgagacga gacgactccc   3240

aaatctctct ctcctctctc ctatgcgcgc cgccgccgcc gccgcagcag cagcagctag   3300

gaggcggagc agcagcagca gcagcagctg agatgatcgt gcgcacctac ggccgcagat   3360

cccgctcctt ctccgacggg ggaggagggg agcgcggcgg cggcggtggg ttctcgtcgt   3420

cgcaagacgc gttcgaattc gacggggagg aggaggacga cctcgtcctg ctggggtcgt   3480

cgtcgcagtc gtcgcacccg cccgcgccgt cgcaggagtc gtcgtcgatg tgggacttcg   3540

acgaggaccc gccgccgccg ccccggcggc ggcgggggag gggtgggggt ggggactacg   3600

cggagcccgc cacggcggcg gcggcggcgg cggcggccac ctcgctcatg gaggcggagg   3660
```

-continued

```
agtacggcga gatgatggag agcgtggacg aggcgaactt cgcgctcgac gggctgcgcg   3720
ccaccgcgcc gaggcgggtg cgccgggcca gcttcctcgc gctgctcggg atctgcgcct   3780
ccgcgccgcg ccgccgcgtc ctccgggccc aggggtcggt acaccaaaga accctccttt   3840
tttttttctt acttgtctgc gctgtaagta aagaataaca attcgcgttc ttgctcttgc   3900
ttcgcgggca atcttggtga ggaatcttgt tagggttatg aaattgggca gccagttctt   3960
gtttcttctg cgtaatcttg gcggaaacag tgggattttg tacgattatg gctccgtaat   4020
cggcatttct gtgggaaatg aaccaccttt agggcatttg accttcgaac agcatgcttg   4080
gtgttgcaat ccgtagctat tgccttcatc ttaggcacaa gaacttgttc tgaattatga   4140
tttaccaact tgtgtttgtt ttcttgttct gagttttctt gcttggttag ggttagggtt   4200
atcaccgtgg tggtgcagaa ttagatgttc gctacttgtc ttaacctctg ccttgcccaa   4260
tttggtaccg agtgttacag ctgggtttag gaagtgtgat ctttgagcat ttctagcatg   4320
ttggtctctt tattttgcta atctcacatg gttgtagagg aaggaagcat agtgactgat   4380
gatgaatgcc tagatactag aaatacatct ttattaactg aattaggatt gcttgggtat   4440
ctatgtagat atgactgtag aatgttactg ctggaaatgc tatccaatat ccattgatct   4500
ctagcctaat atatctctcg aggccaagag atcagtcaat tttgaacttt caggagagtt   4560
tctatttggt acttaatctc ttttatttgt tacttttggt gcctggctct cttttcatga   4620
ttgctaagta gacaggtaaa gttctaccta aaattattct taaaagttca aaatcgcttt   4680
agattaagga gtgccagcca gagccttagg cagagtctta taaaccaaaa gcacaatgct   4740
acaatgttca caaaactttt gtggaatttc cacttgagct gtataaacat cgcaatctac   4800
tgtgaataaa agaagcactt gatggaagtt catgttagca aatgacatgt tttctgtgag   4860
gaggttgatt gcttgaactg ttatggactc ttgcaacttt ttattttact tcgtacccat   4920
ttatgctaat gtgcacaaat aaaattgctg agagtaaaaa tgtacaactt gttacgcacc   4980
agcacacttc ctatttgtat ccattttcct gttgaatttc aaatgtattc aattgctgaa   5040
attgttccat tcaacaaaca catattccgt taatgaaatt attatacatt gcgttttgtt   5100
ttcttactca caagtgtcct cttttcttat atcctataga ttggtgcaac aaattattga   5160
tgcaattttg gttttgaaca ttgatgatcc tccctgcact attggtgcag ctgctcttct   5220
attcgttttg gcaagtgatg tgagtacctc tcaatcccat ccttgtgctt ctgtgcatgc   5280
ttcattctat tttttacgca tatcgattgt tttcttttat ataacagccc ataaaaataa   5340
tcacatcatg gcaaagttat ttatttctcc agtacagtta tataagtatt caccactttt   5400
ccatgaatat cttggcatgt gattacaaag aagattattt aagaaagtcc atgcttttat   5460
ttcatcattt tgtttgaagt tgaactttaa tttatggtgt aaatttcagt taatattgct   5520
agcagctcgt attctttaat ggcataactt cacttgtgct tattctccaa tatctccctt   5580
cttgttgttc aggttcaaga aaatcatttg ttggattcag aatcttgtgt ccattttctt   5640
cttaaattat taaatcctcc agtgaatctt gttgattcca aagcaccatc gataggttcc   5700
aaacttcttg gaatcagtaa agttcaaatg cttaatggat caaataagga ttctgactgc   5760
atttcagagg aaatcctttc aaaagttgaa gagattctct taagctgtca agagatcaag   5820
tcgctcgaca aagatgacaa gaaaacaaca aggccagaac tgtgtccaaa gtggcttgct   5880
ttgttgacaa tggaaaaggc atgcttgtct gctgtttcag tggagggtaa gttttaatca   5940
aatttcttgg tcatgatttc cctttatgac cattataatt atttttatga gccaaataag   6000
```

-continued

```
cagttgccat aagttacata gcacctgttt acaatattca tgggtggttt gcttagccct   6060
ttgcttcacc tgcctttgat tgatgacttc catccgtgtt gcacaactga attggagtaa   6120
ttgactgcac tagaagcacc tatggccatt gtcatactag gaaggttttc ccttatcaaa   6180
tatttgattg ttacagagac ttctgacact gtgtccagag tcggaggaaa ttttaaagag   6240
acattaaggg agttgggcgg tcttgatagt atttttgacg ttatgatgga ttgccattca   6300
acattggagg tgagatctcg ctaacatcgc atattttaca cttcctttgt tcaactctaa   6360
aggatggtgc aagttttgtt cctttttgcc attttagctt taatgtgctt gaagccacat   6420
gaaagcaatg cttgtccaga tacatagcca aaggttgtta tattttggga catggaaaat   6480
gcttgaggta gtaactattt tcatcaggac atggaaaatt ggctgcatca caaattatgt   6540
tgtttcatgt tgcaaaatag ttttttaata ctttttttatt ctgcatgtgg tgttagtgtc   6600
ttacagtgat tcctctgatg attatatccc ccacgataat aatacttgac atatctacac   6660
caagtggaca ttattcattt ggatgttact tttccagcta tacttgctgt tcttgcataa   6720
actttggagt aaattgcgta tccctttaag agataaactg cttggtgctc ctatctgtgt   6780
actttttatg cccccaacta ataatgcaat catattacgc tgataaactg aataaataaa   6840
ttaacaatat acttctggtg gaaaccttgt gtatcagaat ctcataaagg atacctcaac   6900
ttcagctttg gacctaaatg aaggaacatc tttgcaaagt gccgctctcc tcttgaaatg   6960
tttgaaaata ttggaaaatg ccacatttct aagcgatgat aacaaggtaa tgttccttat   7020
atattctgtt tcagtttagt acccattttc ttcttctgta ccatcttctc ccctcatttg   7080
ttctgtgcaa aatgtgcaaa cagtgtgact ttgtatttct gcttaacatt tttctttttt   7140
tcctgaaaag cagtataaac tcttacactc attttgcttc ttgcagaccc atttgcttaa   7200
tatgagtaga aaattgtacc cgaaacgctc ctcgctttct tttgttggtg tcattatcag   7260
tattattgag ttattatcag gtatttttct taataataca atatgtccgc taacacaata   7320
aaatgtttta aacatccagt atgttaaagt tgcagtctga cgcctatttt gttttgctgc   7380
agctctttca atactgcaga attcttctgt tgtttccagc tctacatatc cgaaatcgtc   7440
taaagtctct caacagagtt gctctggtaa taacaaacac caaatttgtt tgatcaactc   7500
gttggctttt ctgtgcactg tttcaatata gtttggtcgc cattcaagtc tcactacaga   7560
tgttgaactt gacctgacac ggtggcacca atatttataa aacgctacct gatattttta   7620
atatttcatg tttcctgacc cagattatct tgttggttcc tcatataagt ttaattagtg   7680
tcgttcttga aactttgtta tgcagcagat gtcatggggg gaacttcatt taatgatgga   7740
aagcgcaaga actcgaagaa aaaaaacctt ttgtcgaacc agacacgcca tagttgctta   7800
tcttcaaaat cagaagtttc tcatattact atatcttctg gtagtgatgc tggtctgtca   7860
cagaaggcat tcaattgttc tccatctata tcaagcaatg gggcatcaag tggttcatta   7920
ggcgagagac atagcaatgg tggtgctttg aagttgaata taaaaaagga tcgtggcaat   7980
gcaaatccaa ttagaggctc aagtgggtgg atttcaataa gagcgcacag ttctgatggg   8040
aactccagag aaatggcaaa aagacgccgt ctatctgaaa atgtaatcac cgacagtggt   8100
ggcggtgatg acccttttgc ttttgatgat gttgatcagg agccttcaaa ttgggaactg   8160
cttggtccaa aaaagaaatc gcctcagaaa catcaagaca aatcaggaaa tggagtgcta   8220
gttgcaagtc atgaaccaga ccaacctgaa gatcttaatc agtcgggtac aacatctctt   8280
tttagtgcta aagatgaatc cagtcttttg gaagactgcc tcttggcatc agttaaggta   8340
attaaatatg tttccttctg atctttcttg tttcttcttc aagagaatat acattcttgg   8400
```

-continued

```
gtcacagttt ctcggtttgt ctttgtgact ttgttgagtg acatattttg aattcacaaa   8460
atttcctttt caatatggct cctcaatcta tagcatctgt cgtgtatgta ttctgtacaa   8520
aatagtattg taacatctcc tagaagaaat tggcaccatc catatcatac agtagcaatt   8580
tatgagacgt gatcctgatt ggaggtttag gacagagcct cgagctaaat tgctattgta   8640
ttgtatctac tatcttttag tacatgatat gtgctgggca ctctgtgtct gagtgtagtg   8700
agtgcttaag tttacatagt tcagctaaca tgcatatgta agacagttta tgattaaatt   8760
taagtgtaga aagaaggtac tttcaaaaga tttttaagga caatataatt gtttcaccgg   8820
gactcatgct tgttctgact gtgagcctaa tgttaccttt acatgccctt acattgtcta   8880
tttttatcg ttttatgaga tcttccaaac aacttgatct gtcttaatgt ttttttgcta   8940
gctcctttct tggatatctg gtaaatggtt aggccgaagt atgaactttg ccttattgtt   9000
tcaaagaaaa tgtaacaact cctggaaaag tctaattttg gttgcccttt attttgctga   9060
ccgtattggc acacatctaa ttctgctgtt cctttctggc aggttcttat gaacttagca   9120
aatgacaacc catctggttg tgaattgatt gcgtcatgtg gtggacttaa caccatggcc   9180
tccttgatca tgaagcattt cccctcattt tgttttgtcg tggacaacaa ctataacacg   9240
agagatgtca atcttgatca tgagttatca tcttctcaaa acagcaaggc acaccaggtc   9300
aaaattaagc aattgcgaga tcatgaactt gattttctgg ttgccatatt gggcttgctt   9360
gttaaccttg tagagaagga tagccttaat aggtaagtcc ctcacatgct tccttccatt   9420
tgctcaattc atatcagtgt tactgttctg gcagttcctt ggggtcagga ctcagaaaca   9480
tccaattaat gttcatgttc tcttaacgac tcagaaatac tttataacct ctccacaggg   9540
tacggctttc atctgcccgt gttcctgttg atctatctca gaatccacag agtgaagaga   9600
cacagagaga tgtcatagca ctcctctgtt ctgtattctt agcaagtcaa ggtgctagtg   9660
aagcttctgg aactatatca ccggtaattc aaaattcttc aagttccttt tgtatgtaga   9720
ttatatcttt gtaaaactcg gcatttatta cctgctcttt gtttcaaaaa gcagtatttt   9780
attttgctcc ttagcatagg tcagcagaac agttgatctt attcagaaaa caatattttg   9840
catgtaacat actgttatct atgagatgaa aattaatgca tgtgtaataa tgtcaatgat   9900
aaatatttgc tatctgaatc cagtctacca actctagtta gaccgaaatt actgaggttc   9960
tatttcaaag aataatttag tgcaccattt gttcaactac tatgaagtaa aatggtattc  10020
ccttctattg acatcgggtt agaagtgaaa ggccatctta atgcaatgtt ctcaatgcca  10080
caaacccaca aatttcatta acacatacag attattatta acatagctat aaattggatt  10140
tccagaagct tgagttgaat ttattttgtt acaattgaaa gcactgggaa cattagcatt  10200
tttttttagt tcttggttat tgcaatttat aatgttatac agaactgtgt acctcacaat  10260
gcattcatta tgacattcta tgaaccattt gattgactgt tgcttgtaaa caacaggatg  10320
atgaggagtc tttgatgcaa ggagcacggg aagctgaaat gatgatcgta gaggcctatg  10380
cagcccttct tcttgcgttt ctttcaactg aaaggtttgc aatctgtagt tgatggattg  10440
ttttattaat gtctaactac ttgcataatg tcagcactat ggcatttaac ttatactgtc  10500
tgttaactgc aacagcatga aggttcgtgg agccatttcc agctgccttc caaataacag  10560
cttaaaaatc cttgtgcctg cgctagagaa atttgtggta tgtctccata attcttgaac  10620
tactgtttgt ataaaaaagt atggatgatc tttgaattta ctccattttg gaaatcatta  10680
atttttcatg tctgaggtgt gaggtgtcac cataattgta cttcccatcc aggaagcctg  10740
```

-continued

```
tttgcaaaat ttcacataaa taaggaaaat ttgaacttgt ttcaagtttg aatagtaaca  10800
ggatgtttta tttctcaact ggagaaaaca ttccggctgg gacttttaac ccttaaaatg  10860
ctagtgtgct cccactgtaa gattgtctgc tgtcacattt gaaactttgt gtaatacctt  10920
tatcactacc cttgagatga gagacacaat ctggtaccga gttaagttat tgataactcc  10980
cagttgaagt acagcaccaa atcaagccaa catgttggct acgtaattaa atgttctctt  11040
acaacagata gaggtaaaaa gggagtttct aagtatctaa cctcttaccc tcttggctta  11100
gcactccagg cacaactctt tcttaacttg cgatttagga cttgactctg agaatattgt  11160
gtgcccacac tggttgagtg catgcctatc taagctgcta gtttttgttc attttgatta  11220
actctgaagc tgcctgagct tattctgctt ccatcattta ttaatccatc atgtttctct  11280
ttcagtcgtt ccatctgcag ctcaatatga tcacagagga aacgcactca gctgtcacag  11340
aagttatcga gaaatgcaaa ctttcataga aagagtgaag aggggcctgt acagatcaac  11400
taacaacctc tttgcagcaa aaaagcatac acacaagtgt ttgtcttggc ctggggctct  11460
gcagatggac tgatactctg acctgcagtg ggcttgggag ctaacaatgg tttcattctt  11520
ttttttttta tgttttcccc tgttgttttt gctcatgttt tgtgtaattt tttcttctca  11580
tctagcgatg ttatttttct tagcatgatg ggagtagccc tccttttttt tttctctaat  11640
taagtgtaaa gtagcaacag catagggatg aatgttcagt gtagtgtgtg gtgtttcagt  11700
tattcagaga cgtccataca gtttgtacct tgtgaccaca cgtcttaatc tgatgaagct  11760
tagaataaat cacatgttag caatgcaata tcatctgcgt cttctctcac tttggtggcc  11820
atcaaattct gtgtagaagt gtatggttgg tgtgctgttg caaatgccgt attccgctct  11880
gttttgtgga agttaagaag tccctagttg aaataccgat ttttcatgat ctcggagatt  11940
gatgcaactc tgattgcagc atttcttttt attagaatgt acactccatg ctatcatgat  12000
gtttattgtt tagtactaca agatttggtt aaccattatt ttaatatcat aataatttta  12060
taaaatcttg gagtaacaag ttcataatac atgatagcat aactttttga ggctagtcta  12120
tgtatattgt ctcctttgtt tttaaactaa gcactcaata aattattgat ggctgtaatt  12180
ttctgaaggt ttcaccggtt tcggcccgtg ctttataaat agcttcggca caaaagacaa  12240
aacggtccct ccaacacata aatggttgag tttacgtttt cattatcttt ggtaaaatca  12300
agtccaccac gtagacactc ataacaaaag tttgaatatc ctcagaaatt ttgacttgag  12360
tctatcttac ctttgatatc ggacatccaa ccctccctcc ctccctgaac tttatattat  12420
tcatattaca cctgaacttt atattattca tattacaccc tgaagtggtt ttcatttaat  12480
tgcatacatg ctgaaatagt ttgacaacgt gagatgcaca aaatctacac gttcgtctta  12540
agttgcaatt cattttatcc cttttctttt tctctcttac ataggaatat caatagtact  12600
aattcacatt acaatatagt ataaattggt gatcgattat tggcaatata ctatattaaa  12660
tattcaaaac tagtcattta agctgccaaa taagtaaacc actatcgaaa accacaatat  12720
aaatggcatt acaaaactta gggggttgaa tatccaattt taaagttcat gatgctagag  12780
gaatttctat caaaagttta tgggtacata tggacttttt cctttttaaa agaagctatt  12840
cttatcgtaa acgttaaata ttttttgtac tttatttttt atgattgaaa aaaaaactta  12900
gttttcaaaa tgattggtct gtatacaagc atcaattaga cttaataaat tcatctaaca  12960
gtttcctggc agaaactgta atttgttttt gttattagac tacgtttatt atttcaaatg  13020
tgtgtacgta tatccgatgt gacaaccaaa cccaaaaatt ttccctaact ccatgaggcc  13080
ttacagatat atttgatggg tgtaaagttt tttaagttct ttgggtgcaa agtttttaaa  13140
```

-continued

```
gtatacggac acacatttga agtattaaat atagacaaat aacaaaacat attacatatt  13200
ctgcctgtaa acaacgagac aaatttatta agcctaatta atctgtcatt agcaaacgtt  13260
tactgcagca tcacattgtc aaatcatagc gtaattaggc tcaaaaatat tcgtctcgta  13320
atttacatgc aaactgtgta attggttttt tttttcgtca acatttaata ctccatgcat  13380
gtccaaatat ttgatgcgat ctttttggcc aaattttgtt ggaatctaaa caaggatcaa  13440
atttgctgaa tttttccaga cgtcacggct tgttcatcca tcgttcgcat cgcgattcgc  13500
caccgacgcc ttggtttcca acgaatttta tcatccgctt aaatacatcc aaagctctcc  13560
atcgccatcg gcggccaacg gcgaccgctc cgctctaccc aatccaccca tccactcgcc  13620
gccgccccct gatccaaagc ctccgccgcg ccgccgtcga gaggaggagg aggaggagga  13680
ggaggaggag gaggcgtgag cccctatggg gaccctcctc cggccgcgtc cgctcgccca  13740
cgccgccggc gccggcgacg ccacgccgtc gaccgcgcac ggtagccacg cgcctctcga  13800
gaggcccccc ccccgccgct cgctgatctc tcttctcatc ctgtttgggt ttgggtttgt  13860
gatttgggtg tttttttttt tccgcagcgg tggtggtgag cggtggccgc ggccgtggcg  13920
tggagtgcca gccgcatcgg gtgcgccgcc gcccgggtcc gcaggttgcg gtggcgacgg  13980
cgagctggag gaggcggagg gagaccgtgg tgagatcgga tttcgccgct ggtggtgccg  14040
ctaccatggg ggattcgccg caggcgctct caggtttgca gcctcctcca ctctcttctc  14100
gcaaaatgtg ttgctatgtt cctctcgctg ggctggcctc atagccatta atgtagtttg  14160
ctggaacatt acattcggaa cgttgttggc aattgcttga caaaatgtgg aattgtggag  14220
gggagaaaaa tcgtttgaac ctgcagtgac aaaattgcca tctataattt taaaactgaa  14280
ggtgtggaaa tcaaacataa tcattgccag cacatcattc ttgttaacca ccttgacata  14340
ttgttggctt ataacagtta gctccacacc aacttggaag gtgtcaatgg aatgtaagta  14400
taaattgagg ataactggca gttgttaaga ctttctacag aacttgtagc agctaaaact  14460
agctattgtg catttatgtt tcatggaatt tgagcggcaa tggatatttc ttactaagac  14520
gtataatgca aaacaaaaaa aaaaaaaact atgtctatgc agtttacatg taatgtgcgg  14580
atgcaaataa aatcatgttc atggacaaac taatgggatt cataccaaat tccagaattg  14640
catttcttat gtggttactt ttgtttgttg atttggttac cagacatcga tgtggtttca  14700
agggtcagag ggtttgcttt ctacgcggtg actgcagttg cagcaatctt tttgtttgtc  14760
gccatggttg tggttcatcc acttgtgctc ctatttgacc gataccggag gagagctcag  14820
cactacattg caaagatttg ggcaactctg acaatttcca tgttctacaa gcttgacgtc  14880
gagggaatgg agaacctgcc accgaatagt agccctgctg tctatgttgc gaaccatcag  14940
agtttcttgg atatctatac ccttctaact ctaggaaggt gtttcaagtt tataagcaag  15000
acaagtatat ttatgttccc aattattgga tgggcaatgt atctcttagg agtaattcct  15060
ttgcggcgta tggacagcag gagccagctg gtatggctgt agtctcatcc ctgctttctt  15120
aagtagacat atatacattt acagtatttg gtaaataaac aagattttat gaatcatata  15180
tgattttggg gaaaacacaa aactctcttt gttggctgcc ttgaacatag ttctgttcac  15240
acagttatag caccttcttt aaaatgaaga actttgttgc atacacataa ggccaaacca  15300
cataatgaat tttgtttatt tctatctttg aatgttagca tcgtttttgt ttaatgcatg  15360
atcgccttcc tatatatttg tagtatgtca acattgtatt ccatgctgag cataacaaat  15420
ggtttgttaa aattcaggac tgtcttaaac ggtgtgtgga tttggtgaaa aaaggagcat  15480
```

-continued

```
ctgtattttt ctttccagag gggactagaa gcaaagatgg aaagctaggt gcatttaagg  15540
ttcagtaacc aaacttaggt tacattacat ctaatgagat ttttatattc agtatataat  15600
gttaaccttc tcatggtgta ctgacgtggt tataaatgtc cccagagagg tgcattcagt  15660
gtggctacaa agaccggtgc tcctgtgata cctattactc ttctcgggac agggaaactg  15720
atgccttctg gaatggaagg catccttaat tcaggttcag taaagctcat tattcaccat  15780
ccaattgaag ggaatgatgc tgagaaatta tgttctgaag caaggaaggt gatagctgac  15840
actcttattc taaacggtta tggagtgcac taaagaaaga tggtgttttt ttttattata  15900
tggaacctat tcaaaggcac agacaggctt tcaaggctaa gcttgttaca ggtactgata  15960
ctagttacta attactttcg taatcagtat aaataagctt gtgtagtgta atggcattgt  16020
acatttctgc acttggtaaa tttacagaag aggcaagtaa tattttagag gattgagttt  16080
attcacccag tcatatagtt gaagaggcaa gtaacctgta agagaggact gaacattaac  16140
acctcttgtt cgattaaaaa tgaccaaaga gcatcaaaca tgtattcgag gctgttactt  16200
tagatatggc ccattaattt gtttagttgt ctatgtacat cctagttggt gtaaatgcca  16260
gttaccattt ctatgatcta aaacaatcaa ctcttttagt atattttcaa aaacgaaaat  16320
tcagtacaca tgtatgaatc ttaatattct tctctagctc gttacaaaag caacaaaggc  16380
accgtgtcag ctggttcaca ttagctagtt tgtacttagc attatccact agcaccttat  16440
tttcatgcat atcatgctaa tttgcttgcc cacgttgagt gggaattttt ttcatgtttt  16500
ataatttata tatgttttag acttctagtc cacaatttat gtacttcatg ttcctgagcc  16560
tctagtatgg ctgatagcag actaggtgct gagtgctgtc ctttttgca gactgaagag  16620
agaagaaata caagactgtc cattgttagt cagatttgta aaaatagact ctgatgtagt  16680
ttacttttgc ccctatttta tttttaacaa tacaaatata taacagatcc taagaactta  16740
tcttaattta ggagaagttg ctcgtttcat taaattaaat tgtgaagtaa aaatgtgtgc  16800
tcgagtctgt caatgcaatc ctgtgttctt gtttgaagat atggtgtagg gcaggccagg  16860
attgaacact gaatggtaag actgcttctg ccttcagacg ttattgctaa atttttagct  16920
acttgcagtt agtgctgcca cgccgattaa gcagtagaac aaagtagttt tgtcgtgcac  16980
aaatgagtta tatttcattg gaaatcgaag cgaaaacgaa tcaaaagtta gaagaaaagg  17040
ggaaacttgg taattactcc ataaagagag tgcattttat tggtaagatg gtatccggaa  17100
gctgtgagct ccgggctgta tgtattctgg caaatttgat atgagatgct cgattattgg  17160
cttaagttag cgatatcaaa tttggggaag caccaaagga attattgtga aggagttatg  17220
ggtgcgtgac gttatctgct aggttcaaat ccttgtggct atgaatattt atctgctagg  17280
ttcaaatcct agtgactatg aatattaatg ggtaaggtaa gggatttatt gttaatttta  17340
gtttctttaa gattgtgcca tcggacgcca ttcggtaact gtaataatgc tttgtattgg  17400
attcacttgt gttacatgca cgcactaaac atgtgcttta ccttttcatc tgtttttgcg  17460
ttctgggcta gaaactcaaa cgttgaattt tccatggtct gctcaacttg acaattactg  17520
cgtgtcaagc gatcttatac gcatactatg cgcacaagtg attgtatacg gatatgatga  17580
cagtataacg tgtgatattg attttttaa taaaaaaatg atgttccttt ccttgatgaa  17640
ggaacaaaga cttttttaa aagaagggta ttactaaaaa caaaaatgac aaaaacaaaa  17700
tatcagtgca catggcaagt gtgctcggca attttttctc tgtactttaa acaaaaatac  17760
ttctatatgt tcttttttat aagggtggca caaatctttt aaatgagcca aatatctaca  17820
ttggatttat taaaaactgt ataaattata atttatactc tgaaaggttg tgtgcatctc  17880
```

-continued tcttggagaa aatgtataag ttgcaaacaa acattaatcc acgttatgta actttttttc 17940
gccggaaagg ccgaaggagg cctgacggag cgtggggctc ctcaccggga gaccgcgcag 18000 gcccccccttt gccggttcgg ccggggactc agggtgaaat tctaagctct ctgtatgtgg 18060
aaggttcgcg accgtcgaaa gagcataaga cacgggcgat gtatacaggt tcgggccgct 18120
gagaagcgta ataccctact cctgtgtttt ggggggatct gtgtatgaag gagctacaaa 18180
gtatgagcca gcctctccct tgttctgggt tccgaatctg gaaaagtcca gtccagtccc 18240
cccctctaag tgggcaaggt cctcctttta tatcttaagg ggataccaca tgcaccatct 18300
ccctcctttc tgtggggact taccctacct tttcataaat ggacggagat ttgtatagtt 18360
gccgtccgaa tgaccttctg ataggacggc ccatacctac ctccacttcc gccgaaagca 18420
ggtgcgacgt gggattatgg ctgtctgctg acgacatgac cagtgtcaga ctggtcacaa 18480
attgctcatt cctgtccacc acgcgtcagt ttagcaatct acatgttggc ccttcttcac 18540
acaacatctt gcctgtaatg gttaggatga agcctggcat atatctaacc aggactaacg 18600
tgccatctct aggaggtaac acgctagctc cagctgggga cgagcgccta gaagccctcg 18660
tcctgacggg atggggcgag gcgtgcgtca gatcgcctgt cgccacctaa cccgcgatct 18720
gaccggtctg tgactggtca cagaccggat aaacgagtgc actgcacttc gttacatgcc 18780
gcgtgacacg ctcagccaaa ccgcaataaa tgtggttagg tgagccccgc tgtgctcacc 18840
taacccatac acgcggagca aaaacccacg aggggtcggg gcgcctcggc cctcggggcc 18900
gaggcgggtg cggtccgacc ccctcggggg gactaagagg agggcgaaca catcaccctc 18960
gggcccgacg tcccccgagg gtgccaggcc acgtgggcga ttgtgtctgc ctcaaacctc 19020
tagtcatgat actcctgatc ccatgtcacc gacagtagcc cccggcgtta tgccagggcg 19080
atcgccctct ttaagggaag cggtcgggcg tgacgccact cctaaggcct ggtgacaggt 19140
gggaccggtc tccacaattg ggcagaaacc caacggtcac aaatcacgca catcggcaat 19200
ggtaactcta ctatcaataa tgagcggtct cttcaagact gccacattac tcgagtagca 19260
cacgaatctg gacatggcga ttcgtttcgt ctggagatat ggtaacgtcg ctttggtcgg 19320
cgagcgtaat taacgcgcgc acgatatgat ctatctcgac tgccacaacc gcatatccac 19380
ctcatgcgcc gcaagcgggc gaatgggatt agtggaagcg tgggcgcgag aaacgagggg 19440
gcgaaatagt gggcgcgaga agcgaggagc cgggcacagc gttggcaaga gtataaaggc 19500
actgaggaaa ggatctgttt ccttcctttc gccatcattt cccttgtctt cgccgcttgc 19560
gccctaactc cttctttcct gtgctctact ttcgccacac gcgctcgctc tcaatcttct 19620
cttcctccgg cgccatggca cggggctccg ctctgctcga tggtagcgtg ctgccgcctt 19680
cccgcatcgt gagcgagagg caggctgggc tgccgcgccg cttcatgccg gaatctgcca 19740
ccggccggga gatagtcacg ctgggtgagg gacgcccggc gccagactac ccggggcggt 19800
ccgtcttctt tctccccttt gcaatggcag ggctggttcc gccattttct tctttcttca 19860
tggatgttct gaagttctac gatctccaga tggcgcacct cacccccaac gcggtgatga 19920
cattggccat cttcgcgcat ctgtgcgaga tgttcattgg ggtgcgccca tctcttcggc 19980
tgttccggtg gttcttcacc gtgcagtcgg tgtcgccgcc atcggtagtt ggtggctgct 20040
acttccagcc atgggggccg gtgctgaatc gctacatccc ctgcgccctc cgcaagaagt 20100
gggacgactg gaagagcgac tggttctaca cccccctcgc cgacgaagcg cgcctctgac 20160
ttccgagcca gcccccggcg caggcctcca gctggcgggc gccggtagat ctgggggatg 20220

-continued

```
gctatgacgc cgtcctcgac cgcctggcgg gcctacgatc ccaggggctc acaggggcca  20280
tggtgtacgg cgactacctc cgtcgtcgga ttgcgccgct ccagcggcgc gctcggggcg  20340
cctgggagta caccgggtcc gaagactaca tgaggaccca ccagggagtc agatgggact  20400
gggctcctga ggatttcaag atagtggtcc aacgggtgct gaatctcaac tccatggagg  20460
cgtccctcat tccccaagga atcctccctc tctgcagcga tccagaccgc gcctccatcc  20520
tgaccattat gacggcggtc ggggcctcag aggagtgagc tccaaagggc cacgacggcg  20580
caggcgggag ccgtaggggg gatcaatcta ccccgggagg gggtcgtgct tctgggtctc  20640
gcgacggagg cccgaggagc agccgccctg ccgacgcccg ggggaagagg aagcagggag  20700
gaacacctcc cccatctcct ccccgagggg gcggggcggt gcgtgccaac agcaggcgcc  20760
cggagggggc cgcgccgaca tcgcagcccg agggggagcg caagaagaag cggctccgca  20820
agatggggga gacagaacca tctcggggaa accttatttc ccctccaaag tggtcgttta  20880
accgaccccc tcgcaggttc gtctctcacc catcgtggct gtattcattc tctcaacgcg  20940
agttttcact cacccatctt gttcgtcttc tggtcttttc ttctgtttca gcgagatccc  21000
gtcgcgtccc tcccgccatt ccaagtccgg ccagtctgag gccgaggatc cggcggccgc  21060
agaggcccgg aggcgggaat ctgaccggcg agaggccgcg gatcgcctac gggaagccga  21120
ggaggccgcc caggaggccg cccgggctcg ccagggcgag gaaaccgctc gggaggaggc  21180
cgcccgggcc cgccaggccg aggaagccgc tcgggaggag gccgcccgag cccaccaggc  21240
cgaggaagcc gctcgggaga aagccggatt tcgccaggac gaggcaatgg cgacttccga  21300
ggcagctcgc gatgaggtcg cgggcgcgtc gcttgagccc gcttcctcgg gcgacgctca  21360
ggcgacaact tccggggcag ctggcgacga ggctgcgggc gcgtcgcttg ggcccactcc  21420
ctcaggcgac gcccaggacc aaccaggtct gagggacatc cccgagtccg gcacttccat  21480
cggcggcccg agccgcgtgg catcctctcc aaggcggctc ttccccacgc cttctatcgc  21540
cccgctgagc gcagagcccc ttctgcaggc cttggccgcc gcaaacatcg cggtgttgga  21600
cgggcttagt gcccaggtgg aggccctgca agcagagtgg gcggagctcg acgccgcgtg  21660
ggcgcgtgtc gaggaggggc ggcgctcagt ggaggccatg gtggaggtgg gccgcaaggc  21720
acaccgccgg catgtctcgg agcttgaagc ccgtaagaag gtgttggcgg aaatcgccaa  21780
ggaagtggag gaggagcggg gggctgccct cattgccacc agcgtgatga acgaggcgca  21840
ggacaccctc cgccttcaat acgggagctg ggaggcggag ctagggaaaa agctcgacgc  21900
cgcccagggg gtgcttgacg ttgccgctgc ccgagaacag cgggcggggg agaccgaagc  21960
ggcgtcccga cggcgcgaag agacccttga ggcgcgcgcc atggcgctgg aagagcgcgc  22020
ctgcgtcgtg gagagggatc tggcggaccg cgaggccgcc gtcactatcc gggaggcaac  22080
actggcggcg cacgagtccg cctgtgccga agaggagtcc gcactccgcc tccacgagga  22140
cgcgctcacc gagcgggagc gagctctcga ggaggccgag gccgcggcgc aacggctggc  22200
ggacagcctg tccctccgcg aggcagcgca ggaggagcag gcgcgccgca ctctggaatg  22260
tgtccgcgcc gagaggaccg cactaaacca gcgggccgct gacctcgagg cgcgggagaa  22320
ggagctggac gcgagggcgc gcagcggcgg ggcggctgcg ggcgaaaacg acttagccgc  22380
ccgcctcgct gctgccgaac ataccatcgc cgatctgcag ggcacgctaa actcgtccgc  22440
cggggaggtc gaggccctcc gcttggcagg cgaggtaggg cccggcatgc tttgggacgc  22500
cgtctcccgc ctagatcgcg ccggtcggca ggtgggcctc tggagagggc ggaccgtaaa  22560
gtacgccgcc aaccatggag gcctcgccca gcgcctctcg aagatggccg gggctctcca  22620
```

-continued

```
acggctcccc gaggagctcg agaagacaat taagtcatcc tcgagggacc tcgcccaagg  22680
agcggtggag ctcgtactgg cgagttacca ggccagggac cccaatttct ctccatggat  22740
ggcgctggat gagttccctc ctgggaccga ggacagcgcg cgcgcaggtc cgggatgccg  22800
ccgaccatat cgtccacagc ttcgagggct cagcccctcg gctcgcgttc gcccccaact  22860
ccgacgagga ggacaatgcc ggtggtgcag acgacagtga cgatgaggcc ggcgacccgg  22920
gcgtatcgga ttgatccccc aagcccccgc cattcttcag ttttttcttc ttttccttct  22980
tctaaggcct tcgggcctct tttttgtata gatcaactta atctgtaatc aaaaatgaag  23040
aaatttttgt gtcaatttca tcttgctgtg tgtatgagat gaggatgatc tgtgacgtgg  23100
tccttttgcg tcttagcttg attaagggct cgtgcccagg tcccagtcct caaaaggcgt  23160
gggtcggggc tagtgcctgg ggagatccac atgtcgagac tggccaggcc gggaacgtgg  23220
tgaccgaggg ttatgggtga cccgattgtg ggtttttgcc gattcccccc cggagttcac  23280
cacgccccgg ggcacggctc ggttctgggc cccgtttggc gattttagcc gacccgagcc  23340
cccgagggca ggattgagca cgagtgacct atttcaagtc aagattcttc aaaaggaaaa  23400
aaaaacacag atacagcctt taggaaattg aaactgcttt tattgaaata ctgaaataag  23460
agaaataaga atgtgcatgt gtggcagccc ccggccaacc ctgcacgccc gagggggtgc  23520
ggggttggcc cgagcccgaa acctgacacc cgaccccccc cctcaggggt agaagcgacg  23580
aaggtgttcg atgttccacg ggttaggcag ctcaatgccg tcgcccgtgg ccagccgtat  23640
ggagcccggc cgggggacgc cgaccactcg atacggaccc tcccacattg gtgagagctt  23700
gctcaatcca gcacgcgttt ggacgcggcg taggacgagg tcgtcgacgc agagtgatcg  23760
ggcccggacg tgacgctgat ggtagcgccg caggctctgc tggtagcgcg cggctctgag  23820
ggccgcgcgt cgccttcgct cttccaagta gtcgaggtca tctctgcgaa gctgatcttg  23880
atcagcctcg cagtacatgg tggcccgagg agacctcagg gtgagctcgg atgggagaac  23940
cgcttccgcg ccgtagacga ggaagaaagg cgtttccccg gttgctcggc ttggtgtagt  24000
tcggtttgcc cagagcaccg ctggcaactc ctcgatccat gaatcgccgt gcttcttgag  24060
tatgttgaag gtcttggttt taaggccttt gaggatttct gaattggcgc gctccacttg  24120
gccattgctt ctggggtggg caggtgaggc gaagcagagc ttgatgccca tgtcttcgca  24180
gtagtcgccg aagagttcac tagtgaattg ggtgccatta tccgtaataa tacggttagg  24240
cactccaaac cgggccgtga tgcccttaat gaatttaagt gcggagtgct tatcgatctt  24300
gacgaccgga taagcctcgg gccacttagt gaacttgtcg atcgcgacat acagatactc  24360
aaacccgccc ggggcccgcc taaacggtcc caggatatcg agcccccaga cagcaaatgg  24420
ccacgaaagt ggtatggtct gcagggcctg ggccggctga tggatttgct tggcgtggaa  24480
ttgacacgct ctacatcgcc ggaccaggtc gaccgcatca ttgagagctg tcggccaata  24540
gaaaccctgg cgaaaagctt taccaaccaa ggtgcgcgag gcggagtggg ctccgcattc  24600
gccttcatgg atatcggcaa gaagcacaac gccttgttcc cgaggaatgc acttcaggag  24660
gattccatta gccgcgcgcc gatagagggt cccttctacc agcacgtagc gtttggagat  24720
gcgatggacg cgttcactcc cttcgcggtc ctcgggtaaa gtcttatctg tgaggtatgc  24780
ttggatctcg gcaatccaag caatcaatct aagggagctg ggagcgctcc cctcgggtcc  24840
cgaggcctgg acttcaacgg gcctcggggg ccggtcaggc gcgtccgtct cccctaaggg  24900
gtcgggtcgc gccgacggct gggcaagcct ttcttcaaag gcgcccggtg gggtctgggc  24960
```

-continued

```
tcgcgtggac gcgagccgtg agagttcgtc ggcaatcatg ttatcccgtc tgggcacatg  25020
ccgaagctca atcccgtcaa aatggcgctc catacgccgt acttggcgca cgtaggcgtc  25080
catctgcggg tcagagcacc ggtactcctt acagacttgg ttaacgacca gctgggagtc  25140
gcctaacacc aggaggcggc ggatccccag tccagctgcc actctgagtc cggcaaggag  25200
tccctcgtac tctgccatat tgttggtcgc tcgaaagtcg aggcggacca agtatctgag  25260
gacgtctccg ctcggagagg tcaacgtgac ccccgcaccg gcgccctgaa gagacaggga  25320
gccgtcgaac tgcattaccc agtgggcggt gtgaggcagc tgcgaggggt ccgtgctggc  25380
ctcggggatt gagacgggct cgggagccgg ggtccactct gccacaaaat cggcgagagc  25440
ctggctcttg atagcgtggc gtggttcaaa gtgcaaatcg aactcagaaa gttcgattgc  25500
ccatttcacc acccgtcctg taccgtctcg attatgcaag atttgaccga gggggtaaga  25560
cgtaaccaca gtgacccgat gcgcctggaa ataatggcgc agtttcctcg aggccatcag  25620
aatagcgtaa agcatcttct gggcctgagg gtatcgggtt ttggcgtccc ggagggcctc  25680
actaacaaag tagacgggcc gctgcacctt tcggtggggc cgatcctctt cgctaggggc  25740
cgcatccctg gggcactctt cgtccaagca gcctcgcggg gcgcacttgt cttctgtgct  25800
gatgacctcg gggtcggagg ataacagggg cggccttccc acagtggctt tggggccgtc  25860
ctgggggtca ggggctcctg gcgtcgtcgg acaagcgggc aaagggccaa ctccggtcgt  25920
caggggcctt aggcctccgt tcggctcggg ggcctcttct ccctgctctt tcccgggtcg  25980
agtcagcaca gggttagcct cggggtcaaa gggcgatagg tgcggccttc ccacagtggc  26040
ctcagggcct tcctgggggt cgggggctcc tagcaccgtc tgacaagcgg gcagagggcc  26100
aactccggtc gtcgggggcc tcgggccacc gttcggctcg ggggcctctc ctccctgctc  26160
tctcccgggc caagtcggca cagggtgggg aagcgcgaaa tgagaattgt cctcatcgcg  26220
ctccacaacc aatgccgcac taactacttg cggggtcgcc gctaagtaga gtagcaaggg  26280
ctcgtctggc tccggggcga ccagaactgg gggagagctt agatacgcct tcaactgggt  26340
gagggcattt tcagcttcct tcgtccaggt aaacggtccg gagcgtttga gaagcttaaa  26400
taagggtaac gccttctctc ccagcctcga tatgaaccga cttagggcgg ccatgcaacc  26460
ggtgacgtat tgcacatccc taagtttgct ggggggggcgc atccgctcta tagcccgtat  26520
cttctcgggg ttggcctcaa tgccccgggc agagaccaag aacccgagaa gcttgcccgc  26580
aggtacaccg aacacacact tatcggggtt taattttatg cgggcggagc ggagactctc  26640
aaaagtttcc gctagatcta tgagtaacgt ttcctggttg cgcgtcttta caaccaagtc  26700
atcgacataa gcttcaatat tacgtcctaa ttggctaccc aaagaaattc gagtagtacg  26760
ttgaaaagta ggacctgcat tctttaaccc gaagggcatt gtcgtataac aataggttcc  26820
tatgggggta atgaacgcag ttttttcctc atcctcccta gccatgcgaa tctgatggta  26880
accagagtat gcatctagaa aacacaaaag gtcgcacccc gcagtggagt cgacaatctg  26940
atctatgcga ggcagggggt aaggatcctt aggacatgcc ttgttaaggt cggtgtagtc  27000
gatgcacatc cgaagcttgc cgttcgcctt gggaacgacc accgggttcg ctagccactc  27060
ggcggggttg acgctgccat catatttttc ggcgatggtg ggccggaacc ttgggggcca  27120
acggacattc cgaagactcg ccacaaaggc tctacagccg acaccaccaa ccgggggcac  27180
ggagggctga ttcccgcgtc cgtgttgagg tgacactctg gacgaggaag cgccctccgt  27240
tgcgtgggca gcacttcggt cattacgccg gcgctcgatg ctggtgcggg cgtccggccc  27300
cccacgcaga tctttctggg tcgaaggagt cgacgaagga gtggcggccg aatggcgaac  27360
```

-continued

```
agcggctgcc gctcgtcgtg ccctccgtct tgacgacgcg gagccggtgg tagcagcacc  27420
agaggccttg gtggcggagg accgcccacc agcatctagg cgctgccgta ccgtcatgac  27480
taatttggcc acgtcgtcca gccatcgttg ggctggagac tccgggtcag ggacgacagg  27540
cgggtgacgt aagagcgcgc ccgcagcttg gagcgcgccc tggggcgtgc tgccgtcgcc  27600
gtagacgagg aggcgacgct ccccatctcg ccgttcttct ccatcgcccg cgatcggtga  27660
agtcgcggat ctttcgaccc tctcgagcgc ctccccccgc ttaggacttt ggcgtggagg  27720
gagcggtgga gtacgagctc gacggcgtgg gttcggctcc ccgtcgtcgc cactcacact  27780
cggagagagg tcgtgcgcct ttgcttgctc ggccatcagg ctgaacagga aaagcttggc  27840
gcacacggaa gagtacgaga gctcagaaaa acacacactg agtcccctac ctggcgcgcc  27900
agatgacgga gcgtggggct cctcaccggg agaccgcgca ggcccccctt tgccggttcg  27960
gccggggact cagggtgaaa ttctaagctc tctgtatgtg gaaggttcgc gaccgtcgaa  28020
agagcataag acacgggcga tgtatacagg ttcgggccgc tgagaagcgt aataccctac  28080
tcctgtgttt tggggggatc tgtgtatgaa ggagctacaa agtatgagcc agcctctccc  28140
ttgttctggg ttccgaatct ggaaaagtcc agtccagtcc ccccctctaa gtgggcaagg  28200
tcctcctttt atatcttaag gggataccac atgcaccatc tccctccttt ctgtggggac  28260
ttaccctacc ttttcataaa tggacggaga tttgtatagt tgccgtccga atgaccttct  28320
gataggacgg cccataccta cctccacttc cgccgaaagc aggtgcgacg tgggattatg  28380
gctgtctgct gacgacatga ccagtgtcag actggtcaca aattgctcat tcctgtccac  28440
cacgcgtcag tttagcaatc tacatgttgg cccttcttca cacaacatct tgcctgtaat  28500
ggttaggatg aagcctggca tatatctaac caggactaac gtgccatctc taggaggtaa  28560
cacgctagct ccagctgggg acgagcgcct agaagccctc gtcctgacgg gatggggcga  28620
ggcgtgcgtc agatcgcctg tcgccaccta acccgcgatc tgaccggtct gtgactggtc  28680
acagaccgga taaacgagtg cactgcactt cgttacatgc ggcgtgacac gctcagccaa  28740
accgcaataa atgtggttag gtgagccccg ctgtgctcac ctaacccata cacgcggagc  28800
aaaaacccac gaggggtcgg ggcgcctcgg ccctcggggc cgaggcgggt gcggtccgac  28860
cccctcgggg ggactaagag gagggcgaac acatcaccct cgggcccgac gtcccccgag  28920
ggtgccaggc cacgtgggcg attgtgtctg cctcaaacct ctagtcatga tactcctgat  28980
cccatgtcat cgacaaggcc atccgaatgt attaaggagt aaaagttaca agaaaaaaca  29040
ccacaatgca ccaaggtgca tgaccacaca ccatacacta cccccaagca caaaccactg  29100
agggtgaagc ctagcaccaa acgaccgcca ctaagtgtga ccaaacgccg ctaggcctac  29160
ggcagcaaca catagatgag acttcgaaaa cgatgccacc aaggtggtca cgacatgtag  29220
gatgctgcca tcgtccatct aaaaagatgt ggttttcacc cagagaaact catcaagaag  29280
gggagagggt aacccttgac agcgccccaa ggaggttacg acgcccgaag gcgtagccgc  29340
tgccggtccg gtgaaccacc ggactaggct tccgcctagg accctatagc cttgatcgca  29400
gatcaccgtc caccactcag aaccaccaca cagacaaaag gtagcacgta gcttccaccg  29460
caccgcaccg acgccccttc gtcggccgac tccatcgaac caccatccct gagagctggc  29520
ccaggacccc tccgttccac cacccgccgg ccgccttgcc agttttggcc aaaggagaac  29580
ccgggactgg gtgacattgc ttcggcagcc tgagcttccc ccgctggcga gctgctgtct  29640
caatccaacc tagaaactcc ccgcaaaaga aggggatgag ctctaggaag ggcgagggtg  29700
```

-continued

```
ccgaccggca acgaggaaga caacccatcg actccagctc cctttgcact accatctggg  29760
cctgcgccaa tgccggatac gctgtcgctc cggctccggc gccacccacc tgcacccccct  29820
ttgcctggtc tccgcgcccc tcctggctgc gtcgcgccgc ccagctggcc gctaagggca  29880
ccacgacggc cgcccggcta ccgaggcctg gccgcgccat gggacagctc gcgctggcac  29940
cagcgagcca cggccgtcgc gctgttgccg gcgccagcga gcacaaccgc cagctccaag  30000
ggccgagcat gccactgagc cgccgccgct gccgcccggg ccggctgcac gtcaccggcg  30060
cacacgaccg cacgccgcca cgctccgcct ccgcgcccga ggcagcccca tgccattgcc  30120
gcgcacctcg cccgcccgct gccgagccgc caccgcgcac cttgctgagc cgccaccgcc  30180
gtccctagcc gcctcgtgcc gccgccacgc cagatccagg cgcgggatgg ccggatccgg  30240
ccttgggggc gccggatccg ccgcctcccc acaccgccac ggcgtcacca cctccgaccg  30300
cagtgagggc ttcgtcgttt gccccatcct catcgcgtcg aggaggaaga cgccaagaaa  30360
aaagggcctc gccgctgcct tccttgctcg ctgccggctt cgccgccggc gagctccggc  30420
ggcggcgagg tgggggagaa gaagtgggga gtgggcagct agggtttttt cgcccccccaa  30480
gccgcccgtg cgagagcgac ggtggggggg gggggacttt ccaacctctt ccagtgttct  30540
agttctccac gttatgtaac tcaatttgtt taaccataga aagtaagaaa cctaccagcg  30600
tgttaagctc tctttcattc cctttcttct tcctggtttt gcttccatca catgtcaagt  30660
gaagggttct taactaccat tactcctaca catctaattt ttttctcaga tctttcgcag  30720
gtatatattg atgctacatt ttatgatctt aagataatct ccttcacatt accctctgct  30780
gaaactttag cttgaaccgt catcttcacc acaatttgag cccaatttgc acagagcaca  30840
acgagcaata gcttgccctt acgttcatta tttagcatga actactacta actacccaag  30900
aatcaataca ccggtttaat aacgccattt tatcacgtta atatatgttt cattcaacac  30960
accggttttg gcacagttgc aaacttgcaa taaattcttt cctacttctc catcccataa  31020
tataacaaat tggtatgtct cgtctggtac taagttgcta tattatgaga tggagggagc  31080
acttcttttc ttccaaaata taagaatata gtattggatt agatattatc tagattcacg  31140
aattcgatta ggttgtctag atttatagtt gtatgtaatg tataattcgg taataggtta  31200
ttacctctcg ggatggaggg agtagttttg actttttttt ttcttataaa tcgctttgat  31260
ttttatatta gtcaaatttt atcgagttta actaagttta tagaaaaaaa ttagcaacat  31320
ttaagcacca cactagtttc attaaattta gcatggaata tattttgata atatatttgt  31380
tctgtgttaa aaatgctgct atatttttct ataaacgtag tcaaatttaa ataagttaga  31440
ctaaaaaaaa tcaaaacgac ttataatatg aaatggagga agtagtagac tataacaaat  31500
ttaaaccgtg ctttgatttt agagcatcac taatatgtta gcaataatct atccctaaaa  31560
tttatttttt ttcctaaact gaaaatagga agtggaaata ctcctccatc taagagagag  31620
cctaaattca ataaaaaact aaaaaactaa aggtggatcc ctctattaaa ctaccgcaaa  31680
aaatttatgt tttttttctc ttccacgcgc gcagaacaga tatctcgatc aagttagcat  31740
gtaaaatttt taaagagata ccttatacga ctccttccgt atttccaaaa gcaaacggat  31800
ttaaaatctg actcaaataa agatctatat atccaattta catgacacat gtttcgccga  31860
atttttatat taataataat taatattttt aaaattaaat tattagcaat ttgtttggag  31920
gatttatcaa aacaggatgg acgttgttta taacagcgtc tagacctaga cgcgcttgca  31980
aactgcggcc acccttttat cacacaaatt tttgacaatt tgacactttc caaaaattaa  32040
ttttataaat taaccgtgac caaaacttat ttaaaaataa tctttttgtt gagcgcaaaa  32100
```

-continued

```
tcgtatactt cagcgccaaa tagcacggcg ccgacctccc ccttcccctc ccctctatcc  32160
tccactgctg ccgcccacct ctccgtatca gctgcgtcgc gttggtttcc gccggcgctg  32220
ctgctgctgc accagtccgc tagggcgggc gggcatggcg cgccgcgccg cttcccgcgt  32280
ccgcgccggc gctgttggcg cccttcgctc ggagggctcg acccaagggc gagggggccg  32340
cacggggggc agtggcgccg aggacgcacg ccacgtgttc gacgaattgc tccggcgtgg  32400
caggggcgcc tcgatctacg gcttgaactg cgccctcgcc gacgtcgcgc gtcacagccc  32460
cgcggccgcc gtgtcccgct acaaccgcat ggcccgagcc ggcgccgacg aggtaactcc  32520
caacttgtgc acctacggca ttctcatcgg ttcctgctgc tgcgcgggcc gcttggacct  32580
cggtttcgcg gccttgggca atgtcattaa gaagggattt agagtggacg ccatcgcctt  32640
cactcctctg ctcaagggcc tctgtgctga caagaggacg agcgacgcaa tggacatagt  32700
gctccgcaga atgacccagc ttggctgcat accaaatgtc ttctcctaca atattcttct  32760
caaggggctg tgtgatgaga acagaagcca agaagctctc gagctgctcc aaatgatgcc  32820
tgatgatgga ggtgactgcc cacctgatgt ggtgtcgtat accactgtca tcaatggctt  32880
cttcaaggag ggggatctgg acaaagctta cggtacatac catgaaatgc tggaccgggg  32940
gattttacca aatgttgtta cctacagctc tattattgct gcgttatgca aggctcaagc  33000
tatggacaaa gccatggagg tacttaccag catggttaag aatggtgtca tgcctaattg  33060
caggacgtat aatagtatcg tgcatgggta ttgctcttca gggcagccga aagaggctat  33120
tggatttctc aaaaagatgc acagtgatgg tgtcgaacca gatgttgtta cttataactc  33180
gctcatggat tatctttgca agaacggaag atgcacggaa gctagaaaga tgttcgattc  33240
tatgaccaag aggggcctaa agcctgaaat tactacctat ggtaccctgc ttcaggggta  33300
tgctaccaaa ggagcccttg ttgagatgca tggtctcttg gatttgatgg tacgaaacgg  33360
tatccacccct aatcattatg ttttcagcat tctaatatgt gcatacgcta aacaagggaa  33420
agtagatcag gcaatgcttg tgttcagcaa aatgaggcag caaggattga atccggatac  33480
agtgacctat ggaacagtta taggcatact ttgcaagtca ggcagagtag aagatgctat  33540
gcgttatttt gagcagatga tcgatgaaag actaagccct ggcaacattg tttataactc  33600
cctaattcat agtctctgta tctttgacaa atgggacaag gctaaagagt taattcttga  33660
aatgttggat cgaggcatct gtctggacac tattttcttt aattcaataa ttgacagtca  33720
ttgcaaagaa gggagggtta tagaatctga aaaactcttt gacctgatgg tacgtattgg  33780
tgtgaagccc gatatcatta cgtacagtac tctcatcgat ggatattgct tggcaggtaa  33840
gatggatgaa gcaacgaagt tacttgccag catggtctca gttggaatga aacctgattg  33900
tgttacatat aatactttga ttaatggcta ctgtaaaatt agcaggatgg aagatgcgtt  33960
agttcttttt agggagatgg agagcagtgg tgttagtcct gatattatta cgtataatat  34020
aattctgcaa ggtttatttc aaaccagaag aactgctgct gcaaaagaac tctatgtcgg  34080
gattaccgaa agtggaacgc agcttgaact tagcacatac aacataatcc ttcatgggct  34140
ttgcaaaaac aatctcactg acgaggcact tcgaatgttt cagaacctat gtttgacgga  34200
tttacagctg gagactagga cttttaacat tatgattggt gcattgctta aagttggcag  34260
aaatgatgaa gccaaggatt tgtttgcagc tctctcggct aacggtttag tgccagatgt  34320
taggacctac agtttaatgg cagaaaatct tatagagcag ggttgctag aagaattgga  34380
tgatctattt ctttcaatgg aggagaatgg ctgtactgcc aactcccgca tgctaaattc  34440
```

-continued

```
cattgttagg aaactgttac agaggggtga tataaccagg gctggcactt acctgttcat  34500
gattgatgag aagcacttct ccctcgaagc atccactgct tccttgtttt tagatctttt  34560
gtctggggga aaatatcaag aatatcatag gtttctccct gaaaaatata agtcctttat  34620
agaatctttg agctgctgaa gccttttgca gctttgaaat tctgtgttgg agttcttttc  34680
tcctacagtt gtattagagg agggatcttc tctttatgtg taaatagcga ggtatgtatg  34740
tcacctctcc gaattatttt tactctggtt cctagacggt aaacaagcaa ttatgttctg  34800
cctttgatgc cagaaaaaac acaaaagttt gtcgttatct ctactaacgg atcataaagg  34860
aatttgtaac tggagtttca aacttaattt gtctaggcag tagttttggc attagatcca  34920
acattgtgta ggattcattt gtgtgtatca atctataggg tttcattaaa tttcgttaat  34980
gtgtactgtt taggtgttga atagtttgac ttgtttttta actgaacaaa agatactgaa  35040
atcgttccat tcaacaaaca catgttccgt taatgaaatt attgtacgtt accttttgtt  35100
ttcttactca caagtgtcct cttttcttat atcctataga ttggtacaac aaattattga  35160
ttcaattttg gttttgaaca ttgatgatcc tccctgcact attggtgcag ctgctcttct  35220
attcattttg tgaagtgatg tgagtacctc tcaatcccat ccttatgctt ctgtgcatgc  35280
ttcattccaa ttttttacgc atatcgattg ttttctttta tataacagtc cataaagata  35340
atcacatcat gacaaagtta tttatttcta cagtatagtt atataagtat tcaccagttt  35400
tccatgaata ttttggcatg tgattacaaa gaagattatt tgagaaaatc catgctttta  35460
tttcatcttt ttgtttgaag ttgaacttta atttatggtg taaatttcag ttattattgc  35520
tagcagctcg tactctttaa tggtataact tcacttgtgc ttattctcca atatctccct  35580
tcttgttgtt caggttcaag aaaatcattt gttggattca gaatctggtg tccattttct  35640
tcttaaatta ttaaatcctc cagtgaatct tgttgattcc aaagcaccat cgataggttc  35700
caaacttctt ggaatcagta aagttcaaat gcttaatgga tcaaataagg attctgactg  35760
catttcagag gaaatccttt caaaagttga agagattctc ttaagctgtc aagtgatcaa  35820
gtcgctcgac aaagatgaca agaaaacaac aaggccagaa ctgtgtccaa agtggcttgc  35880
tttgttgaca atggaaaatg catgcttgtc tgctgtttca gtagagggta agttttaatc  35940
aaatttcttg gtcatgattt ccctttatga ccattatatt tatttatatg agccaaataa  36000
gcagttgtca acttgtcata agttacatag cacctatttg caatattcat gggtggtttg  36060
cttagccctt ttcttcacct gcttttgatt gatgacttcc atctgtgttg cagaattgaa  36120
ttggagtagt ggactgcact agaagcacct atggccattg tcatactagg aaggttttcc  36180
cttatcaaat atttgattgt tacagagact tctgacacag tgtccagagt tggaggaaat  36240
tttaaagaga cattaaggga gatgggaggt cttgatagta tttttgacgt tatggtggat  36300
tttcattcaa cattggaggt gagatctcgc taacatcgca tattttacat ttcctttgtt  36360
caactctaat ggattgtgca ggcttgttcc ttttcgccat tttagcttta atgtgcttga  36420
agccacatga aagtaatgct tgtccagata catagccaaa ggttgttata ttttggggca  36480
tggaaaatgc ttgaggtagt aactattttc atcaggacat ggaaaattgg ctgcaacaca  36540
aattatgttg ttttatgttg caaaaatagt tttttaatac ttttttattc tgcatgtggt  36600
gttagtatct tacagttcct ctgatgatta tatcccccac gataataaca cttgaaacga  36660
taataacact tgacatatct acaccaagtg aacattattc atttggatgt tacttttcca  36720
gctatacttg ctgttcttgc atgtgtaagc aagtttggag taaattgcgc attaatttaa  36780
atgcttggtg ttcctatctg tgtacttttt attccccaac taataatgca atcatattac  36840
```

-continued

```
gctgataaac tgaataaata aattaacaat atacttctgg tggcaaacct tgtgtatcag  36900
aatctcataa aggatacatc cacttcagct ttggaccgaa atgaaggaac atctttgcaa  36960
agtgctgctc tcctcttgaa atgtttgaaa atattggaaa atgccatatt tctaagcgat  37020
gataacaagg taatgctcct tatatgttct gtttcagttt agtacccatt tccttcttct  37080
gtactatctt ctctcctgat ttgttctgtg caaaatgtgc aaacagtgcg actttgtatg  37140
tctgcttaac aattttcttt tcttcctgaa aaagcaatat gaactcttac attcattttg  37200
cttcttgcag acccatttgc ttaatatgag tagaaaattg aacccgaaac gctccttgct  37260
ttcttttgtt ggtgtcatta tcaatactat tgagttatta tcaggtattt ttcttaataa  37320
tacaatgtgt tcgctaacac aataaaatgt tttaaacatc cagtatgtta aagttgcagt  37380
ctgacgccta ttttgttttg ctgcagctct ttcaatactt cagaattctt ctgttgtttc  37440
cagctctaca tatccgaaat cgtctaaagt ctctcaacag agttactctg gtaataacaa  37500
acaccaattt tgtttgatca gttgatctcg ttggcttttc tatgcactgt ctcaatatag  37560
tttggtcgcc attcaagtct cactacagat gttgaacttg gcctgacacc aaatatttat  37620
aaaatgctac ctgatatttt taatatttca tgtttcctga cccagattat cttgttggtt  37680
cctcgtataa gtttaattag tgacattctt gaagctttgt tatgcagcag atgtcatggg  37740
gggaacttca tttaatgatg gaaagagcaa gaactcgaaa aaaaaaaact tttgtcgaac  37800
cagacacgtc attgttgctt atcttcaaaa tcagaagttt ctcatattac tatatcttct  37860
ggtagtgatg ctggtctgtc acagaaggca ttcaattgtt ctccatttat atcaagcaat  37920
ggggcatcaa gtggttcatt aggcgagagg cacagcaatg gtagtggttt gaagttgaat  37980
ataaaaaagg atcgtggcaa tgcaaatcca attagaggct caactggatg gatttcaata  38040
agagcgcaca gttctgatgg gaactccaga gaaatggcaa aaagactccg tctatcttaa  38100
aatgtaatca ccgacagtgg tggtggtgat gaccctttttg catttgaccg ccgcgtcggc  38160
gtcgccacca cgtaatcgcc cacgtcgctg cccccgctgc cacgtcgtcg accgcgcacg  38220
gtaatcacac gcatctcgag gccgccgcta gctgatatct tctcatccgg ttgatttgtg  38280
attttggcgt ttttgcagtg gtgatggcgg ggggcgaccg tggccgaggc gtggagtgcc  38340
atccgcatca gggtgtatcg gccgcgctgc tccgccctgg tccgcaggct ttggcggcga  38400
gctggcggcg gagggagact gtggtgagat cggatttcgc cgctggtggt gtcgctacca  38460
tgggggattc gccgcaggcg ctctcaggtt tgcagcctcc tccactctct tccctttttt  38520
attttttttt ctcgcaaaat gtgttgtgat gttcgtctcg ctgggcaggc ctcatagcca  38580
ttaatgtagt ttgctggaac atttacattt ggaacgttgt tggcaattgc ttgacaaaat  38640
gtggaattgt ggaggggaga aaaatcattt gaacctgcag tgacaaaatt gccatctcta  38700
attttaaaac tgaaggtgtg gaaatcaaac ataatcattg ccagcgcatc attcttgtta  38760
accaccatga tatattgttg gttataacag ttagctccac accaaccttg aaggtgtcaa  38820
tagaatgttt agtataaatt gaggagaaca ggcagttgtt aagactttct aaagaacttg  38880
tagcagctaa tactagctat tgtgcatttg tgtttcatgg aatttgagca gcaatggata  38940
tttcttacta agatgtatga tgcaaaacaa aaaactatgt ctatacagtt tacatgtaat  39000
gtgcggatgc aaataaaatc atgtacatgg acaaactcat gggattcata ccgaattcca  39060
gaattgcatt tcttatgtgg ttacttttgt tgttgatttg gttaccagac atcgatgtga  39120
tttcaagggt cagaggggtt tgcttctacg cggtggctgc agttgcagca atctttttgt  39180
```

-continued

```
ttgtcgccat ggttgtggtt catccacttg tgctcctatt tgaccgatac cggaggagag  39240
ttcaggaaaa aaatttgaaa atacccattt tttgaaaaag atttacgttt atatacacta  39300
gtatgaagaa tttgcgaaaa tataactaat ccgcagatcg gttatgcggg agcgcaacaa  39360
aagtatggcg tggcggcgcg gagtggacgg ccgaggcgtt cgcgcggaat ggggctgcgg  39420
gaccgagcca gtctcgcttg ccggtaacgc ggaaccggta cgctcccgca gcgccagtgt  39480
gcggaaccgc ggcgccaaca tttttttact gcatggcact gtgtttaata ctgtttgaca  39540
ctgtttctgg tactgtttta cacagttccc gggtcagttc cgcacaatgg aggcgcggca  39600
ccgaccatga acaatgtgtg aacagtgctg cacagggtta aaacagtgta taaactgcgc  39660
tgcacagtgc tggagtcgct ggccactgcg gttccgcgtt ttggaaccgc gggaccgtcg  39720
cgattccgcg ttttggagct gccggaccat gacggttccg cgcaggatcg tcggtcccgt  39780
attttgaatc tgcggaaccg tcgctgtccc gcgtttccgt ttcgcgggat gcgtatattt  39840
ttataaaacc tctccatgca tgtatataaa cataaattat tgaaaaaata agtatatttg  39900
caaatttttt tcgagagctc agcactacat tgcaaagatt tgggcaactc tgacaatttc  39960
catgttctac aagcttgacg tcgagggaat ggagaacctg ccaccgaata gtagccctgc  40020
tatctatgtt gcgaaccatc agagtttttt ggatatctat acccttctaa ctctaggaag  40080
gtgtttcaag tttataagca agacaagtat atttatgttc cgaattattt gatgggcaat  40140
gtatctctta ggagtaattc ctttgcggcg tatggacagc aggagccagc tggtatggct  40200
gtagtctcat ccctgctttc ttaagtagac atatatgcaa ttacagaatt tggtaaacaa  40260
acaagatttt atgaatcata tatgattttg ggaaaaacac caaactctct ttggtggctg  40320
ccttgaacat agttctattc acacagttat agcaccttct ttaaaatgaa gaactttgtt  40380
gcatacacat atggccaaac cacataatga attttgttta tttctatctt tgaatgttag  40440
caccttattt tcatgcatat catgctaatt tgcttgccca cgttgagtgg gaattttttt  40500
ccatgtttta taatttatat atgttctaga cttctagtcc acaatttatc tacttcatgt  40560
tcctgagcct ctagtatggc tggtagcaga ctaggtgctg agtgctgtcc atttttgcag  40620
actgaagaga ggagaaatac aggactgtcc gttgttagtc agatttgtaa aaatagactc  40680
tgatgtagtt tattttagcc cctattttat atttaacaat acaaatatat aacgtatcct  40740
aagaacttat cgtaatttag gagaagttgc tcgtttcatt aaattaaact gtgaagtaaa  40800
aatgtgtgct cgagtctgtc aatgcaatcc tgtgttcttg tttgaagata tggtgtaggg  40860
caggctagga tcgaacactg aatggtaaga ctgcttctgc cttcatttgt gcacttggtg  40920
ctgccacgcc gattaagcag tagaacaaag taattttgtc gtgcacaaat gagttatatt  40980
tcattgaaaa tcgaagtgaa aatgaaccaa aagatagaag aaaaggggaa acttggtaat  41040
tatatactcc acaaatttat tggtaagatt tgatattaga cgctcgatta cttggcttaa  41100
gttaaggata tcaaatttgg ggaagcacca aaggaattat tgtgaaggag ttgtgggtgc  41160
ataacgttat ctactaggtt caaatcctag tgactatgaa tattaatgag taaggtaagg  41220
gatttattgt taattttagt ttctttaaga ttgtgtccgg gtacaccatt cggtaagtgt  41280
aataatgttt tgtattggat tcacttgtgt tacgtgcatg tgatttacct tttcatttgt  41340
ttctgcgttc tgggtatgaa tttgacgaga ttccatggtc agctcaacat atcagttact  41400
gcgtgtcaag cgatcttata tggtatgcgc acaagcgatt gtatacggat atgacagtat  41460
aacgtgtgat attgatacga tgttcctttc ctttataaag gaacaaagac tttttaaaa  41520
aaaagaaggg gtattactaa aaaccaaaat gtcaaaaaca aaatatcagt gcacatggca  41580
```

-continued agtgtgcacg agcaatagct tgcccttacg ttcattattt agcatgtact actactaact 41640
acgcaaaaat caattcaccg attattaaac tgttaacatc attttagcac gttaacatat 41700
gtttcattca acacaccggt tttggcacat ttacaaactt gcaaagttgc aatactccct 41760
tcgttacata gcataagaga ttttaggtga atgtgacaca tctatccaaa ttcattatac 41820
tagaatgtat caccgcctcc acgccgggag ggagagcgcc gccggtggag aaagggggag 41880
ggagtggtcg aggggaacca gtagggtgcc ctccccgtcg ccgcctcccc gtggccgcgc 41940
cggcgagaca ggaggaagag ggggatatgg agcggcgccg ccggtgaggg cgcgcgcgcg 42000
ggggggagcg gcgacgccgg tgaggaaggg aaggggagtg gtggctttga gagagatagg 42060
ggggaggaaa aatgatttta gagttagggt ttgggctgct gagtttttat atagatcggg 42120
atcaatcagg accgtccatc agatcggaca actacggctt ctcccgcgtt gggccgggtg 42180
ccactcctag gttgcccaca ctattgggcc acatgtacgc tccgcgtgaa ataagttcac 42240
tttaggtcct ttaagttgcc tctgaattgt tcccaggccg gccgcactat tgggccaccc 42300
cataggccat gtgtacgctc cgcacagaat aatttcgctt tagctccctt aatttgtccc 42360
ctcaaactcc taaaaccagt gcaaatcttt aatttttagt tcacccattg caactcacgg 42420
gcatatttgc tagtgacata taatatgaaa cgaaggatgt agcagactat agaatttaaa 42480
ctgtgctttc attttagagc atcactaact gttatttaga tttttattta aataaatgct 42540
gaaatgatgt ttttattatg aaaattagca ataaagctcc caaaatttca aaaaaaaatt 42600
aaaagagatt tattaatcat ggttaattta attaaaaatt aaatctaacc atatcatatt 42660
atttcacggt ccgtgatgag gaaatggcag ctgctatcac ttacggtggg agagaagggg 42720
cattgtttat ttttataact atctcttata actcccatga aactataaaa taaatataat 42780
cattatcata acattagttt tttttccatt gcaacgcaag ggtaattttt cagtacaata 42840
aaaaaaataa aagtgggcca ttctgaacgg aaatttctgg tttttttttcc caagagcgcc 42900
gcacacaact gcgcaagaga tcgatcgcga tcaccctgct cgtcgccgat ctcctacacc 42960
atccctgcca tctccttccc ctccactggc tgctgctgca cctgtcagct agggcgggca 43020
tggcgcgccg cgccgcttcc cgcgctgctg gcgcccttcg ctcggagggc tcgatccaag 43080
ggcgaggggg ccgcgcgggg ggcagtggcg gtggcgcgga ggacgcacgc cacgtgttcg 43140
acgaattgct ccgtcgtggc ataccagatg tcttctccta caatattctt ctcaacgggc 43200
tgtgtgatga gaacagaagc caagaagctc tcgagttact gcacataatg gctgatgatg 43260
gaggtgactg cccacctgat gtggtgtcgt acagcaccgt catcaatggc ttcttcaagg 43320
agggggatct ggacaaaatg cttgaccaga ggatttcgcc aaatgttgtg acctacaact 43380
ctattattgc tgcgctatgc aaggctcaaa ctgtggacaa ggccatggag gtacttacca 43440
ccatggttaa gagtggtgtc atgcctgatt gcatgacata taatagtatt gtgcatgggt 43500
tttgctcttc agggcagccg aaagaggcta ttgtatttct caaaaagatg cgcagtgatg 43560
gtgtcgaacc agatgttgtt acttataact cgctcatgga ttatctttgc aagaacggaa 43620
gatgcacgga agcaagaaag atttttgatt ctatgaccaa gaggggccta aagcctgata 43680
ttactaccta tggtaccctg cttcaggggt atgctaccaa aggagccctt gttgagatgc 43740
atggtctctt ggatttgatg gtacgaaacg gtatccaccc taatcattat gttttcagca 43800
ttctagtatg tgcatacgct aaacaagaga aagtagaaga ggcaatgctt gtattcagca 43860
aaatgaggca gcaaggattg aatccgaatg cagtgaccta tggaacagtt atagatgtac 43920

-continued

```
tttgcaagtc aggtagagta gaagatgcta tgctttattt tgagcagatg atcgatgaag  43980
gactaagacc tgacagcatt gtttataact ccctaattca tagtctctgt atctttgaca  44040
aatgggagaa ggctgaagag ttatttcttg aaatgttgga tcgaggcatc tgtcttagca  44100
ctattttctt taattcaata attgacagtc attgcaaaga agggagggtt atagaatctg  44160
gaaaactctt tgacttgatg gtacgaattg gtgtgaagcc cgatatcatt acccttggca  44220
ggtaagatgg atgaagcaat gaagttactt tctggcatgg tctcagttgg gttgaaacct  44280
aatactgtta cttatagcac tttgattaat ggctactgca aaattagtag gatggaagac  44340
gcgttagttc tttttaagga gatggagagc agtggtgtta gtcctgatat tattacgtat  44400
aacataattc tgcaaggttt atttcaaacc agaagaactg ctgctgcaaa agaactctat  44460
gtcaggatta ccgaaagtgg aatgcagatt gaactttgtt agatttaatt ggataattaa  44520
tccatttaaa tcaattaaat caaataaatt ccaaggctca ttatgctagg aattcatgtg  44580
aattcattct tctatgggat atcaatggga tgaagagttt tgagaattaa tccatttgat  44640
taaggaattg gtaacttata tcaattaatc ctaattgatg gatggttgat ggttgtgtag  44700
tggaggatgg ttcatggcta gttgatgaca attagttgct ctattcctct tcctattcca  44760
ttggtaactt acatcaatta ctcttaattg attgttggtt gatggttgtg tagtggagga  44820
tggttcatgg ctagttgatg acaattagtt gctccattcc tcttcctatt ccatgactct  44880
tactcttcat cttccattcc tcttataaaa tgagaatgga tttgatctcc cgcgagaaga  44940
agaagacaca ctttcatcca ttttcaaaag ctgttgctgc tacggtaatc ccatcccgac  45000
gagtgtgtgc acacgcgttg ggagagtagg cctccgaaac cacgcgttgc tgcgacgttt  45060
gcacagacgg gcgggcgatc aggtttttgg ggagcgcaag gcgcgactac tcactgttcg  45120
tcaacatcta cttcatcttc accaacatgt cgaacactgg agacaaggag aaggagactc  45180
ccgtcaacac caacggaggc aatactgcct caaactccag cggaggacca ttcttggggt  45240
ataaccttat tacattattt caattagaag ttttactgtt aatgttcatc gcaatgtcaa  45300
cattgtgtca ttatgtgatt gttgatgctt attcaacgtt aagcatgctc atgttgatta  45360
cattcaccac tatcactgga tcaaatccta ttgtaaatat catgtttatt atcttgttat  45420
tttggattaa aatatgccga attatgacca aatttccaac aaacttagca catacaacat  45480
aatccttcat ggactttgca aaaacaaact cactgatgat gcacttcgaa tgtttcagaa  45540
cctatgtttg atggatttga agcttgaggc taggactttc aacattatga ttgatgcatt  45600
gcttaaagtt ggcagaaatg atgaagccaa ggatttgttt gttgctttct cgtctaacgg  45660
tttagtgccg aattattgga cgtacagatt gatggctgaa aatattatag gacaggggtt  45720
gctagaagaa ttggatcaac tctttctttc aatggaggac aatggctgta ctgttgactc  45780
tggcatgcta aatttcattg ttagggaact gttgcagaga ggtgagataa ccagggctgg  45840
cacttacctt tccatgattg atgagaagca cttttccctc gaagcatcca ctgcttcctt  45900
gtttatagat cttttgtctg gggaaaaata tcaagaatat catatatttc tccctgaaaa  45960
atacaagtcc tttatagaat ctttgagctg ctgaagcatt ttgcagcttt gaaattctgt  46020
gttggaattc ttttctccta cagtccgatt agaggaggga tcttctctgt atgtgtaaat  46080
agcgaggtat gtatgtcacc tctccgaatt attttgactg tggttcctgg actgtaaaca  46140
agctattatc ttctggtgtt gatgccagaa aaaacacaaa agtttgtcgt tatctctact  46200
aacggatcat aaaggggttt gtaactggag tttcaaactt aaggtatcta ggcagtaggt  46260
atatattgat cctacatctt atgatcttaa gatgatatcc ttctcattat cctctgctga  46320
```

-continued

```
aactttagct tgaaccgtca tctacaccac aatttgagcc ccttagcaca gagcacaacg  46380
agcaatagct tgcccttacg ttcattattt agcatgcact actactaact acccaataat  46440
caatacatcg gttattaaac tgtttgtaca gtttaataat gtcattttat cacgttaaca  46500
tatgtttcat tcaacaccac accggttttg gcacagttgc aaacttgcaa taacattttt  46560
actacttctc cgccccataa tataacaatc tcgttccata ctatattgct atattacggg  46620
acggatgaag tacttctttc cttccaaaat ataagaatct agtcctagat tagatattat  46680
ttggattcac gaatttgatt aggctatcta gatttgtagt cgtatgtaat gtctaattcg  46740
gtaataggtt attacctctt tggatggagg gagtagtttt tatttcgtac tccctctgtt  46800
tcatattata agttgttttg actttttcct tagtcaaatt ttattgagtt tgactaaatt  46860
tatagaaaaa aaattagcaa catttaagca ccacattagt ttcattaaat gtagcatgga  46920
atatattttt ataatatgtt tgttttttta ttaaaatgct actatatttt tctataaatg  46980
tagccaaatt taaagaagtt tgattacgaa aaaaaatcaa aatgacatat aatatgaaac  47040
tgaggatgta gcagactata gcaaatttaa actatgcttt tattttagag catcaccaaa  47100
agagatagcc taaatcttat cttaactaat taaaatattc ataattttcc tttcgtcaca  47160
ttaaattttc gtccgtaaat ccgattgaaa tccaactaga caatccaaaa aatagagaaa  47220
aagaacagaa aaaataataa aaagcacaca aatcttatct caatcccgcg ggaagctgcc  47280
gatgccgccg aatccgctcg agcgccgccg ccgccgctca cggggaacga tgtcgctgct  47340
atcgcacgtg gtatgggagg gcgccgccgc cgctgcttgg gagataggat atggagagag  47400
aaggaaatgt gagggagggt taggtttttc cccattcgta tcttcagcga cacggaggcg  47460
atccaagctg tccatcagat cagacggctc agaacgcctc catcttcagg ccgcgcatgc  47520
ttgatgggcc gagggaaggc cggagggtcg aacaaacgta gtcagaggag gagttggagg  47580
aggtaaagta gaatttattt gcgggctgag atagtaaatg gactgaaaat ggcccataga  47640
gaaattggga attttattta aataaatgtt gaaaaggtgt ttatattatc aaaattagaa  47700
attaagctcc gaaaatttta aaaaatattc aaagagcatt attaatcatg attaatttaa  47760
taaaaattaa atccaaccat atcatattat ttcacggcgc gcagtaggaa aatgcgcagc  47820
tgttgtcgct tacggtggga gagaagggac attgtttatt ttcagaacta tcttttataa  47880
ctcccatgga actttaaaat aaatataatc attattatag cattagtttt tttctgtctt  47940
ttttttcccc aagagcgccg cgcagaagag atcgatcgcg atctccctgc cccgacgtcg  48000
ccggccgatc tctcattctc tccacgccct gctcgtcgcc gatctcctac accatccctg  48060
ccatctcctc cttcccctcc cctctatcct ccactggtgc cgcccacctc tccgtataag  48120
acaaactgcg ttgcggcgtt ggtttccgcc ggcgctgctg ctgcacctgt cagctagggc  48180
gggcatggcg cgccgcgccg cttcccgcgc tgttggcgcc cttcgctcgg acggctcgat  48240
ccaagggcga ggaggccgcg cggggggcag tggcgccgag gacgcacgcc acgtgttcga  48300
cgaattgctc cggcgtggca ggggcgcctc gatctacggc ttgaaccgcg ccctcgccga  48360
cgtcgcgcgt cacagccccg cggccgccgt gtcccgctac aaccgcatgg cccgagctgg  48420
cgccgacgag gtaactcccg acttgtgcac ctacggcatt ctcatcggtt gctgctgccg  48480
cgcgggccgc ttggacctcg gtttcgcggc cttgggcaat gtcattaaga agggatttag  48540
agtggaagcc atcaccttca ctcctctgct caagggcctc tgtgccgaca agaggacgag  48600
cgacgcaatg gacatagtgc tccgcagaat gaccgagctc ggttgcatac caaatgtctt  48660
```

-continued

```
ctcctacaat aatcttctca acgggctgtg tgatgagaac agaagccaag aagctctcga  48720
gttgctgcac atgatggctg atgatcgagg aggaggtagc ccacctgatg tggtgtcgta  48780
taccactgtc atcaatggct tcttcaaaga gggggattca gacaaagctt acagtacata  48840
ccatgaaatg ctggaccggg ggattttacc tgatgttgtg acctacagct ctattattgc  48900
tgcgttatgc aagggtcaag ctatggacaa gccatggagg tacttaccac gatggttaag  48960
aatggtgtca tgcctgattg catgacatat aatagttatt tcttgaaatg ttggatcgag  49020
gcatttgtct ggacactatt ttctttaatt caataattga cagtcattgc aaagaaggga  49080
gggttataga atctgaaaaa ctctttgacc tgatggtacg tattggtgtg aagcctgata  49140
tcattacata cagtacactc atcgatggat attgcttggc aggtaagatg gatgaagcaa  49200
tgaagttact ttctggcatg gtctcagttg ggttgaaacc taatactgtt acttatagca  49260
ctttgattaa tggctactgc aaaattagta ggatggaaga cgcgttagtt ctttttaagg  49320
agatggagag cagtggtgtt agtcctgata ttattacgta taacataatt ctgcaaggtt  49380
tatttcaaac cagaagaact gctgctgcaa aagaactcta tgtcaggatt accgaaagtg  49440
gaacgcagat tgaacttagc acatacaaca taatccttca tggactttgc aaaaacaaac  49500
tcactgatga tgcacttcag atgtttcaga acctatgttt gatggatttg aagcttgagg  49560
ctaggacttt caacattatg attgatgcat tgcttaaagt tggcagaaat gatgaagcca  49620
aggatttgtt tgttgctttc tcgtctaacg gtttagtgcc gaattattgg acgtacaggt  49680
tgatggctga aaatattata ggacaggggt tgctagaaga attggatcaa ctctttcttt  49740
caatggagga caatggctgt actgttgact ctggcatgct aaatttcatt gttagggaac  49800
tgttgcagag aggtgagata accagggctg gcacttacct ttccatgatt gatgagaagc  49860
acttttccct cgaagcatcc actgcttcct tgtttataga tcttttgtct gggggaaaat  49920
atcaagaata ttataggttt ctccctgaaa aatacaagtc ctttatagaa tctttgagct  49980
gctgaagcat tttgcagctt tgaaattctg tgttggaatt cttttctcct acagtcctat  50040
tagaggaggg atcttctctg tatgtgtaaa tagcgaggta tgtatgccac ctctccgaat  50100
tatttttact gtggttccta gactgtaaac aagcaattat gttatgctgt tgatgccaga  50160
aaaaacataa aagtttgtcg ttatctctac taacggatca taaagggatt tgtgactgga  50220
gtttcaaact taatgtgtct aggcagtaat tttgacatta gatccaaaac aatttatagg  50280
gtttcattaa atttcatcta tgtgtactgt ttaggtgttg aatagtttga cttgtttttt  50340
aactgaacaa aagatatgtc tgaagctttg ttctttacca aatgcagtac tgatcatcac  50400
aatatatttt ttatggaaca agattggatt gtatagaatg gtttccgatc tgattatctt  50460
atctcaacgt attattatgc acatgtacta atcatgaaat atctgatgga atgatgtttc  50520
tatttacctg tgtgaggcag caaggagtga gatggataac accacatact ccctctatcc  50580
cagaatataa gaagttttag agttggacac gattattaag aaagtaggta gaagtgagta  50640
gtggagggtt gtgattgcat gagtagtgga ggtaggtggg aaaagtgaat ggtggagggt  50700
tgtgattggt tgggaagaga atgttggtag agaagttgtt atattttggg gagtacatta  50760
ttattctaga acaatactgt tgtgctcaag aagcgttcca aagatgtttc acaacctgtg  50820
ctcgatgggt tttgagctta atcctgggac attcagtatc atgatctgtc tcattcttaa  50880
acatggaata aaggatgaca gcatgatttc tttgtctcta taatcttttg gctacccaca  50940
gataatagct gtaaatctat actactttaa aaggagtagt ggtggtggtg agtggtgaat  51000
ctgccaccac cccaccacca actctcaaaa ttctgacatg tgggatcact gtcaatccct  51060
```

-continued

```
tctccaagac atgtgggatc actgtcaatc ccttctccaa accaattgta tgatagaaca  51120
gtggaaatca cggacagacc atggagctct caaccataat catccttgcg agttaataac  51180
aaatggagcg taaacttggc aagcaaaaaa ctcaaattaa ttctaaaatt aagctctagg  51240
attcaaaata gatttcctct ctgcattgtg ctgttatgat ttttaattcc gtaacaacgc  51300
aaatgcattt tgctagtctt ataaagaagg gttaatgcaa atattctgat taaatgattg  51360
tatctatgaa gtttgaatgc tagtggaagc tcctttgacc atgttttgtt gtgcgagcat  51420
ttaagagagt gaagagaatg cttctttggt gctgttctgg tatggaagga tccacagata  51480
aaattcaggt tctactgctt ctctgcttgt aattttcatg aagctgcagt gaataccttg  51540
ttgaccactt gatctgttgc tttgaaggag aatatagtag tggccaaggt tggtgacggt  51600
gatggtggca tgtgatcccc cagatcttca gtgacccaga gaggagggga cggcgcgtgg  51660
tgagctacaa ggcatactca gtggagggca agatcaaggc ctcccgtccg taggggactc  51720
cgctgcatca aggccaactg ctccgaactg atcaatttct ggtacggatc acttctcctt  51780
tccttttttt tttcacctta agcactctct tgattcttcg ctgctacctc ccttaatttc  51840
tttcaatata ttgtggcact tgatcatggc ggagacccac cttccagtgt gaatggattt  51900
tgtcaaagaa ctaaatttat tccattagct tattttctga ttacatggaa gacattcttt  51960
tctggaataa atacagaact aaatcctgtt tcctgaataa aagttgttag tgtgtggcat  52020
ggtgcatttc cgcgcttcta aattttataa aacctgttca ttcaatttga acctgcatcc  52080
aatccaatat tttaggtgca gacaggtgct tgcggtcagg ttaaagaagt tggcaaaaat  52140
gcttctgaag aaaggttaat tgttgtttca tctcaggagg taatatgcag atgattattc  52200
caattggcat tgccttgcca tttttatcac gagtctttac aattttatat cctcctacat  52260
attctttcca gattccagat gatccagtgt ctccaacaat tgaggcgctt attttgctcc  52320
atagtaaagc aagtacactt gctgagaacc accagttgac aacacggctt gttgtaccat  52380
caaacaaagt tggttgtatt cttggggaag gtggaaaggt aattactgaa atgagaagac  52440
ggactggggc tgaaatccga gtctactcaa aagcagataa acctaagtac ctgtcttttg  52500
atgaggagct tgtgcaggta atttatttgg ccatacctac accagagatc catatattac  52560
ttttataact gcagttttta cttgttaaca tttcattgtg cttttacatt tgttccaagc  52620
tttcaggttg ctgggcttcc agctattgaa agaggagccc tgacagagat tgcttcgagg  52680
ctttgaacta ggacactcag agatggaagt tcttccaata atccgacacc ttttgcccct  52740
gttgatggtc ctcctgttga tatcttgcct aacaaggaat tcatgctata tggacgatct  52800
gctaatagtc ccccatatgg agggcctgct aatgatccac catatggaag acctgccatt  52860
gatccaccat atggaagacc aatatccaca atatggaaga cctgccaatg atccaccata  52920
tagaagacct gtcaatgata catcatattg agggttggac aatgatgggc ctcgtgatca  52980
ggcccggtcc tgaggggggt cgaatggggc gatcgctccg ggcccccgat tcccagggcc  53040
cccacctatc tgtgcaacga gtagtagcga tcttccagcg cgcaacgtga ggcgatgttt  53100
ctccgtgatt tcgccggcct gcaactgcga gatcgcgagt ataacgatca gccgatcgat  53160
ctcatctgcc gactgccatg ctgatgccac acgcaagcgc agcatatcag ccttatcttg  53220
gttgatcggc atgctggacg agcacatctg ttgtcgcatc aactgctgac tgctatatat  53280
gtgctggtgc tgaatcgatc gattgtcgtc gcggaagtga agaacaacca cggcactgct  53340
gcctgctggg ctctagccgc catcagtaag tacgctatac tgcctatcta gatctagatc  53400
```

-continued

```
gagattacat agtggaatta tctgtttata acaaaattac aaggtatcaa ttgataattt  53460

aaggttataa ccgtacaaac ttcagtgatt tgctggtttc acattggtta gatttgtttc  53520

aactaatttg gtacttctgt agccttgtaa tttacgaatc tagtattaat attttcttaa  53580

gtattagcct gttccttgat attatgctgt tgagaaagta tgcaatagat aacaaaaaca  53640

agtaggtgtg ttgaggatgc tcaagagtaa tacagccact tcaataattc tgatattatc  53700

aggacatcat caataattct gcgcctacaa atcttcaaag aaaattttaa tataatgcgt  53760

atgatttttt aaatacgaat attgattgct atttaaagat atttatatta tatggtaatt  53820

attatttgaa ggtttataat aaaggcctcc gtttttagtt tcacgctggg ccttcagaat  53880

ctcaggaccg gccctgctca tgatc                                        53905


<210> SEQ ID NO 29
<211> LENGTH: 24
<212> TYPE: DNA
<213> ORGANISM: Artificial Sequence
<220> FEATURE:
<223> OTHER INFORMATION: Synthetic oligonucleotide primer for
      amplification

<400> SEQUENCE: 29

atcaggagcc ttcaaattgg gaac                                            24


<210> SEQ ID NO 30
<211> LENGTH: 24
<212> TYPE: DNA
<213> ORGANISM: Artificial Sequence
<220> FEATURE:
<223> OTHER INFORMATION: Synthetic oligonucleotide primer for
      amplification

<400> SEQUENCE: 30

ctcgcaaatt gcttaatttt gacc                                            24


<210> SEQ ID NO 31
<211> LENGTH: 24
<212> TYPE: DNA
<213> ORGANISM: Artificial Sequence
<220> FEATURE:
<223> OTHER INFORMATION: Synthetic oligonucleotide primer for
      amplification

<400> SEQUENCE: 31

tgaaggagtt atgggtgcgt gacg                                            24


<210> SEQ ID NO 32
<211> LENGTH: 24
<212> TYPE: DNA
<213> ORGANISM: Artificial Sequence
<220> FEATURE:
<223> OTHER INFORMATION: Synthetic oligonucleotide primer for
      amplification

<400> SEQUENCE: 32

ttgccgagca cacttgccat gtgc                                            24


<210> SEQ ID NO 33
<211> LENGTH: 24
<212> TYPE: DNA
<213> ORGANISM: Artificial Sequence
<220> FEATURE:
<223> OTHER INFORMATION: Synthetic oligonucleotide primer for
      amplification
```

-continued

<400> SEQUENCE: 33
gcgacgcaat ggacatagtg ctcc 24

<210> SEQ ID NO 34
<211> LENGTH: 24
<212> TYPE: DNA
<213> ORGANISM: Artificial Sequence
<220> FEATURE:
<223> OTHER INFORMATION: Synthetic oligonucleotide primer for amplification

<400> SEQUENCE: 34
ttacctgcca agcaatatcc atcg 24

<210> SEQ ID NO 35
<211> LENGTH: 24
<212> TYPE: DNA
<213> ORGANISM: Artificial Sequence
<220> FEATURE:
<223> OTHER INFORMATION: Synthetic oligonucleotide primer for amplification

<400> SEQUENCE: 35
aaggcatact cagtggaggg caag 24

<210> SEQ ID NO 36
<211> LENGTH: 24
<212> TYPE: DNA
<213> ORGANISM: Artificial Sequence
<220> FEATURE:
<223> OTHER INFORMATION: Synthetic oligonucleotide primer for amplification

<400> SEQUENCE: 36
ttaacctgac cgcaagcacc tgtc 24

<210> SEQ ID NO 37
<211> LENGTH: 24
<212> TYPE: DNA
<213> ORGANISM: Artificial Sequence
<220> FEATURE:
<223> OTHER INFORMATION: Synthetic oligonucleotide primer for amplification

<400> SEQUENCE: 37
tggatggact atgtggggtc agtc 24

<210> SEQ ID NO 38
<211> LENGTH: 24
<212> TYPE: DNA
<213> ORGANISM: Artificial Sequence
<220> FEATURE:
<223> OTHER INFORMATION: Synthetic oligonucleotide primer for amplification

<400> SEQUENCE: 38
agtggaagtg gagagagtag ggag 24

<210> SEQ ID NO 39
<211> LENGTH: 24
<212> TYPE: DNA
<213> ORGANISM: Artificial Sequence
<220> FEATURE:
<223> OTHER INFORMATION: Synthetic oligonucleotide primer for amplification

<400> SEQUENCE: 39

-continued ccctccaaca cataaatggt tgag 24

<210> SEQ ID NO 40
<211> LENGTH: 24
<212> TYPE: DNA
<213> ORGANISM: Artificial Sequence
<220> FEATURE:
<223> OTHER INFORMATION: Synthetic oligonucleotide primer for amplification

<400> SEQUENCE: 40
tttctgccag gaaactgtta gatg 24

<210> SEQ ID NO 41
<211> LENGTH: 24
<212> TYPE: DNA
<213> ORGANISM: Artificial Sequence
<220> FEATURE:
<223> OTHER INFORMATION: Synthetic oligonucleotide primer for amplification

<400> SEQUENCE: 41
gcgatcttat acgcatacta tgcg 24

<210> SEQ ID NO 42
<211> LENGTH: 24
<212> TYPE: DNA
<213> ORGANISM: Artificial Sequence
<220> FEATURE:
<223> OTHER INFORMATION: Synthetic oligonucleotide primer for amplification

<400> SEQUENCE: 42
aaagtctttg ttccttcacc aagg 24

<210> SEQ ID NO 43
<211> LENGTH: 26
<212> TYPE: DNA
<213> ORGANISM: Artificial Sequence
<220> FEATURE:
<223> OTHER INFORMATION: Synthetic oligonucleotide primer for amplification

<400> SEQUENCE: 43
gaggatttat caaaacagga tggacg 26

<210> SEQ ID NO 44
<211> LENGTH: 24
<212> TYPE: DNA
<213> ORGANISM: Artificial Sequence
<220> FEATURE:
<223> OTHER INFORMATION: Synthetic oligonucleotide primer for amplification

<400> SEQUENCE: 44
tgggcggcag cagtggagga taga 24

<210> SEQ ID NO 45
<211> LENGTH: 24
<212> TYPE: DNA
<213> ORGANISM: Artificial Sequence
<220> FEATURE:
<223> OTHER INFORMATION: Synthetic oligonucleotide primer for amplification

<400> SEQUENCE: 45

-continued

```
aagaagggag ggttatagaa tctg                                              24


<210> SEQ ID NO 46
<211> LENGTH: 24
<212> TYPE: DNA
<213> ORGANISM: Artificial Sequence
<220> FEATURE:
<223> OTHER INFORMATION: Synthetic oligonucleotide primer for
      amplification

<400> SEQUENCE: 46

atatcaggac taacaccact gctc                                              24


<210> SEQ ID NO 47
<211> LENGTH: 24
<212> TYPE: DNA
<213> ORGANISM: Artificial Sequence
<220> FEATURE:
<223> OTHER INFORMATION: Synthetic oligonucleotide primer for
      amplification

<400> SEQUENCE: 47

acgagtagta gcgatcttcc agcg                                              24


<210> SEQ ID NO 48
<211> LENGTH: 24
<212> TYPE: DNA
<213> ORGANISM: Artificial Sequence
<220> FEATURE:
<223> OTHER INFORMATION: Synthetic oligonucleotide primer for
      amplification

<400> SEQUENCE: 48

cagcgtgaaa ctaaaaacgg aggc                                              24


<210> SEQ ID NO 49
<211> LENGTH: 24
<212> TYPE: DNA
<213> ORGANISM: Artificial Sequence
<220> FEATURE:
<223> OTHER INFORMATION: Synthetic oligonucleotide primer for
      amplification

<400> SEQUENCE: 49

atcccacatc atcataatcc gacc                                              24


<210> SEQ ID NO 50
<211> LENGTH: 25
<212> TYPE: DNA
<213> ORGANISM: Artificial Sequence
<220> FEATURE:
<223> OTHER INFORMATION: Synthetic oligonucleotide primer for
      amplification

<400> SEQUENCE: 50

agcttctccc ttggatacgg tggcg                                             25


<210> SEQ ID NO 51
<211> LENGTH: 24
<212> TYPE: DNA
<213> ORGANISM: Artificial Sequence
<220> FEATURE:
<223> OTHER INFORMATION: Synthetic oligonucleotide primer for
      amplification

<400> SEQUENCE: 51

atttgttggt tagttgcggc tgag                                              24
```

-continued

<210> SEQ ID NO 52
<211> LENGTH: 24
<212> TYPE: DNA
<213> ORGANISM: Artificial Sequence
<220> FEATURE:
<223> OTHER INFORMATION: Synthetic oligonucleotide primer for
amplification

<400> SEQUENCE: 52
gcccaaactc aaaaggagag aacc 24

<210> SEQ ID NO 53
<211> LENGTH: 24
<212> TYPE: DNA
<213> ORGANISM: Artificial Sequence
<220> FEATURE:
<223> OTHER INFORMATION: Synthetic oligonucleotide primer for
amplification

<400> SEQUENCE: 53
cctcaagtct cccctaaagc cact 24

<210> SEQ ID NO 54
<211> LENGTH: 24
<212> TYPE: DNA
<213> ORGANISM: Artificial Sequence
<220> FEATURE:
<223> OTHER INFORMATION: Synthetic oligonucleotide primer for
amplification

<400> SEQUENCE: 54
gctctactgc tgataaaccg tgag 24

<210> SEQ ID NO 55
<211> LENGTH: 24
<212> TYPE: DNA
<213> ORGANISM: Artificial Sequence
<220> FEATURE:
<223> OTHER INFORMATION: Synthetic oligonucleotide primer for
amplification

<400> SEQUENCE: 55
tggatggact atgtggggtc agtc 24

<210> SEQ ID NO 56
<211> LENGTH: 24
<212> TYPE: DNA
<213> ORGANISM: Artificial Sequence
<220> FEATURE:
<223> OTHER INFORMATION: Synthetic oligonucleotide primer for
amplification

<400> SEQUENCE: 56
agtggaagtg gagagagtag ggag 24

<210> SEQ ID NO 57
<211> LENGTH: 24
<212> TYPE: DNA
<213> ORGANISM: Artificial Sequence
<220> FEATURE:
<223> OTHER INFORMATION: Synthetic oligonucleotide primer for
amplification

<400> SEQUENCE: 57
tacgacgcca tttcactcca ttgc 24

-continued

<210> SEQ ID NO 58
<211> LENGTH: 24
<212> TYPE: DNA
<213> ORGANISM: Artificial Sequence
<220> FEATURE:
<223> OTHER INFORMATION: Synthetic oligonucleotide primer for amplification

<400> SEQUENCE: 58
catttctcta tgggcgttgc tctg 24

<210> SEQ ID NO 59
<211> LENGTH: 26
<212> TYPE: DNA
<213> ORGANISM: Artificial Sequence
<220> FEATURE:
<223> OTHER INFORMATION: Synthetic oligonucleotide primer for amplification

<400> SEQUENCE: 59
acctgtaggt atggcacctt caacac 26

<210> SEQ ID NO 60
<211> LENGTH: 26
<212> TYPE: DNA
<213> ORGANISM: Artificial Sequence
<220> FEATURE:
<223> OTHER INFORMATION: Synthetic oligonucleotide primer for amplification

<400> SEQUENCE: 60
ccaaggaacg aagttcaaat gtatgg 26

<210> SEQ ID NO 61
<211> LENGTH: 24
<212> TYPE: DNA
<213> ORGANISM: Artificial Sequence
<220> FEATURE:
<223> OTHER INFORMATION: Synthetic oligonucleotide primer for amplification

<400> SEQUENCE: 61
tgatgtgttt gggcatccct ttcg 24

<210> SEQ ID NO 62
<211> LENGTH: 24
<212> TYPE: DNA
<213> ORGANISM: Artificial Sequence
<220> FEATURE:
<223> OTHER INFORMATION: Synthetic oligonucleotide primer for amplification

<400> SEQUENCE: 62 gagataggggg acgacagaca cgac 24

<210> SEQ ID NO 63
<211> LENGTH: 26
<212> TYPE: DNA
<213> ORGANISM: Artificial Sequence
<220> FEATURE:
<223> OTHER INFORMATION: Synthetic oligonucleotide primer for amplification

<400> SEQUENCE: 63
tcctatggct gtttagaaac tgcaca 26

-continued

<210> SEQ ID NO 64
<211> LENGTH: 24
<212> TYPE: DNA
<213> ORGANISM: Artificial Sequence
<220> FEATURE:
<223> OTHER INFORMATION: Synthetic oligonucleotide primer for amplification

<400> SEQUENCE: 64
caagttcaaa cataactggc gttg 24

<210> SEQ ID NO 65
<211> LENGTH: 24
<212> TYPE: DNA
<213> ORGANISM: Artificial Sequence
<220> FEATURE:
<223> OTHER INFORMATION: Synthetic oligonucleotide primer for amplification

<400> SEQUENCE: 65
cactgtcctg taagtgtgct gtgc 24

<210> SEQ ID NO 66
<211> LENGTH: 24
<212> TYPE: DNA
<213> ORGANISM: Artificial Sequence
<220> FEATURE:
<223> OTHER INFORMATION: Synthetic oligonucleotide primer for amplification

<400> SEQUENCE: 66
caagcgtgtg ataaaatgtg acgc 24

<210> SEQ ID NO 67
<211> LENGTH: 24
<212> TYPE: DNA
<213> ORGANISM: Artificial Sequence
<220> FEATURE:
<223> OTHER INFORMATION: Synthetic oligonucleotide primer for amplification

<400> SEQUENCE: 67
tgcctactgc cattactatg tgac 24

<210> SEQ ID NO 68
<211> LENGTH: 24
<212> TYPE: DNA
<213> ORGANISM: Artificial Sequence
<220> FEATURE:
<223> OTHER INFORMATION: Synthetic oligonucleotide primer for amplification

<400> SEQUENCE: 68
acatactacc gtaaatggtc tctg 24

<210> SEQ ID NO 69
<211> LENGTH: 4820
<212> TYPE: DNA
<213> ORGANISM: rice

<400> SEQUENCE: 69
atcgatcgcg atctccctgc cccgacgtcg ccggccgatc tctcattctc tccacgccct 60
gctcgtcgcc gatctcctac accatccctg ccatctcctc cttcccctcc cctctatcct 120
ccactggtgc cgcccacctc tccgtataag acaaactgcg ttgcggcgtt ggtttccgcc 180
ggcgctgctg ctgcacctgt cagctagggc gggcatggcg cgccgcgccg cttcccgcgc 240

-continued

```
tgttggcgcc cttcgctcgg acggctcgat ccaagggcga ggaggccgcg cggggggcag    300
tggcgccgag gacgcacgcc acgtgttcga cgaattgctc cgccgtggca ggggcgcctc    360
gatctacggc ttgaaccgcg ccctcgccga cgtcgcgcgt gacagccccg cggccgccgt    420
gtcccgctac aaccgcatgg cccgagccgg cgccgacgag gtaactcccg acttgtgcac    480
ctacggcatt ctcatcggtt gctgctgccg cgcgggccgc ttggacctcg gtttcgcggc    540
cttgggcaat gtcattaaga agggatttag agtggacgcc atcgccttca ctcctctgct    600
caagggcctc tgtgccgaca agaggacgag cgacgcaatg gacatagtgc tccgcagaat    660
gaccgagctc ggctgcatac caaatgtctt ctcctacaat attcttctca aggggctgtg    720
tgatgagaac agaagccaag aagctctcga gctgctgcac atgatggctg atgatcgagg    780
aggaggtagc ccacctgatg tggtgtcgta taccactgtc atcaatggct tcttcaaaga    840
gggggattca gacaaagctt acagtacata ccatgaaatg ctggaccggg ggattttacc    900
tgatgttgtg acctacaact ctattattgc tgcgttatgc aaggctcaag ctatggacaa    960
agccatggag gtacttaaca ccatggttaa gaatggtgtc atgcctgatt gcatgacata   1020
taatagtatt ctgcatggat attgctcttc agggcagccg aaagaggcta ttggatttct   1080
caaaaagatg cgcagtgatg gtgtcgaacc agatgttgtt acttatagct tgctcatgga   1140
ttatctttgc aagaacggaa gatgcatgga agctagaaag attttcgatt ctatgaccaa   1200
gaggggccta aagcctgaaa ttactaccta tggtaccctg cttcaggggt atgctaccaa   1260
aggagccctt gttgagatgc atggtctctt ggatttgatg gtacgaaacg gtatccaccc   1320
tgatcattat gttttcagca ttctaatatg tgcatacgct aaacaaggga aagtagatca   1380
ggcaatgctt gtgttcagca aaatgaggca gcaaggattg aatccgaatg cagtgacgta   1440
tggagcagtt ataggcatac tttgcaagtc aggcagagta gaagatgcta tgctttattt   1500
tgagcagatg atcgatgaag gactaagccc tggcaacatt gtttataact ccctaattca   1560
tggtttgtgc acctgtaaca aatgggagag ggctgaagag ttaattcttg aaatgttgga   1620
tcgaggcatc tgtctgaaca ctattttctt taattcaata attgacagtc attgcaaaga   1680
agggagggtt atagaatctg aaaaactctt tgagctgatg gtacgtattg gtgtgaagcc   1740
caatgtcatt acctacaata ctcttatcaa tggatattgc ttggcaggta agatggatga   1800
agcaatgaag ttactttctg gcatggtctc agttgggttg aaacctaata ctgttactta   1860
tagcactttg attaatggct actgcaaaat tagtaggatg gaagacgcgt tagttctttt   1920
taaggagatg gagagcagtg gtgttagtcc tgatattatt acgtataaca taattctgca   1980
aggtttattt caaaccagaa gaactgctgc tgcaaaagaa ctctatgtta ggattaccga   2040
aagtggaacg cagattgaac ttagcacata caacataatc cttcatggac tttgcaaaaa   2100
caaactcact gatgatgcac ttcagatgtt tcagaaccta tgtttgatgg atttgaagct   2160
tgaggctagg actttcaaca ttatgattga tgcattgctt aaagttggca gaaatgatga   2220
agccaaggat ttgtttgttg ctttctcgtc taacggttta gtgccgaatt attggacgta   2280
caggttgatg gctgaaaata ttataggaca ggggttgcta gaagaattgg atcaactctt   2340
tctttcaatg gaggacaatg gctgtactgt tgactctggc atgctaaatt tcattgttag   2400
ggaactgttg cagagaggtg agataaccag ggctggcact tacctttcca tgattgatga   2460
gaagcacttt tccctcgaag catccactgc ttccttgttt atagatcttt tgtctggggg   2520
aaaatatcaa gaatattata ggtttctccc tgaaaaatac aagtccttta tagaatcttt   2580
```

-continued

```
gagctgctga agcattttgc agctttgaaa ttctgtgttg gaattctttt ctcctacagt   2640
cctattagag gagggatctt ctctgtatgt gtaaatagcg agtttgaatg ctagtggaag   2700
ctcctttgac catgttttgt tgtgcgagca tttaagagag tgaagagaat gcttctttgg   2760
tgctgttctg gtatggaagg atccacagat aaaattcagt agtggccaag gttggtgacg   2820
gtgatggtgg catgtgatcc cccagatctt cagtgaccca gagaggaggg gacggcgcgt   2880
ggtgagctac aaggcatact cagtggaggg caagatcaag gcctcccgtc cgtaggggac   2940
tccgctgcat caaggccaac tgctccgaac tgatcaattt ctggtgcaga caggtgcttg   3000
cggtcaggtt aaagaagttg gcaaaaatgc ttctgaagaa aggttaattg ttgtttcatc   3060
tcaggagatt ccagatgatc cagtgtctcc aacaattgag gcgcttattt tgctccatag   3120
taaagtaagt acacttgctg agaaccacca gttgacaaca cggcttgttg taccatcaaa   3180
caaagttggt tgtattcttg ggaaggtggg aaaggtaatt actgaaatga gaagacggac   3240
tggggctgaa atccgagtct actcaaaagc agataaacct aagtacctgt cttttgatga   3300
ggagcttgtg caggttgctg ggcttccagc tattgaaaga ggagccctga cagagattgc   3360
ttcgaggctt tgaactagga cactcagaga tggaagttct tccaataatc cgacaccttt   3420
tgcccctgtt gatggtcctc ctgttgatat cttgcctaac aaggaattca tgctatatgg   3480
acgatctgct aatagtcccc catatggagg gcctgctaat gatccaccat atggaagacc   3540
tgccattgat ccaccatatg gaagaccaat atccacaata tggaagacct gccaatgatc   3600
caccatatag aagacctgtc aatgatacat catattgagg gttgaacaat gatgggcctc   3660
gtgatcaggc ccggtcctga ggggggtcga atggggcgat cgctccgggc cccccgattc   3720
ccagggcccc cacctatctg tgcaacgagt agtagcgatc ttccagcgcg caacgtgagg   3780
cgatgtttct ccgtgatttc gccggcctgc aactgcgaga tcgcgagtat aacgatcagc   3840
cgatcgatct catctgccga ctgccatgct gatgccacac gcaagcgcag catatcagcc   3900
ttatcttggt tgatcggcat gctggacgag cacatctgtt gtcgcatcaa ctgctgactg   3960
ctatatatgt gctggtgctg aatcgatcga ttgtcgtcac ggaagtgaag aacaaccacg   4020
gcactgctgc ctgctgggct ctagccgcca tcagctgcgg agctgatcca tggacgtgag   4080
gattaccgaa gactgtcagg tctcactggg tatccaggtg gctctgtcga attgtggatt   4140
ccaaatagtt aactggagtc tgtcattggt gttggtggtg tcaatctagc tgagatccgt   4200
ctggtatagc gtaagagaaa catcatgcac tatccccagt cataaccatg ccccaatggc   4260
caccaatagt tttcctcgtg aaaatctccc cttgatccca gatctctggt gcgagagtga   4320
agttgcacga agcccatcct ggttcttccg agtccattgt ggagatccag ggcattccgg   4380
atcaagtgaa agccgcacag agccttctgc aaggcttcat cggcgcaagc agcaacagca   4440
ggcaggcgcc ccagtcctct cgcatggccc attattttta gtaagctgga ggacattcgc   4500
aacagggggg tcagtggtca ctgcaaagct gagtttgttc ttcagttcaa ctgcagaaaa   4560
ttgcagatcg gttgccgtag ttgctagaac ggtacatagt tgccacctaa ctgtagcgag   4620
tggcataact tattgtgtgt tactgcccaa tgttgtctct ccttgtgttc atggattcag   4680
acttgtgatt gtagtatttc tggatcagac tggagtaaaa gaaaaaaaaa aaggaagaca   4740
tgggtttaac agtaagctca aaacgttgac agtagtaaaa taaaaggggt ttgttcactt   4800
taaaaaaaaa aaaaaaaaaa                                               4820
```

<210> SEQ ID NO 70
<211> LENGTH: 4821

-continued

<212> TYPE: DNA
<213> ORGANISM: rice

<400> SEQUENCE: 70
cgatcgcgat ctccctgccc cgacgtcgcc ggccgatctc tcattctctc cacgccctgc 60
tcgtcgccga tctcctacac catccctgcc atctcctcct tcccctcccc tctatcctcc 120
actggtgccg cccacctctc cgtataagac aaactgcgtt gcggcgttgg tttccgccgg 180
cgctgctgct gcacctgtca gctagggcgg gcatggcgcg ccgcgccgct tcccgcgctg 240
ttggcgccct tcgctcggac ggctcgatcc aagggcgagg aggccgcgcg gggggcagtg 300
gcgccgagga cgcacgccac gtgttcgacg aattgctccg ccgtggcagg ggcgcctcga 360
tctacggctt gaaccgcgcc ctcgccgacg tcgcgcgtga cagccccgcg gccgccgtgt 420
cccgctacaa ccgcatggcc cgagccggcg ccgacgaggt aactcccgac ttgtgcacct 480
acggcattct catcggttgc tgctgccgcg cgggccgctt ggacctcggt ttcgcggcct 540
tgggcaatgt cattaagaag ggatttagag tggacgccat cgccttcact cctctgctca 600
agggcctctg tgccgacaag aggacgagcg acgcaatgga catagtgctc cgcagaatga 660
ccgagctcgg ctgcatacca aatgtcttct cctacaatat tcttctcaag ggctgtgtg 720 atgagaacag aagccaagaa gctctcgagc tgctgcacat gatggctgat gatcgaggag 780
gaggtagccc acctgatgtg gtgtcgtata ccactgtcat caatggcttc ttcaaagagg 840
gggattcaga caaagcttac agtacatacc atgaaatgct ggaccggggg attttacctg 900
atgttgtgac ctacaactct attattgctg cgttatgcaa ggctcaagct atggacaaag 960
ccatggaggt acttaacacc atggttaaga atggtgtcat gcctgattgc atgacatata 1020
atagtattct gcatggatat tgctcttcag ggcagccgaa agaggctatt ggatttctca 1080
aaaagatgcg cagtgatggt gtcgaaccag atgttgttac ttatagcttg ctcatggatt 1140
atctttgcaa gaacggaaga tgcatggaag ctagaaagat tttcgattct atgaccaaga 1200
ggggcctaaa gcctgaaatt actacctatg gtaccctgct tcaggggtat gctaccaaag 1260
gagcccttgt tgagatgcat ggtctcttgg atttgatggt acgaaacggt atccaccctg 1320
atcattatgt tttcagcatt ctaatatgtg catacgctaa acaagggaaa gtagatcagg 1380
caatgcttgt gttcagcaaa atgaggcagc aaggattgaa tccgaatgca gtgacgtatg 1440
gagcagttat aggcatactt tgcaagtcag gcagagtaga agatgctatg ctttattttg 1500
agcagatgat cgatgaagga ctaagccctg gcaacattgt ttataactcc ctaattcatg 1560
gtttgtgcac ctgtaacaaa tgggagaggg ctgaagagtt aattcttgaa atgttggatc 1620
gaggcatctg tctgaacact attttcttta attcaataat tgacagtcat tgcaaagaag 1680
ggagggttat agaatctgaa aaactctttg agctgatggt acgtattggt gtgaagccca 1740
atgtcattac ctacaatact cttatcaatg gatattgctt ggcaggtaag atggatgaag 1800
caatgaagtt actttctggc atggtctcag ttgggttgaa acctaatact gttacttata 1860
gcactttgat taatggctac tgcaaaatta gtaggatgga agacgcgtta gttcttttta 1920
aggagatgga gagcagtggt gttagtcctg atattattac gtataacata attctgcaag 1980
gtttatttca aaccagaaga actgctgctg caaaagaact ctatgttagg attaccgaaa 2040
gtggaacgca gattgaactt agcacataca acataatcct tcatggactt tgcaaaaaca 2100
aactcactga tgatgcactt cagatgtttc agaacctatg tttgatggat ttgaagcttg 2160
aggctaggac tttcaacatt atgattgatg cattgcttaa agttggcaga aatgatgaag 2220

-continued

```
ccaaggattt gtttgttgct ttctcgtcta acggtttagt gccgaattat tggacgtaca   2280

ggttgatggc tgaaaatatt ataggacagg ggttgctaga agaattggat caactctttc   2340

tttcaatgga ggacaatggc tgtactgttg actctggcat gctaaatttc attgttaggg   2400

aactgttgca gagaggtgag ataaccaggg ctggcactta cctttccatg attgatgaga   2460

agcacttttc cctcgaagca tccactgctt ccttgtttat agatcttttg tctgggggaa   2520

aatatcaaga atattatagg tttctccctg aaaaatacaa gtcctttata gaatctttga   2580

gctgctgaag cattttgcag ctttgaaatt ctgtgttgga attcttttct cctacagtcc   2640

tattagagga gggatcttct ctgtatgtgt aaatagcgag tttgaatgct agtggaagct   2700

cctttgacca tgttttgttg tgcgagcatt taagagagtg aagagaatgc ttctttggtg   2760

ctgttctggt atggaaggat ccacagataa aattcagtag tggccaaggt tggtgacggt   2820

gatggtggca tgtgatcccc cagatcttca gtgacccaga gaggagggga cggcgcgtgg   2880

tgagctacaa ggcatactca gtggagggca agatcaaggc ctcccgtccg taggggactc   2940

cgctgcatca aggccaactg ctccgaactg atcaatttct ggtgcagaca ggtgcttgcg   3000

gtcaggttaa agaagttggc aaaaatgctt ctgaagaaag gttaattgtt gtttcatctc   3060

aggagattcc agatgatcca gtgtctccaa caattgaggc gcttattttg ctccatagta   3120

aagtaagtac acttgctgag aaccaccagt tgacaacacg gcttgttgta ccatcaaaca   3180

aagttggttg tattcttggg gaaggtggaa aggtaattac tgaaatgaga agacggactg   3240

gggctgaaat ccgagtctac tcaaaagcag ataaacctaa gtacctgtct tttgatgagg   3300

agcttgtgca ggttgctggg cttccagcta ttgaaagagg agccctgaca gagattgctt   3360

cgaggctttg aactaggaca ctcagagatg gaagttcttc caataatccg acaccttttg   3420

cccctgttga tggtcctcct gttgatatct tgcctaacaa ggaattcatg ctatatggac   3480

gatctgctaa tagtccccca tatggagggc ctgctaatga tccaccatat ggaagacctg   3540

ccattgatcc accatatgga agaccaatat ccacaatatg gaagacctgc caatgatcca   3600

ccatatagaa gacctgtcaa tgatacatca tattgagggt tgaacaatga tgggcctcgt   3660

gatcaggccc ggtcctgagg ggggtcgaat ggggcgatcg ctccgggccc cccgattccc   3720

agggccccca cctatctgtg caacgagtag tagcgatctt ccagcgcgca acgtgaggcg   3780

atgtttctcc gtgatttcgc cggcctgcaa ctgcgagatc gcgagtataa cgatcagccg   3840

atcgatctca tctgccgact gccatgctga tgccacacgc aagcgcagca tatcagcctt   3900

atcttggttg atcggcatgc tggacgagca catctgttgt cgcatcaact gctgactgct   3960

atatatgtgc tggtgctgaa tcgatcgatt gtcgtcacgg aagtgaagaa caaccacggc   4020

actgctgcct gctgggctct agccgccatc agctgcggag ctgatccatg gacgtgagga   4080

ttaccgaaga ctgtcaggtc tcactgggta tccaggtggc tctgtcgaat tgtggattcc   4140

aaatagttaa ctggagtctg tcattggtgt tggtggtgtc aatctagctg agatccgtct   4200

ggtatagcgt aagagaaaca tcatgcacta tccccagtca taaccatgcc ccaatggcca   4260

ccaatagttt tcctcgtgaa aatctcccct tgatcccaga tctctggtgc gagagtgaag   4320

ttgcacgaag cccatcctgg ttcttccgag tccattgtgg agatccaggg cattccggat   4380

caagtgaaag ccgcacagag ccttctgcaa ggcttcatcg gcgcaagcag caacagcagg   4440

caggcgcccc agtcctctcg catggcccat tatttttagt aagctggagg acattcgcaa   4500

caggggggtc agtggtcact gcaaagctga gtttgttctt cagttcaact gcagaaaatt   4560

gcagatcggt tgccgtagtt gctagaacgg tacatagttg ccacctaact gtagcgagtg   4620
```

-continued gcataactta ttgtgtgtta ctgcccaatg ttgtctctcc ttgtgttcat ggattcagac 4680
ttgtgattgt agtatttctg gatcagactg gagtaaaaga aaaaaaaaaa ggaagacatg 4740
ggtttaacag taagctcaaa acgttgacag tagtaaaata aaaggggttt gttcacttta 4800
aaaaaaaaaa aaaaaaaaaa a 4821

<210> SEQ ID NO 71
<211> LENGTH: 5005
<212> TYPE: DNA
<213> ORGANISM: rice

<400> SEQUENCE: 71
gagatcgatc gcgatctccc tgccccgacg tcgccggccg atctctcatt ctctccacgc 60
cctgctcgtc gccgatctcc tacaccatcc ctgccatctc ctccttcccc tcccctctat 120
cctccactgg tgccgcccac ctctccgtat aagacaaact gcgttgcggc gttggtttcc 180
gccggcgctg ctgctgcacc tgtcagctag ggcgggcatg gcgcgccgcg ccgcttcccg 240
cgctgttggc gcccttcgct cggacggctc gatccaaggg cgaggaggcc gcgcgggggg 300
cagtggcgcc gaggacgcac gccacgtgtt cgacgaattg ctccgccgtg gcaggggcgc 360
ctcgatctac ggcttgaacc gcgccctcgc cgacgtcgcg cgtgacagcc ccgcggccgc 420
cgtgtcccgc tacaaccgca tggcccgagc cggcgccgac gaggtaactc ccgacttgtg 480
cacctacggc attctcatcg gttgctgctg ccgcgcgggc cgcttggacc tcggtttcgc 540
ggccttgggc aatgtcatta agaagggatt tagagtggac gccatcgcct tcactcctct 600
gctcaagggc ctctgtgccg acaagaggac gagcgacgca atggacatag tgctccgcag 660
aatgaccgag ctcggctgca taccaaatgt cttctcctac aatattcttc tcaaggggct 720
gtgtgatgag aacagaagcc aagaagctct cgagctgctg cacatgatgg ctgatgatcg 780
aggaggaggt agcccacctg atgtggtgtc gtataccact gtcatcaatg gcttcttcaa 840
agagggggat tcagacaaag cttacagtac ataccatgaa atgctggacc gggggatttt 900
acctgatgtt gtgacctaca actctattat tgctgcgtta tgcaaggctc aagctatgga 960
caaagccatg gaggtactta acaccatggt taagaatggt gtcatgcctg attgcatgac 1020
atataatagt attctgcatg gatattgctc ttcagggcag ccgaaagagg ctattggatt 1080
tctcaaaaag atgcgcagtg atggtgtcga accagatgtt gttacttata gcttgctcat 1140
ggattatctt tgcaagaacg gaagatgcat ggaagctaga aagattttcg attctatgac 1200
caagaggggc ctaaagcctg aaattactac ctatggtacc ctgcttcagg ggtatgctac 1260
caaaggagcc cttgttgaga tgcatggtct cttggatttg atggtacgaa acggtatcca 1320
ccctgatcat tatgttttca gcattctaat atgtgcatac gctaaacaag ggaaagtaga 1380
tcaggcaatg cttgtgttca gcaaaatgag gcagcaagga ttgaatccga atgcagtgac 1440
gtatggagca gttataggca tactttgcaa gtcaggcaga gtagaagatg ctatgcttta 1500
ttttgagcag atgatcgatg aaggactaag ccctggcaac attgtttata actccctaat 1560
tcatggtttg tgcacctgta acaaatggga gagggctgaa gagttaattc ttgaaatgtt 1620
ggatcgaggc atctgtctga acactatttt ctttaattca ataattgaca gtcattgcaa 1680
agaagggagg gttatagaat ctgaaaaact ctttgagctg atggtacgta ttggtgtgaa 1740
gcccaatgtc attacctaca atactcttat caatggatat tgcttggcag gtaagatgga 1800
tgaagcaatg aagttacttt ctggcatggt ctcagttggg ttgaaaccta atactgttac 1860

-continued

```
ttatagcact ttgattaatg gctactgcaa aattagtagg atggaagacg cgttagttct   1920
ttttaaggag atggagagca gtggtgttag tcctgatatt attacgtata acataattct   1980
gcaaggttta tttcaaacca gaagaactgc tgctgcaaaa gaactctatg ttaggattac   2040
cgaaagtgga acgcagattg aacttagcac atacaacata atccttcatg gactttgcaa   2100
aaacaaactc actgatgatg cacttcagat gtttcagaac ctatgtttga tggatttgaa   2160
gcttgaggct aggactttca acattatgat tgatgcattg cttaaagttg gcagaaatga   2220
tgaagccaag gatttgtttg ttgctttctc gtctaacggt ttagtgccga attattggac   2280
gtacaggttg atggctgaaa atattatagg acaggggttg ctagaagaat tggatcaact   2340
ctttctttca atggaggaca atggctgtac tgttgactct ggcatgctaa atttcattgt   2400
tagggaactg ttgcagagag gtgagataac cagggctggc acttaccttt ccatgattga   2460
tgagaagcac ttttccctcg aagcatccac tgcttccttg tttatagatc ttttgtctgg   2520
gggaaaatat caagaatatt ataggtttct ccctgaaaaa tacaagtcct ttatagaatc   2580
tttgagctgc tgaagcattt tgcagctttg aaattctgtg ttggaattct tttctcctac   2640
agtcctatta gaggagggat cttctctgta tgtgtaaata gcgagtttga atgctagtgg   2700
aagctccttt gaccatgttt tgttgtgcga gcatttaaga gagtgaagag aatgcttctt   2760
tggtgctgtt ctggtatgga aggatccaca gataaaattc aggagaatat agtagtggcc   2820
aaggttggtg acggtgatgg tggcatgtga tcccccagat cttcagtgac ccagagagga   2880
ggggacggcg cgtggtgagc tacaaggcat actcagtgga gggcaagatc aaggcctccc   2940
gtccgtaggg gactccgctg catcaaggcc aactgctccg aactgatcaa tttctggtgc   3000
agacaggtgc ttgcggtcag gttaaagaag ttggcaaaaa tgcttctgaa gaaaggttaa   3060
ttgttgtttc atctcaggag attccagatg atccagtgtc tccaacaatt gaggcgctta   3120
ttttgctcca tagtaaagta agtacacttg ctgagaacca ccagttgaca acacggcttg   3180
ttgtaccatc aaacaaagtt ggttgtattc ttggggaagg tggaaaggta attactgaaa   3240
tgagaagacg gactggggct gaaatccgag tctactcaaa agcagataaa cctaagtacc   3300
tgtcttttga tgaggagctt gtgcaggttg ctgggcttcc agctattgaa agaggagccc   3360
tgacagagat tgcttcgagg ctttgaacta ggacactcag agatggaagt tcttccaata   3420
atccgacacc ttttgcccct gttgatggtc ctcctgttga tatcttgcct aacaaggaat   3480
tcatgctata tggacgatct gctaatagtc ccccatatgg agggcctgct aatgatccac   3540
catatggaag acctgccatt gatccaccat atggaagacc aatatccaca atatggaaga   3600
cctgccaatg atccaccata tagaagacct gtcaatgata catcatattg agggttgaac   3660
aatgatgggc ctcgtgatca ggcccggtcc tgaggggggt cgaatggggc gatcgctccg   3720
ggccccccga ttcccagggc ccccacctat ctgtgcaacg agtagtagcg atcttccagc   3780
gcgcaacgtg aggcgatgtt tctccgtgat ttcgccggcc tgcaactgcg agatcgcgag   3840
tataacgatc agccgatcga tctcatctgc cgactgccat gctgatgcca cacgcaagcg   3900
cagcatatca gccttatctt ggttgatcgg catgctggac gagcacatct gttgtcgcat   3960
caactgctga ctgctatata tgtgctggtg ctgaatcgat cgattgtcgt cacggaagtg   4020
aagaacaacc acggcactgc tgcctgctgg gctctagccg ccatcagctg cggagctgat   4080
ccatggacgt gaggattacc gaagactgtc aggtctcact gggtatccag gtggctctgt   4140
cgaattgtgg attccaaata gttaactgga gtctgtcatt ggtgttggtg gtgtcaatct   4200
agctgagatc cgtctggtat agcgtaagag aaacatcatg cactatcccc agtcataacc   4260
```

-continued

```
atgccccaat ggccaccaat agttttcctc gtgaaaatct ccccttgatc ccagatctct   4320
ggtgcgagag tgaagttgca cgaagcccat cctggttctt ccgagtccat tgtggagatc   4380
cagggcattc cggatcaagt gaaagccgca cagagccttc tgcaaggctt catcggcgca   4440
agcagcaaca gcaggcaggc gccccagtcc tctcgcatgg cccattattt ttagtaagct   4500
ggaggacatt cgcaacaggg gggtcagtgg tcactgcaaa gctgagtttg ttcttcagtt   4560
caactgcaga aaattgcaga tcggttgccg tagttgctag aacggtacat agttgccacc   4620
taactgtagc gagtggcata acttattgtg tgttactgcc caatgttgtc tctccttgtg   4680
ttcatggatt cagacttgtg attgtagtat ttctggatca gactggagta aaagaaaaaa   4740
aaaaaggaag acatgggttt aacagtaagc tcaaaacgtt gacagtagta aaataaaagg   4800
ggtttgttca ctttatttcc aatatcaacc ttaccaacat ttggcgttga atcatttata   4860
ccacatcgct tgtgcagctg aatttggggc tgtttaaaag atggtctctt ggattgctaa   4920
ttgcctcgcg gcaagcgtgg taccttgtac aatataaata taattataac tatttaattt   4980
cataaaaaaa aaaaaaaaaa aaaaa                                         5005
```

<210> SEQ ID NO 72
<211> LENGTH: 4978
<212> TYPE: DNA
<213> ORGANISM: rice

<400> SEQUENCE: 72

```
gcgatctccc tgccccgacg tcgccggccg atctctcatt ctctccacgc cctgctcgtc     60
gccgatctcc tacaccatcc ctgccatctc ctccttcccc tcccctctat cctccactgg    120
tgccgcccac ctctccgtat aagacaaact gcgttgcggc gttggtttcc gccggcgctg    180
ctgctgcacc tgtcagctag ggcgggcatg gcgcgccgcg ccgcttcccg cgctgttggc    240
gcccttcgct cggacggctc gatccaaggg cgaggaggcc gcgcgggggg cagtggcgcc    300
gaggacgcac gccacgtgtt cgacgaattg ctccgccgtg gcaggggcgc ctcgatctac    360
ggcttgaacc gcgccctcgc cgacgtcgcg cgtgacagcc ccgcggccgc cgtgtcccgc    420
tacaaccgca tggcccgagc cggcgccgac gaggtaactc ccgacttgtg cacctacggc    480
attctcatcg gttgctgctg ccgcgcgggc cgcttggacc tcggtttcgc ggccttgggc    540
aatgtcatta agaagggatt tagagtggac gccatcgcct tcactcctct gctcaagggc    600
ctctgtgccg acaagaggac gagcgacgca atggacatag tgctccgcag aatgaccgag    660
ctcggctgca taccaaatgt cttctcctac aatattcttc tcaaggggct gtgtgatgag    720
aacagaagcc aagaagctct cgagctgctg cacatgatgg ctgatgatcg aggaggaggt    780
agcccacctg atgtggtgtc gtataccact gtcatcaatg gcttcttcaa agagggggat    840
tcagacaaag cttacagtac ataccatgaa atgctggacc gggggatttt acctgatgtt    900
gtgacctaca actctattat tgctgcgtta tgcaaggctc aagctatgga caaagccatg    960
gaggtactta acaccatggt taagaatggt gtcatgcctg attgcatgac atataatagt   1020
attctgcatg gatattgctc ttcagggcag ccgaaagagg ctattggatt tctcaaaaag   1080
atgcgcagtg atggtgtcga accagatgtt gttacttata gcttgctcat ggattatctt   1140
tgcaagaacg gaagatgcat ggaagctaga aagatttttcg attctatgac caagaggggc   1200
ctaaagcctg aaattactac ctatggtacc ctgcttcagg ggtatgctac caaaggagcc   1260
cttgttgaga tgcatggtct cttggatttg atggtacgaa acggtatcca ccctgatcat   1320
```

-continued

```
tatgttttca gcattctaat atgtgcatac gctaaacaag ggaaagtaga tcaggcaatg   1380
cttgtgttca gcaaaatgag gcagcaagga ttgaatccga atgcagtgac gtatggagca   1440
gttataggca tactttgcaa gtcaggcaga gtagaagatg ctatgcttta ttttgagcag   1500
atgatcgatg aaggactaag ccctggcaac attgtttata actccctaat tcatggtttg   1560
tgcacctgta acaaatggga gagggctgaa gagttaattc ttgaaatgtt ggatcgaggc   1620
atctgtctga acactatttt ctttaattca ataattgaca gtcattgcaa agaagggagg   1680
gttatagaat ctgaaaaact ctttgagctg atggtacgta ttggtgtgaa gcccaatgtc   1740
attacctaca atactcttat caatggatat tgcttggcag gtaagatgga tgaagcaatg   1800
aagttacttt ctggcatggt ctcagttggg ttgaaaccta atactgttac ttatagcact   1860
ttgattaatg gctactgcaa aattagtagg atggaagacg cgttagttct ttttaaggag   1920
atggagagca gtggtgttag tcctgatatt attacgtata acataattct gcaaggttta   1980
tttcaaacca gaagaactgc tgctgcaaaa gaactctatg ttaggattac cgaaagtgga   2040
acgcagattg aacttagcac atacaacata atccttcatg gactttgcaa aaacaaactc   2100
actgatgatg cacttcagat gtttcagaac ctatgtttga tggatttgaa gcttgaggct   2160
aggactttca acattatgat tgatgcattg cttaaagttg gcagaaatga tgaagccaag   2220
gatttgtttg ttgctttctc gtctaacggt ttagtgccga attattggac gtacaggttg   2280
atggctgaaa atattatagg acaggggttg ctagaagaat tggatcaact ctttctttca   2340
atggaggaca atggctgtac tgttgactct ggcatgctaa atttcattgt tagggaactg   2400
ttgcagagag gtgagataac cagggctggc acttaccttt ccatgattga tgagaagcac   2460
ttttccctcg aagcatccac tgcttccttg tttatagatc ttttgtctgg gggaaaatat   2520
caagaatatt ataggtttct ccctgaaaaa tacaagtcct ttatagaatc tttgagctgc   2580
tgaagcattt tgcagctttg aaattctgtg ttggaattct tttctcctac agtcctatta   2640
gaggagggat cttctctgta tgtgtaaata gcgagtttga atgctagtgg aagctccttt   2700
gaccatgttt tgttgtgcga gcatttaaga gagtgaagag aatgcttctt tggtgctgtt   2760
ctggtatgga aggatccaca gataaaattc aggttctact gcttctctgc ttgtaatttt   2820
catgaagctg cagtgaatac cttgttgacc acttgatctg ttgctttgaa ggagaatata   2880
gtagtggcca aggttggtga cggtgatggt ggcatgtgat cccccagatc ttcagtgacc   2940
cagagaggag gggacggcgc gtggtgagct acaaggcata ctcagtggag ggcaagatca   3000
aggcctcccg tccgtagggg actccgctgc atcaaggcca actgctccga actgatcaat   3060
ttctggtgca gacaggtgct tgcggtcagg ttaaagaagt tggcaaaaat gcttctgaag   3120
aaaggttaat tgttgtttca tctcaggaga ttccagatga tccagtgtct ccaacaattg   3180
aggcgcttat tttgctccat agtaaagtaa gtacacttgc tgagaaccac cagttgacaa   3240
cacggcttgt tgtaccatca aacaaagttg gttgtattct tggggaaggt ggaaaggtaa   3300
ttactgaaat gagaagacgg actggggctg aaatccgagt ctactcaaaa gcagataaac   3360
ctaagtacct gtcttttgat gaggagcttg tgcaggttgc tgggcttcca gctattgaaa   3420
gaggagccct gacagagatt gcttcgaggc tttgaactag gacactcaga gatggaagtt   3480
cttccaataa tccgacacct tttgcccctg ttgatggtcc tcctgttgat atcttgccta   3540
acaaggaatt catgctatat ggacgatctg ctaatagtcc cccatatgga gggcctgcta   3600
atgatccacc atatggaaga cctgccattg atccaccata tggaagacca atatccacaa   3660
tatggaagac ctgccaatga tccaccatat agaagacctg tcaatgatac atcatattga   3720
```

-continued

```
gggttgaaca atgatgggcc tcgtgatcag gcccggtcct gagggggggtc gaatggggcg   3780
atcgctccgg gcccccccgat tcccagggcc cccacctatc tgtgcaacga gtagtagcga   3840
tcttccagcg cgcaacgtga ggcgatgttt ctccgtgatt tcgccggcct gcaactgcga   3900
gatcgcgagt ataacgatca gccgatcgat ctcatctgcc gactgccatg ctgatgccac   3960
acgcaagcgc agcatatcag ccttatcttg gttgatcggc atgctggacg agcacatctg   4020
ttgtcgcatc aactgctgac tgctatatat gtgctggtgc tgaatcgatc gattgtcgtc   4080
acggaagtga agaacaacca cggcactgct gcctgctggg ctctagccgc catcagtaag   4140
ctgcggagct gatccatgga cgtgaggatt accgaagact gtcaggtctc actgggtatc   4200
caggtggctc tgtcgaattg tggattccaa atagttaact ggagtctgtc attggtgttg   4260
gtggtgtcaa tctagctgag atccgtctgg tatagcgtaa gagaaacatc atgcactatc   4320
cccagtcata accatgcccc aatggccacc aatagttttc ctcgtgaaaa tctccccttg   4380
atcccagatc tctggtgcga gagtgaagtt gcacgaagcc catcctggtt cttccgagtc   4440
cattgtggag atccagggca ttccggatca agtgaaagcc gcacagagcc ttctgcaagg   4500
cttcatcggc gcaagcagca acagcaggca ggcgccccag tcctctcgca tggcccatta   4560
tttttagtaa gctggaggac attcgcaaca ggggggtcag tggtcactgc aaagctgagt   4620
ttgttcttca gttcaactgc agaaaattgc agatcggttg ccgtagttgc tagaacggta   4680
catagttgcc acctaactgt agcgagtggc ataacttatt gtgtgttact gcccaatgtt   4740
gtctctcctt gtgttcatgg attcagactt gtgattgtag tatttctgga tcagactgga   4800
gtaaaagaaa aaaaaaaagg aagacatggg tttaacagta agctcaaaac gttgacagta   4860
gtaaaataaa aggggtttgt tcactttaaa aaaaaaaaaa aaaaaaaaaa aaaaaaaaaa   4920
aaaaaaaaaa aaaaaaaaaa aaaaaaaaaa aaaaaaaaaa aaaaaaaaaa aaaaaaaa     4978
```

<210> SEQ ID NO 73
<211> LENGTH: 4722
<212> TYPE: DNA
<213> ORGANISM: rice

<400> SEQUENCE: 73

```
cgccgatctc ctacaccatc cctgccatct cctccttccc ctcccctcta tcctccactg     60
gtgccgccca cctctccgta taagacaaac tgcgttgcgg cgttggtttc cgccggcgct    120
gctgctgcac ctgtcagcta gggcgggcat ggcgcgccgc gccgcttccc gcgctgttgg    180
cgccccttcgc tcggacggct cgatccaagg gcgaggaggc cgcgcggggg gcagtggcgc    240
cgaggacgca cgccacgtgt tcgacgaatt gctccgccgt ggcaggggcg cctcgatcta    300
cggcttgaac cgcgccctcg ccgacgtcgc gcgtgacagc cccgcggccg ccgtgtcccg    360
ctacaaccgc atggcccgag ccggcgccga cgaggtaact cccgacttgt gcacctacgg    420
cattctcatc ggttgctgct gccgcgcggg ccgcttggac ctcggtttcg cggccttggg    480
caatgtcatt aagaagggat ttagagtgga cgccatcgcc ttcactcctc tgctcaaggg    540
cctctgtgcc gacaagagga cgagcgacgc aatggacata gtgctccgca gaatgaccga    600
gctcggctgc ataccaaatg tcttctccta caatattctt ctcaaggggc tgtgtgatga    660
gaacagaagc caagaagctc tcgagctgct gcacatgatg gctgatgatc gaggaggagg    720
tagcccacct gatgtggtgt cgtataccac tgtcatcaat ggcttcttca aagaggggga    780
ttcagacaaa gcttacagta cataccatga aatgctggac cgggggattt tacctgatgt    840
```

-continued

```
tgtgacctac aactctatta ttgctgcgtt atgcaaggct caagctatgg acaaagccat    900
ggaggtactt aacaccatgg ttaagaatgg tgtcatgcct gattgcatga catataatag    960
tattctgcat ggatattgct cttcagggca gccgaaagag gctattggat ttctcaaaaa   1020
gatgcgcagt gatggtgtcg aaccagatgt tgttacttat agcttgctca tggattatct   1080
ttgcaagaac ggaagatgca tggaagctag aaagattttc gattctatga ccaagagggg   1140
cctaaagcct gaaattacta cctatggtac cctgcttcag ggtatgcta ccaaaggagc    1200
ccttgttgag atgcatggtc tcttggattt gatggtacga aacggtatcc accctgatca   1260
ttatgttttc agcattctaa tatgtgcata cgctaaacaa gggaaagtag atcaggcaat   1320
gcttgtgttc agcaaaatga ggcagcaagg attgaatccg aatgcagtga cgtatggagc   1380
agttataggc atactttgca agtcaggcag agtagaagat gctatgcttt attttgagca   1440
gatgatcgat gaaggactaa gccctggcaa cattgtttat aactccctaa ttcatggttt   1500
gtgcacctgt aacaaatggg agagggctga agagttaatt cttgaaatgt tggatcgagg   1560
catctgtctg aacactattt tctttaattc aataattgac agtcattgca aagaagggag   1620
ggttatagaa tctgaaaaac tctttgagct gatggtacgt attggtgtga agcccaatgt   1680
cattacctac aatactctta tcaatggata ttgcttggca ggtaagatgg atgaagcaat   1740
gaagttactt tctggcatgg tctcagttgg gttgaaacct aatactgtta cttatagcac   1800
tttgattaat ggctactgca aaattagtag gatggaagac gcgttagttc tttttaagga   1860
gatggagagc agtggtgtta gtcctgatat tattacgtat aacataattc tgcaaggttt   1920
atttcaaacc agaagaactg ctgctgcaaa agaactctat gttaggatta ccgaaagtgg   1980
aacgcagatt gaacttagca catacaacat aatccttcat ggactttgca aaaacaaact   2040
cactgatgat gcacttcaga tgtttcagaa cctatgtttg atggatttga agcttgaggc   2100
taggactttc aacattatga ttgatgcatt gcttaaagtt ggcagaaatg atgaagccaa   2160
ggatttgttt gttgctttct cgtctaacgg tttagtgccg aattattgga cgtacaggtt   2220
gatggctgaa aatattatag gacaggggtt gctagaagaa ttggatcaac tctttctttc   2280
aatggaggac aatggctgta ctgttgactc tggcatgcta aatttcattg ttagggaact   2340
gttgcagaga ggtgagataa ccagggctgg cacttacctt tccatgattg atgagaagca   2400
cttttccctc gaagcatcca ctgcttcctt gtttatagat cttttgtctg gggaaaata    2460
tcaagaatat tataggtttc tccctgaaaa atacaagtcc tttatagaat ctttgagctg   2520
ctgaagcatt ttgcagcttt gaaattctgt gttggaattc ttttctccta cagtcctatt   2580
agaggaggga tcttctctgt atgtgtaaat agcgagtttg aatgctagtg gaagctcctt   2640
tgaccatgtt ttgttgtgcg agcatttaag agagtgaaga gaatgcttct ttggtgctgt   2700
tctggtatgg aaggatccac agataaaatt caggttctac tgcttctctg cttgtaattt   2760
tcatgaagct gcagtgaata ccttgttgac cacttgatct gttgctttga aggagaatat   2820
agtagtggcc aaggttggtg acggtgatgg tggcatgtga tcccccagat cttcagtgac   2880
ccagagagga ggggacggcg cgtggtgagc tacaaggcat actcagtgga gggcaagatc   2940
aaggcctccc gtccgtaggg gactccgctg catcaaggcc aactgctccg aactgatcaa   3000
tttctggtgc agacaggtgc ttgcggtcag gttaaagaag ttggcaaaaa tgcttctgaa   3060
gaaaggttaa ttgttgtttc atctcaggag attccagatg atccagtgtc tccaacaatt   3120
gaggcgctta ttttgctcca tagtaaagtg gaaaggtaat tactgaaatg agaagacgga   3180
ctggggctga aatccgagtc tactcaaaag cagataaacc taagtacctg tcttttgatg   3240
```

-continued

```
aggagcttgt gcaggttgct gggcttccag ctattgaaag aggagccctg acagagattg   3300

cttcgaggct ttgaactagg acactcagag atggaagttc ttccaataat ccgacacctt   3360

ttgcccctgt tgatggtcct cctgttgata tcttgcctaa caaggaattc atgctatatg   3420

gacgatctgc taatagtccc ccatatggag ggcctgctaa tgatccacca tatggaagac   3480

ctgccattga tccaccatat ggaagaccaa tatccacaat atggaagacc tgccaatgat   3540

ccaccatata gaagacctgt caatgataca tcatattgag ggttgaacaa tgatgggcct   3600

cgtgatcagg cccggtcctg aggggggtcg aatggggcga tcgctccggg ccccccgatt   3660

cccagggccc ccacctatct gtgcaacgag tagtagcgat cttccagcgc gcaacgtgag   3720

gcgatgtttc tccgtgattt cgccggcctg caactgcgag atcgcgagta taacgatcag   3780

ccgatcgatc tcatctgccg actgccatgc tgatgccaca cgcaagcgca gcatatcagc   3840

cttatcttgg ttgatcggca tgctggacga gcacatctgt tgtcgcatca actgctgact   3900

gctatatatg tgctggtgct gaatcgatcg attgtcgtca cggaagtgaa gaacaaccac   3960

ggcactgctg cctgctgggc tctagccgcc atcagctgcg gagctgatcc atggacgtga   4020

ggattaccga agactgtcag gtctcactgg gtatccaggt ggctctgtcg aattgtggat   4080

tccaaatagt taactggagt ctgtcattgg tgttggtggt gtcaatctag ctgagatccg   4140

tctggtatag cgtaagagaa acatcatgca ctatccccag tcataaccat gccccaatgg   4200

ccaccaatag ttttcctcgt gaaaatctcc ccttgatccc agatctctgg tgcgagagtg   4260

aagttgcacg aagcccatcc tggttcttcc gagtccattg tggagatcca gggcattccg   4320

gatcaagtga aagccgcaca gagccttctg caaggcttca tcggcgcaag cagcaacagc   4380

aggcaggcgc cccagtcctc tcgcatggcc cattattttt agtaagctgg aggacattcg   4440

caacaggggg gtcagtggtc actgcaaagc tgagtttgtt cttcagttca actgcagaaa   4500

attgcagatc ggttgccgta gttgctagaa cggtacatag ttgccaccta actgtagcga   4560

gtggcataac ttattgtgtg ttactgccca atgttgtctc tccttgtgtt catggattca   4620

gacttgtgat tgtagtattt ctggatcaga ctggagtaaa agaaaaaaaa aaaggaagac   4680

atgggtttaa cagtaaaaaa aaaaaaaaaa aaaaaaaaaa aa                      4722
```

<210> SEQ ID NO 74
<211> LENGTH: 6164
<212> TYPE: DNA
<213> ORGANISM: rice

<400> SEQUENCE: 74

```
cgcagaagag atcgatcgcg atctccctgc cccgacgtcg ccggccgatc tctcattctc     60

tccacgccct gctcgtcgcc gatctcctac accatccctg ccatctcctc cttcccctcc    120

cctctatcct ccactggtgc cgcccacctc tccgtataag acaaactgcg ttgcggcgtt    180

ggtttccgcc ggcgctgctg ctgcacctgt cagctagggc gggcatggcg cgccgcgccg    240

cttcccgcgc tgttggcgcc cttcgctcgg acggctcgat ccaagggcga ggaggccgcg    300

cggggggcag tggcgccgag gacgcacgcc acgtgttcga cgaattgctc cgccgtggca    360

ggggcgcctc gatctacggc ttgaaccgcg ccctcgccga cgtcgcgcgt gacagccccg    420

cggccgccgt gtcccgctac aaccgcatgg cccgagccgg cgccgacgag gtaactcccg    480

acttgtgcac ctacggcatt ctcatcggtt gctgctgccg cgcgggccgc ttggacctcg    540

gtttcgcggc cttgggcaat gtcattaaga agggatttag agtggacgcc atcgccttca    600
```

-continued

```
ctcctctgct caagggcctc tgtgccgaca agaggacgag cgacgcaatg gacatagtgc    660
tccgcagaat gaccgagctc ggctgcatac caaatgtctt ctcctacaat attcttctca    720
aggggctgtg tgatgagaac agaagccaag aagctctcga gctgctgcac atgatggctg    780
atgatcgagg aggaggtagc ccacctgatg tggtgtcgta taccactgtc atcaatggct    840
tcttcaaaga gggggattca gacaaagctt acagtacata ccatgaaatg ctggaccggg    900
ggattttacc tgatgttgtg acctacaact ctattattgc tgcgttatgc aaggctcaag    960
ctatggacaa agccatggag gtacttaaca ccatggttaa gaatggtgtc atgcctgatt   1020
gcatgacata taatagtatt ctgcatggat attgctcttc agggcagccg aaagaggcta   1080
ttggatttct caaaaagatg cgcagtgatg gtgtcgaacc agatgttgtt acttatagct   1140
tgctcatgga ttatctttgc aagaacggaa gatgcatgga agctagaaag attttcgatt   1200
ctatgaccaa gaggggccta aagcctgaaa ttactaccta tggtaccctg cttcaggggt   1260
atgctaccaa aggagccctt gttgagatgc atggtctctt ggatttgatg gtacgaaacg   1320
gtatccaccc tgatcattat gttttcagca ttctaatatg tgcatacgct aaacaaggga   1380
aagtagatca ggcaatgctt gtgttcagca aaatgaggca gcaaggattg aatccgaatg   1440
cagtgacgta tggagcagtt ataggcatac tttgcaagtc aggcagagta gaagatgcta   1500
tgctttattt tgagcagatg atcgatgaag gactaagccc tggcaacatt gtttataact   1560
ccctaattca tggtttgtgc acctgtaaca aatgggagag ggctgaagag ttaattcttg   1620
aaatgttgga tcgaggcatc tgtctgaaca ctattttctt taattcaata attgacagtc   1680
attgcaaaga agggagggtt atagaatctg aaaaactctt tgagctgatg gtacgtattg   1740
gtgtgaagcc caatgtcatt acctacaata ctcttatcaa tggatattgc ttggcaggta   1800
agatggatga agcaatgaag ttactttctg gcatggtctc agttgggttg aaacctaata   1860
ctgttactta tagcactttg attaatggct actgcaaaat tagtaggatg gaagacgcgt   1920
tagttctttt taaggagatg gagagcagtg gtgttagtcc tgatattatt acgtataaca   1980
taattctgca aggtttattt caaaccagaa gaactgctgc tgcaaaagaa ctctatgtta   2040
ggattaccga aagtggaacg cagattgaac ttagcacata caacataatc cttcatggac   2100
tttgcaaaaa caaactcact gatgatgcac ttcagatgtt tcagaaccta tgtttgatgg   2160
atttgaagct tgaggctagg actttcaaca ttatgattga tgcattgctt aaagttggca   2220
gaaatgatga agccaaggat ttgtttgttg ctttctcgtc taacggttta gtgccgaatt   2280
attggacgta caggttgatg gctgaaaata ttataggaca ggggttgcta gaagaattgg   2340
atcaactctt tctttcaatg gaggacaatg gctgtactgt tgactctggc atgctaaatt   2400
tcattgttag ggaactgttg cagagaggtg agataaccag ggctggcact tacctttcca   2460
tgattgatga gaagcacttt tccctcgaag catccactgc ttccttgttt atagatcttt   2520
tgtctggggg aaaatatcaa gaatattata ggtttctccc tgaaaaatac aagtccttta   2580
tagaatcttt gagctgctga agcattttgc agctttgaaa ttctgtgttg gaattctttt   2640
ctcctacagt cctattagag gagggatctt ctctgtatgt gtaaatagcg aggtatgtat   2700
gccacctctc cgaattattt ttactgtggt tcctagactg taaacaagca attatgttat   2760
gctgttgatg ccagaaaaaa cataaaagtt tgtcgttatc tctactaacg gatcataaag   2820
ggatttgtga ctggagtttc aaacttaatg tgtctaggca gtaattttga cattagatcc   2880
aaaacaattt atagggtttc attaaatttc atctatgtgt actgtttagg tgttgaatag   2940
tttgacttgt tttttaactg aacaaaagat atgtctgaag ctttgttctt taccaaatgc   3000
```

-continued

```
agtactgatc atcacaatat attttttatg gaacaagatt ggattgtata gaatggtttc   3060
tgatctgatt atcttatctc aacgtattat tatgcacatg tactaatcat gaaatatctg   3120
atggaatgat gtttctattt acctgtgtga ggcagcaagg agtgagatgg ataacaccac   3180
atactccctc tgtcccagaa tataagaagt tttagagttg gacacgatta ttaagaaagt   3240
aggtagaagt gagtagtgga gggttgtgat tgcatgagta gtggaggtag gtgggaaaag   3300
tgaatggtgg agggttgtga ttggttggga agagaatgtt ggtagagaag ttgttatatt   3360
ttggggagta cattattatt ctagaacaat actgttgtgc tcaagaagcg ttccaaagat   3420
gtttcacaac ctgtgctcga tgggttttga gcttaatcct gggacattca gtatcatgat   3480
ctgtctcatt cttaaacatg gaataaagga tgacagcatg atttctttgt ctctataatc   3540
ttttggctac ccacagataa tagctgtaaa tctatactac tttaaaagga gtagtggtgg   3600
tggtgagtgg tgaatctgcc accaccccac caccaactct caaaattctg acatgtggga   3660
tcactgtcaa tcccttctcc aagacatgtg ggatcactgt caatcccttc tccaaaccaa   3720
ttgtatgata gaacagtgga aatcacggac agaccatgga gctctcaacc ataatcatcc   3780
ttgcgagtta ataacaaatg gagcgtaaac ttggcaagca aaaaactcaa attaattcta   3840
aaattaagct ctaggattca aaatagattt cctctctgca ttgtgctgtt atgattttta   3900
attccgtaac aacgcaaatg cattttgcta gtcttataaa gaagggttaa tgcaaatatt   3960
ctgattaaat gattgtatct atgaagtttg aatgctagtg gaagctcctt tgaccatgtt   4020
ttgttgtgcg agcatttaag agagtgaaga gaatgcttct ttggtgctgt tctggtatgg   4080
aaggatccac agataaaatt caggttctac tgcttctctg cttgtaattt tcatgaagct   4140
gcagtgaata ccttgttgac cacttgatct gttgctttga aggagaatat agtagtggcc   4200
aaggttggtg acggtgatgg tggcatgtga tcccccagat cttcagtgac ccagagagga   4260
ggggacggcg cgtggtgagc tacaaggcat actcagtgga gggcaagatc aaggcctccc   4320
gtccgtaggg gactccgctg catcaaggcc aactgctccg aactgatcaa tttctggtgc   4380
agacaggtgc ttgcggtcag gttaaagaag ttggcaaaaa tgcttctgaa gaaaggttaa   4440
ttgttgtttc atctcaggag attccagatg atccagtgtc tccaacaatt gaggcgctta   4500
ttttgctcca tagtaaagta agtacacttg ctgagaacca ccagttgaca acacggcttg   4560
ttgtaccatc aaacaaagtt ggttgtattc ttggggaagg tggaaaggta attactgaaa   4620
tgagaagacg gactggggct gaaatccgag tctactcaaa agcagataaa cctaagtacc   4680
tgtcttttga tgaggagctt gtgcaggttg ctgggcttcc agctattgaa agaggagccc   4740
tgacagagat tgcttcgagg ctttgaacta ggacactcag agatggaagt tcttccaata   4800
atccgacacc ttttgcccct gttgatggtc ctcctgttga tatcttgcct aacaaggaat   4860
tcatgctata tggacgatct gctaatagtc ccccatatgg agggcctgct aatgatccac   4920
catatggaag acctgccatt gatccaccat atggaagacc aatatccaca atatggaaga   4980
cctgccaatg atccaccata tagaagacct gtcaatgata catcatattg agggttgaac   5040
aatgatgggc ctcgtgatca ggcccggtcc tgaggggggt cgaatggggc gatcgctccg   5100
ggccccccga ttcccagggc ccccacctat ctgtgcaacg agtagtagcg atcttccagc   5160
gcgcaacgtg aggcgatgtt tctccgtgat ttcgccggcc tgcaactgcg agatcgcgag   5220
tataacgatc agccgatcga tctcatctgc cgactgccat gctgatgcca cacgcaagcg   5280
cagcatatca gccttatctt ggttgatcgg catgctggac gagcacatct gttgtcgcat   5340
```

-continued

```
caactgctga ctgctatata tgtgctggtg ctgaatcgat cgattgtcgt cacggaagtg   5400

aagaacaacc acggcactgc tgcctgctgg gctctagccg ccatcagctg cggagctgat   5460

ccatggacgt gaggattacc gaagactgtc aggtctcact gggtatccag gtggctctgt   5520

cgaattgtgg attccaaata gttaactgga gtctgtcatt ggtgttggtg gtgtcaatct   5580

agctgagatc cgtctggtat agcgtaagag aaacatcatg cactatcccc agtcataacc   5640

atgccccaat ggccaccaat agttttcctc gtgaaaatct ccccttgatc ccagatctct   5700

ggtgcgagag tgaagttgca cgaagcccat cctggttctt ccgagtccat tgtggagatc   5760

cagggcattc cggatcaagt gaaagccgca cagagccttc tgcaaggctt catcggcgca   5820

agcagcaaca gcaggcaggc gccccagtcc tctcgcatgg cccattattt ttagtaagct   5880

ggaggacatt cgcaacaggg gggtcagtgg tcactgcaaa gctgagtttg ttcttcagtt   5940

caactgcaga aaattgcaga tcggttgccg tagttgctag aacggtacat agttgccacc   6000

taactgtagc gagtggcata acttattgtg tgttactgcc caatgttgtc tctccttgtg   6060

ttcatggatt cagacttgtg attgtagtat ttctggatca gactggagta aaagaaaaaa   6120

aaaaaggaag acatgggttt aacagtaaaa aaaaaaaaaa aaaa                    6164
```

```
<210> SEQ ID NO 75
<211> LENGTH: 791
<212> TYPE: PRT
<213> ORGANISM: rice

<400> SEQUENCE: 75

Met Ala Arg Arg Ala Ala Ser Arg Ala Val Gly Ala Leu Arg Ser
  1               5                  10                  15

Asp Gly Ser Ile Gln Gly Arg Gly Gly Arg Ala Gly Gly Ser Gly
                 20                  25                  30

Ala Glu Asp Ala Arg His Val Phe Asp Glu Leu Leu Arg Arg Gly
                 35                  40                  45

Arg Gly Ala Ser Ile Tyr Gly Leu Asn Arg Ala Leu Ala Asp Val
                 50                  55                  60

Ala Arg Asp Ser Pro Ala Ala Ala Val Ser Arg Tyr Asn Arg Met
                 65                  70                  75

Ala Arg Ala Gly Ala Asp Glu Val Thr Pro Asp Leu Cys Thr Tyr
                 80                  85                  90

Gly Ile Leu Ile Gly Cys Cys Cys Arg Ala Gly Arg Leu Asp Leu
                 95                 100                 105

Gly Phe Ala Ala Leu Gly Asn Val Ile Lys Lys Gly Phe Arg Val
                110                 115                 120

Asp Ala Ile Ala Phe Thr Pro Leu Leu Lys Gly Leu Cys Ala Asp
                125                 130                 135

Lys Arg Thr Ser Asp Ala Met Asp Ile Val Leu Arg Arg Met Thr
                140                 145                 150

Glu Leu Gly Cys Ile Pro Asn Val Phe Ser Tyr Asn Ile Leu Leu
                155                 160                 165

Lys Gly Leu Cys Asp Glu Asn Arg Ser Gln Glu Ala Leu Glu Leu
                170                 175                 180

Leu His Met Met Ala Asp Asp Arg Gly Gly Gly Ser Pro Pro Asp
                185                 190                 195

Val Val Ser Tyr Thr Thr Val Ile Asn Gly Phe Phe Lys Glu Gly
                200                 205                 210

Asp Ser Asp Lys Ala Tyr Ser Thr Tyr His Glu Met Leu Asp Arg
```

-continued

```
                215                 220                 225

Gly Ile Leu Pro Asp Val Val Thr Tyr Asn Ser Ile Ile Ala Ala
                230                 235                 240

Leu Cys Lys Ala Gln Ala Met Asp Lys Ala Met Glu Val Leu Asn
                245                 250                 255

Thr Met Val Lys Asn Gly Val Met Pro Asp Cys Met Thr Tyr Asn
                260                 265                 270

Ser Ile Leu His Gly Tyr Cys Ser Ser Gly Gln Pro Lys Glu Ala
                275                 280                 285

Ile Gly Phe Leu Lys Lys Met Arg Ser Asp Gly Val Glu Pro Asp
                290                 295                 300

Val Val Thr Tyr Ser Leu Leu Met Asp Tyr Leu Cys Lys Asn Gly
                305                 310                 315

Arg Cys Met Glu Ala Arg Lys Ile Phe Asp Ser Met Thr Lys Arg
                320                 325                 330

Gly Leu Lys Pro Glu Ile Thr Thr Tyr Gly Thr Leu Leu Gln Gly
                335                 340                 345

Tyr Ala Thr Lys Gly Ala Leu Val Glu Met His Gly Leu Leu Asp
                350                 355                 360

Leu Met Val Arg Asn Gly Ile His Pro Asp His Tyr Val Phe Ser
                365                 370                 375

Ile Leu Ile Cys Ala Tyr Ala Lys Gln Gly Lys Val Asp Gln Ala
                380                 385                 390

Met Leu Val Phe Ser Lys Met Arg Gln Gln Gly Leu Asn Pro Asn
                395                 400                 405

Ala Val Thr Tyr Gly Ala Val Ile Gly Ile Leu Cys Lys Ser Gly
                410                 415                 420

Arg Val Glu Asp Ala Met Leu Tyr Phe Glu Gln Met Ile Asp Glu
                425                 430                 435

Gly Leu Ser Pro Gly Asn Ile Val Tyr Asn Ser Leu Ile His Gly
                440                 445                 450

Leu Cys Thr Cys Asn Lys Trp Glu Arg Ala Glu Glu Leu Ile Leu
                455                 460                 465

Glu Met Leu Asp Arg Gly Ile Cys Leu Asn Thr Ile Phe Phe Asn
                470                 475                 480

Ser Ile Ile Asp Ser His Cys Lys Glu Gly Arg Val Ile Glu Ser
                485                 490                 495

Glu Lys Leu Phe Glu Leu Met Val Arg Ile Gly Val Lys Pro Asn
                500                 505                 510

Val Ile Thr Tyr Asn Thr Leu Ile Asn Gly Tyr Cys Leu Ala Gly
                515                 520                 525

Lys Met Asp Glu Ala Met Lys Leu Leu Ser Gly Met Val Ser Val
                530                 535                 540

Gly Leu Lys Pro Asn Thr Val Thr Tyr Ser Thr Leu Ile Asn Gly
                545                 550                 555

Tyr Cys Lys Ile Ser Arg Met Glu Asp Ala Leu Val Leu Phe Lys
                560                 565                 570

Glu Met Glu Ser Ser Gly Val Ser Pro Asp Ile Ile Thr Tyr Asn
                575                 580                 585

Ile Ile Leu Gln Gly Leu Phe Gln Thr Arg Arg Thr Ala Ala Ala
                590                 595                 600

Lys Glu Leu Tyr Val Arg Ile Thr Glu Ser Gly Thr Gln Ile Glu
                605                 610                 615
```

-continued

```
Leu Ser Thr Tyr Asn Ile Ile Leu His Gly Leu Cys Lys Asn Lys
                620                 625                 630

Leu Thr Asp Asp Ala Leu Gln Met Phe Gln Asn Leu Cys Leu Met
                635                 640                 645

Asp Leu Lys Leu Glu Ala Arg Thr Phe Asn Ile Met Ile Asp Ala
                650                 655                 660

Leu Leu Lys Val Gly Arg Asn Asp Glu Ala Lys Asp Leu Phe Val
                665                 670                 675

Ala Phe Ser Ser Asn Gly Leu Val Pro Asn Tyr Trp Thr Tyr Arg
                680                 685                 690

Leu Met Ala Glu Asn Ile Ile Gly Gln Gly Leu Leu Glu Glu Leu
                695                 700                 705

Asp Gln Leu Phe Leu Ser Met Glu Asp Asn Gly Cys Thr Val Asp
                710                 715                 720

Ser Gly Met Leu Asn Phe Ile Val Arg Glu Leu Leu Gln Arg Gly
                725                 730                 735

Glu Ile Thr Arg Ala Gly Thr Tyr Leu Ser Met Ile Asp Glu Lys
                740                 745                 750

His Phe Ser Leu Glu Ala Ser Thr Ala Ser Leu Phe Ile Asp Leu
                755                 760                 765

Leu Ser Gly Gly Lys Tyr Gln Glu Tyr Tyr Arg Phe Leu Pro Glu
                770                 775                 780

Lys Tyr Lys Ser Phe Ile Glu Ser Leu Ser Cys
                785                 790 791
```

<210> SEQ ID NO 76
<211> LENGTH: 24
<212> TYPE: DNA
<213> ORGANISM: Artificial Sequence
<220> FEATURE:
<223> OTHER INFORMATION: Synthetic oligonucleotide primer for amplification

<400> SEQUENCE: 76
tctcattctc tccacgccct gctc 24

<210> SEQ ID NO 77
<211> LENGTH: 24
<212> TYPE: DNA
<213> ORGANISM: Artificial Sequence
<220> FEATURE:
<223> OTHER INFORMATION: Synthetic oligonucleotide primer for amplification

<400> SEQUENCE: 77
acggcggagc aattcgtcga acac 24

<210> SEQ ID NO 78
<211> LENGTH: 24
<212> TYPE: DNA
<213> ORGANISM: Artificial Sequence
<220> FEATURE:
<223> OTHER INFORMATION: Synthetic oligonucleotide primer for amplification

<400> SEQUENCE: 78
agtgtgtggc atggtgcatt tccg 24

<210> SEQ ID NO 79
<211> LENGTH: 24

-continued

<212> TYPE: DNA
<213> ORGANISM: Artificial Sequence
<220> FEATURE:
<223> OTHER INFORMATION: Synthetic oligonucleotide primer for amplification

<400> SEQUENCE: 79
ctctacagga tacacggtgt aagg 24

<210> SEQ ID NO 80
<211> LENGTH: 4746
<212> TYPE: DNA
<213> ORGANISM: rice

<400> SEQUENCE: 80
gccgcgcaga agagatcgat cgcgatctcc ctgccccgac gtcgccggcc gatctctcat 60
tctctccacg ccctgctcgt cgccgatctc ctacaccatc cctgccatct cctccttccc 120
ctcccctcta tcctccactg gtgccgccca cctctccgta taagacaaac tgcgttgcgg 180
cgttggtttc cgccggcgct gctgctgcac ctgtcagcta gggcgggcat ggcgcgccgc 240
gccgcttccc gcgctgttgg cgcccttcgc tcggacggct cgatccaagg gcgaggaggc 300
cgcgcggggg gcagtggcgc cgaggacgca cgccacgtgt tcgacgaatt gctccgccgt 360
ggcaggggcg cctcgatcta cggcttgaac cgcgccctcg ccgacgtcgc gcgtgacagc 420
cccgcggccg ccgtgtcccg ctacaaccgc atggcccgag ccggcgccga cgaggtaact 480
cccgacttgt gcacctacgg cattctcatc ggttgctgct gccgcgcggg ccgcttggac 540
ctcggtttcg cggccttggg caatgtcatt aagaagggat ttagagtgga cgccatcgcc 600
ttcactcctc tgctcaaggg cctctgtgcc gacaagagga cgagcgacgc aatggacata 660
gtgctccgca gaatgaccga gctcggctgc ataccaaatg tcttctccta caatattctt 720
ctcaaggggc tgtgtgatga gaacagaagc caagaagctc tcgagctgct gcacatgatg 780
gctgatgatc gaggaggagg tagcccacct gatgtggtgt cgtataccac tgtcatcaat 840
ggcttcttca aagaggggga ttcagacaaa gcttacagta cataccatga aatgctggac 900
cgggggattt tacctgatgt tgtgacctac aactctatta ttgctgcgtt atgcaaggct 960
caagctatgg acaaagccat ggaggtactt aacaccatgg ttaagaatgg tgtcatgcct 1020
gattgcatga catataatag tattctgcat ggatattgct cttcagggca gccgaaagag 1080
gctattggat ttctcaaaaa gatgcgcagt gatggtgtcg aaccagatgt tgttacttat 1140
agcttgctca tggattatct ttgcaagaac ggaagatgca tggaagctag aaagattttc 1200
gattctatga ccaagagggg cctaaagcct gaaattacta cctatggtac cctgcttcag 1260
gggtatgcta ccaaaggagc ccttgttgag atgcatggtc tcttggattt gatggtacga 1320
aacggtatcc accctgatca ttatgttttc agcattctaa tatgtgcata cgctaaacaa 1380
gggaaagtag atcaggcaat gcttgtgttc agcaaaatga ggcagcaagg attgaatccg 1440
aatgcagtga cgtatggagc agttataggc atactttgca agtcaggcag agtagaagat 1500
gctatgcttt attttgagca gatgatcgat gaaggactaa gccctggcaa cattgtttat 1560
aactccctaa ttcatggttt gtgcacctgt aacaaatggg agagggctga agagttaatt 1620
cttgaaatgt tggatcgagg catctgtctg aacactattt tctttaattc aataattgac 1680
agtcattgca aagaagggag ggttatagaa tctgaaaaac tctttgagct gatggtacgt 1740
attggtgtga agcccaatgt cattacctac aatactctta tcaatggata ttgcttggca 1800
ggtaagatgg atgaagcaat gaagttactt tctggcatgg tctcagttgg gttgaaacct 1860

-continued

```
aatactgtta cttatagcac tttgattaat ggctactgca aaattagtag gatggaagac   1920
gcgttagttc tttttaagga gatggagagc agtggtgtta gtcctgatat tattacgtat   1980
aacataattc tgcaaggttt atttcaaacc agaagaactg ctgctgcaaa agaactctat   2040
gttaggatta ccgaaagtgg aacgcagatt gaacttagca catacaacat aatccttcat   2100
ggactttgca aaaacaaact cactgatgat gcacttcaga tgtttcagaa cctatgtttg   2160
atggatttga agcttgaggc taggactttc aacattatga ttgatgcatt gcttaaagtt   2220
ggcagaaatg atgaagccaa ggatttgttt gttgctttct cgtctaacgg tttagtgccg   2280
aattattgga cgtacaggtt gatggctgaa aatattatag gacaggggtt gctagaagaa   2340
ttggatcaac tctttctttc aatggaggac aatggctgta ctgttgactc tggcatgcta   2400
aatttcattg ttagggaact gttgcagaga ggtgagataa ccagggctgg cacttacctt   2460
tccatgattg atgagaagca cttttccctc gaagcatcca ctgcttcctt gtttatagat   2520
cttttgtctg gggaaaaata tcaagaatat tataggtttc tccctgaaaa atacaagtcc   2580
tttatagaat ctttgagctg ctgaagcatt ttgcagcttt gaaattctgt gttggaattc   2640
ttttctccta cagtcctatt agaggaggga tcttctctgt atgtgtaaat agcgagtttg   2700
aatgctagtg gaagctcctt tgaccatgtt ttgttgtgcg agcatttaag agagtgaaga   2760
gaatgcttct ttggtgctgt tctggtatgg aaggatccac agataaaatt cagtagtggc   2820
caaggttggt gacggtgatg gtggcatgtg atcccccaga tcttcagtga cccagagagg   2880
aggggacggc gcgtggtgag ctacaaggca tactcagtgg agggcaagat caaggcctcc   2940
cgtccgtagg ggactccgct gcatcaaggc caactgctcc gaactgatca atttctggtg   3000
cagacaggtg cttgcggtca ggttaaagaa gttggcaaaa atgcttctga agaaaggtta   3060
attgttgttt catctcagga gattccagat gatccagtgt ctccaacaat tgaggcgctt   3120
attttgctcc atagtaaagt aagtacactt gctgagaacc accagttgac aacacggctt   3180
gttgtaccat caaacaaagt tggttgtatt cttggggaag gtggaaaggt aattactgaa   3240
atgagaagac ggactggggc tgaaatccga gtctactcaa aagcagataa acctaagtac   3300
ctgtcttttg atgaggagct tgtgcaggtt gctgggcttc cagctattga aagaggagcc   3360
ctgacagaga ttgcttcgag gctttgaact aggacactca gagatggaag ttcttccaat   3420
aatccgacac cttttgcccc tgttgatggt cctcctgttg atatcttgcc taacaaggaa   3480
ttcatgctat atggacgatc tgctaatagt cccccatatg gagggcctgc taatgatcca   3540
ccatatggaa gacctgccat tgatccacca tatggaagac caatatccac aatatggaag   3600
acctgccaat gatccaccat atagaagacc tgtcaatgat acatcatatt gagggttgaa   3660
caatgatggg cctcgtgatc aggcccggtc ctgagggggg tcgaatgggg cgatcgctcc   3720
gggccccccg attcccaggg cccccaccta tctgtgcaac gagtagtagc gatcttccag   3780
cgcgcaacgt gaggcgatgt ttctccgtga tttcgccggc ctgcaactgc gagatcgcga   3840
gtataacgat cagccgatcg atctcatctg ccgactgcca tgctgatgcc acacgcaagc   3900
gcagcatatc agccttatct tggttgatcg gcatgctgga cgagcacatc tgttgtcgca   3960
tcaactgctg actgctatat atgtgctggt gctgaatcga tcgattgtcg tcacggaagt   4020
gaagaacaac cacggcactg ctgcctgctg ggctctagcc gccatcagct gcggagctga   4080
tccatggacg tgaggattac cgaagactgt caggtctcac tgggtatcca ggtggctctg   4140
tcgaattgtg gattccaaat agttaactgg agtctgtcat tggtgttggt ggtgtcaatc   4200
```

-continued

```
tagctgagat ccgtctggta tagcgtaaga gaaacatcat gcactatccc cagtcataac   4260

catgccccaa tggccaccaa tagttttcct cgtgaaaatc tccccttgat cccagatctc   4320

tggtgcgaga gtgaagttgc acgaagccca tcctggttct tccgagtcca ttgtggagat   4380

ccagggcatt ccggatcaag tgaaagccgc acagagcctt ctgcaaggct tcatcggcgc   4440

aagcagcaac agcaggcagg cgccccagtc ctctcgcatg gcccattatt tttagtaagc   4500

tggaggacat tcgcaacagg ggggtcagtg gtcactgcaa agctgagttt gttcttcagt   4560

tcaactgcag aaaattgcag atcggttgcc gtagttgcta gaacggtaca tagttgccac   4620

ctaactgtag cgagtggcat aacttattgt gtgttactgc ccaatgttgt ctctccttgt   4680

gttcatggat tcagacttgt gattgtagta tttctggatc agactggagt aaaagaaaaa   4740

aaaaaa                                                              4746
```

<210> SEQ ID NO 81
<211> LENGTH: 4779
<212> TYPE: DNA
<213> ORGANISM: rice

<400> SEQUENCE: 81

```
tctcattctc tccacgccct gctcgtcgcc gatctcctac accatccctg ccatctcctc     60

cttcccctcc cctctatcct ccactggtgc cgcccacctc tccgtataag acaaactgcg    120

ttgcggcgtt ggtttccgcc ggcgctgctg ctgcacctgt cagctagggc gggcatggcg    180

cgccgcgccg cttcccgcgc tgttggcgcc cttcgctcgg acggctcgat ccaagggcga    240

ggaggccgcg cggggggcag tggcgccgag gacgcacgcc acgtgttcga cgaattgctc    300

cgccgtggca ggggcgcctc gatctacggc ttgaaccgcg ccctcgccga cgtcgcgcgt    360

gacagccccg cggccgccgt gtcccgctac aaccgcatgg cccgagccgg cgccgacgag    420

gtaactcccg acttgtgcac ctacggcatt ctcatcggtt gctgctgccg cgcgggccgc    480

ttggacctcg gtttcgcggc cttgggcaat gtcattaaga agggatttag agtggacgcc    540

atcgccttca ctcctctgct caagggcctc tgtgccgaca agaggacgag cgacgcaatg    600

gacatagtgc tccgcagaat gaccgagctc ggctgcatac caaatgtctt ctcctacaat    660

attcttctca aggggctgtg tgatgagaac agaagccaag aagctctcga gctgctgcac    720

atgatggctg atgatcgagg aggaggtagc ccacctgatg tggtgtcgta taccactgtc    780

atcaatggct tcttcaaaga gggggattca gacaaagctt acagtacata ccatgaaatg    840

ctggaccggg ggattttacc tgatgttgtg acctacaact ctattattgc tgcgttatgc    900

aaggctcaag ctatggacaa agccatggag gtacttaaca ccatggttaa gaatggtgtc    960

atgcctgatt gcatgacata taatagtatt ctgcatggat attgctcttc agggcagccg   1020

aaagaggcta ttggatttct caaaaagatg cgcagtgatg gtgtcgaacc agatgttgtt   1080

acttatagct tgctcatgga ttatctttgc aagaacggaa gatgcatgga agctagaaag   1140

attttcgatt ctatgaccaa gaggggccta aagcctgaaa ttactaccta tggtaccctg   1200

cttcaggggt atgctaccaa aggagccctt gttgagatgc atggtctctt ggatttgatg   1260

gtacgaaacg gtatccaccc tgatcattat gttttcagca ttctaatatg tgcatacgct   1320

aaacaaggga aagtagatca ggcaatgctt gtgttcagca aaatgaggca gcaaggattg   1380

aatccgaatg cagtgacgta tggagcagtt ataggcatac tttgcaagtc aggcagagta   1440

gaagatgcta tgctttattt tgagcagatg atcgatgaag gactaagccc tggcaacatt   1500

gtttataact ccctaattca tggtttgtgc acctgtaaca aatgggagag ggctgaagag   1560
```

-continued

```
ttaattcttg aaatgttgga tcgaggcatc tgtctgaaca ctattttctt taattcaata   1620
attgacagtc attgcaaaga agggagggtt atagaatctg aaaaactctt tgagctgatg   1680
gtacgtattg gtgtgaagcc caatgtcatt acctacaata ctcttatcaa tggatattgc   1740
ttggcaggta agatggatga agcaatgaag ttactttctg gcatggtctc agttgggttg   1800
aaacctaata ctgttactta tagcactttg attaatggct actgcaaaat tagtaggatg   1860
gaagacgcgt tagttctttt taaggagatg gagagcagtg gtgttagtcc tgatattatt   1920
acgtataaca taattctgca aggtttattt caaaccagaa gaactgctgc tgcaaaagaa   1980
ctctatgtta ggattaccga aagtggaacg cagattgaac ttagcacata caacataatc   2040
cttcatggac tttgcaaaaa caaactcact gatgatgcac ttcagatgtt tcagaaccta   2100
tgtttgatgg atttgaagct tgaggctagg actttcaaca ttatgattga tgcattgctt   2160
aaagttggca gaaatgatga agccaaggat ttgtttgttg ctttctcgtc taacggttta   2220
gtgccgaatt attggacgta caggttgatg gctgaaaata ttataggaca ggggttgcta   2280
gaagaattgg atcaactctt tctttcaatg gaggacaatg gctgtactgt tgactctggc   2340
atgctaaatt tcattgttag ggaactgttg cagagaggtg agataaccag ggctggcact   2400
tacctttcca tgattgatga gaagcacttt tccctcgaag catccactgc ttccttgttt   2460
atagatcttt tgtctggggg aaaatatcaa gaatattata ggtttctccc tgaaaaatac   2520
aagtccttta tagaatcttt gagctgctga agcattttgc agctttgaaa ttctgtgttg   2580
gaattctttt ctcctacagt cctattagag gagggatctt ctctgtatgt gtaaatagcg   2640
agtttgaatg ctagtggaag ctcctttgac catgttttgt tgtgcgagca tttaagagag   2700
tgaagagaat gcttctttgg tgctgttctg gtatggaagg atccacagat aaaattcagg   2760
agaatatagt agtggccaag gttggtgacg gtgatggtgg catgtgatcc cccagatctt   2820
cagtgaccca gagaggaggg gacggcgcgt ggtgagctac aaggcatact cagtggaggg   2880
caagatcaag gcctcccgtc cgtaggggac tccgctgcat caaggccaac tgctccgaac   2940
tgatcaattt ctggtgcaga caggtgcttg cggtcaggtt aaagaagttg gcaaaaatgc   3000
ttctgaagaa aggttaattg ttgtttcatc tcaggagatt ccagatgatc cagtgtctcc   3060
aacaattgag gcgcttattt tgctccatag taaagtaagt acacttgctg agaaccacca   3120
gttgacaaca cggcttgttg taccatcaaa caaagttggt tgtattcttg ggaaggtgg    3180
aaaggtaatt actgaaatga gaagacggac tggggctgaa atccgagtct actcaaaagc   3240
agataaacct aagtacctgt cttttgatga ggagcttgtg caggttgctg ggcttccagc   3300
tattgaaaga ggagccctga cagagattgc ttcgaggctt tgaactagga cactcagaga   3360
tggaagttct tccaataatc cgacaccttt tgcccctgtt gatggtcctc ctgttgatat   3420
cttgcctaac aaggaattca tgctatatgg acgatctgct aatagtcccc catatggagg   3480
gcctgctaat gatccaccat atggaagacc tgccattgat ccaccatatg gaagaccaat   3540
atccacaata tggaagacct gccaatgatc caccatatag aagacctgtc aatgatacat   3600
catattgagg gttgaacaat gatgggcctc gtgatcaggc ccggtcctga ggggggtcga   3660
atggggcgat cgctccgggc cccccgattc ccagggcccc cacctatctg tgcaacgagt   3720
agtagcgatc ttccagcgcg caacgtgagg cgatgtttct ccgtgatttc gccggcctgc   3780
aactgcgaga tcgcgagtat aacgatcagc cgatcgatct catctgccga ctgccatgct   3840
gatgccacac gcaagcgcag catatcagcc ttatcttggt tgatcggcat gctggacgag   3900
```

-continued

```
cacatctgtt gtcgcatcaa ctgctgactg ctatatatgt gctggtgctg aatcgatcga   3960

ttgtcgtcac ggaagtgaag aacaaccacg gcactgctgc ctgctgggct ctagccgcca   4020

tcagctgcgg agctgatcca tggacgtgag gattaccgaa gactgtcagg tctcactggg   4080

tatccaggtg gctctgtcga attgtggatt ccaaatagtt aactggagtc tgtcattggt   4140

gttggtggtg tcaatctagc tgagatccgt ctggtatagc gtaagagaaa catcatgcac   4200

tatccccagt cataaccatg ccccaatggc caccaatagt tttcctcgtg aaaatctccc   4260

cttgatccca gatctctggt gcgagagtga agttgcacga agcccatcct ggttcttccg   4320

agtccattgt ggagatccag ggcattccgg atcaagtgaa agccgcacag agccttctgc   4380

aaggcttcat cggcgcaagc agcaacagca ggcaggcgcc ccagtcctct cgcatggccc   4440

attattttta gtaagctgga ggacattcgc aacagggggg tcagtggtca ctgcaaagct   4500

gagtttgttc ttcagttcaa ctgcagaaaa ttgcagatcg gttgccgtag ttgctagaac   4560

ggtacatagt tgccacctaa ctgtagcgag tggcataact tattgtgtgt tactgcccaa   4620

tgttgtctct ccttgtgttc atggattcag acttgtgatt gtagtatttc tggatcagac   4680

tggagtaaaa gaaaaaaaaa aaggaagaca tgggtttaac agtaaaaaaa aaaaaaaaaa   4740

aaaaaaaaaa aaaaaaaaaa aaaaaaaaaa aaaaaaaaa                          4779
```

<210> SEQ ID NO 82
<211> LENGTH: 6158
<212> TYPE: DNA
<213> ORGANISM: rice

<400> SEQUENCE: 82

```
cgcgcagaag agatcgatcg cgatctccct gccccgacgt cgccggccga tctctcattc     60

tctccacgcc ctgctcgtcg ccgatctcct acaccatccc tgccatctcc tccttcccct    120

cccctctatc ctccactggt gccgcccacc tctccgtata agacaaactg cgttgcggcg    180

ttggtttccg ccggcgctgc tgctgcacct gtcagctagg gcgggcatgg cgcgccgcgc    240

cgcttcccgc gctgttggcg cccttcgctc ggacggctcg atccaagggc gaggaggccg    300

cgcggggggc agtggcgccg aggacgcacg ccacgtgttc gacgaattgc tccgccgtgg    360

caggggcgcc tcgatctacg gcttgaaccg cgccctcgcc gacgtcgcgc gtgacagccc    420

cgcggccgcc gtgtcccgct acaaccgcat ggcccgagcc ggcgccgacg aggtaactcc    480

cgacttgtgc acctacggca ttctcatcgg ttgctgctgc cgcgcgggcc gcttggacct    540

cggtttcgcg gccttgggca atgtcattaa gaagggattt agagtggacg ccatcgcctt    600

cactcctctg ctcaagggcc tctgtgccga caagaggacg agcgacgcaa tggacatagt    660

gctccgcaga atgaccgagc tcggctgcat accaaatgtc ttctcctaca atattcttct    720

caaggggctg tgtgatgaga acagaagcca agaagctctc gagctgctgc acatgatggc    780

tgatgatcga ggaggaggta gcccacctga tgtggtgtcg tataccactg tcatcaatgg    840

cttcttcaaa gagggggatt cagacaaagc ttacagtaca taccatgaaa tgctggaccg    900

ggggatttta cctgatgttg tgacctacaa ctctattatt gctgcgttat gcaaggctca    960

agctatggac aaagccatgg aggtacttaa caccatggtt aagaatggtg tcatgcctga   1020

ttgcatgaca tataatagta ttctgcatgg atattgctct tcagggcagc cgaaagaggc   1080

tattggattt ctcaaaaaga tgcgcagtga tggtgtcgaa ccagatgttg ttacttatag   1140

cttgctcatg gattatcttt gcaagaacgg aagatgcatg gaagctagaa agattttcga   1200

ttctatgacc aagaggggcc taaagcctga aattactacc tatggtaccc tgcttcaggg   1260
```

-continued

```
gtatgctacc aaaggagccc ttgttgagat gcatggtctc ttggatttga tggtacgaaa   1320
cggtatccac cctgatcatt atgttttcag cattctaata tgtgcatacg ctaaacaagg   1380
gaaagtagat caggcaatgc ttgtgttcag caaaatgagg cagcaaggat tgaatccgaa   1440
tgcagtgacg tatggagcag ttataggcat actttgcaag tcaggcagag tagaagatgc   1500
tatgctttat tttgagcaga tgatcgatga aggactaagc cctggcaaca ttgtttataa   1560
ctccctaatt catggtttgt gcacctgtaa caaatgggag agggctgaag agttaattct   1620
tgaaatgttg gatcgaggca tctgtctgaa cactattttc tttaattcaa taattgacag   1680
tcattgcaaa gaagggaggg ttatagaatc tgaaaaactc tttgagctga tggtacgtat   1740
tggtgtgaag cccaatgtca ttacctacaa tactcttatc aatggatatt gcttggcagg   1800
taagatggat gaagcaatga agttactttc tggcatggtc tcagttgggt tgaaacctaa   1860
tactgttact tatagcactt tgattaatgg ctactgcaaa attagtagga tggaagacgc   1920
gttagttctt tttaaggaga tggagagcag tggtgttagt cctgatatta ttacgtataa   1980
cataattctg caaggtttat ttcaaaccag aagaactgct gctgcaaaag aactctatgt   2040
taggattacc gaaagtggaa cgcagattga acttagcaca tacaacataa tccttcatgg   2100
actttgcaaa aacaaactca ctgatgatgc acttcagatg tttcagaacc tatgtttgat   2160
ggatttgaag cttgaggcta ggactttcaa cattatgatt gatgcattgc ttaaagttgg   2220
cagaaatgat gaagccaagg atttgtttgt tgctttctcg tctaacggtt tagtgccgaa   2280
ttattggacg tacaggttga tggctgaaaa tattatagga caggggttgc tagaagaatt   2340
ggatcaactc tttctttcaa tggaggacaa tggctgtact gttgactctg gcatgctaaa   2400
tttcattgtt agggaactgt tgcagagagg tgagataacc agggctggca cttacctttc   2460
catgattgat gagaagcact ttccctcga agcatccact gcttccttgt ttatagatct   2520
tttgtctggg ggaaaatatc aagaatatta taggtttctc cctgaaaaat acaagtcctt   2580
tatagaatct ttgagctgct gaagcatttt gcagctttga aattctgtgt tggaattctt   2640
ttctcctaca gtcctattag aggagggatc ttctctgtat gtgtaaatag cgaggtatgt   2700
atgccacctc tccgaattat ttttactgtg gttcctagac tgtaaacaag caattatgtt   2760
atgctgttga tgccagaaaa aacataaaag tttgtcgtta tctctactaa cggatcataa   2820
agggatttgt gactggagtt tcaaacttaa tgtgtctagg cagtaatttt gacattagat   2880
ccaaaacaat tttatagggtt tcattaaatt tcatctatgt gtactgttta ggtgttgaat   2940
agtttgactt gttttttaac tgaacaaaag atatgtctga agctttgttc tttaccaaat   3000
gcagtactga tcatcacaat atattttta tggaacaaga ttggattgta tagaatggtt   3060
tctgatctga ttatcttatc tcaacgtatt attatgcaca tgtactaatc atgaaatatc   3120
tgatggaatg atgtttctat ttacctgtgt gaggcagcaa ggagtgagat ggataacacc   3180
acatactccc tctgtcccag aatataagaa gttttagagt tggacacgat tattaagaaa   3240
gtaggtagaa gtgagtagtg gagggttgtg attgcatgag tagtggaggt aggtgggaaa   3300
agtgaatggt ggagggttgt gattggttgg gaagagaatg ttggtagaga agttgttata   3360
ttttggggag tacattatta ttctagaaca atactgttgt gctcaagaag cgttccaaag   3420
atgtttcaca acctgtgctc gatgggtttt gagcttaatc ctgggacatt cagtatcatg   3480
atctgtctca ttcttaaaca tggaataaag gatgacagca tgatttcttt gtctctataa   3540
tcttttggct acccacagat aatagctgta aatctatact actttaaaag gagtagtggt   3600
```

-continued

```
ggtggtgagt ggtgaatctg ccaccacccc accaccaact ctcaaaattc tgacatgtgg   3660
gatcactgtc aatcccttct ccaagacatg tgggatcact gtcaatccct tctccaaacc   3720
aattgtatga tagaacagtg gaaatcacgg acagaccatg gagctctcaa ccataatcat   3780
ccttgcgagt taataacaaa tggagcgtaa acttggcaag caaaaaactc aaattaattc   3840
taaaattaag ctctaggatt caaaatagat ttcctctctg cattgtgctg ttatgatttt   3900
taattccgta acaacgcaaa tgcattttgc tagtcttata aagaagggtt aatgcaaata   3960
ttctgattaa atgattgtat ctatgaagtt tgaatgctag tggaagctcc tttgaccatg   4020
ttttgttgtg cgagcattta agagagtgaa gagaatgctt ctttggtgct gttctggtat   4080
ggaaggatcc acagataaaa ttcaggagaa tatagtagtg gccaaggttg gtgacggtga   4140
tggtggcatg tgatccccca gatcttcagt gacccagaga ggaggggacg gcgcgtggtg   4200
agctacaagg catactcagt ggagggcaag atcaaggcct cccgtccgta ggggactccg   4260
ctgcatcaag gccaactgct ccgaactgat caatttctgg tgcagacagg tgcttgcggt   4320
caggttaaag aagttggcaa aaatgcttct gaagaaaggt taattgttgt ttcatctcag   4380
gagattccag atgatccagt gtctccaaca attgaggcgc ttattttgct ccatagtaaa   4440
gtaagtacac ttgctgagaa ccaccagttg acaacacggc ttgttgtacc atcaaacaaa   4500
gttggttgta ttcttgggga aggtggaaag gtaattactg aaatgagaag acggactggg   4560
gctgaaatcc gagtctactc aaaagcagat aaacctaagt acctgtcttt tgatgaggag   4620
cttgtgcagg ttgctgggct tccagctatt gaaagaggag ccctgacaga gattgcttcg   4680
aggctttgaa ctaggacact cagagatgga agttcttcca ataatccgac accttttgcc   4740
cctgttgatg gtcctcctgt tgatatcttg cctaacaagg aattcatgct atatggacga   4800
tctgctaata gtcccccata tggagggcct gctaatgatc caccatatgg aagacctgcc   4860
attgatccac catatggaag accaatatcc acaatatgga agacctgcca atgatccacc   4920
atatagaaga cctgtcaatg atacatcata ttgagggttg aacaatgatg ggcctcgtga   4980
tcaggcccgg tcctgagggg ggtcgaatgg ggcgatcgct ccgggccccc cgattcccag   5040
ggcccccacc tatctgtgca acgagtagta gcgatcttcc agcgcgcaac gtgaggcgat   5100
gtttctccgt gatttcgccg gcctgcaact gcgagatcgc gagtataacg atcagccgat   5160
cgatctcatc tgccgactgc catgctgatg ccacacgcaa gcgcagcata tcagccttat   5220
cttggttgat cggcatgctg gacgagcaca tctgttgtcg catcaactgc tgactgctat   5280
atatgtgctg gtgctgaatc gatcgattgt cgtcacggaa gtgaagaaca accacggcac   5340
tgctgcctgc tgggctctag ccgccatcag ctgcggagct gatccatgga cgtgaggatt   5400
accgaagact gtcaggtctc actgggtatc caggtggctc tgtcgaattg tggattccaa   5460
atagttaacc ggagtctgtc attggtgttg gtggtgtcaa tctagctgag atccgtctgg   5520
tatagcgtaa gagaaacatc atgcactatc cccagtcata accatgcccc aatggccacc   5580
aatagttttc ctcgtgaaaa tctccccttg atcccagatc tctggtgcga gagtgaagtt   5640
gcacgaagcc catcctggtt cttccgagtc cattgtggag atccagggca ttccggatca   5700
agtgaaagcc gcacagagcc ttctgcaagg cttcatcggc gcaagcagca acagcaggca   5760
ggcgccccag tcctctcgca tggcccatta tttttagtaa gctggaggac attcgcaaca   5820
ggggggtcag tggtcactgc aaagctgagt ttgttcttca gttcaactgc agaaaattgc   5880
agatcggttg ccgtagttgc tagaacggta catagttgcc acctaactgt agcgagtggc   5940
ataacttatt gtgtgttact gcccaatgtt gtctctcctt gtgttcatgg attcagactt   6000
```

-continued gtgattgtag tatttctgga tcagactgga gtaaaagaaa aaaaaaaagg aagacatggg 6060
tttaacagta aaaaaaaaaa aaaaaaaaaa aaaaaaaaaa aaaaaaaaaa aaaaaaaaaa 6120
aaaaaaaaaa aaaaaaaaaa aaaaaaaaaa aaaaaaaa 6158

<210> SEQ ID NO 83
<211> LENGTH: 2864
<212> TYPE: DNA
<213> ORGANISM: rice

<400> SEQUENCE: 83
aagagatcga tcgcgatctc cctgccccga cgtcgccggc cgatctctca ttctctccac 60
gccctgctcg tcgccgatct cctacaccat ccctgccatc tcctccttcc cctcccctct 120
atcctccact ggtgccgccc acctctccgt ataagacaaa ctgcgttgcg gcgttggttt 180
ccgccggcgc tgctgctgca cctgtcagct agggcgggca tggcgcgccg cgccgcttcc 240
cgcgctgttg gcgcccttcg ctcggacggc tcgatccaag ggcgaggagg ccgcgcgggg 300
ggcagtggcg ccgaggacgc acgccacgtg ttcgacgaat tgctccgccg tggcaggggc 360
gcctcgatct acggcttgaa ccgcgccctc gccgacgtcg cgcgtgacag ccccgcggcc 420
gccgtgtccc gctacaaccg catggcccga gccggcgccg acgaggtaac tcccgacttg 480
tgcacctacg gcattctcat cggttgctgc tgccgcgcgg gccgcttgga cctcggtttc 540
gcggccttgg gcaatgtcat taagaaggga tttagagtgg acgccatcgc cttcactcct 600
ctgctcaagg gcctctgtgc cgacaagagg acgagcgacg caatggacat agtgctccgc 660
agaatgaccg agctcggctg cataccaaat gtcttctcct acaatattct tctcaagggg 720
ctgtgtgatg agaacagaag ccaagaagct ctcgagctgc tgcacatgat ggctgatgat 780
cgaggaggag gtagcccacc tgatgtggtg tcgtatacca ctgtcatcaa tggcttcttc 840
aaagaggggg attcagacaa agcttacagt acataccatg aaatgctgga ccgggggatt 900
ttacctgatg ttgtgaccta caactctatt attgctgcgt tatgcaaggc tcaagctatg 960
gacaaagcca tggaggtact taacaccatg gttaagaatg gtgtcatgcc tgattgcatg 1020
acatataata gtattctgca tggatattgc tcttcagggc agccgaaaga ggctattgga 1080
tttctcaaaa agatgcgcag tgatggtgtc gaaccagatg ttgttactta tagcttgctc 1140
atggattatc tttgcaagaa cggaagatgc atggaagcta gaaagatttt cgattctatg 1200
accaagaggg gcctaaagcc tgaaattact acctatggta ccctgcttca ggggtatgct 1260
accaaaggag cccttgttga gatgcatggt ctcttggatt tgatggtacg aaacggtatc 1320
caccctgatc attatgtttt cagcattcta atatgtgcat acgctaaaca agggaaagta 1380
gatcaggcaa tgcttgtgtt cagcaaaatg aggcagcaag gattgaatcc gaatgcagtg 1440
acgtatggag cagttatagg catactttgc aagtcaggca gagtagaaga tgctatgctt 1500
tattttgagc agatgatcga tgaaggacta agccctggca acattgttta taactcccta 1560
attcatggtt tgtgcacctg taacaaatgg gagagggctg aagagttaat tcttgaaatg 1620
ttggatcgag gcatctgtct gaacactatt ttctttaatt caataattga cagtcattgc 1680
aaagaaggga gggttataga atctgaaaaa ctctttgagc tgatggtacg tattggtgtg 1740
aagcccaatg tcattaccta caatactctt atcaatggat attgcttggc aggtaagatg 1800
gatgaagcaa tgaagttact ttctggcatg gtctcagttg ggttgaaacc taatactgtt 1860
acttatagca ctttgattaa tggctactgc aaaattagta ggatggaaga cgcgttagtt 1920

-continued

```
cttttaagg agatggagag cagtggtgtt agtcctgata ttattacgta taacataatt   1980

ctgcaaggtt tatttcaaac cagaagaact gctgctgcaa aagaactcta tgttaggatt   2040

accgaaagtg gaacgcagat tgaacttagc acatacaaca taatccttca tggactttgc   2100

aaaaacaaac tcactgatga tgcacttcag atgtttcaga acctatgttt gatggatttg   2160

aagcttgagg ctaggacttt caacattatg attgatgcat tgcttaaagt tggcagaaat   2220

gatgaagcca aggatttgtt tgttgctttc tcgtctaacg gtttagtgcc gaattattgg   2280

acgtacaggt tgatggctga aaatattata ggacaggggt tgctagaaga attggatcaa   2340

ctctttcttt caatggagga caatggctgt actgttgact ctggcatgct aaatttcatt   2400

gttagggaac tgttgcagag aggtgagata accagggctg gcacttacct ttccatgatt   2460

gatgagaagc acttttccct cgaagcatcc actgcttcct tgtttataga tcttttgtct   2520

gggggaaaat atcaagaata ttataggttt ctccctgaaa aatacaagtc ctttatagaa   2580

tctttgagct gctgaagcat tttgcagctt tgaaattctg tgttggaatt cttttctcct   2640

acagtcctat tagaggaggg atcttctctg tatgtgtaaa tagcgaggta tgtatgccac   2700

ctctccgaat tatttttact gtggttccta gactgtaaac aagcaattat gttatgctgt   2760

tgatgccaga aaaaacataa aagtttgtcg ttatctctac taacggatca taaagggatt   2820

tgtgactgga gtttcaaaaa aaaaaaaaaa aaaaaaaaaa aaaa                    2864
```

<210> SEQ ID NO 84
<211> LENGTH: 2819
<212> TYPE: DNA
<213> ORGANISM: rice

<400> SEQUENCE: 84

```
ctcattctct ccacgccctg ctcgtcgccg atctcctaca ccatccctgc catctcctcc     60

ttcccctccc ctctatcctc cactggtgcc gcccacctct ccgtataaga caaactgcgt    120

tgcggcgttg gtttccgccg gcgctgctgc tgcacctgtc agctagggcg ggcatggcgc    180

gccgcgccgc ttcccgcgct gttggcgccc ttcgctcgga cggctcgatc caagggcgag    240

gaggccgcgc ggggggcagt ggcgccgagg acgcacgcca cgtgttcgac gaattgctcc    300

gccgtggcag gggcgcctcg atctacggct tgaaccgcgc cctcgccgac gtcgcgcgtg    360

acagccccgc ggccgccgtg tcccgctaca accgcatggc ccgagccggc gccgacgagg    420

taactcccga cttgtgcacc tacggcattc tcatcggttg ctgctgccgc gcgggccgct    480

tggacctcgg tttcgcggcc ttgggcaatg tcattaagaa gggatttaga gtggacgcca    540

tcgccttcac tcctctgctc aagggcctct gtgccgacaa gaggacgagc gacgcaatgg    600

acatagtgct ccgcagaatg accgagctcg gctgcatacc aaatgtcttc tcctacaata    660

ttcttctcaa ggggctgtgt gatgagaaca gaagccaaga agctctcgag ctgctgcaca    720

tgatggctga tgatcgagga ggaggtagcc cacctgatgt ggtgtcgtat accactgtca    780

tcaatggctt cttcaaagag ggggattcag acaaagctta cagtacatac catgaaatgc    840

tggaccgggg gattttacct gatgttgtga cctacaactc tattattgct gcgttatgca    900

aggctcaagc tatggacaaa gccatggagg tacttaacac catggttaag aatggtgtca    960

tgcctgattg catgacatat aatagtattc tgcatggata ttgctcttca gggcagccga   1020

aagaggctat tggatttctc aaaaagatgc gcagtgatgg tgtcgaacca gatgttgtta   1080

cttatagctt gctcatggat tatctttgca agaacggaag atgcatggaa gctagaaaga   1140

ttttcgattc tatgaccaag aggggcctaa agcctgaaat tactacctat ggtaccctgc   1200
```

-continued

```
ttcaggggta tgctaccaaa ggagcccttg ttgagatgca tggtctcttg gatttgatgg   1260

tacgaaacgg tatccaccct gatcattatg ttttcagcat tctaatatgt gcatacgcta   1320

aacaagggaa agtagatcag gcaatgcttg tgttcagcaa aatgaggcag caaggattga   1380

atccgaatgc agtgacgtat ggagcagtta taggcatact ttgcaagtca ggcagagtag   1440

aagatgctat gctttatttt gagcagatga tcgatgaagg actaagccct ggcaacattg   1500

tttataactc cctaattcat ggtttgtgca cctgtaacaa atgggagagg gctgaagagt   1560

taattcttga aatgttggat cgaggcatct gtctgaacac tattttcttt aattcaataa   1620

ttgacagtca ttgcaaagaa gggagggtta tagaatctga aaaactcttt gagctgatgg   1680

tacgtattgg tgtgaagccc aatgtcatta cctacaatac tcttatcaat ggatattgct   1740

tggcaggtaa gatggatgaa gcaatgaagt tactttctgg catggtctca gttgggttga   1800

aacctaatac tgttacttat agcactttga ttaatggcta ctgcaaaatt agtaggatgg   1860

aagacgcgtt agttcttttt aaggagatgg agagcagtgg tgttagtcct gatattatta   1920

cgtataacat aattctgcaa ggtttatttc aaaccagaag aactgctgct gcaaaagaac   1980

tctatgttag gattaccgaa agtggaacgc agattgaact tagcacatac aacataatcc   2040

ttcatggact ttgcaaaaac aaactcactg atgatgcact tcagatgttt cagaacctat   2100

gtttgatgga tttgaagctt gaggctagga ctttcaacat tatgattgat gcattgctta   2160

aagttggcag aaatgatgaa gccaaggatt tgtttgttgc tttctcgtct aacggtttag   2220

tgccgaatta ttggacgtac aggttgatgg ctgaaaatat tataggacag ggttgctag    2280

aagaattgga tcaactcttt ctttcaatgg aggacaatgg ctgtactgtt gactctggca   2340

tgctaaattt cattgttagg gaactgttgc agagaggtga gataaccagg gctggcactt   2400

acccttccat gattgatgag aagcactttt ccctcgaagc atccactgct tccttgttta   2460

tagatctttt gtctggggga aaatatcaag aatattatag gtttctccct gaaaaataca   2520

agtcctttat agaatctttg agctgctgaa gcattttgca gctttgaaat tctgtgttgg   2580

aattcttttc tcctacagtc ctattagagg agggatcttc tctgtatgtg taaatagcga   2640

ggtatgtatg ccacctctcc gaattatttt tactgtggtt cctagactgt aaacaagcaa   2700

ttatgttatg ctgttgatgc cagaaaaaac ataaaagttt gtcgttatct ctactaacgg   2760

atcataaagg gatttgtgac tggagtttca aaaaaaaaaa aaaaaaaaaa aaaaaaaaa    2819
```

<210> SEQ ID NO 85
<211> LENGTH: 2649
<212> TYPE: DNA
<213> ORGANISM: rice

<400> SEQUENCE: 85

```
ggtgccgccc acctctccgt ataagacaaa ctgcgttgcg gcgttggttt ccgccggcgc     60

tgctgctgca cctgtcagct agggcgggca tggcgcgccg cgccgcttcc cgcgctgttg    120

gcgcccttcg ctcggacggc tcgatccaag ggcgaggagg ccgcgcgggg ggcagtggcg    180

ccgaggacgc acgccacgtg ttcgacgaat tgctccgccg tggcaggggc gcctcgatct    240

acggcttgaa ccgcgccctc gccgacgtcg cgcgtgacag ccccgcggcc gccgtgtccc    300

gctacaaccg catggcccga gccggcgccg acgaggtaac tcccgacttg tgcacctacg    360

gcattctcat cggttgctgc tgccgcgcgg gccgcttgga cctcggtttc gcggccttgg    420

gcaatgtcat taagaaggga tttagagtgg acgccatcgc cttcactcct ctgctcaagg    480
```

-continued

```
gcctctgtgc cgacaagagg acgagcgacg caatggacat agtgctccgc agaatgaccg    540
agctcggctg cataccaaat gtcttctcct acaatattct tctcaagggg ctgtgtgatg    600
agaacagaag ccaagaagct ctcgagctgc tgcacatgat ggctgatgat cgaggaggag    660
gtagcccacc tgatgtggtg tcgtatacca ctgtcatcaa tggcttcttc aaagaggggg    720
attcagacaa agcttacagt acataccatg aaatgctgga ccgggggatt ttacctgatg    780
ttgtgaccta caactctatt attgctgcgt tatgcaaggc tcaagctatg gacaaagcca    840
tggaggtact taacaccatg gttaagaatg gtgtcatgcc tgattgcatg acatataata    900
gtattctgca tggatattgc tcttcagggc agccgaaaga ggctattgga tttctcaaaa    960
agatgcgcag tgatggtgtc gaaccagatg ttgttactta tagcttgctc atggattatc   1020
tttgcaagaa cggaagatgc atggaagcta gaaagatttt cgattctatg accaagaggg   1080
gcctaaagcc tgaaattact acctatggta ccctgcttca ggggtatgct accaaaggag   1140
cccttgttga gatgcatggt ctcttggatt tgatggtacg aaacggtatc caccctgatc   1200
attatgtttt cagcattcta atatgtgcat acgctaaaca agggaaagta gatcaggcaa   1260
tgcttgtgtt cagcaaaatg aggcagcaag gattgaatcc gaatgcagtg acgtatggag   1320
cagttatagg catactttgc aagtcaggca gagtagaaga tgctatgctt tattttgagc   1380
agatgatcga tgaaggacta agccctggca acattgttta taactcccta attcatggtt   1440
tgtgcacctg taacaaatgg gagagggctg aagagttaat tcttgaaatg ttggatcgag   1500
gcatctgtct gaacactatt ttctttaatt caataattga cagtcattgc aaagaaggga   1560
gggttataga atctgaaaaa ctctttgagc tgatggtacg tattggtgtg aagcccaatg   1620
tcattaccta caatactctt atcaatggat attgcttggc aggtaagatg gatgaagcaa   1680
tgaagttact ttctggcatg gtctcagttg ggttgaaacc taatactgtt acttatagca   1740
ctttgattaa tggctactgc aaaattagta ggatggaaga cgcgttagtt ctttttaagg   1800
agatggagag cagtggtgtt agtcctgata ttattacgta taacataatt ctgcaaggtt   1860
tatttcaaac cagaagaact gctgctgcaa aagaactcta tgttaggatt accgaaagtg   1920
gaacgcagat tgaacttagc acatacaaca taatccttca tggactttgc aaaaacaaac   1980
tcactgatga tgcacttcag atgtttcaga acctatgttt gatggatttg aagcttgagg   2040
ctaggacttt caacattatg attgatgcat tgcttaaagt tggcagaaat gatgaagcca   2100
aggatttgtt tgttgctttc tcgtctaacg gtttagtgcc gaattattgg acgtacaggt   2160
tgatggctga aaatattata ggacaggggt tgctagaaga attggatcaa ctctttcttt   2220
caatggagga caatggctgt actgttgact ctggcatgct aaatttcatt gttagggaac   2280
tgttgcagag aggtgagata accagggctg gcacttacct ttccatgatt gatgagaagc   2340
acttttccct cgaagcatcc actgcttcct tgtttataga tcttttgtct gggggaaaat   2400
atcaagaata ttataggttt ctccctgaaa aatacaagtc ctttatagaa tctttgagct   2460
gctgaagcat tttgcagctt tgaaattctg tgttggaatt cttttctcct acagtcctat   2520
tagaggaggg atcttctctg tatgtgtaaa tagcgaggta tgtatgccac ctctccgaat   2580
tatttttact gtggttccta gactgtaaac aagcaattat gttatgctgt tgatgccaga   2640
aaaaaaaaa                                                           2649
```

<210> SEQ ID NO 86
<211> LENGTH: 24
<212> TYPE: DNA
<213> ORGANISM: Artificial Sequence -continued

```
<220> FEATURE:
<223> OTHER INFORMATION: Synthetic oligonucleotide primer for
      amplification

<400> SEQUENCE: 86

cagttgggtt gaaacctaat actg                                    24


<210> SEQ ID NO 87
<211> LENGTH: 24
<212> TYPE: DNA
<213> ORGANISM: Artificial Sequence
<220> FEATURE:
<223> OTHER INFORMATION: Synthetic oligonucleotide primer for
      amplification

<400> SEQUENCE: 87

cactaaaccg ttagacgaga aagc                                    24
```

RICE RESTORER GENE TO THE RICE BT TYPE CYTOPLASMIC MALE STERILITY

FIELD OF THE INVENTION

The present invention relates to the rice restorer gene to the rice BT type cytoplasmic male sterility.

The present application claims priority based on Japanese Patent Application No. 2002-107560 filed on Jul. 5, 2002. The entire disclosures of the patent application are incorporated herein.

PRIOR ART

Rice is a self-fertilizing plant, so in order to perform crossing between varieties, self-fertilization must first be avoided by removing all stamens in a glumaceous flower just before flowering and, then fertilization is effected with pollens from the parent variety with which it is to be crossed. However, this manual crossing method is entirely unsuitable for producing a large quantity of hybrid seeds on a commercial scale.

Accordingly, hybrid rice is produced by the triple-crossing system which makes use of cytoplasmic male sterility. In the triple-crossing system, the following three lines are employed, i.e., a sterile line having male sterile cytoplasm, a restorer line having Rf-1 gene and a maintainer line having the same nuclear gene as that of the sterile line but not having any sterile cytoplasm. By using these three lines, (i) hybrid seeds can be obtained through fertilization of the sterile line with the pollen of the restorer line whereas (ii) the sterile line can be maintained through its fertilization with the pollen of the maintainer line.

When employing the BT type male sterile cytoplasm in the triple-crossing system, it is important to breed rice of the restorer line and to this end, it is necessary to ensure that the rice at every stage of breeding maintains Rf-1 gene and that the Rf-1 gene is homozygous at the final stage. It also becomes necessary in the triple-crossing system to check to ensure that the variety used as the restorer line possesses Rf-1 gene, or to check for the presence of Rf-1 gene in order to ensure that the resulting hybrid seeds have restored fertility.

In order to genotype the locus of Rf-1 gene in a plant, it has been necessary that F1 plants be first formed from hybrid seeds obtained by crossing the plant to be genotyped to a standard line and then self-fertilized, followed by investigating the incidence of individuals that can produce seeds at a frequency higher than a certain level (e.g. 70~80% or more). The standard line refers to the maintainer line, the sterile line or a set of the two lines, and it is appropriately chosen depending upon whether the cytoplasm of the individual under test is of BT type or normal type or unknown. If the standard line is a sterile line, it is crossed to the individual under test as the female parent and if the standard line is a maintainer line, it is crossed as the male parent.

However, these techniques require a huge amount of labor and time to carry out. As a further problem, fertilization for seed production is sensitive to environmental factors and if an investigation is made in an unfavorable environment such as cold climate or insufficient daylight, sterility may be caused irrespective of the genotype constitution, with the result that genotyping of the locus of Rf-1 gene cannot be performed accurately.

With a view to solving these problems, it has recently been proposed that Rf-1 gene be checked for its presence by a technique of molecular biology. The technical idea of this technique lies in checking for the presence or absence of Rf-1 gene by detecting base sequences linked to Rf-1 gene (such sequences are hereunder referred to as DNA markers). Note that it is not possible to directly detect Rf-1 gene since the DNA sequence of Rf-1 gene has not been clarified so far.

For example, it has been reported that the locus of Rf-1 gene in rice is present on chromosome 10 and located between DNA marker (RFLP marker) loci G291 and G127 which can be used in restriction fragment length polymorphism analysis (RFLP) (Fukuta et al., 1992, Jpn J. Breed. 42 (supl. 1) 164-165). This is a known method of genotyping the locus of Rf-1 gene by investigating the genotypes of DNA marker loci G291 and G127 which are linked to Rf-1 gene.

However, the conventional molecular biology techniques have several problems. First, they use RFLP markers which need to be detected by Southern blot analysis. In order to perform Southern blot analysis, DNA at the microgram level needs to be purified from the individual under test and, in addition, there is a need to carry out a sequence of steps comprising treatment with restriction enzymes, electrophoresis, blotting, hybridization with a probe and signal detection; this not only involves considerable labor but it also takes about one week to obtain the test results.

The second problem is that since the gene map distance between RFLP marker loci G291 and G127 is as long as about 30 cM (corresponding to about 9000 kbp in rice DNA), the probability for the occurrence of double recombination in the region would be a few percent and hence, it is not always guaranteed that the genotype of the locus of Rf-1 gene can be estimated correctly by the markers.

Thirdly, when the presence of Rf-1 gene is estimated by detecting RFLP marker loci G291 and G127, not only Rf-1 gene but also the gene region between those loci are introduced into the fertility restorer line selected as the result of breeding. As a consequence, the introduced DNA sequence will have a chromosomal region of 30 cM or longer from the Rf-1 gene donor parent, and this presents the risk of introducing a deleterious gene that may potentially be present within that region.

In order to solve these problems, there have been developed a dominant DNA marker (Japanese Patent Public Disclosure No. 222588/1995) and a co-dominant DNA marker (Japanese Patent Public Disclosure No. 313187/1997), both of which are linked to the locus of Rf-1 gene. These markers are linked to the locus of Rf-1 gene, their genetic distances from Rf-1 gene respectively being 1.6±0.7 cM (corresponding to about 480 kbp in rice DNA) and 3.7±1.1 cM (corresponding to about 1110 kbp in rice DNA), and their loci being on opposite sides of the locus of Rf-1 gene. Hence, the presence of Rf-1 gene can be estimated by detecting the presence of both the locus of the dominant PCR marker and that of the co-dominant PCR marker. The use of the co-dominant PCR marker also enables us to estimate as to whether the locus of Rf-1 gene is homozygous or heterozygous.

However, the use of these PCR markers still involve several problems. The co-dominant marker has a genetic distance of 3.7±1.1 cM from the locus of Rf-1 gene, and the problem of potentially high frequency of recombination with the locus of Rf-1 gene has not been fully dissolved. As a result, speaking of the co-dominant marker itself, correct detection can be made as to whether it is homozygous or a heterozygous. However, if recombination occurs between the locus of the co-dominant marker and that of Rf-1 gene, the genotype of Rf-1 gene locus cannot be determined correctly, particularly as to whether it is homozygous or heterozygous. On the other hand, if the dominant marker is used to genotype the locus of Rf-1 gene, the marker will detect individuals indiscriminately irrespective of whether they are homozygous (Rf-1/Rf-1) or heterozygous (Rf-1/rf-1) with respect to Rf-1 gene. Therefore, even if the co-dominant marker is used in combination with the dominant marker in order to genotype the locus of Rf-1 gene, it is not possible to correctly distinguish individuals having Rf-1 gene homozygously from those having the gene heterozygously. Further, if no amplification product is obtained in PCR using the dominant marker, one cannot deny the possibility that this is due to some problems in the experimental procedure. As a further problem, since the genetic distance between the co-dominant marker and the dominant marker is as great as about 5.3 cM (around 1590 kbp), the size of the chromosomal region introduced from the Rf-1 gene donor parent cannot be limited to a sufficiently small value to prevent any concomitant introduction of a deleterious gene which may be contained in that region.

Japanese Patent Public Disclosure No. 139465/2000 describes co-dominant PCR markers that were developed on the basis of the base sequences of RFLP markers located in the neighborhood of Rf-1 gene on chromosome 10 of rice. However, most of those PCR markers are spaced from the Rf-1 gene by a genetic distance greater than about 1 cM.

DISCLOSURE OF THE INVENTION

An object of the present invention is to provide methods for restoring rice fertility. A method of the present invention comprises introducing a nucleic acid into rice, wherein the nucleic acid encodes the amino acid sequence of SEQ ID NO. 75, or an amino acid sequence which is identical to at least 70% of the amino acid sequence of SEQ ID NO. 75, and which functions to restore fertility. In one of the preferred embodiments of the present invention, the nucleic acid encoding the amino acid sequence of SEQ ID NO. 75, or an amino acid sequence which is identical to at least 70% of the amino acid sequence of SEQ ID NO. 75 is selected from nucleic acids of the following a)-p):

a) a nucleic acid comprising the bases 215-2587 of SEQ ID NO:69;

b) a nucleic acid comprising the bases 213-2585 of SEQ ID NO:70;

c) a nucleic acid comprising the bases 218-2590 of SEQ ID NO:71;

d) a nucleic acid comprising the bases 208-2580 of SEQ ID NO:72;

e) a nucleic acid comprising the bases 149-2521 of SEQ ID NO:73;

f) a nucleic acid comprising the bases 225-2597 of SEQ ID NO:74;

g) a nucleic acid comprising the bases 43907-46279 of SEQ ID NO:27;

h) a nucleic acid comprising the bases 229-2601 of SEQ ID NO:80;

i) a nucleic acid comprising the bases 175-2547 of SEQ ID NO:81;

j) a nucleic acid comprising the bases 227-2599 of SEQ ID NO:82;

k) a nucleic acid comprising the bases 220-2592 of SEQ ID NO:83;

l) a nucleic acid comprising the bases 174-2546 of SEQ ID NO:84;

m) a nucleic acid comprising the bases 90-2462 of SEQ ID NO:85;

n) a nucleic acid which is identical to at least 70% of the nucleic acid of any of a)-m), and which functions to restore fertility;

o) a nucleic acid which hybridizes to the nucleic acid of any of a)-m) under a moderate or high stringent condition, and which functions to restore fertility; and p) a nucleic acid wherein one or a plurality of base(s) is deleted from, added to or substituted from the nucleic acid of any of a)-m), and which functions to restore fertility.

Preferably, in the method of the present invention, the nucleic acid encoding the amino acid sequence of SEQ ID NO. 75, or an amino acid sequence which is identical to at least 70% of the amino acid sequence of SEQ ID NO. 75, and which functions to restore fertility, meets at least one of the following requirements 1)-12):

1) a base corresponding to the base 1769 of SEQ ID NO. 69 is A;

2) a base corresponding to the base 1767 of SEQ ID NO. 70 is A;

3) a base corresponding to the base 1772 of SEQ ID NO. 71 is A;

4) a base corresponding to the base 1762 of SEQ ID NO. 72 is A;

5) a base corresponding to the base 1703 of SEQ ID NO. 73 is A;

6) a base corresponding to the base 1779 of SEQ ID NO. 74 is A;

7) a base corresponding to the base 1783 of SEQ ID NO. 80 is A;

8) a base corresponding to the base 1729 of SEQ ID NO. 81 is A;

9) a base corresponding to the base 1781 of SEQ ID NO. 82 is A;

10) a base corresponding to the base 1774 of SEQ ID NO. 83 is A;

11) a base corresponding to the base 1728 of SEQ ID NO. 84 is A; or 12) a base corresponding to the base 1644 of SEQ ID NO. 85 is A.

Another object of the present invention is to provide a method for discerning whether a subject rice individual or a seed thereof has the Rf-1 gene or not, utilizing a nucleic acid encoding the amino acid sequence of SEQ ID NO. 75, or an amino acid sequence which is identical to at least 70% of the amino acid sequence of SEQ ID NO. 75, and which functions to restore fertility. Preferably, in an embodiment of the present method, the subject rice individual or the seed thereof is determined to have the Rf-1 gene, in the case that the nucleic acid encoding the amino acid sequence of SEQ ID NO. 75, or an amino acid sequence which is identical to at least 70% of the amino acid sequence of SEQ ID NO. 75, and which functions to restore fertility, meets at least one of the following requirements 1)-12):

1) a base corresponding to the base 1769 of SEQ ID NO. 69 is A;

2) a base corresponding to the base 1767 of SEQ ID NO. 70 is A;

3) a base corresponding to the base 1772 of SEQ ID NO. 71 is A;

4) a base corresponding to the base 1762 of SEQ ID NO. 72 is A;

5) a base corresponding to the base 1703 of SEQ ID NO. 73 is A;

6) a base corresponding to the base 1779 of SEQ ID NO. 74 is A;

7) a base corresponding to the base 1783 of SEQ ID NO. 80 is A;

8) a base corresponding to the base 1729 of SEQ ID NO. 81 is A;

9) a base corresponding to the base 1781 of SEQ ID NO. 82 is A;

10) a base corresponding to the base 1774 of SEQ ID NO. 83 is A;

11) a base corresponding to the base 1728 of SEQ ID NO. 84 is A; or 12) a base corresponding to the base 1644 of SEQ ID NO. 85 is A.

Another object of the present invention is to provide a method for inhibiting the function of the Rf-1 gene to restore fertility. The inhibition method of the present invention comprises, in an embodiment, introducing an antisense having at least 100 bases in length, and being selected from base sequences complementary to a nucleic acid encoding the amino acid sequence of SEQ ID NO. 75, or an amino acid sequence which is identical to at least 70% of the amino acid sequence of SEQ ID NO. 75, and which functions to restore fertility.

Still another object of the present invention is to provide a nucleic acid encoding the amino acid sequence of SEQ ID NO. 75, or an amino acid sequence which is identical to at least 70% of the amino acid sequence of SEQ ID NO. 75, and which functions to restore fertility. The present invention provides, in an embodiment, a nucleic acid selected from nucleic acids of the following a)-p):

a) a nucleic acid comprising the bases 215-2587 of SEQ ID NO:69;

b) a nucleic acid comprising the bases 213-2585 of SEQ ID NO:70;

c) a nucleic acid comprising the bases 218-2590 of SEQ ID NO:71;

d) a nucleic acid comprising the bases 208-2580 of SEQ ID NO:72;

e) a nucleic acid comprising the bases 149-2521 of SEQ ID NO:73;

f) a nucleic acid comprising the bases 225-2597 of SEQ ID NO:74;

g) a nucleic acid comprising the bases 43907-46279 of SEQ ID NO:27;

h) a nucleic acid comprising the bases 229-2601 of SEQ ID NO:80;

i) a nucleic acid comprising the bases 175-2547 of SEQ ID NO:81;

j) a nucleic acid comprising the bases 227-2599 of SEQ ID NO:82;

k) a nucleic acid comprising the bases 220-2592 of SEQ ID NO:83;

l) a nucleic acid comprising the bases 174-2546 of SEQ ID NO:84;

m) a nucleic acid comprising the bases 90-2462 of SEQ ID NO:85;

n) a nucleic acid which is identical to at least 70% of the nucleic acid of any of a)-m), and which functions to restore fertility;

o) a nucleic acid which hybridizes to the nucleic acid of any of a)-m) under a moderate or high stringent condition, and which functions to restore fertility; and p) a nucleic acid wherein one or a plurality of base(s) is deleted from, added to or substituted from the nucleic acid of any of a)-m), and which functions to restore fertility.

BEST MODES FOR PERFORMING THE INVENTION

Figure 1:
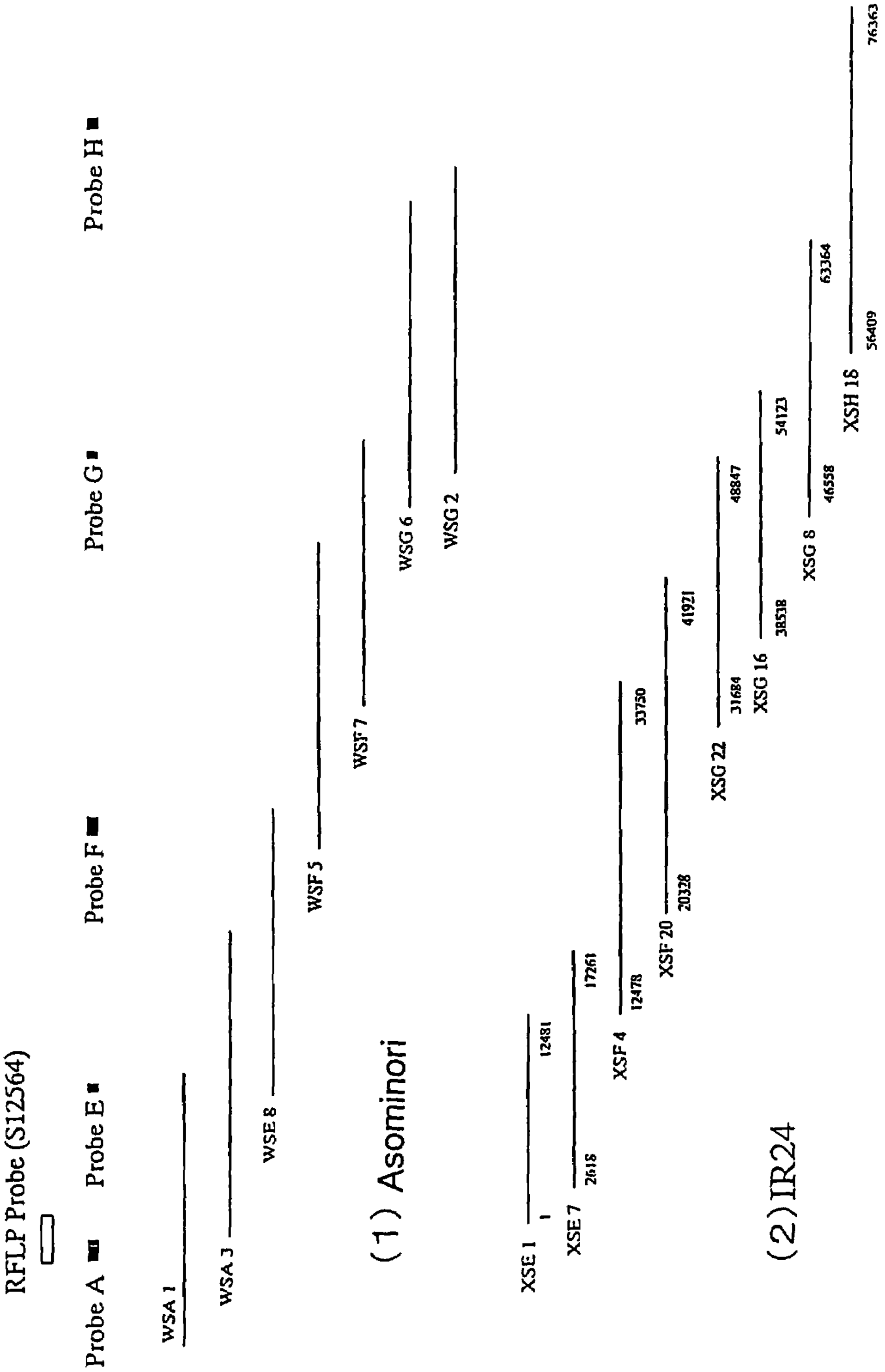
FIG. 1 shows the results of chromosomal walking started from the RFLP marker locus S12564.

We began by restricting the Rf-1 locus to a very small region on chromosome 10. On this basis, we developed PCR markers proximal to the Rf-1 locus and found a method for detecting the Rf-1 gene by utilizing on the linkage of these PCR markers to the Rf-1 locus. Specifically, the presence of the Rf-1 gene is tested and individuals homozygous for the Rf-1 gene are selected by genotyping at the novel PCR marker loci proximal to the Rf-1 locus on the basis that the Rf-1 locus is mapped between the PCR marker loci S12564 Tsp509I and C1361 MwoI on chromosome 10 of rice. We previously filed a patent application for the method for detecting the Rf-1 gene under Japanese Patent Application No. 2000-247204 on Aug. 17, 2000. The entire disclosure of the patent application is incorporated herein by reference.

I. Methods for Estimating the Genotype at the Rf-1 Locus Described in Japanese Patent Application No. 2000-247204

Japanese Patent Application No. 2000-247204 describes methods for determining whether or not a rice individual or seed under test has the Rf-1 gene on the basis that the Rf-1 locus is mapped between the PCR marker loci S12564 and C1361 on chromosome 10 of rice.

Markers

Primer pairs designed to be specific to particular regions near the locus of Rf-1 gene are used in PCR and the amplification products are treated with particular restriction enzymes; upon electrophoresis, rice of indica lines in some cases provide an observable band of a different size from that of rice of Japonica lines. This band which is characteristic of indica lines is herein referred to as the Rf-1 linked band. Now that it has been made clear by the present inventors that the locus of Rf-1 gene is located between PCR markers S12564 Tsp509I and C1361 MwoI on chromosome 10 of rice, the skilled artisan can appropriately develop and employ PCR markers that are present in the neighborhood of Rf-1 gene.

For instance, according to the invention, a rice individual under test is checked to see if its genome contains at least one of the PCR markers listed below, thereby determining whether the individual under test has Rf-1 gene linked to those PCR markers:

(1) marker 1: PCR marker R1877 EcoRI which, when rice genomic DNA is subjected to PCR with DNA primers having the sequences of SEQ ID NO:1 and SEQ ID NO:2, can detect polymorphisms between rice individuals of the japonica and indica lines depending on whether the amplification products have a recognition site for restriction enzyme EcoRI;

(2) marker 2: PCR marker G4003 HindIII (SEQ ID NO:19) which, when rice genomic DNA is subjected to PCR with DNA primers having the sequences of SEQ ID NO:3 and SEQ ID NO:4, can detect polymorphisms between rice individuals of the japonica and indica lines depending on whether the amplification products have a recognition site for restriction enzyme HindIII;

(3) marker 3: PCR marker C1361 MwoI (SEQ ID NO:20) which, when rice genomic DNA is subjected to PCR employing DNA primers having the sequences of SEQ ID NO:5 and SEQ ID NO:6, can detect polymorphisms between rice individuals of the japonica and indica lines depending on whether the amplification products have a recognition site for restriction enzyme MwoI;

(4) marker 4: PCR marker G2155 MwoI (SEQ ID NO:21) which, when rice genomic DNA is subjected to PCR with DNA primers having the sequences of SEQ ID NO:7 and SEQ ID NO:8, can detect polymorphisms between rice individuals of the japonica and indica lines depending on whether the amplification products have a recognition site for restriction enzyme MwoI;

(5) marker 5: PCR marker G291 MspI (SEQ ID NO:22) which, when rice genomic DNA is subjected to PCR with DNA primers having the sequences of SEQ ID NO:9 and SEQ ID NO:10, can detect polymorphisms between rice individuals of the japonica and indica lines depending on whether the amplification products have a recognition site for restriction enzyme MspI;

(6) marker 6: PCR marker R2303 BslI (SEQ ID NO:23) which, when rice genomic DNA is subjected to PCR with DNA primers having the sequences of SEQ ID NO:11 and SEQ ID NO:12, can detect polymorphisms between rice individuals of the japonica and indica lines depending on whether the amplification products have a recognition site for restriction enzyme BslI;

(7) marker 7: PCR marker S10019 BstUI (SEQ ID NO:24) which, when rice genomic DNA is subjected to PCR with DNA primers having the sequences of SEQ ID NO:13 and SEQ ID NO:14, can detect polymorphisms between rice individuals of the japonica and indica lines depending on whether the amplification products have a recognition site for restriction enzyme BstUI;

(8) marker 8: PCR marker S10602 KpnI (SEQ ID NO:25) which, when rice genomic DNA is subjected to PCR with DNA primers having the sequences of SEQ ID NO:15 and SEQ ID NO:16, can detect polymorphisms between rice individuals of the japonica and indica lines depending on whether the amplification products have a recognition site for restriction enzyme KpnI; and (9) marker 9: PCR marker S12564 Tsp509I (SEQ ID NO:26) which, when rice genomic DNA is subjected to PCR with DNA primers having the sequences of SEQ ID NO:17 and SEQ ID NO:18, can detect polymorphisms between rice individuals of the japonica and indica lines depending on whether the amplification products have a recognition site for restriction enzyme Tsp509I.

Assuming that the locus of Rf-1 gene was highly likely to be located near the nine RFLP marker regions R1877, G291, R2303, S12564, C1361, S10019, G4003, S10602 and G2155 on chromosome 10 of rice (see the results of RFLP linkage analysis described in Fukuta et al., 1992, Jpn. J. Breed. 42 (supl. 1) 164-165 and the RFLP linkage map of rice described in Harushima et al., 1998, Genetics, 148, 479-494), the present inventors converted those RFLP markers to co-dominant PCR markers such as CAPS markers or dCAPS markers as described below in Reference example 1 (Michaels and Amasino, 1998, The Plant Journal, 14(3), 381-385; Neff et al., 1998, The Plant Journal, 14(3), 387-392). As a result of this conversion, the PCR markers above have been obtained.

Among these PCR markers, one group consisting of PCR markers R1877 EcoRI, G291 MspI (SEQ ID NO:22), R2303 BslI (SEQ ID NO:23) and S12564 Tsp509I (SEQ ID NO:26) and the other group consisting of PCR markers C1361 MwoI (SEQ ID NO:20), S10019 BstUI (SEQ ID NO:24), G4003 HindIII (SEQ ID NO:19), S10602 KpnI (SEQ ID NO:25) and G2155 MwoI (SEQ ID NO:21) are on opposite sides of the locus of Rf-1 gene on chromosome 10 of rice.

Therefore, in one embodiment, the presence of the Rf-1 gene is detected by detecting Rf-1 linked bands by (a) at least one PCR marker selected from the group consisting of PCR markers R1877 EcoRI, G291 MspI, R2303 BslI and S12564 Tsp509I, and (b) at least one PCR marker selected from the group consisting of PCR markers C1361 MwoI, S10019 BstUI, G4003 HindIII, S10602 KpnI and G2155 MwoI. In this case, at least S12564 Tsp509I from group (a) and at least C1361 MwoI from group (b) are preferably used as the closest PCR markers to the Rf-1 gene. If Rf-1 linked bands are detected with PCR markers of both (a) and (b) in the genome of the rice under test, it can be estimated with a high probability that the rice contains Rf-1 gene.

In another embodiment, Rf-1 linked bands are detected by at least two PCR markers of group (a) and at least two PCR markers of group (b) above. For example, a rice individual carrying the Rf-1 gene with a minimum of unwanted gene regions can be selected by picking up an individual in which Rf-1 linked bands are detected by markers of groups (a) and (b) more proximal to the Rf-1 gene but not detected by markers of groups (a) and (b) more distal from the Rf-1 gene on the gene map shown in FIG. 1. Again, it is preferred that at least one PCR marker of group (a) is S12564 Tsp509I and at least one PCR marker of group (b) is C1361 MwoI. Thus, the two PCR marker loci S12564 Tsp509I and C1361 MwoI are separated by a genetic distance of 0.3 cM. By utilizing this characteristic, the chromosomal region that is introduced from the Rf-1 gene donor parent can be narrowed down to a size of about 1 cM. This helps minimize the possibility of introducing into the restorer line a deleterious gene that may be present in the neighborhood of Rf-1 gene in the donor parent.

Detection of the Rf-1 Gene

In order to detect Rf-1 gene in the genome of a rice under test, any one of the above PCR markers is amplified from the genome of the rice by PCR using primers of SEQ ID NOS: 1-18 above and then detected by the polymerase chain reaction-restriction fragment length polymorphism method (PCR-RFLP). PCR-RFLP is a method that is applicable to the case where polymorphisms exist among variety lines at recognition sites of restriction enzymes in the sequences of PCR amplified DNA fragments and by which specific polymorphisms can conveniently be identified on the basis of cleavage patterns with those restriction enzymes (D. E. Harry et al., Theor. Appl. Genet. (1998), 97:327-336)

Restriction enzyme cleavage patterns show the bands as shown in Table 1 below on a visualized gel depending on the primer pair used.

TABLE 1

| | Approximate size (bp) of detected band |
|---|---|
| **Detection of marker 1 (R1877 EcoRI) with primer pair 1** | |
| When the genome of test rice has Rf-1 gene homozygously: | 1500 and 1700 |
| When the genome of test rice has Rf-1 gene heterozygously: | 1500, 1700 and 3200 |
| When the genome of test rice has no Rf-1 gene: | 3200 |
| **Detection of marker 2 (G4003 HindIII) with primer pair 2** | |
| When the genome of test rice has Rf-1 gene homozygously: | 362 |
| When the genome of test rice has Rf-1 gene heterozygously: | 95, 267 and 362 |
| When the genome of test rice has no Rf-1 gene: | 95 and 267 |
| **Detection of marker 3 (C1361 MwoI) with primer pair 3** | |
| When the genome of test rice has Rf-1 gene homozygously: | 50 and 107 |
| When the genome of test rice has Rf-1 gene heterozygously: | 25, 50, 79 and 107 |
| When the genome of test rice has no Rf-1 gene: | 25, 50 and 79 |
| **Detection of marker 4 (G2155 MwoI) with primer pair 4** | |
| When the genome of test rice has Rf-1 gene homozygously: | 25, 27 and 78 |
| When the genome of test rice has Rf-1 gene heterozygously: | 25, 27, 78 and 105 |
| When the genome of test rice has no Rf-1 gene: | 25 and 105 |
| **Detection of marker 5 (G291 MspI) with primer pair 5** | |
| When the genome of test rice has Rf-1 gene homozygously: | 25, 49 and 55 |
| When the genome of test rice has Rf-1 gene heterozygously: | 25, 49, 55 and 104 |
| When the genome of test rice has no Rf-1 gene: | 25 and 104 |
| **Detection of marker 6 (R2303 BslI) with primer pair 6** | |
| When the genome of test rice has Rf-1 gene homozygously: | 238, 655 and 679 |
| When the genome of test rice has Rf-1 gene heterozygously: | 238, 655, 679 and 1334 |
| When the genome of test rice has no Rf-1 gene: | 238 and 1334 |
| **Detection of marker 7 (S10019 BstUI) with primer pair 7** | |
| When the genome of test rice has Rf-1 gene homozygously: | 130, 218 and 244 |
| When the genome of test rice has Rf-1 gene heterozygously: | 130, 218, 244 and 462 |
| When the genome of test rice has no Rf-1 gene: | 130 and 462 |
| **Detection of marker 8 (S10602 KpnI) with primer pair 8** | |
| When the genome of test rice has Rf-1 gene homozygously: | 724 |
| When the genome of test rice has Rf-1 gene heterozygously: | 117, 607 and 724 |
| When the genome of test rice has no Rf-1 gene: | 117 and 607 |
| **Detection of marker 9 (S12564 Tsp509I) with primer pair 9** | |
| When the genome of test rice has Rf-1 gene homozygously: | 41 and 117 |
| When the genome of test rice has Rf-1 gene heterozygously: | 26, 41, 91 and 117 |
| When the genome of test rice has no Rf-1 gene: | 26, 41 and 91 |

II. Identification of the Rf-1 Locus

As described above, Japanese Patent Application No. 2000-247204 discloses RFLP-PCR markers based on our finding that the Rf-1 locus is mapped between DNA marker loci S12564 Tsp509I and C1361 MwoI. Fertility-restoring lines are established by backcrossing the Rf-1 gene into a normal japonica variety not containing the Rf-1 gene. If the method for identifying the Rf-1 locus described in Japanese Patent Application No. 2000-247204 is used during this process, not only the restoring lines can be established efficiently (within 2-3 years) but also the length of insert fragments can be controlled.

However, introduction by crossing inevitably introduce regions proximal to Rf-1 at the same time. Japanese Patent Application No. 2000-247204 showed that the Rf-1 locus is mapped between DNA marker loci S12564 Tsp509I and C1361 MwoI, but the distance between both loci is about 0.3 cM, i.e. about 90 kbp. If a deleterious gene existed proximal to Rf-1, it would be undeniable that the deleterious gene might be inserted together with the Rf-1 gene.

Thus, we searched for regions linked to the Rf-1 gene between DNA marker loci S12564 Tsp509I and C1361 MwoI by chromosomal walking and genetic analysis based on the close linkage between the Rf-1 locus and the DNA marker locus S12564 Tsp509I. As a result, we successfully identified the region of the Rf-1 locus including the Rf-1 gene up to about 76 kb and determined the entire base sequence of said region. According to the present invention, it is possible to introduce the function of a fertility restorer gene into BT male sterile cytoplasms by genetic engineering techniques.

Specifically, in Japanese Patent Application No. 2000-247204, linkage analyses on a population of 1042 individuals prepared by pollinating MS Koshihikari with MS-FR Koshihikari (heterozygous at the Rf-1 locus) revealed one recombinant between the Rf-1 and S12564 Tsp509I loci and two recombinants between the Rf-1 and C1361 MwoI loci (Reference examples 1-2 herein). In the present invention, 4103 individuals were added to the population to analyze a total of 5145 individuals. As a result, one recombinant between the Rf-1 and S12564 Tsp509I loci and six recombinants between the Rf-1 and C1361 MwoI loci were newly found with a total of 2 and 8 recombinants. These 10 individuals were tested by the high-precision segregation analysis of the present invention as recombinants proximal to the Rf-1 locus (Example 1).

The frequency of 8 recombinants between the Rf-1 and C1361 MwoI loci as compared with 2 recombinants between the Rf-1 and S12564 Tsp509I loci means that the S12564 Tsp509I locus is genetically closer to the Rf-1 locus than the C1361 MwoI locus. Genetic distance (expressed in recombination frequency: cM) and physical distance (expressed in the number of base pairs: bp) are not always proportional to each other, but it can be normally expected that physical distance decreases with genetic distance.

Thus, we tried to isolate the Rf-1 locus by chromosomal walking started from the S12564 Tsp509I locus (Example 2). Chromosomal walking was performed on a genomic library prepared from λ DASH II vector using the genomic DNA of an indica variety IR24 and a japonica variety Asominori. IR24 is a variety carrying Rf-1, while Asominori is a variety not carrying Rf-1. As a result of chromosomal walking, contigs covering a chromosomal region of about 76 kb (ordered sets of overlapping clones on a chromosome) were able to be prepared from genomic clones of IR24, and the entire base sequence (76363 bp) thereof was determined.

Then, 12 markers were newly developed on the basis of the base sequence data or the like obtained and a high-precision segregation analysis was performed on the 10 recombinants proximal to Rf-1 locus described above (Example 3). As a result, a 65 kb sequence included in the chromosomal region of about 76 kb above was shown to contain a sequence determining the presence of the function of the Rf-1 gene. This region is covered by a contig consisting of 8 genomic clones. Each clone has a length of about 12-22 kb and has overlapping domains of at least 4.7 kb. Genes for rice are known to have a wide range of lengths (from short ones to large ones), but most of them seem to have a length of several kb or less. Thus, at least one of these 8 genomic clones is expected to contain the full-length Rf-1 gene.

We further restricted the Rf-1 gene region in the chromosomal region of about 76 kb above and performed complementation assays to directly demonstrate the presence of a fertility restoring ability.

Figure 5:
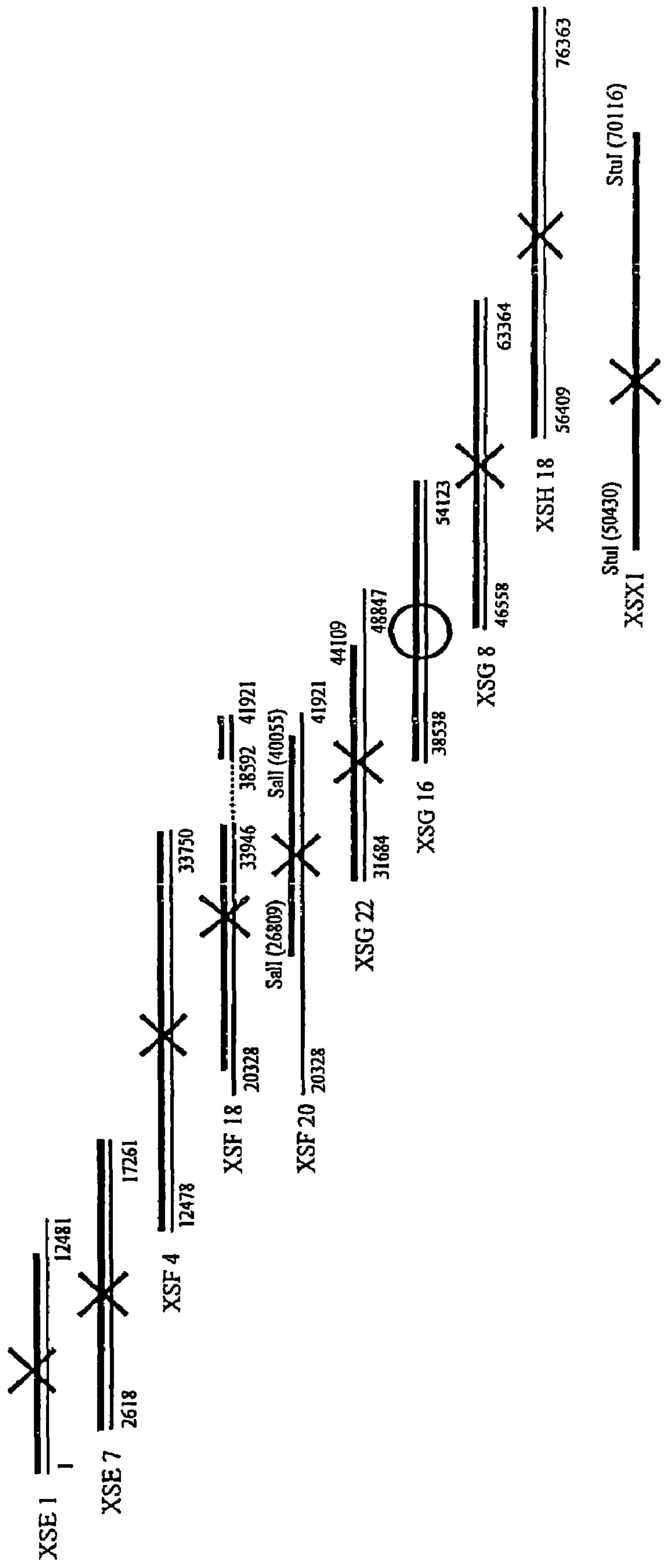
FIG. 5 shows fragments from 10 genomic clones used for the identification of the Rf-1 region by complementation assays. Lambda clones obtained by chromosomal walking (thin lines) were used for complementation assays of the chromosomal regions shown by bold lines. XSF18 was found to contain a deletion shown by dotted line.

Specifically, 10 partial fragments (each 10-21 kb) in the above region of 76 kb were separately introduced into immature seeds of a male sterility line MS Koshihikari by genetic engineering techniques (FIG. 5). Of the 10 partial fragments used, 8 fragments are derived from 8 genomic clones previously obtained by chromosomal walking (XSE1, XSE7, XSF4, XSF20, XSG22, XSG16, XSG8 and XSH18 shown in FIG. 1 and described in Example 3). Additionally, fragments derived from 2 clones XSF18 and XSX1 were also analyzed by complementation assays. XSF18 is identical to XSF20 at the 5' and 3' ends (bases 20328 and 41921 of SEQ ID NO:27, respectively), but lacks internal bases 33947-38591. This is because clone XSF18 was initially isolated but found to contain the above deletion during amplification after isolation, and therefore, the amplification step was freshly taken to isolate a complete clone designated XSF20 (Example 8). XSX1 is a clone freshly prepared from clones XSG8 and XSH18 by restriction enzyme treatment and ligation to contain sufficient overlapping domains because of the overlapping domains of both clones are relatively small (about 7 kb) (Example 13).

If the insert fragment completely contains the Rf-1 gene, transformed individuals at this generation restore fertility because Rf-1 is a dominant gene. In complementation assays plants transformed with each fragment were evaluated for seed fertility to find that those transformed with a 15.6 kb fragment (including bases 38538-54123 of SEQ ID NO:27) derived from the λ phage clone XSG16 restored seed fertility (Example 10). Plants transformed with the other fragments were all sterile. These results showed that the above 15.6 kb fragment completely contains the Rf-1 gene. Moreover, a method for introducing the Rf-1 gene by genetic engineering techniques was provided by the present invention and demonstrated to be effective.

To further specify the region of the λ phage clone XSG16 in which the Rf-1 gene is contained, we evaluated seed fertility of shorter fragments than the 15.6 kb fragment (including bases 38538-54123 of SEQ ID NO:27) by complementation assays. As a result, plants transformed with a 11.4 kb fragment derived from XSG16 (including bases 42357-53743 of SEQ ID NO:27) were shown to restore seed fertility (Example 10(2)). Plants transformed with a further shorter 6.8 kb fragment (including bases 42132-48883 of SEQ ID NO:27) also restored seed fertility (Example 10(3)). These results showed that the above 6.8 kb fragment contains the Rf-1 gene.

The present inventors further continued studying, and identified the nucleic acid having the function to restore fertility. The amino acid sequence encoded by the nucleic acid then has been clarified. Specifically, DNA fragments corresponding to bases 43733-44038 and 48306-50226 of SEQ ID NO:27 were first prepared by using PCR as described in Examples 14-15. The cDNA library prepared from the line wherein Rf-1 is introduced to Koshihikari was screened by using the above two DNA fragments as probes (Probe P and Q). As a result, terminal base sequences of 6 clones are identical to the sequence of XSG16, and these 6 clones were isolated as those containing the Rf-1 gene, and base sequences thereof were analyzed (SEQ ID NOS:69-74).

All of the sequences, SEQ ID NOS:69-74 encode a protein having the amino acids 1-791 of SEQ ID NO:75. Specifically, all and each of the 215-2587 of SEQ ID NO:69, the bases 213-2585 of SEQ ID NO:70, the bases 218-2590 of SEQ ID NO:71, the bases 208-2580 of SEQ ID NO:72, the bases 149-2521 of SEQ ID NO:73 and the bases 225-2597 of SEQ ID NO:74 encodes a protein having amino acids 1-791 of SEQ ID NO:75. The above base sequences correspond to the bases 43907-46279 of SEQ ID NO:27.

The amino acid sequence of SEQ ID NO:75 was compared with the presumed amino acid sequence of the corn fertility restorer gene (Rf2), and the N-terminal 7 amino acid residues (Met-Ala-Arg-Arg-Ala-Ala-Ser) in both amino acid sequences were concurred. These 7 amino acid residues are considered to be a portion of a targeting signal to mitochondria (Liu et al., 2001). Based on the above facts, the cDNAs isolated on this occasion are considered to contain the full coding region of the Rf-1 gene. No homology between the amino acid sequences of the rice Rf-1 and the corn Rf-2 can be found except for the above region.

Figure 7:
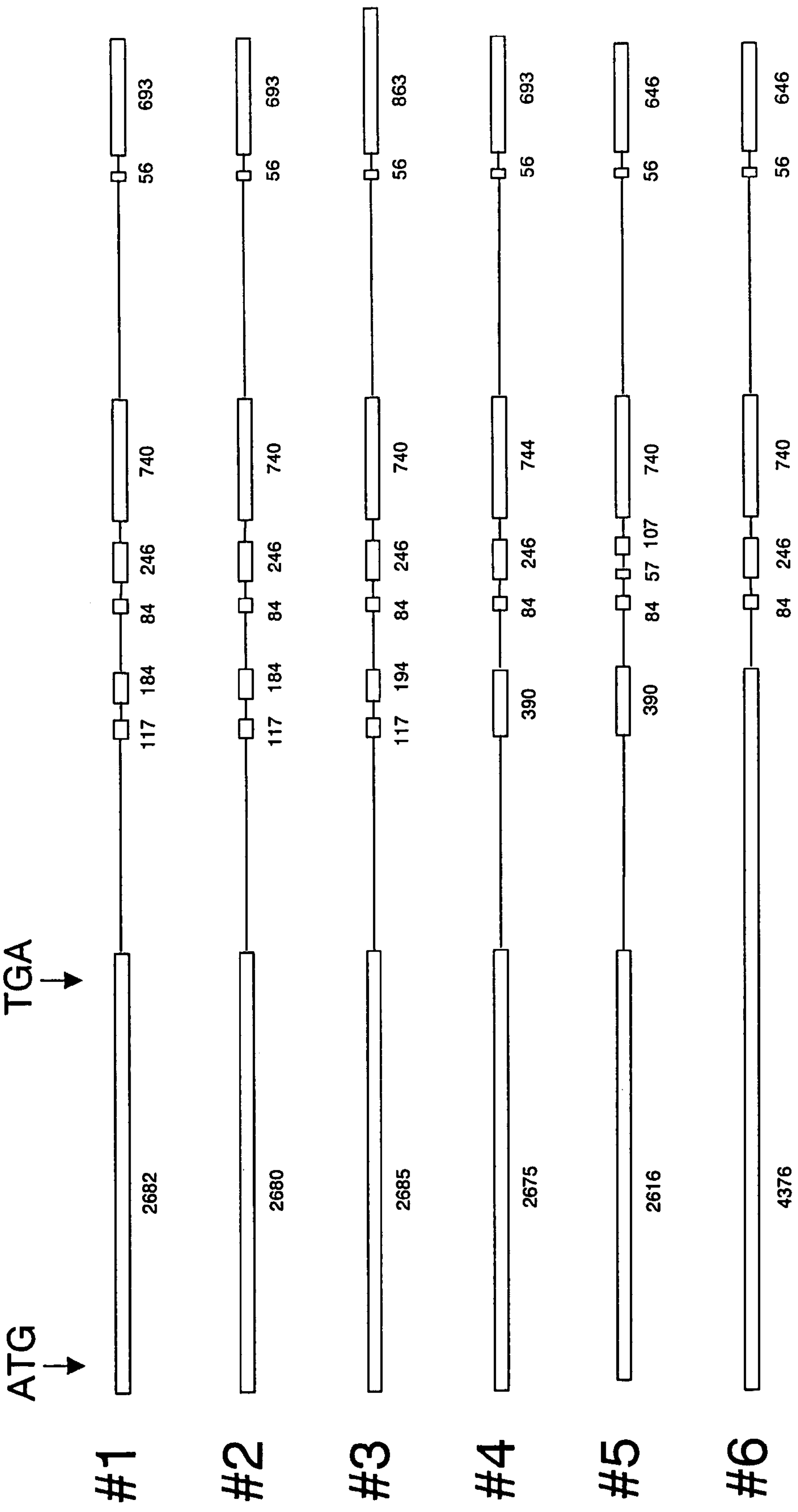
FIG. 7 is a schematic picture showing the Rf-1 gene structure. White bars and black bars represent exons and introns, respectively. Numbers of base pairs are shown for the exon portions.

In addition, the sequences of cDNAs isolated on this occasion were compared with the genome sequence of IR24 (SEQ ID NO:27), and the structures of exons and introns of the Rf-1 gene were clarified (FIG. 7). As a result, it was shown that various transcription products wherein the splicing patterns and the poly A addition positions are different, are present in a plant body. There is no intron in the coding region of the Rf-1 gene.

As for the 6.8 kb fragment which restored seed fertility in the complementary assay of Example 10 (3), the present inventors further pursued a complementary assay. Specifically, in Example 16, a 4.2 kb fragment (the bases 42132-46318 of SEQ ID NO:27) containing the promoter region and the presumed translation region of the Rf-1 gene within the above 6.8 kb fragment was subjected to a complementary assay, and the 4.2 kb fragment restored the seed fertility.

Further, in Example 17, six new clones containing the nucleic acid having the fertility restorer function were obtained. Specifically, PCR was performed by using two primers corresponding to the bases 45522-45545 and 45955-45932 of SEQ ID NO:27, and the genomic clone XSG16 of IR24 as a template to obtain a DNA fragment. Plaque hybridization assays were performed by using the DNA fragment as Probe R and the above mentioned Probe P. Six clones were newly obtained (#7-#12) from plaques which are positive for both Probe P and Probe R. The results were shown in SEQ ID NOS:80-85.

All of the sequences, SEQ ID NOS:80-85 are presumed to encode a protein having the amino acids 1-791 of SEQ ID NO:75. Specifically, all and each of the 229-2601 of SEQ ID NO:80, the bases 175-2547 of SEQ ID NO:81, the bases 227-2599 of SEQ ID NO:82, the bases 220-2592 of SEQ ID NO:83, the bases 174-2546 of SEQ ID NO:84 and the bases 90-2462 of SEQ ID NO:85 encodes a protein having amino acids 1-791 of SEQ ID NO:75. The above base sequences correspond to the bases 43907-46279 of SEQ ID NO:27.

Figure 8:
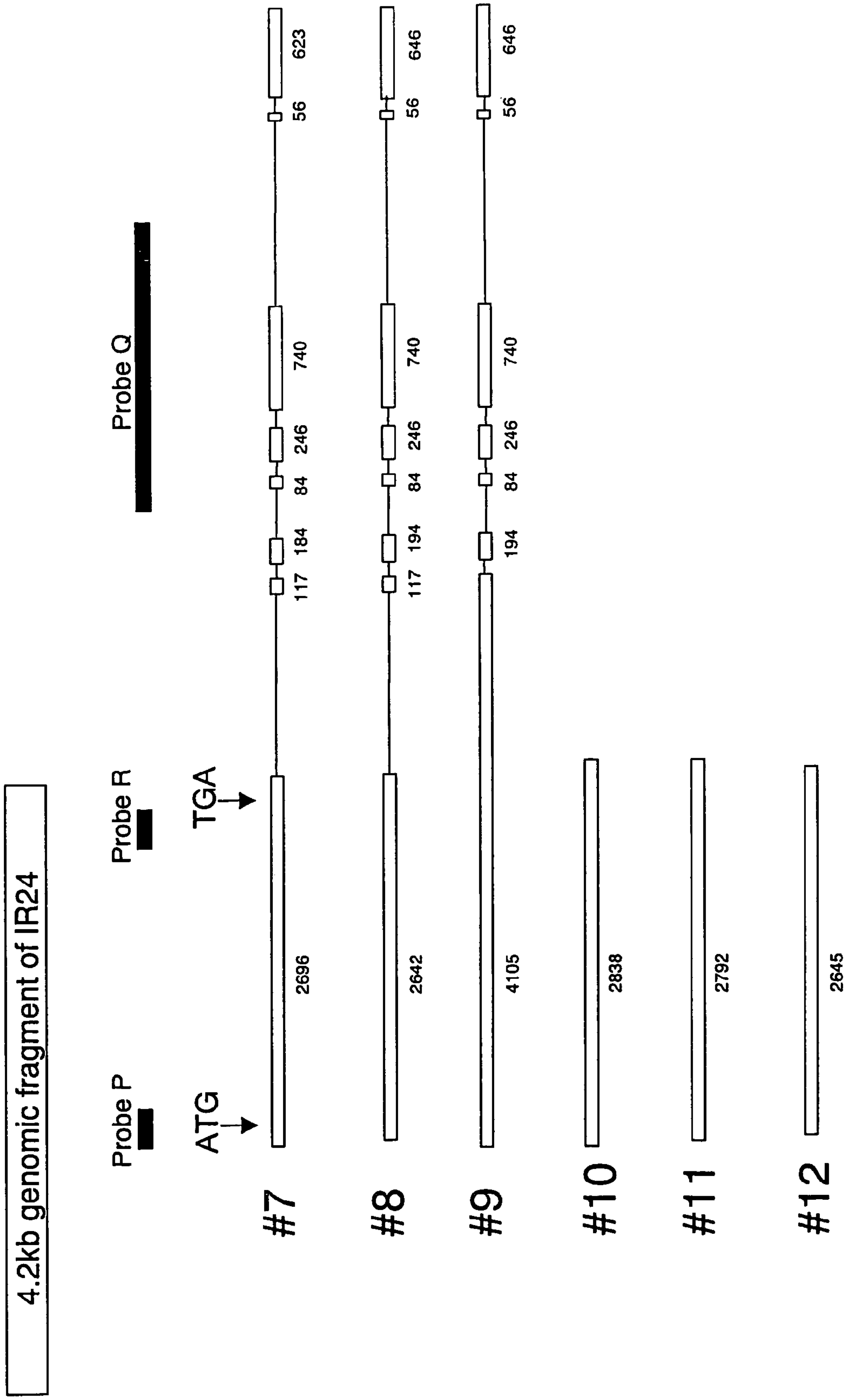
FIG. 8 is a schematic picture showing positional relationships between the IR24 genome fragment subjected to the complementation assays, probes used for the cDNA library screening and the Rf-1 gene deduced from the isolated cDNAs. White bars and black bars in the Rf-1 gene represent exons and introns, respectively. Numbers of base pairs are shown for the exon portions.

The sequences of cDNAs isolated on this occasion were compared with the genome sequence of IR24 (The Japanese Patent Application No. 2001-285247, SEQ ID NO:27), and the structures of exons and introns were clarified (FIG. 8). Among the cDNAs isolated on this occasion, there are three cDNAs which do not have any exons irrelevant to the presumed translation region, and consist of a single exon (#10-#12, SEA ID NOS: 83-85).

III. Nucleic Acids Containing the Rf-1 Locus

The present invention provides nucleic acids containing the locus of a fertility restorer gene (Rf-1). The nucleic acids containing the locus of a fertility restorer gene (Rf-1) of the present invention include a nucleic acid having the base sequence of SEQ ID NO. 27, or a nucleic acid having a base sequence which is identical to at least 70% of the base sequence of SEQ ID NO. 27, and which functions to restore fertility. Further, as described in Example 10, it was confirmed that the Rf-1 gene is completely contained in especially the bases 38538-54123 of the base sequence of SEQ ID NO:27. Still further, the region containing the Rf-1 gene is determined to be, preferably the bases 38538-54123 of SEQ ID NO:27, more preferably the bases 42357-53743, still preferably the bases 42132-48883, and still more preferably the bases 42132-46318.

The present inventors further pursued the study, and determined that the following regions as being nucleic acids containing the Rf-1 gene.

a) the bases 215-2587 of SEQ ID NO:69;
b) the bases 213-2585 of SEQ ID NO:70;
c) the bases 218-2590 of SEQ ID NO:71;
d) the bases 208-2580 of SEQ ID NO:72;
e) the bases 149-2521 of SEQ ID NO:73;
f) the bases 225-2597 of SEQ ID NO:74;
h) the bases 229-2601 of SEQ ID NO:80;
i) the bases 175-2547 of SEQ ID NO:81;
j) the bases 227-2599 of SEQ ID NO:82;
k) the bases 220-2592 of SEQ ID NO:83;
l) the bases 174-2546 of SEQ ID NO:84; and
m) the bases 90-2462 of SEQ ID NO:85.

The above base sequences correspond to g) the bases 43907-46279 of SEQ ID NO:27, and all of the bases encode the amino acid sequence 1-791 of SEQ ID NO:75.

Hereinafter, in the present specification, the term "the base sequence of SEQ ID NO:27" refers to the whole SEQ ID NO:27 or a portion thereof which takes part in the fertility restorer function, especially the bases 38538-54123. The term refers to more preferably the bases 42357-53743, still preferably the bases 42132-48883, and still more preferably the bases 42132-46318. And most preferably, it refers to g) the bases 43907-46279 of SEQ ID NO:27, or alternatively, a) the bases 215-2587 of SEQ ID NO:69, b) the bases 213-2585 of SEQ ID NO:70, c) the bases 218-2590 of SEQ ID NO:71, d) the bases 208-2580 of SEQ ID NO:72, e) the bases 149-2521 of SEQ ID NO:73, f) the bases 225-2597 of SEQ ID NO:74, h) the bases 229-2601 of SEQ ID NO:80, i) the bases 175-2547 of SEQ ID NO:81, j) the bases 227-2599 of SEQ ID NO:82, k) the bases 220-2592 of SEQ ID NO:83, l) the bases 174-2546 of SEQ ID NO:84 or m) the bases 90-2462 of SEQ ID NO:85 corresponding thereto.

In the examples below, a nucleic acid was isolated from a genomic library of indica rice IR24 containing the Rf-1 gene as a nucleic acid containing a fertility restorer gene (Rf-1) and determined to have the base sequence of SEQ ID NO:27. However, the nucleic acid containing a fertility restorer gene (Rf-1) of the present invention can be derived from any indica variety carrying the Rf-1 gene. The indica varieties carrying the Rf-1 gene include, but not specifically limited to, e.g. IR24, IR8, IR36, IR64, Chinsurah and BoroII. Known japonica varieties not carrying the Rf-1 gene include, but not limited to, Asominori, Koshihikari, Kirara 397, Akihikari, Akitakomachi, Sasanishiki, Kinuhikari, Nipponbare, Hatsuboshi, Koganebare, Hinohikari, Mineasahi, Aichinokaori, Hatsushimo, Akebono, Fujihikari, Minenoyukimochi, Kokonoemochi, Fukuhibiki, Dontokoi, Gohyakumangoku, Hanaechizen, Todorokiwase, Haenuki, Domannaka, Yamakikari, etc. The "indica" and "japonica" varieties are well known to those skilled in the art and the rice varieties encompassed by the present invention can be readily determined by those skilled in the art.

Nucleic acids of the present invention include DNA in both single-stranded and double-stranded forms, as well as the RNA complement thereof. DNA includes, for example, genomic DNA (including corresponding cDNA), chemically synthesized DNA, DNA amplified by PCR, and combinations thereof.

Nucleic acids containing the Rf-1 gene of the present invention preferably have the base sequence of SEQ ID NO:27. More than one codon may encode the same amino acid, and this is called degeneracy of the genetic code. Thus, a DNA sequence not completely identical to SEQ ID NO:27 may encode a protein having an amino acid sequence completely identical to SEQ ID NO:27. Such a variant DNA sequence may result from silent mutation (e.g., occurring during PCR amplification), or can be a product of deliberate mutagenesis of a native sequence.

Preferably, the Rf-1 gene of the present invention encodes the amino acid sequence described in SEQ ID NO:75. However, it is not limited thereto, and may encode an amino acid sequence wherein one or more amino acid residues are deleted, added or substituted.

The protein of the present invention is intended to include any homologous proteins as long as they have the fertility restorer function. The "amino acid variation" occurs at one or a plurality of amino acids residues, preferably 1-20, more preferably 1-10, most preferably 1-5 amino acid residues. The amino acid sequence encoded by the Rf-1 gene has an identity of at least about 70%, preferably about 80% or more, more preferably about 90% or more, still preferably about 95% or more, and most preferably about 98% or more with the amino acid sequence of SEQ ID NO:75.

The percent identity of the amino acids can be determined by visual inspection and mathematical calculation. The percent identity between two protein sequences may be determined by comparing sequence information based on the algorithm of Needleman, S. B. and Wunsch, C. D. (J. Mol. Biol., 48: 443-453, 1970) and using the GAP computer program available from University of Wisconsin Genetics Computer Group (UWGCG). The preferred default parameters for the "GAP" program include: (1) a scoring matrix as described in Henikoff, S and Henikoff, J. G. (Proc. Natl. Acad. Sci. USA, 89: 10915-10919, 1992), blosum 62; (2) a penalty of 12 for each gap; (3) a penalty of 4 for each length of each gap; and (4) no penalty for end gaps.

Other programs used by those skilled in the art for sequence comparison can also be used. For example, the percent identity may be determined by comparing sequence information using the BLAST program described in Altschul et al. (Nucl. Acids. Res. 25., p. 3389-3402, 1997). The program is available from the web site of National Center for Biotechnology Information (NCBI), or the web site of DNA Data bank of Japan (DDBJ) on the Internet. Various factors (parameters) for the homology research via the BLAST program are described in detail on the sites. A research is generally performed by using the default parameters, although some setting may be appropriately modified.

It is well known for those skilled in the art that even proteins having the same function may have different amino acid sequences depending on the varieties from which they are derived. The Rf-1 gene of the present invention includes such homologs and variants of the base sequence of SEQ ID NO:27 so far as they function to restore fertility. The expression "function to restore fertility" means that fertility is conferred on a rice individual or seed when such a DNA fragment is introduced. Fertility restoration may result from the expression of a protein by the Rf-1 gene or some function of the nucleic acid (DNA or RNA) per se of the Rf-1 gene in conferring fertility.

Whether or not a homolog or variant of the Rf-1 gene functions to restore fertility can be examined by, but not limited to, the following method, for example. A nucleic acid fragment under test is introduced into immature seeds obtained by pollinating MS Koshihikari (sterile line) with MS-FR Koshihikari according to the method of Hiei et al. (Plant Journal (1994), 6(2), p. 272-282). As the resulting transformants are cultured under normal conditions, the seeds mature only when the nucleic acid fragment under test functions to restore fertility.

The nucleic acid derived from a corresponding region of japonica Asominori not carrying the Rf-1 gene has the base sequence shown in SEQ ID NO:28. Corresponding parts of SEQ ID NO:28 and SEQ ID NO:27 have an overall identity of about 98%. Thus, nucleic acids containing the locus of a fertility restorer gene (Rf-1) of the present invention are at least about 70%, preferably about 80% or more, more preferably 90% or more, still more preferably 95% or more, most preferably 98 or more % identical to SEQ ID NO:27. Especially, the term "SEQ ID NO:27" intends to mean any one of g) the bases 43907-46279 of SEQ ID NO:27, or alternatively, a) the bases 215-2587 of SEQ ID NO:69, b) the bases 213-2585 of SEQ ID NO:70, c) the bases 218-2590 of SEQ ID NO:71, d) the bases 208-2580 of SEQ ID NO:72, e) the bases 149-2521 of SEQ ID NO:73, f) the bases 225-2597 of SEQ ID NO:74, h) the bases 229-2601 of SEQ ID NO:80, i) the bases 175-2547 of SEQ ID NO:81, j) the bases 227-2599 of SEQ ID NO:82, k) the bases 220-2592 of SEQ ID NO:83, l) the bases 174-2546 of SEQ ID NO:84 or m) the bases 90-2462 of SEQ ID NO:85 corresponding thereto.

The percent identity of a nucleic acid may be determined by visual inspection and mathematical calculation. Alternatively, the percent identity of two nucleic acid sequences can be determined by comparing sequence information using the GAP computer program, version 6.0 described by Devereux et al., Nucl. Acids Res., 12:387 (1984) and available from the University of Wisconsin Genetics Computer Group (UWGCG). The preferred default parameters for the GAP program include: (1) a unary comparison matrix (containing a value of 1 for identities and 0 for non-identities) for bases, and the weighted comparison matrix of Gribskov and Burgess, Nucl. Acids Res., 14:6745 (1986), as described by Schwartz and Dayhoff, eds., Atlas of Protein Sequence and Structure, National Biomedical Research Foundation, pp. 353-358 (1979); (2) a penalty of 3.0 for each gap and an additional 0.10 penalty for each symbol in each gap; and (3) no penalty for end gaps. Other programs used by those skilled in the art of sequence comparison may also be used.

Nucleic acids of the present invention also include nucleic acids which are capable of hybridizing to the base sequence of SEQ ID NO:27 under conditions of moderately stringent conditions and functions to restore fertility, and nucleic acids which are capable of hybridizing to the base sequence of SEQ ID NO:27 under conditions of highly stringent conditions and functions to restore fertility.

As used herein, conditions of moderate stringency can be readily determined by those having ordinary skill in the art based on, for example, the length of the DNA. The basic conditions are set forth by Sambrook et al. Molecular Cloning: A Laboratory Manual, 2nd. Vol. 1, pp. 1.101-104, Cold Spring Harbor Laboratory Press, (1989), and include use of a prewashing solution for the nitrocellulose filters 5×SSC, 0.5% SDS, 1.0 mM EDTA (pH 8.0), hybridization conditions of about 1×SSC to 6×SSC at about 40° C. to 60° C. (or other similar hybridization solution, such as Stark's solution, in about 50% formamide at about 42° C.), and washing conditions of about 60° C., 0.5×SSC, 0.1% SDS. The hybridization temperature is about 15-20° C. lower when the hybridization solution contains about 50% formamide. Conditions of high stringency can also be readily determined by the skilled artisan based on, for example, the length of the DNA. Generally, conditions of high stringency include hybridization and/or washing conditions at higher temperatures and/or lower salt concentrations than in the conditions of moderate stringency described above. For example, such conditions include hybridization conditions of 0.1×SSC to 0.2×SSC at about 60-65° C. and/or washing conditions of 0.2×SSC, 0.1% SDS at about 65-68° C. The skilled artisan will recognize that the temperature and wash solution salt concentration can be adjusted as necessary according to factors such as the length of the probe.

Especially preferably, "SEQ ID NO:27" intends to mean any one of g) the bases 43907-46279 of SEQ ID NO:27, or alternatively, a) the bases 215-2587 of SEQ ID NO:69, b) the bases 213-2585 of SEQ ID NO:70, c) the bases 218-2590 of SEQ ID NO:71, d) the bases 208-2580 of SEQ ID NO:72, e) the bases 149-2521 of SEQ ID NO:73, f) the bases 225-2597 of SEQ ID NO:74, h) the bases 229-2601 of SEQ ID NO:80, i) the bases 175-2547 of SEQ ID NO:81, j) the bases 227-2599 of SEQ ID NO:82, k) the bases 220-2592 of SEQ ID NO:83, l) the bases 174-2546 of SEQ ID NO:84 or m) the bases 90-2462 of SEQ ID NO:85 corresponding thereto.

DNAs of the present invention also include nucleic acids that differ from the base sequence of SEQ ID NO:27 due to deletions, insertions or substitutions of one or more bases while retaining a fertility restoring function. So far as a fertility restoring function is retained, the number of bases to be deleted, inserted or substituted is not specifically limited, but preferably 1 to several thousands, more preferably 1-1000, still more preferably 1-500, even more preferably 1-200, most preferably 1-100.

The Rf-1 gene has further been specified on the basis of the descriptions herein, and it can be used by those skilled in the art after nucleic acids such as other regions than the Rf-1 gene or intron regions in the Rf-1 gene are removed. A given amino acid (especially, the amino acid sequence of SEQ ID NO:75) may be replaced, for example, by a residue having similar physicochemical characteristics. Examples of such conservative substitutions include changes from one aliphatic residue to another, such as changes from one to another of Ile, Val, Leu, or Ala; changes from one polar residue to another, such as changes between Lys and Arg, Glu and Asp, or Gln and Asn; or changes from one aromatic residue to another, such as changes from one to another of Phe, Trp, or Tyr. Other well-known conservative substitutions include e.g. changes between entire regions having similar hydrophobic characteristics. Those skilled in the art can introduce desired deletions, insertions or substitutions by well-known gene engineering techniques using e.g. site-specific mutagenesis as described in Sambrook et al., Molecular Cloning: A Laboratory Manual, 2nd edition, Cold Spring Harbor Laboratory Press, (1989).

We compared an indica variety IR24 carrying the Rf-1 gene (SEQ ID NO:27) with japonica varieties not carrying it such as Asominori (SEQ ID NO:28) and a Nipponbare BAC clone deposited with GenBank (Accession No. AC068923). As a result, we found that the Rf-1 region of the indica variety containing the Rf-1 gene has at least the following single bases polymorphisms (SNP).

1) a base corresponding to the base 1239 of SEQ ID NO:27 is A;

2) a base corresponding to the base 6227 of SEQ ID NO:27 is A;

3) a base corresponding to the base 20680 of SEQ ID NO:27 is G;

4) a base corresponding to the base 45461 of SEQ ID NO:27 is A;

5) a base corresponding to the base 49609 of SEQ ID NO:27 is A;

6) a base corresponding to the base 56368 of SEQ ID NO:27 is T;

7) a base corresponding to the base 57629 of SEQ ID NO:27 is C; and 8) a base corresponding to the base 66267 of SEQ ID NO:27 is G.

Thus, nucleic acids containing the Rf-1 region of the present invention preferably meet one to all of the requirements 1)-8) above.

Figure 3:
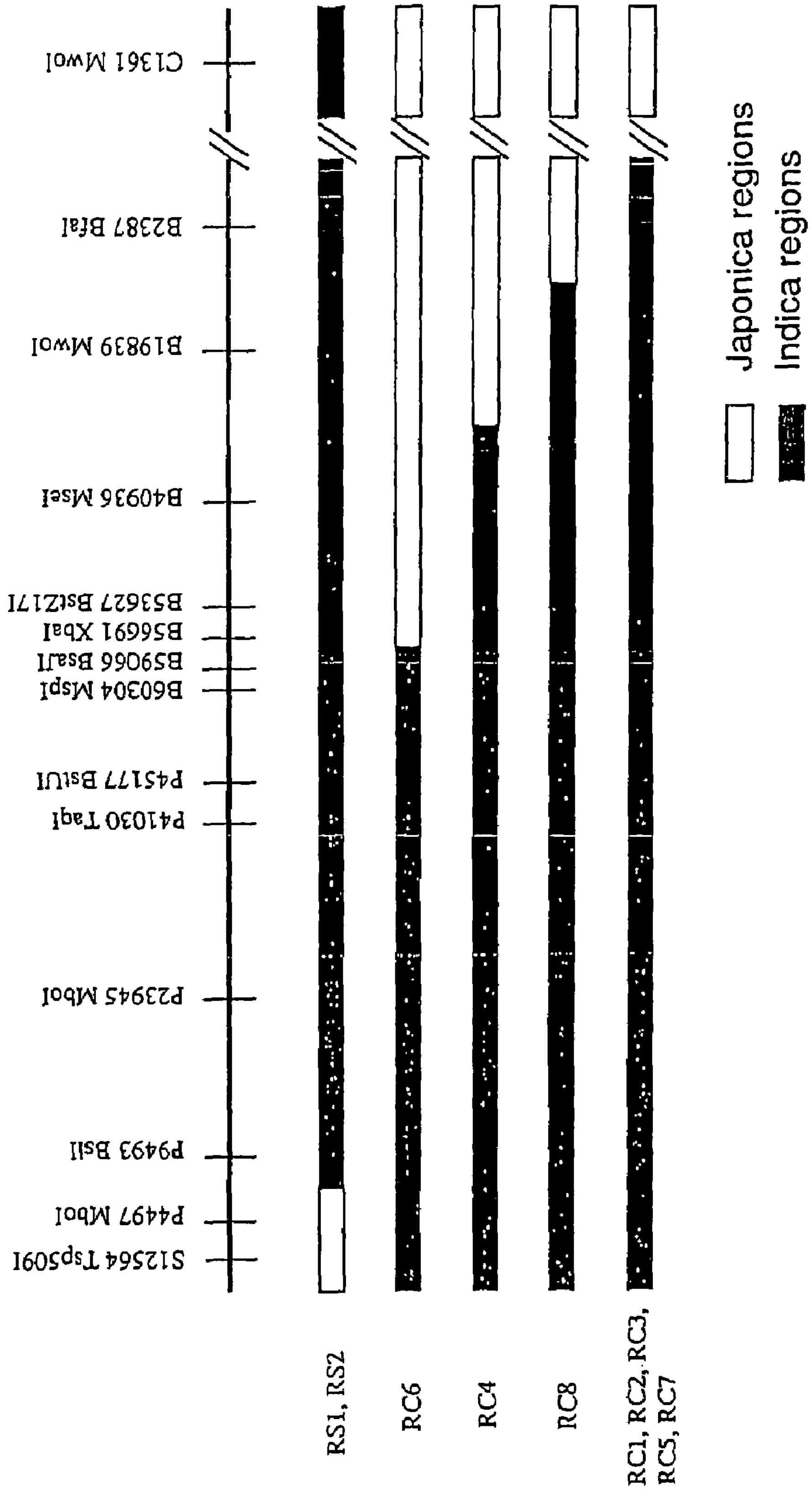
FIG. 3 shows the chromosomal organization of recombinant pollens proximal to the Rf-1 locus (all fertile) as mapped in close proximity to the Rf-1 locus based on the genotypes at the marker loci of 10 individuals (RS1, RS2, RC1-8) generated from the pollens. White bars represent japonica regions and black bars represent indica regions.

In Example 3 below, the chromosomal organizations of recombinants proximal to the Rf-1 gene (RS1-RS2, RC1-RC8) were tested in the Rf-1 region. The results showed that a sequence determining the presence of the function of the Rf-1 gene is contained in the base sequence of bases 1239-66267 of SEQ ID NO:27, i.e. in a region from the P4497 MboI to B56691 XbaI loci (about 65 kb) as estimated at maximum (FIG. 3). However, there is a possibility that it is important for the expression of the genetic function of the Rf-1 gene that the Rf-1 gene is partially of the indica genotype, and that the genetic function may not be significantly changed whether the remaining regions are of the japonica or indica genotype. There may be an extreme case that the coding region is completely identical and only the promoter region is different between japonica and indica, and that the promoter region and the coding region are only partially included in the region from P4497 the MboI to B56691 XbaI loci (about 65 kb). Therefore, it cannot be concluded that the common indica region above (bases 1239-66267 of SEQ ID NO:27) completely contains the entire Rf-1 gene. However, it is thought that at least SEQ ID NO:27 completely contains the entire Rf-1 gene for the following reasons:

1) the size of a gene is normally several kilobases, and rarely exceeds 10 kb;

2) the genomic base sequence of IR24 determined by the present invention (SEQ ID NO:27) completely contains the common indica region above;

3) the 5' end of SEQ ID NO:27 is located 1238 bp upstream of the 5' end of the common indica region above and forms a part of another gene (S12564); and 4) the 3' end of SEQ ID NO:27 is located 10096 bp downstream of the 3' end of the common indica region above.

In this way, we first succeeded in restricting the region of the Rf-1 gene to 76 kb. Thus, nucleic acids containing the region of the Rf-1 gene of the present invention are extremely less likely to contain other genes proximal to the Rf-1 gene as compared with those selected with the co-dominant marker locus at a genetic distance of about 1 cM (about 300 kb) from the Rf-1 gene described in a prior documents such as Japanese Patent Public Disclosure No. 2000-139465. Moreover, they are less likely to contain other genes than those selected with the DNA marker loci S12564 Tsp509I and C1361 MwoI (at a distance of about 0.3 cM between them) described in our prior Japanese Patent Application No. 2000-247204.

We further confirmed by complementation assays that the Rf-1 gene is completely contained in especially bases 38538-54123 of the base sequence of SEQ ID NO:27. In an embodiment of the present invention, therefore, the base sequence at least 70% identical to the base sequence of SEQ ID NO:27 or to the base sequence of bases 38538-54123 of SEQ ID NO:27 meets at least one of the following requirements 1) and 2):

1) a base corresponding to the base 45461 of SEQ ID NO:27 is A;

2) a base corresponding to the base 49609 of SEQ ID NO:27 is A.

The present inventors further determined that the following regions as being nucleic acids containing the Rf-1 gene.

a) the bases 215-2587 of SEQ ID NO:69;

b) the bases 213-2585 of SEQ ID NO:70;

c) the bases 218-2590 of SEQ ID NO:71;

d) the bases 208-2580 of SEQ ID NO:72;

e) the bases 149-2521 of SEQ ID NO:73;

f) the bases 225-2597 of SEQ ID NO:74;

h) the bases 229-2601 of SEQ ID NO:80;

i) the bases 175-2547 of SEQ ID NO:81;

j) the bases 227-2599 of SEQ ID NO:82;

k) the bases 220-2592 of SEQ ID NO:83;

l) the bases 174-2546 of SEQ ID NO:84; and m) the bases 90-2462 of SEQ ID NO:85.

The above base sequences correspond to g) the bases 43907-46279 of SEQ ID NO:27. The nucleic acids of the present invention further include n) a nucleic acid which is identical to at least 70% of the nucleic acid of any of a)-m), and which functions to restore fertility;

o) a nucleic acid which hybridizes to the nucleic acid of any of a)-m) under a moderate or high stringent condition, and which functions to restore fertility; and p) a nucleic acid wherein one or a plurality of base(s) is deleted from, added to or substituted from the nucleic acid of any of a)-m), and which functions to restore fertility.

The base 45461 of SEQ ID NO:27 corresponds to 1) the base 1769 of SEQ ID NO. 69; 2) the base 1767 of SEQ ID NO. 70; 3) the base 1772 of SEQ ID NO. 71; 4) the base 1762 of SEQ ID NO. 72; 5) the base 1703 of SEQ ID NO. 73; 6) the base 1779 of SEQ ID NO. 74; 7) the base 1783 of SEQ ID NO. 80; 8) the base 1729 of SEQ ID NO. 81; 9) the base 1781 of SEQ ID NO. 82; 10) the base 1774 of SEQ ID NO. 83; 11) the base 1728 of SEQ ID NO. 84; and 12) the base 1644 of SEQ ID NO. 85. Accordingly, especially preferably, the nucleic acid used for the method of the present invention meets at least one of the following requirements 1)-12):

1) a base corresponding to the base 1769 of SEQ ID NO. 69 is A;

2) a base corresponding to the base 1767 of SEQ ID NO. 70 is A;

3) a base corresponding to the base 1772 of SEQ ID NO. 71 is A;

4) a base corresponding to the base 1762 of SEQ ID NO. 72 is A;

5) a base corresponding to the base 1703 of SEQ ID NO. 73 is A;

6) a base corresponding to the base 1779 of SEQ ID NO. 74 is A;

7) a base corresponding to the base 1783 of SEQ ID NO. 80 is A;

8) a base corresponding to the base 1729 of SEQ ID NO. 81 is A;

9) a base corresponding to the base 1781 of SEQ ID NO. 82 is A;

10) a base corresponding to the base 1774 of SEQ ID NO. 83 is A;

11) a base corresponding to the base 1728 of SEQ ID NO. 84 is A; or 12) a base corresponding to the base 1644 of SEQ ID NO. 85 is A.

IV. Method for Restoring Rice Fertility

The present invention provides a method for restoring rice fertility comprising introducing a nucleic acid into rice, wherein the nucleic acid has the base sequence of SEQ ID NO. 27, or has a base sequence which is identical to at least 70% of the base sequence of SEQ ID NO. 27, and which functions to restore fertility. The methods of the present invention may comprise introducing a nucleic acid into rice, wherein the nucleic acid has a portion of SEQ ID NO:27, especially the bases 38538-54123, preferably the bases 42357-53743, more preferably the bases 42132-48883 of SEQ ID NO:27 or has a base sequence which is at least 70% identical to the base sequence of bases 38538-54123, preferably the bases 42357-53743, more preferably the bases 42132-48883 of SEQ ID NO:27, still more preferably the bases 42132-46318 and, which functions to restore fertility.

In a particularly preferable embodiment of the present method, the nucleic acid encodes the amino acid sequence of SEQ ID NO. 75, or an amino acid sequence which is identical to at least 70% of the amino acid sequence of SEQ ID NO. 75, and which functions to restore fertility is introduced into rice. Most preferably, the nucleic acid encoding the amino acid sequence of SEQ ID NO. 75, or an amino acid sequence which is identical to at least 70% of the amino acid sequence of SEQ ID NO. 75 is selected from nucleic acids of the following a)-p):

a) a nucleic acid comprising the bases 215-2587 of SEQ ID NO:69;

b) a nucleic acid comprising the bases 213-2585 of SEQ ID NO:70;

c) a nucleic acid comprising the bases 218-2590 of SEQ ID NO:71;

d) a nucleic acid comprising the bases 208-2580 of SEQ ID NO:72;

e) a nucleic acid comprising the bases 149-2521 of SEQ ID NO:73;

f) a nucleic acid comprising the bases 225-2597 of SEQ ID NO:74;

g) a nucleic acid comprising the bases 43907-46279 of SEQ ID NO:27;

h) a nucleic acid comprising the bases 229-2601 of SEQ ID NO:80;

i) a nucleic acid comprising the bases 175-2547 of SEQ ID NO:81;

j) a nucleic acid comprising the bases 227-2599 of SEQ ID NO:82;

k) a nucleic acid comprising the bases 220-2592 of SEQ ID NO:83;

l) a nucleic acid comprising the bases 174-2546 of SEQ ID NO:84;

m) a nucleic acid comprising the bases 90-2462 of SEQ ID NO:85;

n) a nucleic acid which is identical to at least 70% of the nucleic acid of any of a)-m), and which functions to restore fertility;

o) a nucleic acid which hybridizes to the nucleic acid of any of a)-m) under a moderate or high stringent condition, and which functions to restore fertility; and p) a nucleic acid wherein one or a plurality of base(s) is deleted from, added to or substituted from the nucleic acid of any of a)-m), and which functions to restore fertility.

In the present invention, the nucleic acid containing the locus of a fertility restorer gene (Rf-1) that can be introduced into rice can be any one of the nucleic acids described above in "III. Nucleic acids containing the Rf-1 locus". The method for introducing the nucleic acid into rice is not specifically limited but can be any known method. Nucleic acids of the present invention can be introduced by known genetic engineering techniques or crossing. Genetic engineering techniques are preferably used because inclusion of other neighboring genes can be prevented and the period for establishing a line can be shortened.

Any suitable expression system for transduction by genetic engineering techniques can be employed. Recombinant expression vectors comprise a nucleic acid containing a fertility restorer gene (Rf-1) of the invention that can be introduced into rice, operably linked to suitable transcriptional or translational regulatory base sequences, such as those derived from a mammalian, microbial, viral, or insect gene.

Examples of regulatory sequences include transcriptional promoters, operators, or enhancers, an mRNA ribosomal binding site, and appropriate sequences which control transcription and translation initiation and termination. Base sequences are operably linked to a regulatory sequence when the regulatory sequence is functionally associated with the DNA sequences. Thus, a promoter base sequence is operably linked to a DNA sequence if the promoter base sequence controls the transcription of the DNA sequence. An origin of replication that confers the ability to replicate in rice, and a selection gene by which transformants are identified, are generally incorporated into expression vectors. As for selectable markers, those commonly used can be used by standard methods. Examples are genes resistant to antibiotics such as tetracycline, ampicillin, kanamycin, neomycin, hygromycin or spectinomycin.

In addition, a sequence encoding an appropriate signal peptide (native or heterogonous) can be incorporated into expression vectors. A DNA sequence for a signal peptide (secretary leader) may be fused in frame to a nucleic acid sequence of the invention so that the DNA is initially transcribed, and the mRNA translated into a fusion protein containing the signal peptide.

The present invention also provides recombinant vectors containing a gene of the present invention. Methods for integrating a DNA fragment of a gene of the present invention into a vector such as a plasmid are described in e.g. Sambrook, J. et al, Molecular Cloning, A Laboratory Manual (2nd edition), Cold Spring Harbor Laboratory, 1.53 (1989). Commercially available ligation kits (e.g. available from TAKARA) can be conveniently used. Thus obtained recombinant vectors (e.g. recombinant plasmids) are transferred into host rice cells.

Vectors can be conveniently prepared by linking a desired gene to a recombinant vector available in the art (e.g. plasmid DNA) by standard methods. Plant transforming vectors are especially useful for conferring fertility on rice using a nucleic acid fragment of the present invention. Vectors for plants are not specifically limited so far as they can express the gene of interest in plant cells to produce the protein, but preferably include pBI221, pBI121 (Clutch), and vectors derived there from. Especially, examples of vectors for transforming rice belonging to monocotyledons include pIG121Hm and pTOK233 (Hiei et al., Plant J., 6, 271-282 (1994)), and pSB424 (Komari et al., Plant J., 10, 165-174 (1996)).

Transgenic plants can be prepared by replacing the β-glucuronidase (GUS) gene in the above vectors with a nucleic acid fragment of the present invention to construct a plant transforming vector and transfecting it into a plant. The plant transforming vector preferably comprises at least a promoter, a start codon, a desired gene (a nucleic acid sequence of the present invention or a part thereof), a stop codon and a terminator. It may also contain a DNA encoding a signal peptide, an enhancer sequence, non-translated 5' and 3' regions of the desired gene, a selectable marker region, etc., as appropriate. Promoters and terminators are not specifically limited so far as they are functional in plant cells, among which constitutive expression promoters include the 35S promoter initially contained in the above vectors as well as promoters for actin and ubiquitin genes.

Suitable methods for introducing a plasmid into a host cell include the use of calcium phosphate or calcium chloride/rubidium chloride, electroporation, electroinjection, chemical treatment with PEG or the like, the use of a gene gun described in Sambrook, J. et al., Molecular Cloning, A Laboratory Manual (2nd edition), Cold Spring Harbor Laboratory, 1.74 (1989). Plant cells can be transformed by e.g. the leaf disc method [Science, 227, 129 (1985)] or electroporation [Nature, 319, 791 (1986)].

Methods for transferring a gene into a plant include the use of *Agrobacterium* (Horsch et al., Science, 227, 129 (1985); Hiei et al., Plant J., 6, 271-282 (1994)), electroporation (Fromm et al., Nature, 319, 791 (1986)), PEG (Paszkowski et al., EMBO J., 3, 2717 (1984)), microinjection (Crossway et al., Mol. Gen. Genet., 202, 179 (1986)), particle bombardment (McCabe et al., Bio/Technology, 6, 923 (1988)). Methods are not specifically limited so far as they are suitable for transfecting a nucleic acid into a desired plant.

Transduction by crossing can be performed as follows, for example. First, $F_1$ obtained by crossing an Rf-1 donor parent and a japonica variety is backcrossed with the japonica variety. The resulting individuals are screened for those homozygous for japonica at the S12564 Tsp509I locus and heterozygous at the P4497 MboI and B53627 BstZ17I loci and further backcrossed. The resulting individuals are screened for those heterozygous at the P4497 MboI and B56691 XbaI loci and homozygous for japonica at the B53627 BstZ17I locus and further backcrossed. Subsequently, about 10 cycles of screening each backcrossed generation for individuals heterozygous at the P4497 MboI and B56691 XbaI loci and subjecting them to the subsequent backcrossing are repeated. Finally, individuals heterozygous at the P4497 MboI and B56691 XbaI loci are self-fertilized and the resulting individuals are screened for those homozygous for indica at both loci, whereby a restorer line inheriting a limited chromosomal region from the P4497 MboI to B56691 XbaI loci from the Rf-1 donor parent can be obtained.

According to the present invention, nucleic acids containing a fertility restorer gene (Rf-1) were isolated, whereby the Rf-1 gene can be introduced into a rice variety using genetic engineering techniques to establish a restorer line. The present invention succeeded in restricting the Rf-1 region to 76 kb or less in the first place. Therefore, nucleic acids containing the Rf-1 locus of the present invention are extremely less likely to contain other genes neighboring the Rf-1 gene than those of the prior art. Moreover, the entire base sequence of the region containing the Rf-1 gene was determined by the present invention. Those skilled in the art can proceed with analysis of the Rf-1 gene itself on the basis of the description herein. Thus, only the Rf-1 gene can be introduced without including any neighboring gene. This is especially important when neighboring genes bring deleterious traits. Furthermore, restorer lines can be established in a shorter period such as 1-2 years than obtained by crossing.

In complementation assays described in Examples 4-13 and 17 herein, MS Koshihikari (having BT cytoplasm and a core gene substantially identical to Koshihikari) was actually transformed by an *Agrobacterium*-mediated method using fragments from 10 clones described in FIG. 5. The results demonstrated that fertility restorer lines can be established from a nucleic acid containing the base sequence of the bases 38538-54123, preferably the bases 42357-53743, more preferably the bases 42132-48883, still more preferably the bases 42132-46318 of SEQ ID NO:27.

*Agrobacterium*-mediated methods for establishing rice restorer lines are described in, but not limited to, Hiei et al., Plant J., 6, pp. 271-282 (1994), Komari et al., Plant J., 10, p. 165-174 (1996), Ditto et al., Proc. Natl. Acad. Sci. USA 77: pp. 7347-7351 (1980), etc.

First, a plasmid vector containing a nucleic acid fragment of interest to be inserted is prepared. Suitable plasmid vectors include e.g. pSB11, pSB22 and the like having a plasmid map described in Komari et al., Plant J., 10, pp. 165-174 (1996), supra. Alternatively, those skilled in the art can also construct an appropriate vector by themselves on the basis of plasmid vectors such as pSB11, pSB22 described above. In the examples herein below, an intermediate vector pSB200 having a hygromycin-resistant gene cassette was prepared on the basis of pSB11, and used. Specifically, a nonaligned syntheses terminator (Tons) was first fused to a ubiquitin promoter and a ubiquitin intron (Pubi-ubiI). A hygromycin-resistant gene (HYG(R)) was inserted between ubiI and Tons of the resulting Pubi-ubiI-Tnos complex to give a Pubi-ubiI-HYG (R)-Tons assembly. This assembly was fused to a HindIII/EcoRI fragment of pSB11 (Komari et al., supra.) to give pKY205. Linker sequences for adding restriction enzyme sites NotI, NspV, EcoRV, KpnI, SacI, EcoRI were inserted into the Hind III site upstream of Pubi of this pKY205 to give pSB200 having a hygromycin-resistant gene cassette.

Then, *E. coli* cells (e.g. DH5a, JM109, MV1184, all commercially available from e.g. TAKARA) are transformed with the recombinant vector containing the nucleic acid inserted.

Thus transformed *E. coli* cells are used for triparental mating with an *Agrobacterium* strain preferably in combination with a helper *E. coli* strain according to e.g. the method of Ditto et al. (1980). Suitable *Agrobacterium* strains include *Agrobacterium tumefaciens* strains such as LBA4404/pSB1, LBA4404/pNB1, LBA4404/pSB3, etc. They all have a plasmid map described in Komari et al., Plant J., 10, pp. 165-174 (1996), supra. and can be used by those skilled in the art by constructing a vector by themselves. Suitable helper *E. coli* strains include, but not limited to, e.g. HB101/pRK2013 (available from Clutch). A report shows that *E. coli* cells carrying pRK2073 can also be used as helper *E. coli* though they are less common (Lemas et al., Plasmid 1992, 27, pp. 161-163).

Then, the *Agrobacterium* cells mated as intended are transformed into male sterility rice according to e.g. the method of Hiei et al (1994). Necessary immature rice seeds for transformation can be prepared by e.g. pollinating male sterility rice with a japonica variety.

Fertility restoration in transformed plants can be assessed by e.g. evaluating seed fertility in standing plants about one month after heading. Evaluation on standing plants means observation of plants grown in a field or the like. An alternative method is a laboratory study of grain ripening percentages in the ear.

V. Methods for Discerning the Presence of the Rf-1 Gene

According to the present invention, it was shown that a sequence determining the presence of the function of the Rf-1 gene is located between the polymorphism-detecting marker loci P4497 MboI and B56691 XbaI on rice chromosome 10. Moreover, complementation assays confirmed that the Rf-1 gene is completely contained in especially bases 38538-54123 of the base sequence of SEQ ID NO:27.

Comparison of the base sequence of an indica variety carrying the Rf-1 gene (IR24) (SEQ ID NO:27) with those of japonica varieties not carrying said gene (Asominori (SEQ ID NO:28) and Nipponbare BAC clone AC068923) revealed the presence of polymorphisms between both varieties. As a result, it became possible to conveniently, rapidly and exactly discern whether or not a rice plant or seed under test carries the Rf-1 gene on the basis of polymorphisms in base sequence in regions neighboring the Rf-1 gene.

Therefore, the present invention also provides a method for discerning whether or not a subject rice individual or a seed thereof has the Rf-1 gene or not, wherein the method utilizing a fact that a sequence determining the presence of the function of the Rf-1 gene positions between the polymorphism detection marker loci P4497 MboI and B56691 Xba I on rice chromosome 10.

Polymorphisms can be detected by any known method. For example, known methods include assays for restriction fragment length polymorphisms (RFLPs); direct determination by sequencing; cutting a genomic DNA with a 8-base recognizing restriction enzyme, and then radioactively labeling the ends and further cutting the labeled digest with 6-base and 4-bases recognizing restriction enzyme and then developing the digest by two-dimensional electrophoresis (RLGS, Restriction Landmark Genome Scanning); etc. AFLP analysis (amplified fragment length polymorphism; P. Vos et al., Nucleic Acids Res. Vol. 23, pp. 4407-4414 (1995)) has also been developed wherein RFLP is amplified/detected by polymerase chain reaction (PCR).

For example, conventional methods involved detecting RFLPs via PCR amplification (conversion of RFLP markers into PCR markers) or detecting polymorphisms in microsatellites via PCR amplification (microsatellite markers) as illustrated below.

Conversion of RFLP Markers into PCR Markers

A. PCR markers based on polymorphisms in genomic regions corresponding to RFLP probes (D. E. Harry, B. Temesgen, D. B. Neale; Codominant PCR-based markers for Pinus taeda developed from mapped cDNA clones, Theor. Appl. Genet. (1998) 97: pp. 327-336). After performing genomic PCR using primers designed for an RFLP marker probe sequence ("RFLP" is a polymorphism observed by Southern analysis using a DNA fragment as a probe. The base sequence of the DNA fragment used as a probe is called "RFLP marker probe sequence"), a PCR marker can be prepared by either of the following two procedures. A first procedure involves treating the products with a series of restriction enzymes to search for a restriction enzyme causing a fragment length polymorphism, and a second procedure involves searching for a polymorphism by varietal comparison of the base sequences of the products and preparing a PCR marker based on the polymorphism.

B. PCR markers based on identification of RFLP-causing sites. A PCR marker can be obtained by identifying an RFLP-causing site (a restriction enzyme recognition site carried by only one of two varieties compared) present in or near (normally within several kbs) an RFLP marker probe sequence.

Microsatellite Markers

Microsatellites are repeat sequences of about 2 to 4 bases such as $(CA)_n$ that are present in great numbers in genomes. If a varietal polymorphism occurs in repetition number, a polymorphism can be observed in PCR product length by PCR using primers designed in adjacent regions, whereby the DNA polymorphism can be detected. Markers for detecting polymorphisms using microsatellites are called microsatellite markers (O. Parnaud, X. Chen, S. R. McCouch, Mol. Gen. Genet. (1996) 252: pp. 597-607).

Methods for detecting polymorphisms in the present invention are not specifically limited. From the viewpoint of efficiency and convenience, PCR-RFLP is preferred, which is a combination of PCR and RFLP to identify polymorphisms from their restriction enzyme cleavage patterns in cases where they exist among variety lines at restriction enzyme recognition sites in the sequences of DNA fragments amplified by PCR. PCR-RFLP is also called CAPS (cleaved amplified polymorphic sequence). If any suitable restriction enzyme recognition site is not present in a region showing polymorphisms, a modified CAPS called dCAPS (derived cleaved amplified polymorphic sequence) can also be used wherein restriction enzyme sites are introduced during PCR (Michaels, S. D. and Amasino, R. M. (1998), The Plant Journal 14(3) 381-385; A. Konieczny et al., (1993), Plant J. 4(2) pp. 403-410; Neff, M. M., Neff, J. D., Chory, J. and Pepper, A. E. (1998), The Plant Journal 14(3) 387-392). These methods are explained in more detail below.

CAPS, dCAPS

The method for discerning of the present invention comprise, but not limited to:

i) preparing a pair of primers based on the base sequences of a site showing a polymorphism in the base sequences between indica and japonica varieties at the Rf-1 locus and its adjacent regions to amplify said base sequences;

ii) performing nucleic acid amplification reaction(s) using the genomic DNA of the subject rice individual or the seed thereof as a template; and iii) discerning whether or not the subject rice individual or the seed thereof has the Rf-1 gene based on the polymorphism found in the nucleic acid amplification product.

The step of preparing a primer pair in i) preferably comprises any of the following means:

a) when a change containing a deleted region exists in the polymorphism in the nucleic acid amplification product, preparing a pair of primers for nucleic acid amplification to flank the deleted region to form a marker for detecting the polymorphism;

b) when a base change causing a difference in restriction enzyme recognition exists in the polymorphism in the nucleic acid amplification product, preparing a pair of primers for nucleic acid amplification to flank the base change site to form a marker for detecting the polymorphism; or c) when a base change causing no difference in restriction enzyme recognition exists in the polymorphism in the nucleic acid amplification product, preparing a pair of primers for introducing a mismatch, wherein pair of primers contain the base change site and alters a region containing the base change site into a base sequence causing a difference in restriction enzyme recognition in the nucleic acid amplification product to form a marker for detecting the polymorphism.

Suitable polymorphic sites for discerning the presence of the Rf-1 gene in the present invention can be appropriately selected so that a polymorphism detecting marker can be prepared as described below on the basis of comparison of, but not limited to, the base sequence of an indica variety carrying the Rf-1 gene (IR24) (SEQ ID NO:27) with those of japonica varieties not carrying said gene (Asominori (SEQ ID NO:28) and Nipponbare BAC clone AC068923).

If the polymorphism found causes a difference in restriction enzyme recognition, for example, a pair of primers for nucleic acid amplification are prepared to flank the polymorphic site and used for detecting the polymorphism. Primers are preferably designed not to be specific for highly repeated sequences to avoid undesired products. If the polymorphism found does not cause a difference in restriction enzyme recognition, markers can be prepared by applying the dCAPS method described above. Primers for dCAPS markers are preferably designed not to be specific for repeat sequences and to provide a product length of preferably 50-300 bases, more preferably about 100 bases to ease identification of polymorphisms.

If the polymorphism found involves a microsatellite, nucleic acid amplification primers are prepared to flank the microsatellite and used to detect the polymorphism. Again, the primers are preferably designed not to be specific for repeat sequences.

1) Nucleic Acid Amplification

In the present invention, a pair of primers are preferably prepared for amplifying adjacent regions containing polymorphisms on the basis of the determined base sequence of the nucleic acid of a subject rice individual or seed at the Rf-1 locus. The primer pair is used to perform a nucleic acid amplification reaction with the genomic DNA of the subject rice individual or seed as a template. The nucleic acid amplification reaction is preferably polymerase chain reaction (PCR) (Saiki et al., 1985, Science 230, pp. 1350-1354).

The pair of primers for nucleic acid amplification can be prepared by any known method on the basis of the base sequence of a polymorphic site and adjacent regions thereto. Specifically, a primer pair can be prepared on the basis of the base sequence of a polymorphic site and adjacent regions thereto by a process comprising generating a single-stranded DNA having the same base sequence as the base sequence of the polymorphic site and adjacent regions thereto or a base sequence complementary to said regions or, if necessary, generating the single-stranded DNA containing a modification without affecting the binding specificity to the base sequence of the polymorphic site and adjacent regions thereto provided that the following conditions are satisfied:

1) the length of each primer should be 15-30 bases;

2) the proportion of G+C in the base sequence of each primer should be 30-70%;

3) the distribution of A, T, G and C in the base sequence of each primer should not be partially largely uneven;

4) the length of the nucleic acid amplification product amplified by the primer pair should be 50-3000 bases, preferably 50-300 bases; and 5) any complementary sequence segment should not occur with the base sequence of each primer or between the base sequences of the primers.

As used herein, the "adjacent regions" to a polymorphic site mean that an area containing both of a polymorphic site and adjacent regions thereto is within a distance suitable for nucleic acid amplification, preferably PCR. The adjacent regions amplified preferably have a length within the range of, but not limited to, about 50 bases to about 3000 bases, more preferably about 50 bases to about 2000 bases. To facilitate identification of polymorphisms, the product length is preferably 50-300 bases, more preferably about 100 bases. The adjacent regions preferably have a length within the range of, but not limited to, about 0 to about 3000 bases, more preferably about 0 to about 2000 bases, still more preferably about 0 to about 1000 bases on the 5' or 3' side of a polymorphic site.

Procedures and conditions for the nucleic acid amplification reaction are not specifically limited and are well known to those skilled in the art. Appropriate conditions can be applied by those skilled in the art depending on various factors such as the base sequence of the polymorphic site and adjacent regions thereto, the base sequence and length of the primer pair, etc. Generally, the nucleic acid amplification reaction can be performed under more stringent conditions (annealing reaction and nucleic acid elongation reaction at higher temperatures and less cycles) as the primer pair is longer or the proportion of G+C is higher or the distribution of A, T, G and C is evener. The use of more stringent conditions allows an amplification reaction with higher specificity.

The amplification reaction can be performed under conditions of, but not limited to, one cycle of 94° C. for 2 min, 30 cycles of 94° C. for 1 min, 58° C. for 1 min and 72° C. for 2 min, and finally one cycle of 72° C. for 2 min using 50 ng of a genomic DNA as a template, 200 μM of each dNTP and 5 U of ExTaq™ (TAKARA). The reaction can also be performed under conditions of one cycle of 94° C. for 2 min, 30 cycles of 94° C. for 1 min, 58° C. for 1 min and 72° C. for 1 min, and finally one cycle of 72° C. for 2 min. In another embodiment, the reaction can also be performed under conditions of one cycle of 94° C. for 2 min, 35 cycles of 94° C. for 30 sec, 58° C. for 30 sec and 72° C. for 30 sec, and finally one cycle of 72° C. for 2 min.

The subject rice (test rice) genomic DNA used as a template for PCR can be easily extracted from individuals or seeds by the method of Edwards et al. (Nucleic Acids Res. 8(6):1349, 1991). More preferably, DNA purified by standard techniques is used. An especially preferred extraction method is the CTAB method (Murray, M. G. et al., Nucleic Acids Res. 8(19):4321-5, 1980). The DNA is preferably used as a template for PCR at a final concentration of 0.5 ng/μL.

2) Preparation of Markers for Detecting Polymorphisms

After examining whether or not a polymorphism is detected in the amplification product by the nucleic acid amplification reaction with a pair of primers, a marker for detecting the polymorphism is prepared on the basis of the polymorphism found. Non-limiting examples of polymorphisms that can be detected in the amplification product are as follows.

a) A change containing a deleted region exists in the polymorphism in the nucleic acid amplification product.

In this case, a pair of primers for nucleic acid amplification are prepared to flank the deleted region to form a marker for detecting the polymorphism. If the deleted region has a sufficient size, the polymorphism can be detected from the difference in mobility by electrophoresing the amplification product on an agarose gel or an acrylamide gel, for example. The polymorphism can be detected when the difference in base pair numbers is about 5% or more in the case of agarose gel electrophoresis or when the difference in length is about 1 base or more in the case of sequencing acrylamide gel electrophoresis, for example. Alternatively, the polymorphism can be detected by hybridizing the nucleic acid amplification product using an oligobase or a DNA fragment having a complementary sequence to the base sequence excluding the deleted region as an analytical probe. Alternatively, the polymorphism can be confirmed by determining the base sequence of the amplification product, if desired. Known techniques for electrophoresis of nucleic acids, hybridization, sequencing and the like can be used as appropriate by those skilled in the art. In this case, the difference in the length of the amplification product directly reflects the polymorphism and markers for detecting polymorphisms on this basis are called ALP (amplicon length polymorphism) markers.

b) A base change causing a difference in restriction enzyme recognition exists in the polymorphism in the nucleic acid amplification product.

In this case, a pair of primers for nucleic acid amplification are prepared to flank the base change site to form a marker for detecting the polymorphism. In this case, a base change causing a difference in restriction enzyme recognition occurs in the polymorphism of the nucleic acid amplification product, i.e. the nucleic acid amplification product may be cleaved or not with one or more specific restriction enzymes. Thus, the amplification product can be treated with the restriction enzymes and electrophoresed on e.g. an agarose gel to detect the polymorphism from the difference in mobility. The polymorphism can be confirmed by determining the base sequence of the amplification product, if desired.

In this case, the difference in the length of the restriction fragment of the amplification product by PCR or the like reflects the polymorphism and markers for detecting polymorphisms on this basis are called CAPS markers or PCR-RFLP markers (A. Konieczny et al., supra.)

This is exemplified by primer pairs P4497 MboI, P23945 MboI, P41030 TaqI, P45177 BstUI, B59066 BsaJI and B56691 XbaI in Example 1 below. Even if the polymorphism can be detected by the length of the nucleic acid amplification product as described in a) above, the polymorphism can be more easily detected by combination with restriction enzyme treatment.

c) A base change causing no difference in restriction enzyme recognition exists in the polymorphism in the nucleic acid amplification product.

In this case, a pair of primers for introducing a mismatch are prepared that contains the base change site and alters a region containing the base change site into a base sequence causing a difference in restriction enzyme recognition in the nucleic acid amplification product to form a marker for detecting the polymorphism.

Specifically, a pair of primers based on the base sequences of regions naturally proximal to the Rf-1 gene cause a polymorphism in the nucleic acid amplification product but no difference in restriction enzyme recognition, and therefore, a mismatch is introduced into one or both of the primers to alter a region containing the base change site (polymorphism) into a base sequence causing a difference in restriction enzyme recognition in the nucleic acid amplification product. For example, the method described in Mikaelian et al., Nucl. Acids. Res. 20:376. 1992 can be used as a standard technique for substituting, deleting or adding a specific base by PCR-mediated site-specific mutagenesis. The amplification product using the mismatch-introducing primers as a marker for detecting the polymorphism may be cleaved or not with one or more specific restriction enzymes because it has a difference in restriction enzyme recognition at the mismatch-introducing site. Therefore, the amplification product can be treated with the restriction enzymes and electrophoresed on e.g. an agarose gel to detect the polymorphism from the difference in mobility, as described in b) above.

The introduction of a mismatch must not affect not only the binding of the primers to a target plant genome but also the polymorphic base change. The polymorphic base change is used to introduce a mismatch near it so that a difference in restriction enzyme recognition occurs by a combination of both base change and mismatch. Methods for introducing such a mismatch are known to those skilled in the art and described in detail in Michaels, S. D. and Amasino, R. M. (1998), Neff, M. M., Neff, J. D., Chory, J. and Pepper, A. E. (1998), for example.

Markers in this case are improved CAPS markers described in b) above and called dCAPS (derived CAPS) markers. This is exemplified by P9493 BslI in Example 3 below.

If there are many extra restriction sites unrelated to varietal polymorphisms in the case of b) or c) above, it may be difficult to discern any difference in restriction site recognition based on polymorphisms. In this case, a mismatch may be introduced into a primer as appropriate to abolish unnecessary restriction sites. For example, a mismatch was introduced into the R-primer to abolish the MspI site unrelated to polymorphisms in B60304 MspI in Example 3.

Although the invention is not limited to any specific method, CAPS or dCAPS methods have several advantages over other RFLP methods. Specifically, analyses can be made with smaller amounts of samples than in RFLP, for example. Another advantage is that the time and labor required for analyses can be greatly reduced. Polymorphisms detected with PCR markers can be visualized by agarose gel electrophoresis that is easier than acrylamide gel electrophoresis used for microsatellite markers.

Preferred Embodiments of the Discerning Method of the Present Invention

Preferred embodiments of the method for discerning whether or not a subject rice has the Rf-1 gene are described below for illustrative purposes. In the examples herein, it was found that the base sequence of an indica variety IR24 carrying the Rf-1 gene (SEQ ID NO:27) has at least the following polymorphisms 1)-8) as compared with corresponding regions of japonica varieties:

1) a base corresponding to the base 1239 of SEQ ID NO:27 is A;

2) a base corresponding to the base 6227 of SEQ ID NO:27 is A;

3) a base corresponding to the base 20680 of SEQ ID NO:27 is G;

4) a base corresponding to the base 45461 of SEQ ID NO:27 is A;

5) a base corresponding to the base 49609 of SEQ ID NO:27 is A;

6) a base corresponding to the base 56368 of SEQ ID NO:27 is T;

7) a base corresponding to the base 57629 of SEQ ID NO:27 is C; and 8) a base corresponding to the base 66267 of SEQ ID NO:27 is G.

In preferred embodiments of the present invention, therefore, the subject rice individual or seed is judged as carrying the Rf-1 gene when one to all of the requirements 1)-8) above are met.

We further verified that a region essential for the expression of the function of the Rf-1 gene is contained in especially the bases 38538-54123, preferably the bases 42357-53743, more preferably the bases 42132-48883, still more preferably the bases 42132-46318 in the base sequence of SEQ ID NO:27. In an embodiment of the present invention, therefore, the subject rice individual or seed is determined to have the Rf-1 gene in the case that the nucleic acid having a base sequence which is identical to at least 70% of the base sequence of SEQ ID NO. 27 or of the base sequence of bases 38538-54123 of SEQ ID NO. 27, meets at least one of the following requirements 1) and 2):

1) a base corresponding to the base 45461 of SEQ ID NO. 27 is A; and 2) a base corresponding to the base 49609 of SEQ ID NO. 27 is A.

Known polymorphism detecting methods can be used to determine whether or not the above requirements are met. The base sequence of adjacent regions containing said sequence can also be directly determined. However, CAPS or dCAPS methods described above are preferably used because they are rapid and convenient. CAPS or dCAPS methods can be performed by a protocol comprising, for example:

i) preparing a pair of primers based on a base sequence of adjacent regions including any one of the following base;

1) a base corresponding to the base 1239 of SEQ ID NO:27;

2) a base corresponding to the base 6227 of SEQ ID NO:27;

3) a base corresponding to the base 20680 of SEQ ID NO:27;

4) a base corresponding to the base 45461 of SEQ ID NO:27;

5) a base corresponding to the base 49609 of SEQ ID NO:27;

6) a base corresponding to the base 56368 of SEQ ID NO:27;

7) a base corresponding to the base 57629 of SEQ ID NO:27; and 8) a base corresponding to the base 66267 of SEQ ID NO:27 is G.

to amplify both the base of the above and adjacent regions thereto;

ii) performing nucleic acid amplification reaction(s) using the genome DNA of the subject rice individual or the seed thereof as a template; and iii) discerning the presence of the Rf-1 in the subject rice individual or the seed thereof based on polymorphism found in said nucleic acid amplification product.

The detection of polymorphisms in the nucleic acid amplification product is performed by, but not limited to, discerning the subject rice individual or seed to have the Rf-1 gene when one to all of the requirements 1)-8) below are met:

1) a region including a base corresponding to the base 1239 of SEQ ID NO:27 does not have any MboI recognition sequence;

2) a region including a base corresponding to the base 6227 of SEQ ID NO:27 does not have any BslI recognition sequence;

3) a region including a base corresponding to the base 20680 of SEQ ID NO:27 does not have any MboI recognition sequence;

4) a region including a base corresponding to the base 45461 of SEQ ID NO:27 does not have any TaqI recognition sequence;

5) a region including a base corresponding to the base 49609 of SEQ ID NO:27 does not have any BstUI recognition sequence;

6) a region including a base corresponding to the base 56368 of SEQ ID NO:27 does not have any MspI recognition sequence;

7) a region including a base corresponding to the base 57629 of SEQ ID NO:27 does not have any BsaJI recognition sequence; and 8) a region including a base corresponding to the base 66267 of SEQ ID NO:27 does not have any XbaI recognition sequence.

However, the present invention is not limited to the restriction enzymes above so far as each polymorphism in the specific regions 1)-8) above can be detected.

Preferably, identification methods of the present invention comprise:

i) preparing a pair of primers based on a base sequence of adjacent regions including any one of the following base;

1) a base corresponding to the base 45461; or 2) a base corresponding to the base 49609;

to amplify both the base of the above and adjacent regions thereto;

ii) performing nucleic acid amplification reaction(s) using the genome DNA of the subject rice individual or the seed thereof as a template; and iii) discerning the presence of the Rf-1 in the subject rice individual or the seed thereof based on polymorphism found in said nucleic acid amplification product. The subject rice individual or seed thereof is determined to have the Rf-1 gene in step iii), although not limited to, when at least one of the following requirements 1) and 2) is met:

1) a region including a base corresponding to the base 45461 of SEQ ID NO:27 does not have any TaqI recognition sequence;

2) a region including a base corresponding to the base 49609 of SEQ ID NO:27 does not have any BstUI recognition sequence.

The base 45461 of SEQ ID NO:27 discussed above corresponds to 1) the base 1769 of SEQ ID NO. 69; 2) the base 1767 of SEQ ID NO. 70; 3) the base 1772 of SEQ ID NO. 71; 4) the base 1762 of SEQ ID NO. 72; 5) the base 1703 of SEQ ID NO. 73; 6) the base 1779 of SEQ ID NO. 74; 7) the base 1783 of SEQ ID NO. 80; 8) the base 1729 of SEQ ID NO. 81; 9) the base 1781 of SEQ ID NO. 82; 10) the base 1774 of SEQ ID NO. 83; 11) the base 1728 of SEQ ID NO. 84; and 12) the base 1644 of SEQ ID NO. 85.

Primer pairs used for the amplification reaction can be appropriately selected by those skilled in the art to preferably satisfy the conditions above on the basis of the base sequence of SEQ ID NO:27. Preferably, any primer pair having a base sequence selected from the group consisting of SEQ ID NOS: 39 and 40, SEQ ID NOS: 41 and 42, SEQ ID NOS: 43 and 44, SEQ ID NOS: 45 and 46, SEQ ID NOS: 47 and 48, SEQ ID NOS: 49 and 50, SEQ ID NOS: 51 and 52, and SEQ ID NOS: 53 and 54 is used. More preferably, the primer pair is selected from the group consisting of SEQ ID NOS: 45 and 46, and SEQ ID NOS: 47 and 48. If necessary, the sequences of the above primer pairs containing substitutions, deletions or additions while retaining the binding specificity for the base sequence of the polymorphic site and adjacent regions thereto can also be used as primers.

To examine the resulting PCR product for restriction fragment length polymorphisms, it is cleaved with restriction enzymes corresponding to the restriction sites present in PCR markers. Such cleavage is accomplished by incubation for several hours to a day at the recommended reaction temperature for the restriction enzymes used. The PCR amplified sample cleaved with the restriction enzymes can be analyzed by electrophoresis on an about 0.7%-2% agarose gel or an about 3% MetaPhor™ agarose gel. The gel is visualized under UV light in ethidium bromide, for example.

In the most preferred embodiments of the present invention, restriction enzyme cleavage patterns show the bands as shown in Table 2 below on the visualized gel depending on the primer pair used.

TABLE 2

| | Approximate size (bp) of detected band |
|---|---|
| Amplified with P4497 MobI (SEQ ID NOS: 39 and 40) Restriction enzyme MboI | |
| Test rice genome having the Rf-1 gene (homozygous): | 730 |
| no: | 385, 345 |
| Amplified with P9493 BslI (SEQ ID NOS: 41 and 42) Restriction enzyme BslI | |
| Test rice genome having the Rf-1 gene (homozygous): | 126 |
| no: | 100, 26 |
| Amplified with P23945 MboI (SEQ ID NOS: 43 and 44) Restriction enzyme MboI | |
| Test rice genome having the Rf-1 gene (homozygous): | 160, 100 |
| no: | 260 |
| Amplified with P41030 TaqI (SEQ ID NOS: 45 and 46) Restriction enzyme TaqI | |
| Test rice genome having the Rf-1 gene (homozygous): | 280 |
| no: | 90, 190 |
| Amplified with P45177 BstUI (SEQ ID NOS: 47 and 48) Restriction enzyme BstUI | |
| Test rice genome having the Rf-1 gene (homozygous): | 20, 65, 730 |
| no: | 20, 65, 175, 555 |
| Amplified with B60304 MspI (SEQ ID NOS: 49 and 50) Restriction enzyme MspI | |
| Test rice genome having the Rf-1 gene (homozygous): | 330 |
| no: | 220, 110 |
| Amplified with B59066 BsaJI (SEQ ID NOS: 51 and 52) Restriction enzyme BsaJI | |
| Test rice genome having the Rf-1 gene (homozygous): | 420 |
| no: | 65, 355 |
| Amplified with B56691 XbaI (SEQ ID NOS: 53 and 54) Restriction enzyme XbaI | |
| Test rice genome having the Rf-1 gene (homozygous): | 670 |
| no: | 140, 530 |

In Example 3 below, recombinants proximal to the Rf-1 gene having pollen fertility (RS1-RS2, RC1-RC8) were tested for the chromosomal organization of the Rf-1 region using 14 polymorphic markers including the 8 primer pairs described above. As a result, it was confirmed that all the plants carry the Rf-1 gene derived from the indica variety between P9493 BslI and 59066 BsaJI. This result showed that recombinant pollens having the chromosomal organization as shown in FIG. 3 have pollen fertility, i.e. the Rf-1 gene is functional in these pollens. This means that a sequence determining the presence of the function of the Rf-1 gene is included in the indica region common to these recombinant pollens, i.e. in a region from the P4497 MboI to B56691 XbaI loci (about 65 kb) as estimated at maximum.

In the present invention, chromosomal walking was started on the presumption that the S12564 Tsp509I locus should be vary proximal to the Rf-1 locus as judged from the frequency of appearance of individuals by crossing. In fact, the genetic distance between both loci has been calculated to be about 0.04 cM as the result of the high-precision segregation analysis of the present invention. Even one of markers known to be most closely linked to the Rf-1 locus as described in Japanese Patent Public Disclosure No. 2000-139465 is reported to have a genetic distance of 1 cM from the Rf-1 locus. Considering that 1 cM is estimated to be equivalent to 300 kb on average in rice, a considerable time should be required to restrict the Rf-1 gene region if chromosomal walking were started from the marker described in Japanese Patent Public Disclosure No. 2000-139465.

VI. Method for Inhibiting the Function of Rf-1 Gene to Restore Fertility

According to the present invention, the nucleic acid containing the locus of a fertility restorer gene (Rf-1) including the nucleic acids which function to restore fertility was isolated. The entire base sequence thereof was determined, whereby the fertility restoring function of the Rf-1 gene can be controlled by genetic engineering techniques. Thus, the present invention further provides a method for inhibiting the function of Rf-1 to restore fertility.

A method for inhibiting the function of the Rf-1 gene to restore fertility according to one embodiment of the present invention comprises introducing an antisense having at least 100 continuous bases in length, and having a base sequence complementary to a nucleic acid having the base sequence of SEQ ID NO. 27, or to a nucleic acid having a base sequence which is identical to at least 70% of the base sequence of SEQ ID NO. 27, and which functions to restore fertility.

In an embodiment, the method for inhibiting the function of the Rf-1 gene to restore fertility according to the present invention comprises introducing an antisense having at least 100 continuous bases in length, and being selected from base sequences complementary to a nucleic acid having the base sequence of the bases 38538-54123, preferably the bases 42357-53743, more preferably the bases 42132-48883 of SEQ ID NO:27, or to a nucleic acid having a base sequence which is identical to at least 70% of the base sequence of the bases 38538-54123, preferably the bases 42357-53743, more preferably the bases 42132-48883, still more preferably the bases 42132-46318 of SEQ ID NO:27 and, which functions to restore fertility.

In an especially preferable embodiment, the method for inhibiting the function of the Rf-1 gene to restore fertility according to the present invention comprises introducing an antisense having at least 100 bases in length, and being selected from base sequences complementary to a nucleic acid encoding the amino acid sequence of SEQ ID NO. 75, or an amino acid sequence which is identical to at least 70% of the amino acid sequence of SEQ ID NO. 75, and which functions to restore fertility.

Most preferably, the nucleic acid encoding the amino acid sequence of SEQ ID NO. 75, or an amino acid sequence which is identical to at least 70% of the amino acid sequence of SEQ ID NO. 75 is selected from nucleic acids of the following a)-p):

a) a nucleic acid comprising the bases 215-2587 of SEQ ID NO:69;

b) a nucleic acid comprising the bases 213-2585 of SEQ ID NO:70;

c) a nucleic acid comprising the bases 218-2590 of SEQ ID NO:71;

d) a nucleic acid comprising the bases 208-2580 of SEQ ID NO:72;

e) a nucleic acid comprising the bases 149-2521 of SEQ ID NO:73;

f) a nucleic acid comprising the bases 225-2597 of SEQ ID NO:74;

g) a nucleic acid comprising the bases 43907-46279 of SEQ ID NO:27;

h) a nucleic acid comprising the bases 229-2601 of SEQ ID NO:80;

i) a nucleic acid comprising the bases 175-2547 of SEQ ID NO:81;

j) a nucleic acid comprising the bases 227-2599 of SEQ ID NO:82;

k) a nucleic acid comprising the bases 220-2592 of SEQ ID NO:83;

l) a nucleic acid comprising the bases 174-2546 of SEQ ID NO:84;

m) a nucleic acid comprising the bases 90-2462 of SEQ ID NO:85;

n) a nucleic acid which is identical to at least 70% of the nucleic acid of any of a)-m), and which functions to restore fertility;

o) a nucleic acid which hybridizes to the nucleic acid of any of a)-m) under a moderate or high stringent condition, and which functions to restore fertility; and p) a nucleic acid wherein one or a plurality of base(s) is deleted from, added to or substituted from the nucleic acid of any of a)-m), and which functions to restore fertility.

The antisense has a length of at least 100 bases or more, more preferably 500 bases or more, most preferably 1000 bases or more. From the viewpoint of technical convenience of introduction, it preferably has a length of 10000 bases or less, more preferably 5000 bases or less. The antisense can be synthesized by known methods. The antisense can be introduced into rice by known methods as described in e.g. Terada et al. (Plant Cell Physiol. 2000 July, 41(7), pp. 881-888).

It is also anticipated that Rf-1 disrupted lines can be established by screening variant lines containing a transposable element such as, but not limited to, Tos17 (Hirochika H. et al. 1996, Proc. Natl. Acad. Sci. USA 93, pp. 7783-7788) for a line containing the transposable element in the base sequence of SEQ ID NO:27. In plants, gene disruption by homologous recombination has been studied. It may also be possible to inhibit fertility restoring function by establishing such a line in which the Rf-1 gene has been replaced by a variant Rf-1 gene using a nucleic acid having the base sequence of SEQ ID NO. 27, or a nucleic acid having a base sequence which is identical to at least 70% of the base sequence of SEQ ID NO. 27.

REFERENCES

1. Fukuta et al. 1992, Jpn J. Breed. 42 (supl. 1) p. 164-165.

2. Japanese Patent Public Disclosure No. HEI7(1995)-222588.

3. Japanese Patent Public Disclosure No. HEI9(1997)-313187.

4. Japanese Patent Public Disclosure No. 2000-139465.

5. Harushima et al. 1998, Genetics 148 p. 479-494.

6. Michaels and Amasino 1998, The Plant Journal 14(3) p. 381-385.

7. Neff et al. 1998, The plant Journal 14(3) p. 387-392.

8. D. E. Harry, et al., Theor Appl Genet (1998) 97:p. 327-336.

9. Hiei et al., Plant Journal (1994), 6(2), p. 272-282.

10. Komari et al., Plant Journal (1996) 10, p. 165-174.

11. Ditto et al., Proc. Natl. Acad. Sci. USA (1980), 77: p. 7347-7351,

12. P. Vos et al., Nucleic Acids Res. Vol. 23, p. 4407-4414 (1995).

13. O. Parnaud, X. et al, Mol. Gen. Genet. (1996) 252:p. 597-607.

14. A. Konieczny et al., (1993), Plant J. 4(2) p. 403-410.

15. Edwards et al., Nucleic Acids Res. 8(6): 1349, 1991.

16. Murray M. G. et al., Nucleic Acids Res. 8(19):4321-5, 1980.

17. Terada et al., Plant Cell Physiol. 2000, July, 41(7), p. 881-888.

18. Hirochika H. et al. 1996, Proc. Natl. Acad. Sci. USA 93, p. 7783-7788.

19. Cui, X., Wise, R. P. and Schanble, P. S. (1996) The rf2 nuclear restorer gene of male-sterile T-cytoplasm maize. Science, 272, 1334-1336

20. Liu, F., Cui, X., Horner, H. T., Weiner, H. and Schnable, P. S. (2001) Mitochondrial aldehyde dehydrogenase activity is required for male fertility in maize. The Plant Cell, 13, 1063-1078

EXAMPLES

The following examples further illustrate the present invention but are not intended to limit the technical scope of the invention. Those skilled in the art can readily add modifications/changes to the present invention on the basis of the description of the specification, and those modifications/changes are included in the technical scope of the present invention.

Reference Examples

The following reference examples are based on the examples described in our prior application (Japanese Patent Application No. 2000-247204 filed Aug. 17, 2000).

Reference Example 1

Conversion of RFLP Markers Around Rf-1 Gene to PCR Markers

In this reference example, nine RFLP markers (i.e., R1877, G291, R2303, S12564, C1361, S10019, G4003, S10602 and G2155) around the locus of Rf-1 gene were converted to PCR markers.

(1) Materials and Methods

The following nine RFLP markers, R1877, G291, R2303, S12564, C1361, S10019, G4003, S10602 and G2155, were purchased from the National Institute of Agrobiological Sciences, the Ministry of Agriculture, Forestry and Fisheries of Japan. After determining the base sequences of the inserts in the vectors, experiments were conducted according to the following procedures. Among rice varieties herein, Asominori belongs to japonica, and IR24 belongs to indica.

(2) Preparation of Asominori Genomic Library

Total DNA was extracted from green leaves of Asominori by the CTAB method. After partial digestion with MboI, the DNA was fractionated according to size by NaCl density gradient centrifugation (6-20% linear gradient, 20° C., 37,000 rpm, 4 hr, total volume=12 mL). A portion of each fraction (about 0.5 mL) was subjected to electrophoresis and fractions containing 15-20 kb DNA were collected and purified. A library was constructed using Lambda DASH II (Stratagene) as a vector in accordance with the attached protocol. Giga Pack III Gold (Stratagene) was used for packaging. After packaging, 500 μL of SM Buffer and 20 μL of chloroform were added. After centrifugation, 20 μL of chloroform was added to the supernatant to make a library solution.

XL-1 Blue MRA (P2) was infected with 5 μL of a 50-fold dilution of the library solution, whereupon 83 plaques were formed. This corresponded to $4.15\times10^5$ pfu per library, and hence, it was calculated that the plaques covered $8.3\times10^9$ bp assuming that the average length of the inserted fragments was 20 kb. The library was therefore considered to have an adequate size for the rice genome ($4\times10^8$ bp).

(3) Isolation of Genomic Clones Containing R1877-, C1361- and G4003-Marker Regions.

As for C1361 and G4003, plasmids containing the RFLP marker probe were isolated and subjected to restriction enzyme treatment and electrophoresis to separate the RFLP marker probe portion; the desired DNA was recovered on a DNA recovery filter (Takara SUPREC-01). As for R1877, primers were designed that were specific to both ends of the marker probe and PCR was performed with the total DNA of Asominori used as a template; the amplification products were electrophoresed and recovered by the method described above. The recovered DNA was labelled with a Rediprime DNA Labelling System (Amersham Pharmacia) to prepare a probe for screening the library. PCR was performed in the usual manner (this also applies to the following description).

Screening of the library was performed in the usual manner after blotting the plaques onto Hybond-N+ (Amersham Pharmacia). After primary screening, areas of positive plaques were individually punched out, suspended in SM buffer and subjected to the second round of screening. After the second screening, the positive plaques were punched out and subjected to the third round of screening to isolate a single plaque.

The isolated plaque of interest was suspended in SM buffer and primary multiplication of the phage was performed by the plate lysate method. The resulting phage-enriched solution was subjected to secondary multiplication by shake culture and the phage DNA was purified with Lambda starter kit (QIAGEN).

For each marker, primary screening was conducted on eight plates. A 10 μL aliquot of the library solution was employed per plate. After the primary, second and third rounds of screening, four genomic clones in association with R1877 were isolated and three were isolated in association with each of C1361 and G4003.

(4) Conversion of R1877 to PCR Marker

The isolated genomic clones were analyzed to identify the causative site of RFLP, or the EcoRI site that exists in IR24 (indica rice) but not in Asominori (japonica rice), thereby converting R1877 to a PCR marker.

Specifically, the four isolated clones were subjected to the following analyses. First, T3 and T7 primers were used to determine the base sequences at both ends of the insert in each clone. Then, primers extending outwardly from both ends of the marker probe were designed. They were combined with T3 and T7 primers to give a combination of four primers in total, and employed in PCR with each clone used as the template.

In a separate step, each clone was digested with NotI and EcoRI, and electrophoresed to estimate the insert size and the length of each EcoRI fragment.

These analyses revealed the relative positions of the individual clones. In RFLP analysis, marker probe R1877 was reported to detect an EcoRI fragment of 20 kb in Nipponbare (japonica rice) and one of 6.4 kb in Kasalath (indica rice) (ftp://ftp.staff.or.jp/pub/geneticmap98/parentsouthern/chr10/R1877.JPG). This fact, taken together with the results of analysis described above, gave a putative position for the EcoRI site that existed in IR24 but not in Asominori. Hence, a primer combination (SEQ ID NO:1×SEQ ID NO:2) that was designed to amplify the nearby region was employed to perform genomic PCR over 30 cycles, each cycle consisting of 94° C.×1 min, 58° C.×1 min and 72° C.×2 min. The PCR product was treated with EcoRI and subjected to electrophoresis on 0.7% agarose gel.

As a result, the expected polymorphisms were observed between Asominori and IR24. By treatment with EcoRI, the PCR product (~3200 bp) was cleaved to yield 1500 bp and 1700 bp fragments in IR24 but not in Asominori. Mapping of the marker was made with an RIL (recombinant inbred line) of Asominori-IR24 with the results that the PCR marker was located in the same region as that of RFLP marker locus R1877, thereby confirming the conversion of RFLP marker R1877 to a PCR marker, which was named R1877 EcoRI in the present invention.

(5) Conversion of G4003 to PCR Marker

The isolated genomic clones were analyzed to identify the causative site of RFLP, or the HindIII site that existed in Asominori but not in IR24, thereby converting G4003 to a PCR marker.

By performing analyses similar to those employed for R1877, the relative positions of the three isolated clones were revealed. In RFLP analysis, marker probe G4003 was reported to detect a HindIII fragment of 3 kb in Nipponbare (japonica rice) and one of 10 kb in Kasalath (indica rice) (ftp://ftp.staff.or.jp/pub/geneticmap98/parentsouthern/chr10/R1877.JPG). This report, taken together with the analyses described above, led to a temporary conclusion that the HindIII site that existed in Asominori but not in IR24 would be at either one of two candidate sites. Hence, a primer combination (SEQ ID NOS: 3 and 4) that was designed to amplify the area in the neighborhood of each HindIII site was employed to perform genomic PCR over 35 cycles, each cycle consisting of 94° C.×30 sec, 58° C.×30 sec and 72° C.×30 sec. The PCR product was treated with HindIII and subjected to electrophoresis on 2% agarose gel. As a result, the HindIII site within the marker probe was found to have polymorphisms. By treatment with HindIII, the PCR product (362 bp) was cleaved to yield a 95 bp fragment and a 267 bp fragment in Asominori but not in IR24. Mapping of the site demonstrated the conversion of RFLP marker G4003 to a PCR marker, which was named G4003 HindIII (SEQ ID NO:19) in the present invention.

(6) Conversion of C1361 to PCR Marker

Primers were designed on the basis of the base sequence information of the isolated genomic clones. PCR was performed with the total DNAs of Asominori and IR24 being used as a template and the PCR product was recovered by known methods after electrophoresis. Using the recovered DNA as a template, the inventors analyzed the base sequence of each of the rice varieties with ABI Model 310 in search of mutations that would cause polymorphisms.

By performing analyses similar to those employed for R1877, approximate relative positions of the three isolated clones could be established. As it turned out, however, regions around the C1361 marker would be difficult to amplify by PCR or determine their base sequences, and hence, it would not be easy to identify the causative site of RFLP. Hence, the inventors took notice of the region capable of yielding a comparatively long PCR product (2.7 kb) and made an attempt to create a dCAPS marker.

Specifically, upon comparing the base sequences of the genomic PCR products of said region using Asominori and Koshihikari (both japonica rice) and Kasalath and IR24 (both indica rice), the inventors found six sites of polymorphism between japonica and indica. One of these six sites was used to create a dCAPS marker. To this end, with SEQ ID NO:5 and SEQ ID NO:6 used as primers, PCR was performed over 35 cycles, each cycle consisting of 94° C.×30 sec, 58° C.×30 sec and 72° C.×30 sec. The PCR product was treated with MwoI and analyzed by electrophoresis on 3% MetaPhor™ agarose gel. In Asominori, cleavage occurred at two sites to give three observable bands of about 25 bp, 50 bp and 79 bp, but in IR24 cleavage occurred at one site to give two observable bands of about 50 bp and 107 bp. Mapping demonstrated the conversion of RFLP marker C1361 to a PCR marker, which was named C1361 MwoI (SEQ ID NO:20) in the present invention.

(7) Conversion of G2155 to PCR Marker

Primers specific to both ends of the marker probe were designed and PCR was performed with the total DNA of Asominori, Koshihikari, IR24 or IL216 (a line produced by introducing Rf-1 gene into Koshihikari by back crossing; its genotype was Rf-1/Rf-1) being used as a template. Purification of the PCR product and searching for a mutation that would be useful for providing restriction fragment polymorphisms were performed by the methods already described above.

Specifically, as a result of comparing the base sequences of corresponding regions of the varieties under test, mutations were found at three sites between the variety/line (IR24 and IL216) having Rf-1 gene and the variety (Asominori and Koshihikari) not having Rf-1 gene. One of the three sites was utilized to create a dCAPS marker. To this end, SEQ ID NO:7 and SEQ ID NO:8 were used as primers to perform PCR over 35 cycles, each cycle consisting of 94° C.×30 sec, 58° C.×30 sec and 72° C.×30 sec. The PCR product was treated with MwoI and analyzed by electrophoresis on 3% MetaPhor™ agarose gel. In Asominori, cleavage occurred at one site to give two observable bands of about 25 bp and 105 bp, but in IR24, cleavage occurred at two sites to give three observable bands of about 25 bp, 27 bp and 78 bp. Mapping demonstrated the conversion of RFLP marker G2155 to a PCR marker, which was named G2155 MwoI (SEQ ID NO:21) in the present invention.

(8) Conversion of G291 to PCR Marker

Primers specific to internal sequences of the marker probe were designed and used in various combinations to perform PCR to find a primer combination that could yield an amplification product of the expected size. Using the selected primer combination, the inventors performed PCR with the total DNA of Asominori, Koshihikari, IR24 and IL216 used as a template. Purification of the PCR product and searching for a mutation that could be utilized in providing restriction fragment polymorphisms were performed by the methods already described above.

Specifically, using the primers designed to be specific for the marker probe sequence, the inventors performed genomic PCR of each variety under test and compared the base sequences of the products. As a result, mutations were found at four sites between the variety/line having Rf-1 gene (IR24 and IL216) and the variety (Asominori and Koshihikari) not having Rf-1 gene. One of the four sites was used to create a dCAPS marker. To this end, SEQ ID NO:9 and SEQ ID NO:10 were used as primers to perform PCR over 35 cycles, each cycle consisting of 94° C.×30 sec, 58° C.×30 sec and 72° C.×30 sec. The PCR product was treated with MspI and analyzed by electrophoresis on 3% MetaPhor™ agarose gel. In the varieties/lines having Rf-1 gene, cleavage occurred at two sites to give three observable bands of about 25 bp, 49 bp and 55 bp, but in the varieties not having Rf-1 gene, cleavage occurred at one site to give two observable bands of about 25 bp and 104 bp. Mapping demonstrated the conversion of RFLP marker G291 to a PCR marker, which was named G291 MspI (SEQ ID NO:22) in the present invention.

(9) Conversion of R2303 to PCR Marker

Primers specific to internal sequences of the marker probe were designed and PCR was performed with the total DNA of Asominori (japonica rice) and IR24 and Kasalath (indica rice) used as a template. Purification of the PCR product and searching for a mutation that could be used for providing restriction fragment polymorphisms were performed by the methods already described above.

As a result of comparing the base sequences of corresponding regions of the varieties under test, a mutation was found between japonica rice and indica rice. Since the mutation occurred at the BslI recognition site, the site was directly used to create a CAPS marker. To this end, SEQ ID NO:11 and SEQ ID NO:12 were used as primers and PCR was performed over 30 cycles, each cycle consisting of 94° C.×1 min, 58° C.×1 min and 72° C.×2 min. The PCR product was treated with BslI and analyzed by electrophoresis on 2% agarose gel. In japonica rice, cleavage occurred at one site to give two observable bands of about 238 bp and 1334 bp, but in indica rice, cleavage occurred at two sites to give three observable bands of about 238 bp, 655 bp and 679 bp. Mapping demonstrated the conversion of RFLP marker R2303 to a PCR marker, which was named R2303 BslI (SEQ ID NO:23) in the present invention.

(10) Converting S10019 to PCR Marker

S10019 was converted to a PCR marker in accordance with the method (9) of converting R2303 to a PCR marker.

Specifically, as a result of comparing the base sequences of corresponding regions of the varieties under test, a mutation was found between japonica rice and indica rice. Since the mutation occurred at the BstUI recognition site, the site was directly used to create a CAPS marker. To this end, SEQ ID NO:13 and SEQ ID NO:14 were used as primers and PCR was performed over 30 cycles, each cycle consisting of 94° C.×1 min, 58° C.×1 min and 72° C.×1 min. The PCR product was treated with BstUI and analyzed by electrophoresis on 2% agarose gel. In japonica rice, cleavage occurred at one site to give two observable bands of about 130 bp and 462 bp, but in indica rice, cleavage occurred at two sites to give three observable bands of about 130 bp, 218 bp and 244 bp. Mapping demonstrated the conversion of RFLP marker S10019 to a PCR marker, which was named S10019 BstUI (SEQ ID NO:24) in the present invention.

(11) Conversion of S10602 to PCR Marker

S10602 was converted to a PCR marker in accordance with the method (9) of converting R2303 to a PCR marker.

Specifically, as a result of comparing the base sequences of corresponding regions of the varieties under test, a mutation was found between japonica rice and indica rice. The mutation was used to create a CAPS marker. To this end, SEQ ID NO:15 and SEQ ID NO:16 were used as primers and PCR was performed over 33 cycles, each cycle consisting of 94° C.×1 min, 58° C.×1 min and 72° C.×1 min. The PCR product was treated with KpnI and analyzed by electrophoresis on 2% agarose gel. In japonica rice, cleavage occurred at one site to give two observable bands of about 117 bp and 607 bp, but in indica rice, no cleavage occurred, giving only an observable band of 724 bp. Mapping demonstrated the conversion of RFLP marker S10602 to a PCR marker, which was named S10602 KpnI (SEQ ID NO:25) in the present invention.

(12) Conversion of S12564 to PCR Marker

S12564 was converted to a PCR marker in accordance with the method of converting R2303 to a PCR marker.

Specifically, as a result of comparing the base sequences of corresponding regions of the varieties under test, a mutation was found between japonica rice and indica rice. The mutation was used to create a dCAPS marker. To this end, SEQ ID NO:17 and SEQ ID NO:18 were used as primers and PCR was performed over 35 cycles, each cycle consisting of 94° C.×30 sec, 58° C.×30 sec and 72° C.×30 sec. The PCR product was treated with Tsp509I and analyzed by electrophoresis on 3% MetaPhor™ agarose gel. In japonica rice, cleavage occurred at two sites to give three observable bands of 26 bp, 41 bp and 91 bp, but in indica rice, cleavage occurred at one site to give two observable bands of 41bp and 117 bp. Mapping demonstrated the conversion of RFLP marker S12564 to a PCR marker, which was named S12564 Tsp509I (SEQ ID NO:26) in the present invention.

TABLE 3

Genotypes of Marker Loci in Recombinant Individuals Around Rf-1 Locus

| Locus | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|
| R1877 EcoRI | J | J | J | J | J | J | J | J | H | H | H | H | H | H | H | H | H | H | H | H | H | H | H |
| G291 MspI | H | J | J | J | J | J | J | J | H | H | H | H | H | H | H | H | H | H | H | H | H | H | H |
| R2303 BslI | H | H | J | J | J | J | J | J | H | H | H | H | H | H | H | H | H | H | H | H | H | H | H |
| S12564 Tsp509I | H | H | H | H | H | H | H | J | H | H | H | H | H | H | H | H | H | H | H | H | H | H | H |
| C1361 MwoI | H | H | H | H | H | H | H | H | J | J | H | H | H | H | H | H | H | H | H | H | H | H | H |
| S10019 BstUI | H | H | H | H | H | H | H | H | J | J | J | J | J | J | J | J | H | H | H | H | H | H | H |
| G4003 HindIII | H | H | H | H | H | H | H | H | J | J | J | J | J | J | J | J | J | J | J | J | J | J | J |
| S10602 KpnI | H | H | H | H | H | H | H | H | J | J | J | J | J | J | J | J | J | J | J | J | J | J | J |
| G2155 MwoI | H | H | H | H | H | H | H | H | J | J | J | J | J | J | J | J | J | J | J | J | J | J | J |
| **Locus** | **24** | **25** | **26** | **27** | **28** | **29** | **30** | **31** | **32** | **33** | **34** | **35** | **36** | **37** | **38** | **39** | **40** | **41** | **42** | **43** | **44** | **45** | **46** |
| R1877 EcoRI | H | H | H | H | H | H | H | H | H | H | H | H | H | H | H | H | H | H | H | H | H | H | H |
| G291 MspI | H | H | H | H | H | H | H | H | H | H | H | H | H | H | H | H | H | H | H | H | H | H | H |
| R2303 BslI | H | H | H | H | H | H | H | H | H | H | H | H | H | H | H | H | H | H | H | H | H | H | H |
| S12564 Tsp509I | H | H | H | H | H | H | H | H | H | H | H | H | H | H | H | H | H | H | H | H | H | H | H |
| C1361 MwoI | H | H | H | H | H | H | H | H | H | H | H | H | H | H | H | H | H | H | H | H | H | H | H |
| S10019 BstUI | H | H | H | H | H | H | H | H | H | H | H | H | H | H | H | H | H | H | H | H | H | H | H |
| G4003 HindIII | J | J | J | J | J | J | J | J | J | H | H | H | H | H | H | H | H | H | H | H | H | H | H |
| S10602 KpnI | J | J | J | J | J | J | J | J | J | J | J | J | J | J | J | J | J | J | J | J | J | H | H |
| G2155 MwoI | J | J | J | J | J | J | J | J | J | J | J | J | J | J | J | J | J | J | J | J | J | J | J |

J: Homozygous Koshihikari type
H: Heterozygous Koshihikari type/MS-FR Koshihikari type

Reference Example 2

Mapping of Rf-1 Gene Locus

DNA was extracted from 1042 seedlings of the F1 population produced by pollinating MS Koshihikari with MS-FR Koshihikari, and the DNA extract was used in the analysis. MS Koshihikari (generation: BC10F1) was created by replacing the cytoplasm of Koshihikari with BT type male sterility cytoplasm. MS-FR Koshihikari was a line created by introducing Rf-1 gene from IR8 (supplied from National Institute of Agrobiological Sciences) into MS Koshihikari (the locus of Rf-1 gene being heterozygous).

First, each individual was investigated for the genotype at two marker loci R1877 EcoRI and G2155 MwoI described in Reference example 1 that would presumably be located on opposite sides of the locus of Rf-1 gene. Japonica type homozygotes with respect to either locus R1877 EcRI or G2155 MwoI were regarded as recombinants between these two marker loci. Then, each of such recombinants was investigated for the genotypes of G291 MspI, R2303 BslI, S12564 Tsp 509I, C1361 MwoI, S10019 BstUI, G4003 HindIII and S10602 KpnI loci, and the positions of recombination were identified.

The genotype investigation with respect to R1877 EcoRI and G2155 MwoI loci revealed that 46 individuals were recombinants around the locus of Rf-1 gene. Genotypes of the marker loci around the locus of Rf-1 gene were investigated and the results are shown in Table 3.

Figure 4:
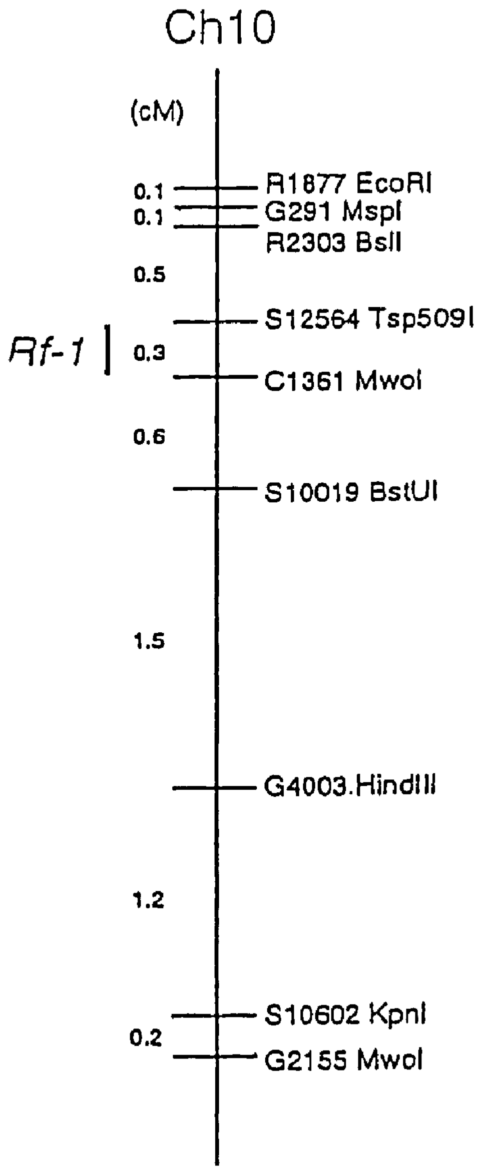
FIG. 4 is a gene map in which the locus of Rf-1 gene on chromosome 10 of rice is positioned on a linkage map in relation to various markers; the values of map distance were calculated from the segregation data from 1042 F1 individuals.

As shown in Table 3, recombinant 8 homozygous for japonica at the S12564 Tsp509I marker locus and recombinants 9 and 10 homozygous for japonica at the C1361 Mwo marker locus were obtained. As all of these recombinants restored fertility, the former was regarded as a recombinant between the Rf-1 and S12564 Tsp509I loci while the latter were regarded as recombinants between the Rf-1 and C1361 MwoI loci, showing that the Rf-1 gene is located between the S12564 Tsp509I and C1361 MwoI loci. Based on the report that only pollens carrying the Rf-1 gene have fertility in individuals having the BT type male sterile cytoplasm in the cross above (C. Shinjyo, JAPAN. J. GENETICS Vol. 44, No. 3:149-156 (1969)), the Rf-1 gene locus could be located on a detailed linkage map (FIG. 4).

Example 1

Acquisition of Recombinant Individuals Proximal to the Rf-1 Locus (Materials and Methods)

DNA was extracted from each of 4103 individuals of BC10F1 population produced by pollinating MS Koshihikari (generation: BC10F1) with MS-FR Koshihikari (generation: BC9F1, heterozygous at the Rf-1 locus), and genotyped at the S12564 Tsp509I and C1361 MwoI loci in the same manner as described in Reference example 2 above. Individuals having a genotype homozygous for Koshihikari at the S12564 Tsp509I locus were regarded as those generated by recombination between the Rf-1 and S12564 Tsp509I loci, while individuals having a genotype homozygous for Koshihikari at the C1361 MwoI locus were regarded as those generated by recombination between the Rf-1 and C1361 MwoI loci.

(Results and Discussion)

A survey of 4103 individuals revealed one recombinant individual between the Rf-1 and S12564 Tsp509I loci and 6 recombinant individuals between the Rf-1 and C1361 MwoI loci. The previous survey of 1042 individuals obtained by crossing in Reference example 2 above had already revealed one recombinant individual between the Rf-1 and S12564 Tsp509I loci and 2 recombinant individuals between the Rf-1 and C1361 MwoI loci as shown in Table 3.

Thus, a total of 2 recombinant individuals between the Rf-1 and S12564 Tsp509I loci and 8 recombinant individuals between the Rf-1 and C1361 MwoI loci were able to be oabtained from 5145 individuals. These 10 individuals were tested by high-precision segregation analysis in the examples below.

Example 2

Chromosomal Walking (1) First Chromosomal Walking (Materials and Methods)

A genomic library was constructed from the genomic DNA of Asominori japonica (not carrying Rf-1) using Lambda DASH II vector as described in Reference example 1 and tested by chromosomal walking.

PCR was routinely performed using total DNA of Asominori as a template in combination with the following primer pair:

```
5'-atcaggagccttcaaattgggaac-3' (SEQ ID NO:29)
and

5'-ctcgcaaattgcttaattttgacc-3' (SEQ ID NO:30)
```

designed for a partial base sequence (Accession No. D47284) of RFLP probe S12564. The resulting amplification products of about 1200 bp were electrophoresed on an agarose gel and then purified by QIAEXII (QIAGEN). The purified DNA was labeled with a rediprime DNA labelling system (Amersham Pharmacia) to give a library screening probe (probe A, FIG. 1).

The library was routinely screened after plaques were blotted onto Hybond-$N^+$ (Amersham Pharmacia). Single plaques were separated, after which phage DNA was purified by the plate lysate method using Lambda Midi kit (QIAGEN).

(Results and Discussion)

The results of terminal base sequence analysis and restriction enzyme fragment length analysis showed that two (WSA1 and WSA3) of 4 clones obtained by screening were in a relative position as shown in FIG. 1. The Asominori genomic base sequences corresponding to WSA1 and WSA3 were determined by primer walking (DNA Sequencer 377, ABI).

(2) Second Chromosomal Walking (Materials and Methods)

In addition to the Asominori genomic library described above, an IR24 genomic library was similarly constructed from the genomic DNA of an indica variety IR24 (carrying Rf-1) and tested by chromosomal walking.

PCR was routinely performed using DNA of WSA3 as a template in combination with the following primer pair:

```
5'-tgaaggagttatgggtgcgtgacg-3' (SEQ ID NO:31)
and

5'-ttgccgagcacacttgccatgtgc-3' (SEQ ID NO:32)
```

designed for the Asominori genomic base sequence determined in (1). The resulting amplification products of 524 bp were purified and labeled by the method described above to give a library screening probe (probe E, FIG. 1).

Library screening and phage DNA purification were performed by the method described above.

(Results and Discussion)

The results of terminal base sequence analysis and restriction enzyme fragment length analysis showed that one (WSE8) of 15 clones obtained by screening of the Asominori genomic library was in a relative position as shown in FIG. 1. The Asominori genomic base sequence corresponding to WSE8 was determined by primer walking.

The results of terminal base sequence analysis and restriction enzyme fragment length analysis showed that two (XSE1 and XSE7) of 7 clones obtained by screening of the IR24 genomic library were in a relative position as shown in FIG. 1. The IR24 genomic base sequences corresponding to XSE1 and XSE7 were determined by primer walking.

(3) Third Chromosomal Walking (Materials and Methods)

The Asominori genomic library and IR24 genomic library described above were tested by chromosomal walking.

PCR was routinely performed using DNA of WSE8 as a template in combination with the following primer pair:

```
5'-gcgacgcaatggacatagtgctcc-3' (SEQ ID NO:33)
and

5'-ttacctgccaagcaatatccatcg-3' (SEQ ID NO:34)
```

designed for the Asominori genomic base sequence determined in (2). The resulting amplification products of 1159 bp were purified and labeled by the method described above to give a library screening probe (probe F, FIG. 1).

Library screening and phage DNA purification were performed by the method described above.

(Results and Discussion)

The results of terminal base sequence analysis and restriction enzyme fragment length analysis showed that two (WSF5 and WSF7) of 8 clones obtained by screening of the Asominori genomic library were in a relative position as shown in FIG. 1. The Asominori genomic base sequences corresponding to WSF5 and WSF7 were determined by primer walking.

The results of terminal base sequence analysis and restriction enzyme fragment length analysis showed that two (XSF4 and XSF20) of 13 clones obtained by screening of the IR24 genomic library were in a relative position as shown in FIG. 1. The IR24 genomic base sequences corresponding to XSF4 and XSF20 were determined by primer walking.

(4) Fourth Chromosomal Walking (Materials and Methods)

The Asominori genomic library and IR24 genomic library described above were tested by chromosomal walking.

PCR was routinely performed using DNA of WSF7 as a template in combination with the following primer pair:

```
5'-aaggcatactcagtggagggcaag-3' (SEQ ID NO:35)
and

5'-ttaacctgaccgcaagcacctgtc-3' (SEQ ID NO:36)
```

designed for the Asominori genomic base sequence determined in (3). The resulting amplification products of 456 bp were purified and labeled by the method described above to give a library screening probe (probe G, FIG. 1).

Library screening and phage DNA purification were performed by the method described above.

(Results and Discussion)

The results of terminal base sequence analysis and restriction enzyme fragment length analysis showed that two (WSG2 and WSG6) of 6 clones obtained by screening of the Asominori genomic library were in a relative position as shown in FIG. 1. The Asominori genomic base sequences corresponding to WSG2 and WSG6 were determined by primer walking.

The results of terminal base sequence analysis and restriction enzyme fragment length analysis showed that three (XSG8, XSG16 and XSG22) of 14 clones obtained by screening of the IR24 genomic library were in a relative position as shown in FIG. 1. The IR24 genomic base sequences corresponding to XSG8, XSG16 and XSG22 were determined by primer walking.

(5) Fifth Chromosomal Walking (Materials and Methods)

The IR24 genomic library described above was tested by chromosomal walking.

Figure 2:
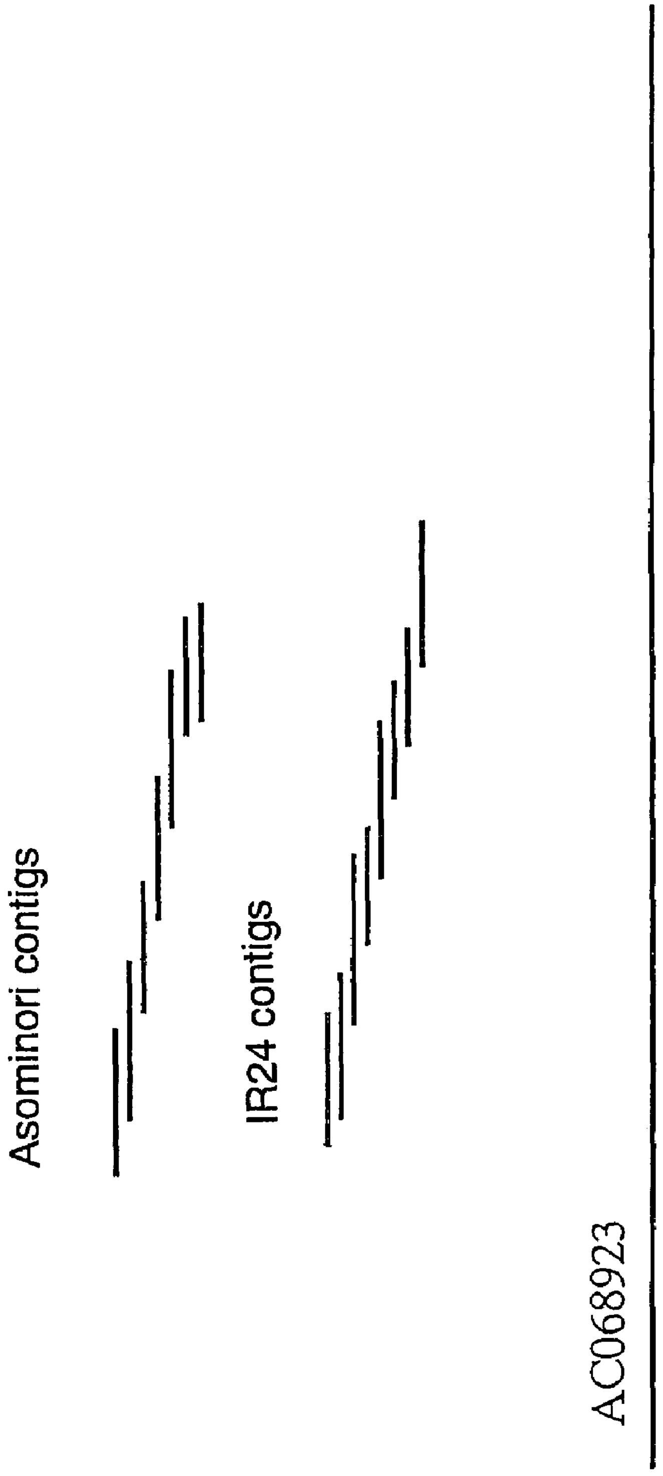
FIG. 2 shows an alignment of lambda clone contigs in relation to the BAC clone AC068923.

We perused the public website of TIGR (The Institute for Genomic Research) and found that a BAC (Bacterial Artificial Chromosome) clone (Accession No. AC068923) containing RFLP marker S12564 had been deposited with a public database (GenBank). This BAC clone contains the genomic DNA of Nipponbare japonica and it was shown from base sequence comparison to completely include the contig regions of Asominori and IR24 prepared in (1)-(4) (FIG. 2).

Thus, PCR was routinely performed using total DNA of IR24 as a template in combination with the following primer pair:

```
5'-tggatggactatgtggggtcagtc-3' (SEQ ID NO:37)
and

5'-agtggaagtggagagagtagggag-3' (SEQ ID NO:38)
```

designed to amplify a part of this BAC clone. The resulting amplification products of about 600 bp were purified and labeled by the method described above to give a library screening probe (probe H, FIG. 1).

Library screening and phage DNA purification were performed by the method described above.

(Results and Discussion)

The results of terminal base sequence analysis and restriction enzyme fragment length analysis showed that one (XSH18) of 15 clones obtained by screening of the IR24 genomic library was in a relative position as shown in FIG. 1. The IR24 genomic base sequence corresponding to XSH18 was determined by primer walking.

Example 3

High Precision Segregation Analysis (1) Development of PCR Marker P4497 MboI

Comparison between the genomic base sequence corresponding to the IR24 contig (SEQ ID NO:27) and the genomic base sequence corresponding to the Asominori contig (SEQ ID NO:28) determined in Example 2 revealed that the 1239th base of SEQ ID NO:27 is A while the 12631st base of SEQ ID NO:28 corresponding to said position is G.

For detecting this change, fragments of about 730 bp are first amplified by PCR from a region surrounding said position using the following primer pair:

P4497 MboI F:

```
5'-ccctccaacacataaatggttgag-3' (SEQ ID NO:39)
```

(corresponding to bases 853-876 of SEQ ID NO:27)
(corresponding to bases 12247-12270 of SEQ ID NO:28)
and P4497 MboI R:

```
5'-tttctgccaggaaactgttagatg-3' (SEQ ID NO:40)
```

(corresponding to bases 1583-1560 of SEQ ID NO:27)
(corresponding to bases 12975-12952 of SEQ ID NO:28).

The amplification products can be visualized by electrophoresis on an agarose gel after treatment with MboI. Thus, the change can be detected as a difference in mobility in the agarose gel due to the difference in the length of DNA after MboI treatment because the amplification products from Asominori DNA having an MboI recognition sequence (GATC) are cleaved with MboI while the amplification products from IR24 DNA are not cleaved with MboI for the lack of the MboI recognition sequence.

(2) Development of PCR Marker P9493 BslI

Comparison between the genomic base sequence corresponding to the IR24 contig (SEQ ID NO:27) and the genomic base sequence corresponding to the Asominori contig (SEQ ID NO:28) determined in Example 2 revealed that the 6227th base of SEQ ID NO:27 is A while the 17627th base of SEQ ID NO:28 corresponding to said position is C.

For detecting this change, fragments of 126 bp are first amplified by PCR from a region surrounding said position using the following primer pair:

P9493 BslI F:

```
5'-gcgatcttatacgcatactatgcg-3' (SEQ ID NO:41)
```

(corresponding to bases 6129-6152 of SEQ ID NO:27)
(corresponding to bases 17529-17552 of SEQ ID NO:28)
and P9493 BslI R:

```
5'-aaagtctttgttccttcaccaagg-3' (SEQ ID NO:42)
```

(corresponding to bases 6254-6231 of SEQ ID NO:27)
(corresponding to bases 17654-17631 of SEQ ID NO:28).

The amplification products can be visualized by electrophoresis on an agarose gel after treatment with BslI. Thus, the change can be detected as a difference in mobility in the agarose gel due to the difference in the length of DNA after BslI treatment because the amplification products from Asominori DNA having a BslI recognition sequence (CCNNNNNNNGG) are cleaved with BslI while the amplification products from IR24 DNA are not cleaved with BslI for the lack of the BslI recognition sequence.

This marker was developed by applying the dCAPS method (Michaels and Amasino 1998, Neff et al., 1998). Specifically, g is substituted for a at the base 6236 of SEQ ID NO:27 and the base 17636 of SEQ ID NO:28 by the use of P9493 BslI R primer described above. Thus, the fragments from Asominori DNA come to have a sequence of CCtttccttG G at 17626-17636 of SEQ ID NO:28 so that they are cleaved with BslI.

(3) Development of PCR Marker P23945 MboI

Comparison between the genomic base sequence corresponding to the IR24 contig (SEQ ID NO:27) and the genomic base sequence corresponding to the Asominori contig (SEQ ID NO:28) determined in Example 2 revealed that the 20680th base of SEQ ID NO:27 is G while the 32079th base of SEQ ID NO:28 corresponding to said position is A.

For detecting this change, fragments of 260 bp are first amplified by PCR from a region surrounding said position using the following primer pair:

P23945 MboI F:

5'-gaggatttatcaaaacaggatggacg-3' (SEQ ID NO:43)

(corresponding to bases 20519-20544 of SEQ ID NO:27)
(corresponding to bases 31918-31943 of SEQ ID NO:28) and P23945 MboI R:

5'-tgggcggcagcagtggaggataga-3' (SEQ ID NO:44)

(corresponding to bases 20778-20755 of SEQ ID NO:27)
(corresponding to bases 32177-32154 of SEQ ID NO:28).

The amplification products can be visualized by electrophoresis on an agarose gel after treatment with MboI. Thus, the change can be detected as a difference in mobility in the agarose gel due to the difference in the length of DNA after MboI treatment because the amplification products from IR24 DNA having an MboI recognition sequence (GATC) are cleaved with MboI while the amplification products from Asominori DNA are not cleaved with MboI for the lack of the MboI recognition sequence.

(4) Development of PCR Marker P41030 TaqI

Comparison between the genomic base sequence corresponding to the IR24 contig (SEQ ID NO:27) and the genomic base sequence corresponding to the Asominori contig (SEQ ID NO:28) determined in Example 2 revealed that the 45461st base of SEQ ID NO:27 is A while the 49164th base of SEQ ID NO:28 corresponding to said position is G.

For detecting this change, fragments of 280 bp are first amplified by PCR from a region surrounding said position using the following primer pair:

P41030 TaqI F:

5'-aagaagggagggttatagaatctg-3' (SEQ ID NO:45)

(corresponding to bases 45369-45392 of SEQ ID NO:27)
(corresponding to bases 49072-49095 of SEQ ID NO:28) and P41030 TaqI R:

5'-atatcaggactaacaccactgctc-3' (SEQ ID NO:46)

(corresponding to bases 45648-45625 of SEQ ID NO:27)
(corresponding to bases 49351-49328 of SEQ ID NO:28).

The amplification products can be visualized by electrophoresis on an agarose gel after treatment with TaqI. Thus, the change can be detected as a difference in mobility in the agarose gel due to the difference in the length of DNA after TaqI treatment because the amplification products from Asominori DNA having a TaqI recognition sequence (TCGA) are cleaved with TaqI while the amplification products from IR24 DNA are not cleaved with TaqI for the lack of the TaqI recognition sequence.

(5) Development of PCR Marker P45177 BstUI

Comparison between the genomic base sequence corresponding to the IR24 contig (SEQ ID NO:27) and the genomic base sequence corresponding to the Asominori contig (SEQ ID NO:28) determined in Example 2 revealed that the 49609th base of SEQ ID NO:27 is A while the 53311st base of SEQ ID NO:28 corresponding to said position is G.

For detecting this change, fragments of 812 bp are first amplified by PCR from a region surrounding said position using the following primer pair:

P45177 BstUI F:

5'-acgagtagtagcgatcttccagcg-3' (SEQ ID NO:47)

(corresponding to bases 49355-49378 of SEQ ID NO:27)
(corresponding to bases 53057-53080 of SEQ ID NO:28) and P45177 BstUI R:

5'-cagcgtgaaactaaaaacggaggc-3' (SEQ ID NO:48)

(corresponding to bases 50166-50143 of SEQ ID NO:27)
(corresponding to bases 53868-53845 of SEQ ID NO:28).

The amplification products can be visualized by electrophoresis on an agarose gel after treatment with BstUI. Thus, the change can be detected as a difference in mobility in the agarose gel due to the difference in the length of DNA after BstUI treatment because the amplification products from IR24 DNA having a BstUI recognition sequence (CGCG) at two positions are cleaved into 3 fragments with BstUI while the amplification products from Asominori DNA having the BstUI recognition sequence at three positions are cleaved with BstUI into four fragments.

(6) Development of PCR Marker B60304 MspI

Comparison between the genomic base sequence corresponding to the IR24 contig (SEQ ID NO:27) determined in Example 2 and the base sequence of the BAC clone described above (Accession No. AC068923) revealed that the 56368th base of SEQ ID NO:27 is T while the base of AC068923 corresponding to said position is C.

For detecting this change, fragments of about 330 bp are first amplified by PCR from a region surrounding said position using the following primer pair:

B60304 MspI F:

5'-atcccacatcatcataatccgacc-3' (SEQ ID NO:49)

(corresponding to bases 56149-56172 of SEQ ID NO:27) and

B60304 MspI R:

5'-agcttctcccttggatacggtggcg-3' (SEQ ID NO:50)

(corresponding to bases 56479-56455 of SEQ ID NO:27).

The amplification products can be visualized by electrophoresis on an agarose gel after treatment with MspI. Thus, the change can be detected as a difference in mobility in the agarose gel due to the difference in the length of DNA after MspI treatment because the amplification products from Nipponbare DNA having an MspI recognition sequence (CCGG) are cleaved with MspI while the amplification products from IR24 DNA are not cleaved with MspI for the lack of the MspI recognition sequence.

This marker was developed by applying the dCAPS method. Specifically, t is substituted for g at base 56463 of SEQ ID NO:27 by the use of B60304 MspI R primer. As a result, the MspI recognition sequence of bases 56460-56463 of SEQ ID NO:27 changes from CCGG into ccgt so that the fragments from SEQ ID NO:27 become unable to be cleaved with MspI. Thus, the fragments from IR24 have no MspI recognition sequence, while DNA from Nipponbare has the MspI recognition sequence at one position in a region corresponding to bases 56367-56370 of SEQ ID NO:27.

(7) Development of PCR Marker B59066 BsaJI

Comparison between the genomic base sequence corresponding to the IR24 contig (SEQ ID NO:27) determined in Example 2 and the base sequence of the BAC clone described above (Accession No. AC068923) revealed that the 57629th base of SEQ ID NO:27 is C while the base of AC068923 corresponding to said position is CC.

For detecting this change, fragments of about 420 bp are first amplified by PCR from a region surrounding said position using the following primer pair:

B59066 BsaJI F:

5'-atttgttggttagttgcggctgag-3' (SEQ ID NO:51)

(corresponding to bases 57563-57586 of SEQ ID NO:27) and

B59066 BsaJI R:

5'-gcccaaactcaaaaggagagaacc-3' (SEQ ID NO:52)

(corresponding to bases 57983-57960 of SEQ ID NO:27).

The amplification products can be visualized by electrophoresis on an agarose gel after treatment with BsaJI. Thus, the change can be detected as a difference in mobility in the agarose gel due to the difference in the length of DNA after BsaJI treatment because the amplification products from Nipponbare DNA having a BsaJI recognition sequence (CCNNGG) are cleaved with BsaJI while the amplification products from IR24 DNA are not cleaved with BsaJI for the lack of the BsaJI recognition sequence.

(8) Development of PCR Marker B56691 XbaI

Comparison between the genomic base sequence corresponding to the IR24 contig (SEQ ID NO:27) determined in Example 2 and the base sequence of the BAC clone described above (Accession No. AC068923) revealed that the 66267th base of SEQ ID NO:27 is G while the base of AC068923 corresponding to said position is C.

For detecting this change, fragments of about 670 bp are first amplified by PCR from a region surrounding said position using the following primer pair:

B56691 XbaI F:

5'-cctcaagtctcccctaaagccact-3' (SEQ ID NO:53)

(corresponding to bases 66129-66152 of SEQ ID NO:27) and

B56691 XbaI R:

5'-gctctactgctgataaaccgtgag-3' (SEQ ID NO:54)

(corresponding to bases 66799-66776 of SEQ ID NO:27).

The amplification products can be visualized by electrophoresis on an agarose gel after treatment with XbaI. Thus, the change can be detected as a difference in mobility in the agarose gel due to the difference in the length of DNA after XbaI treatment because the amplification products from Nipponbare DNA having an XbaI recognition sequence (TCTAGA) are cleaved with XbaI while the amplification products from IR24 DNA are not cleaved with XbaI for the lack of the XbaI recognition sequence.

(9) Development of PCR Marker B53627 BstZ17I

Comparison between the genomic base sequence corresponding to the IR24 contig (SEQ ID NO:27) determined in Example 2 and the base sequence of the BAC clone described above (Accession No. AC068923) revealed that the 69331st base of SEQ ID NO:27 is T while the base of AC068923 corresponding to said position is C.

For detecting this change, fragments of about 620 bp are first amplified by PCR from a region surrounding said position using the following primer pair:

B53627 BstZ17I F:

5'-tggatggactatgtggggtcagtc-3' (SEQ ID NO:55)

(corresponding to bases 68965-68988 of SEQ ID NO:27) and

B53627 BstZ17I R:

5'-agtggaagtggagagagtagggag-3' (SEQ ID NO:56)

(corresponding to bases 69582-69559 of SEQ ID NO:27).

The amplification products can be visualized by electrophoresis on an agarose gel after treatment with BstZ17I. Thus, the change can be detected as a difference in mobility in the agarose gel due to the difference in the length of DNA after BstZ17I treatment because the amplification products from IR24 DNA having a BstZ17I recognition sequence (GTATAC) are cleaved with BstZ17I while the amplification products from Nipponbare DNA are not cleaved with BstZ17I for the lack of the BstZ17I recognition sequence.

(10) Development of PCR Marker B40936 MseI

Development of all the following PCR markers (10)-(12) relates to a study of the base sequences corresponding to further downstream regions (3') of base 76363 at the 3' end of SEQ ID NO:27.

The following primer pair was designed for the base sequence of the BAC clone described above (Accession No. AC068923):

5'-tacgacgccatttcactccattgc-3' (SEQ ID NO:57)
and

5'-catttctctatgggcgttgctctg-3'. (SEQ ID NO:58)

PCR was routinely performed using this primer pair in combination with total DNAs of MS-FR Koshihikari (genotype of the Rf-1 locus: Rf-1 Rf-1) and Koshihikari as templates. The resulting amplification products of about 1300 bp were electrophoresed on an agarose gel and then purified by QIAEXII (QIAGEN). Analysis of the base sequence of the purified DNA by a DNA sequencer 377 (ABI) showed several polymorphisms.

One of them can be detected by PCR amplification of a region surrounding said position using the following primer pair:

B40936 MseI F:

5'-acctgtaggtatggcaccttcaacac-3' (SEQ ID NO:59)

and

B40936 MseI R:

5'-ccaaggaacgaagttcaaatgtatgg-3'. (SEQ ID NO:60)

The amplification products can be visualized by electrophoresis on an agarose gel after treatment with MseI. Thus, the change can be detected as a difference in mobility in the agarose gel due to the difference in the length of DNA after MseI treatment because the amplification products from MS-FR Koshihikari (Rf-1 Rf-1) DNA having an MseI recognition sequence (TTAA) are cleaved with MseI while the amplification products from Koshihikari DNA are not cleaved with MseI for the lack of the MseI recognition sequence.

This marker was developed by applying the dCAPS method.

(11) Development of PCR Marker B19839 MwoI

The following primer pair was designed for the base sequence of the BAC clone described above (Accession No. AC068923):

5'-tgatgtgtttgggcatccctttcg-3' (SEQ ID NO:61)
and

5'-gagataggggacgacagacacgac-3'. (SEQ ID NO:62)

PCR was routinely performed using this primer pair in combination with total DNAs of MS-FR Koshihikari (genotype of the Rf-1 locus: Rf-1 Rf-1) and Koshihikari as templates. The resulting amplification products of about 1200 bp were electrophoresed on an agarose gel and then purified by QIAEXII (QIAGEN). Analysis of the base sequence of the purified DNA by a DNA sequencer 377 (ABI) showed several polymorphisms.

One of them can be detected by PCR amplification of a region surrounding said position using the following primer pair:

B19839 MwoI F:

5'-tcctatggctgtttagaaactgcaca-3' (SEQ ID NO:63)

and

B19839 MwoI R:

5'-caagttcaaacataactggcgttg-3'. (SEQ ID NO:64)

The amplification products can be visualized by electrophoresis on an agarose gel after treatment with MwoI. Thus, the change can be detected as a difference in mobility in the agarose gel due to the difference in the length of DNA after MwoI treatment because the amplification products from Koshihikari DNA having an MwoI recognition sequence (GCNNNNNNNGC) are cleaved with MwoI while the amplification products from MS-FR Koshihikari (Rf-1 Rf-1) DNA are not cleaved with MwoI for the lack of the MwoI recognition sequence.

This marker was developed by applying the dCAPS method.

(12) Development of PCR Marker B2387 BfaI

The following primer pair was designed for the base sequence of the BAC clone described above (Accession No. AC068923):

5'-cactgtcctgtaagtgtgctgtgc-3' (SEQ ID NO:65)
and

5'-caagcgtgtgataaaatgtgacgc-3'. (SEQ ID NO:66)

PCR was routinely performed using this primer pair in combination with total DNAs of MS-FR Koshihikari (genotype of the Rf-1 locus: Rf-1 Rf-1) and Koshihikari as templates. The resulting amplification products of about 1300 bp were electrophoresed on an agarose gel and then purified by QIAEXII (QIAGEN). Analysis of the base sequence of the purified DNA by a DNA sequencer 377 (ABI) showed several polymorphisms.

One of them can be detected by PCR amplification of a region surrounding said position using the following primer pair:

B2387 BfaI F:

5'-tgcctactgccattactatgtgac-3' (SEQ ID NO:67)

and

B2387 BfaI R:

5'-acatactaccgtaaatggtctctg-3'. (SEQ ID NO:68)

The amplification products can be visualized by electrophoresis on an agarose gel after treatment with BfaI. Thus, the change can be detected as a difference in mobility in the agarose gel due to the difference in the length of DNA after BfaI treatment because the amplification products from Koshihikari DNA having an BfaI recognition sequence (CTAG) are cleaved with BfaI while the amplification products from MS-FR Koshihikari (Rf-1 Rf-1) DNA are not cleaved with BfaI for the lack of the BfaI recognition sequence.

(13) Segregation Analysis

Two recombinants between the Rf-1 and S12564 Tsp509I loci (RS1 and RS2) and 8 recombinants between the Rf-1 and C1361 MwoI loci (RC1 to RC8) obtained in Example 1 were genotyped at the 12 DNA marker loci developed in (1) to (12) above. The results are shown in Table 4 along with the genotypes of each recombinant at the S12564 Tsp509I and C1361 MwoI loci.

TABLE 4

| | Genotypes of recombinants proximal to the Rf-1 locus at various marker loci | | | | | | | | | |
|---|---|---|---|---|---|---|---|---|---|---|
| Locus | RS1 | RS2 | RC1 | RC2 | RC3 | RC4 | RC5 | RC6 | RC7 | RC8 |
| S12564 Tsp509I | J | J | H | H | H | H | H | H | H | H |
| P4497 MboI | J | J | H | H | H | H | H | H | H | H |
| P9493 BslI | H | H | H | H | H | H | H | H | H | H |
| P23945 MboI | H | H | H | H | H | H | H | H | H | H |
| P41030 TaqI | H | H | H | H | H | H | H | H | H | H |
| P45177 BstUI | H | H | H | H | H | H | H | H | H | H |
| B60304 MspI | H | H | H | H | H | H | H | H | H | H |
| B59066 BsaJI | H | H | H | H | H | H | H | H | H | H |
| B56691 XbaI | H | H | H | H | H | H | H | J | H | H |
| B53627 BstZ17I | H | H | H | H | H | H | H | J | H | H |
| B40936 MseI | H | H | H | H | H | H | H | J | H | H |
| B19839 MwoI | H | H | H | H | H | J | H | J | H | H |
| B2387 BfaI | H | H | H | H | H | J | H | J | H | J |
| C1361 MwoI | H | H | J | J | J | J | J | J | J | J |

J: Homozygous for Koshihikari
H: Heterozygous for Koshihikari/MS-FR Koshihikari

Table 4 shows that all the recombinants have an indica-derived Rf-1 chromosomal region between P9493 BslI and 59066 BsaJI. This result showed that recombinant pollens having the chromosomal organization as shown in FIG. 3 have pollen fertility, i.e. the Rf-1 gene is functional in these pollens. This means that a sequence determining the presence of the function of the Rf-1 gene is included in the indica region common to these recombinant pollens, i.e. in a region from the P4497 MboI to B56691 XbaI loci (about 65 kb) as estimated at maximum.

However, there is a possibility that it is important for the expression of the genetic function of the Rf-1 gene that the Rf-1 gene is partially of the indica genotype, and that the genetic function may not be significantly changed whether the remaining regions are of the japonica or indica genotype. Therefore, it cannot be concluded that the common indica region above (bases 1239-66267 of SEQ ID NO:27) completely contains the entire Rf-1 gene. However, it is thought that at least SEQ ID NO:27 completely contains the entire Rf-1 gene for the following reasons:

1) the size of a gene is normally several kilobases, and rarely exceeds 10 kb;

2) the genomic base sequence of IR24 determined by the present invention (SEQ ID NO:27) completely contains the common indica region above;

3) the 5' end of SEQ ID NO:27 is located 1238 bp upstream of the 5' end of the common indica region above and forms a part of another gene (S12564); and 4) the 3' end of SEQ ID NO:27 is located 10096 bp downstream of the 3' end of the common indica region above.

Example 4

Complementation Assay for a 9.7 kb Fragment from XSE1

(Materials and Methods)

The λ phage clone XSE1 (FIGS. 1 and 5) was completely digested with NotI and electrophoresed on an agarose gel. The separated 9.7 kb fragment (including bases 1-9657 of SEQ ID NO:27) was purified by QIAEXII (QIAGEN).

On the other hand, an intermediate vector pSB200 having a hygromycin-resistant gene cassette was prepared on the basis of pSB11 (Komari et al., supra.). Specifically, a nopaline synthase terminator (Tnos) was first fused to a ubiquitin promoter and a ubiquitin intron (Pubi-ubiI). A hygromycin-resistant gene (HYG(R)) was inserted between ubiI and Tnos of the resulting Pubi-ubiI-Tnos complex to give an assembly of Pubi-ubiI-HYG(R)-Tnos. This assembly was fused to a HindIII/EcoRI fragment of pSB11 to give pKY205. Linker sites for adding restriction enzyme sites NotI, NspV, EcoRV, KpnI, SacI, EcoRI were inserted into the Hind III site upstream of Pubi of this pKY205 to give pSB200 having a hygromycin-resistant gene cassette.

After the plasmid vector pSB200 was completely digested with NotI, DNA was recovered by ethanol precipitation. The recovered DNA was dissolved in TE solution and then dephosphorylated by CIAP (TAKARA). The reaction solution was electrophoresed on an agarose gel, and then a vector fragment was purified from the gel using QIAEXII (QIAGEN).

The two fragments prepared above, i.e. a 9.7 kb fragment from XSE1 and a vector fragment were subjected to a ligation reaction using DNA Ligation Kit Ver. 1 (TAKARA). After the reaction, DNA was recovered by ethanol precipitation. The recovered DNA was dissolved in pure water (prepared by a Millipore system) and then mixed with *E. coli* DH5a cells, and the mixture was electroporated. After electroporation, the solution was cultured with shaking in LB medium (37° C., 1 hr) and then plated on an LB plate containing spectinomycin and warmed (37° C., 16 hr). Plasmids were isolated from 24 of the resulting colonies. Their restriction enzyme fragment length patterns and boundary base sequences were analyzed to select desired *E. coli* cells transformed with recombinant plasmids.

The *E. coli* cells selected above were used for triparental mating with the *Agrobacterium tumefaciens* strain LBA4404/pSB1 (Komari et al., 1996) and the helper *E. coli* strain HB101/pRK2013 (Ditta et al., 1980) according to the method of Ditta et al. (1980). Plasmids were isolated from 6 of the colonies formed on an AB plate containing spectinomycin and their restriction enzyme fragment length patterns were analyzed to select desired *Agrobacterium* cells.

The *Agrobacterium* cells selected above were used to transform MS Koshihikari (having BT cytoplasm and a nucleus gene substantially identical to Koshihikari) according to the method of Hiei et al. (1994). Necessary immature seeds of MS Koshihikari for transformation can be prepared by pollinating MS Koshihikari with Koshihikari.

Transformed plants were transferred to a greenhouse under long-day conditions after acclimation. 48 individuals grown to a stage suitable for transplantation were transplanted into 1/5000a Wagner pots (4 individuals/pot), and transferred into a greenhouse under short-day conditions 3-4 weeks after transplantation. About one month after heading, seed fertility was tested on standing plants.

(Results and Discussion)

All of the 48 transformed individuals were sterile. This indicates that the 9.7 kb insert fragment does not contain at least the full-length Rf-1 gene.

Example 5

Complementation Assay for a 14.7 kb Fragment from XSE7

(Materials and Methods)

The λ phage clone XSE7 (FIGS. 1 and 5) was completely digested with EcoRI and then DNA was recovered by ethanol precipitation. The recovered DNA was dissolved in TE solution and then blunted by DNA Blunting Kit (TAKARA). The reaction solution was electrophoresed on an agarose gel to separate a 14.7 kb fragment (including bases 2618-17261 of SEQ ID NO:27), which was purified by QIAEXII (QIAGEN).

On the other hand, the plasmid vector pSB200 was completely digested with SacI and then DNA was recovered by ethanol precipitation. The recovered DNA was dissolved in TE solution and then dephosphorylated by CIAP (TAKARA) and DNA was recovered by ethanol precipitation. The recovered DNA was dissolved in TE solution and then blunted by DNA Blunting Kit (TAKARA). The reaction solution was electrophoresed on an agarose gel, and then a vector fragment was purified from the gel using QIAEXII (QIAGEN).

The two fragments prepared above, i.e. the 14.7 kb fragment from XSE7 and the vector fragment were subjected to a ligation reaction using DNA Ligation Kit Ver. 1 (TAKARA). Subsequently, transformed plants were prepared and studied according to the method described in Example 4.

(Results and Discussion)

All of the 48 transformed individuals were sterile. This indicates that the 14.7 kb insert fragment does not contain at least the full-length Rf-1 gene.

Example 6

Complementation Assay for a 21.3 kb Fragment from XSF4

(Materials and Methods)

The λ phage clone XSF4 (FIGS. 1 and 5) was partially digested with NotI and electrophoresed on an agarose gel. The separated 21.3 kb fragment (including bases 12478-33750 of SEQ ID NO:27) was purified by QIAEXII (QIAGEN).

On the other hand, the plasmid vector pSB200 was completely digested with NotI and then DNA was recovered by ethanol precipitation. The recovered DNA was dissolved in TE solution and then dephosphorylated by CIAP (TAKARA). The reaction solution was electrophoresed on an agarose gel, and then a vector fragment was purified from the gel using QIAEXII (QIAGEN).

The two fragments prepared above, i.e. the 21.3 kb fragment from XSF4 and the vector fragment were subjected to a ligation reaction using DNA Ligation Kit Ver. 1 (TAKARA). Subsequently, transformed plants were prepared and studied according to the method described in Example 4.

(Results and Discussion)

All of the 48 transformed individuals were sterile. This indicates that the 21.3 kb insert fragment does not contain at least the full-length Rf-1 gene.

Example 7

Complementation Assay for a 13.2 kb Fragment from XSF20

(Materials and Methods)

The λ phage clone XSF20 (FIGS. 1 and 5) was completely digested with SalI and then DNA was recovered by ethanol precipitation. The recovered DNA was dissolved in TE solution and then blunted by DNA Blunting Kit (TAKARA). The reaction solution was electrophoresed on an agarose gel to separate a 13.2 kb fragment (including bases 26809-40055 of SEQ ID NO:27), which was purified by QIAEXII (QIAGEN).

On the other hand, the plasmid vector pSB200 was completely digested with EcoRV and then DNA was recovered by ethanol precipitation. The recovered DNA was dissolved in TE solution and then dephosphorylated by CIAP (TAKARA). The reaction solution was electrophoresed on an agarose gel, and then a vector fragment was purified from the gel using QIAEXII (QIAGEN).

The two fragments prepared above, i.e. the 13.2 kb fragment from XSF20 and the vector fragment were subjected to a ligation reaction using DNA Ligation Kit Ver. 1 (TAKARA). Subsequently, transformed plants were prepared and studied according to the method described in Example 4.

(Results and Discussion)

All of the 44 transformed individuals were sterile. This indicates that the 13.2 kb insert fragment does not contain at least the full-length Rf-1 gene.

Example 8

Complementation Assay for a 16.2 kb Fragment from XSF18

(Materials and Methods)

The λ phage clone XSF18 is identical to XSF20 at the 5' and 3' ends (bases 20328 and 41921 of SEQ ID NO:27, respectively), but lacks internal bases 33947-38591. Thus, it comprises bases 20328-33946 and 38592-41921 of SEQ ID NO:27. This is because clone XSF18 was initially isolated but found to contain the above deletion during amplification after isolation, and therefore, the amplification step was freshly taken to isolate a complete clone designated XSF20.

The λ phage clone XSF18 (FIG. 5) was completely digested with NotI and electrophoresed on an agarose gel. The separated 16.2 kb fragment (including bases 21065-33946 and 38592-41921 of SEQ ID NO:27) was purified by QIAEXII (QIAGEN).

On the other hand, the plasmid vector pSB200 was completely digested with NotI and then DNA was recovered by ethanol precipitation. The recovered DNA was dissolved in TE solution and then dephosphorylated by CIAP (TAKARA). The reaction solution was electrophoresed on an agarose gel, and then a vector fragment was purified from the gel using QIAEXII (QIAGEN).

The two fragments prepared above, i.e. the 16.2 kb fragment from XSF18 and the vector fragment were subjected to a ligation reaction using DNA Ligation Kit Ver. 1 (TAKARA). Subsequently, transformed plants were prepared and studied according to the method described in Example 4.

(Results and Discussion)

Figure 6:
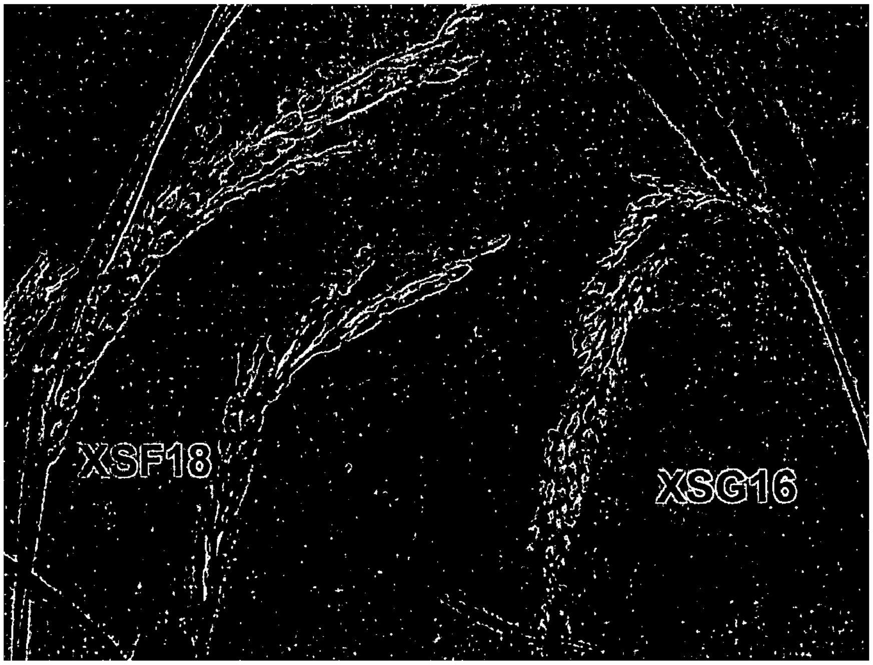
FIG. 6 shows the results of complementation assays using a 15.7 kb fragment from XSG16 (Example 10) and a 16.2 kb fragment from XSF18 (Example 8). The plant transformed with the 15.7 kb fragment from XSG16 has restored fertility as proved by ears bowing.

All of the 48 transformed individuals were sterile (FIG. 6). This indicates that the 16.2 kb insert fragment does not contain at least the full-length Rf-1 gene.

Example 9

Complementation Assay for a 12.6 kb Fragment from XSG22

(Materials and Methods)

The λ phage clone XSG22 (FIGS. 1 and 5) was partially digested with NotI and electrophoresed on an agarose gel. The separated 12.6 kb fragment (including bases 31684-44109 of SEQ ID NO:27) was purified by QIAEXII (QIAGEN).

On the other hand, the plasmid vector pSB200 was completely digested with NotI and then DNA was recovered by ethanol precipitation. The recovered DNA was dissolved in TE solution and then dephosphorylated by CIAP (TAKARA). The reaction solution was electrophoresed on an agarose gel, and then a vector fragment was purified from the gel using QIAEXII (QIAGEN).

The two fragments prepared above, i.e. the 12.6 kb fragment from XSG22 and the vector fragment were subjected to a ligation reaction using DNA Ligation Kit Ver. 1 (TAKARA). Subsequently, transformed plants were prepared and studied according to the method described in Example 4.

(Results and Discussion)

All of the 48 transformed individuals were sterile. This indicates that the 12.6 kb insert fragment does not contain at least the full-length Rf-1 gene.

Example 10

(1) Complementation Assay for a 15.7 kb Fragment from XSG16

(Materials and Methods)

The λ phage clone XSG16 (FIGS. 1 and 5) was partially digested with NotI and electrophoresed on an agarose gel. The separated 15.7 kb fragment (including bases 38538-54123 of SEQ ID NO:27) was purified by QIAEXII (QIAGEN).

On the other hand, the plasmid vector pSB200 was completely digested with NotI and then DNA was recovered by ethanol precipitation. The recovered DNA was dissolved in TE solution and then dephosphorylated by CIAP (TAKARA). The reaction solution was electrophoresed on an agarose gel, and then a vector fragment was purified from the gel using QIAEXII (QIAGEN).

The two fragments prepared above, i.e. the 15.7 kb fragment from XSG16 and the vector fragment were subjected to a ligation reaction using DNA Ligation Kit Ver. 1 (TAKARA). Subsequently, transformed plants were prepared and studied according to the method described in Example 4.

(Results and Discussion)

Of the 47 transformed individuals, at least 37 individuals clearly restored fertility (FIG. 6). This indicates that 15586 bases (bases 38538-54123 of SEQ ID NO:27) derived from rice (IR24) in the 15.7 kb insert fragment include the full-length Rf-1 gene.

(2) Complementation Assay for an Internal 11.4 kb Fragment in XSG16

(Materials and Methods)

The λ phage clone XSG16 was completely digested with AlwNI and BsiWI and then DNA was recovered by ethanol precipitation. The recovered DNA was dissolved in TE solution and then blunted by DNA Blunting Kit (TAKARA). The reaction solution was electrophoresed on an agarose gel to separate a 11.4 kb fragment, which was purified by QIAEXII (QIAGEN).

The plasmid vector pSB11 (Komari et al. Plant Journal, 1996) was completely digested with SmaI and then DNA was recovered by ethanol precipitation. The recovered DNA was dissolved in TE solution and then dephosphorylated by CIAP (TAKARA). The reaction solution was electrophoresed on an agarose gel, and then a vector fragment was purified from the gel using QIAEXII (QIAGEN).

The two fragments prepared above were subjected to a ligation reaction using DNA Ligation Kit Ver. 1 (TAKARA). After the reaction, DNA was recovered by ethanol precipitation. The recovered DNA was dissolved in pure water (prepared by a Millipore system) and then mixed with *E. coli* DH5a cells, and the mixture was electroporated. After electroporation, the solution was cultured with shaking in LB medium (37° C., 1 hr) and then plated on an LB plate containing spectinomycin and warmed (37° C., 16 hr). Plasmids were isolated from 14 of the resulting colonies, and their restriction enzyme fragment length patterns and boundary base sequences were analyzed to select desired *E. coli* cells.

The *E. coli* cells selected above were used for triparental mating with the *Agrobacterium tumefaciens* strain LBA4404/pSB4U (Takakura et al., Japanese Patent Application No. 2001-269982 (WO02/019803 A1)) and the helper *E. coli* strain HB101/pRK2013 (Ditta et al., 1980) according to the method of Ditta et al. (1980). Plasmids were isolated from 12 of the colonies formed on an AB plate containing spectinomycin and their restriction enzyme fragment length patterns were analyzed to select desired *Agrobacterium* cells.

The *Agrobacterium* cells selected above were used to transform MS Koshihikari (having BT cytoplasm and a nucleus gene substantially identical to Koshihikari) according to the method of Hiei et al. (1994). Necessary immature seeds of MS Koshihikari for transformation can be prepared by pollinating MS Koshihikari with Koshihikari.

Transformed plants were transferred to a greenhouse under long-day conditions after acclimation. 120 individuals grown to a stage suitable for transplantation were transplanted into 1/5000a Wagner pots (4 individuals/pot), and transferred into a greenhouse under short-day conditions about one month after transplantation. About one month after heading, one typical ear was sampled from each plant to evaluate seed fertility (the percentage of fertile paddies to total paddies).

(Results and Discussion)

Of the 120 transformed individuals, 59 individuals showed seed fertility of 10% or more, among which 19 individuals showed seed fertility of 70% or more. This indicates that the 11.4 kb insert fragment (bases 42357-53743 of SEQ ID NO:27) contains an essential Rf-1 gene region for expressing a fertility restoring function.

(3) Complementation Assay for an Internal 6.8 kb Fragment in XSG16

(Materials and Methods)

The λ phage clone XSG16 was completely digested with HpaI and AlwNI and electrophoresed on an agarose gel. The separated 6.8 kb fragment was purified by QIAEXII (QIAGEN).

The subsequent procedures including the preparation of the plasmid vector pSB11 were performed according to the method in (2) above.

(Results and Discussion)

Of the 120 transformed individuals, 67 individuals showed seed fertility of 10% or more, among which 26 individuals showed seed fertility of 70% or more. This indicates that the 6.8 kb insert fragment (bases 42132-48883 of SEQ ID NO:27) contains an essential Rf-1 gene region for expressing a fertility restoring function.

Example 11

Complementation Assay for a 16.9 kb Fragment from XSG8

(Materials and Methods)

The λ phage clone XSG8 (FIGS. 1 and 5) was completely digested with NotI and electrophoresed on an agarose gel. The separated 16.9 kb fragment (including bases 46558-63364 of SEQ ID NO:27) was purified by QIAEXII (QIAGEN).

On the other hand, the plasmid vector pSB200 was completely digested with NotI and then DNA was recovered by ethanol precipitation. The recovered DNA was dissolved in TE solution and then dephosphorylated by CIAP (TAKARA). The reaction solution was electrophoresed on an agarose gel, and then a vector fragment was purified from the gel using QIAEXII (QIAGEN).

The two fragments prepared above, i.e. the 16.9 kb fragment from XSG8 and the vector fragment were subjected to a ligation reaction using DNA Ligation Kit Ver. 1 (TAKARA). Subsequently, transformed individuals were prepared and studied according to the method described in Example 4.

(Results and Discussion)

All of the 48 transformed individuals were sterile. This indicates that the 16.9 kb insert fragment does not contain at least the full-length Rf-1 gene.

Example 12

Complementation Assay for a 20.0 kb Fragment from XSH18

(Materials and Methods)

The λ phage clone XSH18 (FIGS. 1 and 5) was completely digested with NotI and electrophoresed on an agarose gel. The separated 20.0 kb fragment (including bases 56409-76363 of SEQ ID NO:27) was purified by QIAEXII (QIAGEN).

On the other hand, the plasmid vector pSB200 was completely digested with NotI and then DNA was recovered by ethanol precipitation. The recovered DNA was dissolved in TE solution and then dephosphorylated by CIAP (TAKARA). The reaction solution was electrophoresed on an agarose gel, and then a vector fragment was purified from the gel using QIAEXII (QIAGEN).

The two fragments prepared above, i.e. the 20.0 kb fragment from XSH18 and the vector fragment were subjected to a ligation reaction using DNA Ligation Kit Ver. 1 (TAKARA). Subsequently, transformed individuals were prepared and studied according to the method described in Example 4.

(Results and Discussion)

All of the 44 transformed individuals were sterile. This indicates that the 20.0 kb insert fragment does not contain at least the full-length Rf-1 gene.

Example 13

Complementation Assay for a 19.7 kb Fragment from an Overlapping Region of XSG8 and XSH18

(Materials and Methods)

A plasmid (XSG8SB200F) isolated from desired *E. coli* cells obtained by ligation in Example 11 was completely digested with SalI and StuI and electrophoresed on an agarose gel. The separated 12.8 kb fragment (including bases 50430-63197 of SEQ ID NO:27) was purified by QIAEXII (QIAGEN).

On the other hand, a plasmid (XSH18SB200R) isolated from desired *E. coli* cells obtained by ligation in Example 12 was completely digested with SalI, StuI and XhoI and electrophoresed on an agarose gel to separate a 6.9 kb fragment (including bases 63194-70116 of SEQ ID NO:27), which was purified by QIAEXII (QIAGEN).

Further, the plasmid vector pSB200 was completely digested with EcoRV and then DNA was recovered by ethanol precipitation. The recovered DNA was dissolved in TE solution and then dephosphorylated by CIAP (TAKARA). The reaction solution was electrophoresed on an agarose gel, and then a vector fragment was purified from the gel using QIAEXII (QIAGEN).

The three fragments prepared above, i.e. the 12.8 kb fragment from XSG8, the 6.9 kb fragment from XSH18 and the vector fragment were subjected to a ligation reaction using DNA Ligation Kit Ver. 1 (TAKARA). The ligation product contains a 19.7 kb fragment from an overlapping region of XSG8 and XSH18 (including 50430-70116 of SEQ ID NO:27) (XSX1 in FIG. 5). Subsequently, transformed individuals were prepared and studied according to the method described in Example 4.

(Results and Discussion)

All of the 40 transformed individuals were sterile. This indicates that the 19.7 kb insert fragment does not contain at least the full-length Rf-1 gene.

Example 14

Preparation of cDNA Library

Firstly, IL216, a line wherein the Rf-1 is introduced into Koshihikari via backcrossing (the genotype, Rf-1/Rf-1), was prepared. The IL216 was grown in a greenhouse by a conventional method, and young panicles were sampled during the growth stage wherein the length between auricles is −5~5 cm. Total RNA was extracted by the SDS-phenol method (Watanabe, A. and Price, C. A. (1982) Translation of mRNAs for subunits of chloroplast coupling factor 1 in spinach. Proceedings of the National Academy of Sciences of the U.S.A., 79, 6304-6308), and the poly $(A)^+$ RNA was purified using QuickPrep mRNA Purification Kit (Amersham Pharmacia Biotech).

The purified poly (A)+ RNA was provided to prepare a cDNA library by ZAP-cDNA Synthesis Kit (Stratagene). The titer of the prepared library (1 ml) was calculated to be 16,000,000 pfu/ml, and was determined to be sufficiently large.

Example 15

Screening of the cDNA Library (1) Preparation of the Screening Primers

PCR was performed by using the following two types of primes:

```
Sense primer
5'-tctcattctctccacgccctgctc-3' (SEQ ID NO:76)

Antisense primer
5'-acggcggagcaattcgtcgaacac-3' (SEQ ID NO:77)
```

and XSG16, a genomic clone of IR24, as a template. SEQ ID NOS:76 and 77 correspond to the bases 43733-43756 and the bases 44038-44015 of SEQ ID NO:27, respectively.

After the electrophoresis, the amplification product of about 300 bp was recovered from the agarose gel by QIAEX II Gel Extraction Kit (QIAGEN). The recovered fragment was $^{32}$P-labeld by Rediprime II DNA labelling system (Amersham Pharmacia Biotech) (The fragment is hereunder referred to as "Probe P").

Further, PCR was performed by using the following two types of primes:

```
Sense primer
5'-agtgtgtggcatggtgcatttccg-3' (SEQ ID NO:78)

Antisense primer
5'-ctctacaggatacacggtgtaagg-3' (SEQ ID NO:79)
```

and XSG16, a genomic clone of IR24, as a template. SEQ ID NOS:78 and 79 correspond to the bases 48306-48329 and the bases 50226-50203 of SEQ ID NO:27, respectively. After the electrophoresis, the amplification product of about 1900 bp was recovered from the agarose gel. The recovered fragment was $^{32}$P-labeld by the method mentioned above (The fragment is hereunder refers to as "Probe Q").

(2) Screening of the cDNA Libbary

The cDNA library prepared in Example 14 was provided to prepare 70 of agar medium wherein about 15000 plaques appeared. Plaque lift was performed twice for each agar medium, and the plaques were transferred to Hybond-N$^+$ (Amersham Pharmacia Biotech). One membrane was used for hybridization with Probe P, and the other membrane was used for hybridization with Probe Q. The whole steps were performed according to the manufacture's instructions.

Probes were added to a hybridization solution containing 250M $Na_2HPO_4$, 1 mM EDTA and 7% SDS, and hybridization was performed at 65° C. for 16 hours. Washing was performed twice with a solution containing 1×SSC and 0.1% SDS, at 65° C. for 15 minutes, and then twice with a solution containing 0.1×SSC and 0.1% SDS, at 65° C. for 15 minutes. After the washing, the membranes were analyzed with FUJIX BAS 1000 (Fuji Photo Films).

As a result, 8 plaques which showed positive for both Probe P and Probe Q were identified. Therefore, those plaques were isolated, subcloned into pBluescript according to the instructions of the manufacture (Stratagene). Among 8 clones, the terminal base sequences of 6 clones were identical to that of XSG16. The entire base sequences of the 6 clones were determined, and the results are shown in SEQ ID NOS:69-74 in the sequence listing.

All of the sequences, SEQ ID NOS:69-74 are presumed to encode a protein having the amino acids 1-791 of SEQ ID NO:75. Specifically, all and each of the 215-2587 of SEQ ID NO:69, the bases 213-2585 of SEQ ID NO:70, the bases 218-2590 of SEQ ID NO:71, the bases 208-2580 of SEQ ID NO:72, the bases 149-2521 of SEQ ID NO:73 and the bases 225-2597 of SEQ ID NO:74 encodes a protein having amino acids 1-791 of SEQ ID NO:75. The above base sequences correspond to the bases 43907-46279 of SEQ ID NO:27.

The amino acid sequence of SEQ ID NO:75 was compared with the presumed amino acid sequence of the corn fertility restorer gene (Rf2), and the N-terminal 7 amino acid residues (Met-Ala-Arg-Arg-Ala-Ala-Ser) in both amino acid sequences were concurred. These 7 amino acid residues are considered to be a portion of a targeting signal to mitochondria (Liu et al., 2001). Based on the above facts, the cDNAs isolated on this occasion are considered to contain the full coding region of the Rf-1 gene. No homology between the amino acid sequences of the rice Rf-1 and the corn Rf2 can be found except for the above region. It is presumed that the mechanisms by which the gene products of the Rf-1 and the Rf2 can restore fertility after being transferred to mitochondria are distinct from each other.

In addition, the sequences of cDNAs isolated on this occasion were compared with the genome sequence of IR24 (SEQ ID NO:27), and the structures of exons and introns of the Rf-1 gene were clarified (FIG. 7). As a result, it was shown that various transcription products wherein the splicing forms and the poly A addition positions are different, are present in a plant body. There is no intron in the coding region of the Rf-1 gene.

Example 16

Complementation Assay

A complementation assay was performed by using a 4.2 kb fragment containing the promoter region and the presumed translation region of the Rf-1 gene. The 4.2 kb fragment is in a plasmid containing the 6.8 kb genome derive from IR24 which proved to have fertility restorer function in Example 10(3).

Firstly, the plasmid described in Example 10(3) was treated with EcoRI, and was subjected to electrophoresis with agarose gel. The 4.2 kb fragment containing the promoter region and the presumed translation region of the Rf-1 (corresponding to the bases 42132-46318 in SEQ ID NO:27) was separated, recovered from the gal using QIAEXII (QIAGEN). The 4.2 kb fragment was subjected to ligation reaction using DNA Ligation Kit Ver. 1 (TAKARA) together with pBluescript II SK (−) which has been treated with EcoRI and then with CIAP (TAKARA). After the reaction, the DNA was recovered by ethanol precipitation.

The recovered DNA was dissolved in pure water (prepared by a Millipore system) and then mixed with *E. coli* DH5a cells, and the mixture was electroporated. After electroporation, the solution was cultured by shaking in LB medium (37° C., 1 hr) and then plated on an LB plate containing ampicillin and warmed (37° C., 16 hr). Plasmids were isolated from 12 of the resulting colonies, and their restriction enzyme fragment length patterns and boundary base sequences were analyzed to select desired *E. coli* cells. Then, plasmids isolated from the selected *E. coli* were treated with BamHI and SalI, and electrophoresed on an agarose gel. The 4.2 kb fragment containing the promoter region and the presumed translation region of Rf-1 was separated, and recovered from the gel using QIAEXII (QIAGEN).

On the other hand, TnosJH0072 (an intermediate vector comprising the nos terminator and a cassette of the ampicillin resistant gene) was treated with BamHI and SalI, and electrophored on a agarose gel. The 3.0 kb fragment containing the nos terminator and the ampicillin-resistant gene was separated, and was recovered from the gel using QIAEXII (QIAGEN).

The 4.2 kb fragment containing the promoter region and the presumed translation region of Rf-1, and the fragment derived from TnosJH0072 were subjected to ligation reaction, and to electroporation by the methods discussed above. The reactant was spread on LB plates containing ampicillin, and incubated (37° C., 16 hr). Plasmids were isolated from 12 of the resulting colonies, and their restriction enzyme fragment length patterns and boundary base sequences were analyzed to select desired *E. coli* cells.

Further, plasmids isolated from the selected *E. coli* were treated with SgfI, and electrophoresed on an agarose gel. The 4.2 kb fragment containing the promoter region and the presumed translation region of Rf-1 was separated, and recovered from the gel using QIAEXII (QIAGEN). The 4.2 kb fragment and pSB200Pac (an intermediate vector comprising a cassette of the hygromycin-resistant gene) which has been treated with PacI and then with CIAP (TAKARA) were subjected to ligation reaction, and to electroporation by the methods discussed above. The reactant was spread on LB plates containing spectinomycin, and incubated (37° C., 16 hr). Plasmids were isolated from 16 of the resulting colonies, and their restriction enzyme fragment length patterns and boundary base sequences were analyzed to select desired *E. coli* cells.

As a result of the above steps, *E. coli* cells were obtained wherein the chimera gene of the fragment containing the promoter region of the Rf-1 and the presumed translation region of the Rf-1 attached with the nos terminator has been inserted within an intermediate vector. The *E. coli* cells were used for triparental mating with the *Agrobacterium tumefaciens* strain LBA4404/pSB1 (Komari et al., 1996) and the helper *E. coli* strain HB101/pRK2013 (Ditta et al., 1980) according to the method of Ditta et al. (1980). Plasmids were isolated from 6 of the colonies formed on an AB plate containing spectinomycin and their restriction enzyme fragment length patterns were analyzed to select desired *Agrobacterium* cells.

The *Agrobacterium* cells selected above were used to transform MS Koshihikari (having BT cytoplasm and a nucleus gene substantially identical to Koshihikari) according to the method of Hiei et al. (1994). Necessary immature seeds of MS Koshihikari for transformation were prepared by pollinating MS Koshihikari with Koshihikari.

Transformed plants were transferred to a greenhouse under long-day conditions after acclimation. 32 individuals grown to a stage suitable for transplantation were transplanted into 1/5000a Wagner pots (4 individuals/pot), and transferred into a greenhouse under short-day conditions 3-4 weeks after transplantation. About one month after heading, seed fertility was tested on standing plants. As a result, 28 individuals among the 32 transformed individuals restored fertility.

By the above procedures, it has been experimentally demonstrated that the function of the Rf-1 gene can be furnished by expressing the presumed translation region.

Example 17

Isolation of cDNA

In Example 15, the cDNA library derived from IL216 young panicles was screened with Probe P and Probe Q. Plaques which are positive for both probes were isolated and analyzed, and 6 cDNA were isolated. In this example, similar screening was performed with Probe P and Probe R as mentioned below, and six additional cDNAs were isolated. Details are as follows.

Firstly, PCR was performed by using the following two types of primes:

```
Sense primer
5'-cagttgggttgaaacctaatactg-3' (SEQ ID NO:86)

Antisense primer
5'-cactaaaccgttagacgagaaagc-3' (SEQ ID NO:87)
```

and a genomic clone of IR24, XSG16 as a template. SEQ ID NOS:86 and 87 correspond to the bases 45522-45545 and the bases 45955-45932 of SEQ ID NO:27, respectively.

After the electrophoresis, the amplification product of about 430 bp was recovered from the agarose gel by QIAEX II (QIAGEN). The recovered fragment was $^{32}$P-labeld by Rediprime II DNA labelling system (Amersham Pharmacia Biotech) (hereinafter referred as "Probe R", FIG. 8).

The cDNA library derived from IL216 young panicles was provided to prepare 20 of agar medium wherein about 15000 plaques appeared. Plaque lift was performed twice for each agar medium, and the plaques were transferred to Hybond-N$^+$ (Amersham Pharmacia Biotech). One membrane was used for hybridization with Probe P of Example 15, and the other membrane was used for hybridization with Probe R. All of the steps were performed according to the manufacture's instructions. As a result, 12 plaques were identified which proved to be positive for both Probe P and Probe R.

Accordingly, those plaques were isolated, and subcloned into pBluescript according to the instructions of the manufacture (Staratagene). The terminal base sequences of the cones were determined. Among 12 clones, the terminal base sequences of 6 clones were identical to that of XSG16, and thus the entire base sequences of those 6 clones were determined (#7-#12). The results were shown in SEQ ID NOS:80-85.

All of the sequences, SEQ ID NOS:80-85 are presumed to encode a protein having the amino acids 1-791 of SEQ ID NO:75. Specifically, all and each of the 229-2601 of SEQ ID NO:80, the bases 175-2547 of SEQ ID NO:81, the bases 227-2599 of SEQ ID NO:82, the bases 220-2592 of SEQ ID NO:83, the bases 174-2546 of SEQ ID NO:84 and the bases 90-2462 of SEQ ID NO:85 encodes a protein having amino acids 1-791 of SEQ ID NO:75. The above base sequences correspond to the bases 43907-46279 of SEQ ID NO:27.

The sequences of cDNAs isolated on this occasion were compared with the genome sequence of IR24 (SEQ ID NO:27), and the structures of exons and introns were clarified (FIG. 8). Among the cDNAs isolated on this occasion, there are three cDNAs which do not have any exons irrelevant to the presumed translation region, and consist of a single exon (#10-#12, SEA ID NOS: 83-85).

The invention claimed is:

1. A method for restoring rice fertility comprising introducing a nucleic acid into rice, wherein the nucleic acid encodes the amino acid sequence of SEQ ID NO. 75, or an amino acid sequence which is identical to at least 95% of the amino acid sequence of SEQ ID NO. 75.

2. The method of claim 1, comprising introducing a nucleic acid into rice, wherein the nucleic acid encodes the amino acid sequence of SEQ ID NO. 75.

3. The method of claim 1 or 2, wherein the nucleic acid encoding the amino acid sequence of SEQ ID NO. 75, or an amino acid sequence which is identical to at least 95% of the amino acid sequence of SEQ ID NO. 75 is selected from nucleic acids of the following a)-p):

a) a nucleic acid comprising the bases 215-2587 of SEQ ID NO:69;

b) a nucleic acid comprising the bases 213-2585 of SEQ ID NO:70;

c) a nucleic acid comprising the bases 218-2590 of SEQ ID NO:71;

d) a nucleic acid comprising the bases 208-2580 of SEQ ID NO:72;

e) a nucleic acid comprising the bases 149-2521 of SEQ ID NO:73;

f) a nucleic acid comprising the bases 225-2597 of SEQ ID NO:74;

g) a nucleic acid comprising the bases 43907-46279 of SEQ ID NO:27;

h) a nucleic acid comprising the bases 229-2601 of SEQ ID NO:80;

i) a nucleic acid comprising the bases 175-2547 of SEQ ID NO:81;

j) a nucleic acid comprising the bases 227-2599 of SEQ ID NO:82;

k) a nucleic acid comprising the bases 220-2592 of SEQ ID NO:83;

l) a nucleic acid comprising the bases 174-2546 of SEQ ID NO:84;

m) a nucleic acid comprising the bases 90-2462 of SEQ ID NO:85;

n) a nucleic acid which is identical to at least 95% of the nucleic acid of any of a)-m);

o) a nucleic acid which hybridizes to the nucleic acid of any of a)-m) underhybridization conditions of 0.1×SSC to 0.2×SSC at about 60-65° C. and/or washing conditions of 0.2×SSC, 0.1% SDS at about 65-68° C.; and p) a nucleic acid wherein one or a plurality of base(s) is deleted from, added to or substituted from the nucleic acid of any of a)-m).

4. The method of claim 3, wherein the nucleic acid encoding the amino acid sequence of SEQ ID NO. 75, or an amino acid sequence which is identical to at least 95% of the amino acid sequence of SEQ ID NO. 75, and which meets at least one of the following requirements 1)-12):

1) a base corresponding to the base 1769 of SEQ ID NO. 69 is A;

2) a base corresponding to the base 1767 of SEQ ID NO. 70 is A;

3) a base corresponding to the base 1772 of SEQ ID NO. 71 is A;

4) a base corresponding to the base 1762 of SEQ ID NO. 72 is A;

5) a base corresponding to the base 1703 of SEQ ID NO. 73 is A;

6) a base corresponding to the base 1779 of SEQ ID NO. 74 is A;

7) a base corresponding to the base 1783 of SEQ ID NO. 80 is A;

8) a base corresponding to the base 1729 of SEQ ID NO. 81 is A;

9) a base corresponding to the base 1781 of SEQ ID NO. 82 is A;

10) a base corresponding to the base 1774 of SEQ ID NO. 83 is A;

11) a base corresponding to the base 1728 of SEQ ID NO. 84 is A; or 12) a base corresponding to the base 1644 of SEQ ID NO. 85 is A.

5. A method for restoring rice fertility comprising introducing a nucleic acid into rice, wherein the nucleic acid comprises SEQ ID NO: 69 bases 215-2587, or a nucleic acid sequence comprising a sequence having at least 95% identity to the nucleic acid of SEQ ID NO. 69 bases 215-2587.

* * * * *